US007951378B2

(12) United States Patent
Larrick et al.

(10) Patent No.: US 7,951,378 B2
(45) Date of Patent: May 31, 2011

(54) IMMUNOADHESIN COMPRISING A CHIMERIC ICAM-1 MOLECULE PRODUCED IN A PLANT

(75) Inventors: James William Larrick, Woodside, CA (US); Keith Lynn Wycoff, Palo Alto, CA (US)

(73) Assignee: Planet Biotechnology Inc., Hayward, CA (US)

( * ) Notice: Subject to any disclaimer, the term of this patent is extended or adjusted under 35 U.S.C. 154(b) by 0 days.

(21) Appl. No.: 10/258,763

(22) PCT Filed: Apr. 28, 2001

(86) PCT No.: PCT/US01/13932
§ 371 (c)(1),
(2), (4) Date: Oct. 25, 2002

(87) PCT Pub. No.: WO01/83529
PCT Pub. Date: Nov. 8, 2001

(65) Prior Publication Data
US 2008/0219999 A1    Sep. 11, 2008

(51) Int. Cl.
*A61K 39/385* (2006.01)
*C07K 14/00* (2006.01)
(52) U.S. Cl. .................. 424/193.1; 530/350; 530/387.1
(58) Field of Classification Search ............. 435/5, 69.7, 435/325, 339; 424/184.1
See application file for complete search history.

(56) References Cited

U.S. PATENT DOCUMENTS

| | | | |
|---|---|---|---|
| 4,443,549 A | 4/1984 | Sadowski | |
| 4,594,244 A | 6/1986 | Lehner et al. | |
| 4,607,388 A | 8/1986 | Koiyumaki et al. | |
| 4,652,448 A | 3/1987 | Sadowski | |
| 4,736,866 A | 4/1988 | Leder et al. | |
| 4,870,009 A | 9/1989 | Evans et al. | |
| 4,873,191 A | 10/1989 | Wagner et al. | |
| 5,034,322 A | 7/1991 | Rogers et al. | |
| 5,116,964 A | 5/1992 | Capon et al. | |
| 5,183,756 A | 2/1993 | Schlom | |
| 5,188,642 A | 2/1993 | Shah et al. | |
| 5,202,422 A | 4/1993 | Hiatt et al. | |
| 5,258,498 A | 11/1993 | Huston et al. | |
| 5,349,124 A | 9/1994 | Fischhoff et al. | |
| 5,352,440 A | 10/1994 | Gilchrest et al. | |
| 5,352,446 A | 10/1994 | Lehner | |
| 5,352,605 A | 10/1994 | Fraley et al. | |
| 5,854,402 A | 12/1998 | Lehner et al. | |
| 5,959,177 A | 9/1999 | Hein et al. | |
| 6,034,223 A | 3/2000 | Maddon et al. | |
| 6,046,037 A * | 4/2000 | Hiatt et al. ................... | 435/70.1 |
| 6,303,341 B1 | 10/2001 | Hiatt et al. | |
| 6,417,429 B1 | 7/2002 | Hein et al. | |
| 6,808,709 B1 | 10/2004 | Hiatt et al. | |
| 6,852,319 B2 | 2/2005 | Hein et al. | |
| 7,074,913 B2 | 7/2006 | Young et al. | |
| 7,211,389 B2 | 5/2007 | Hiatt et al. | |

| | | |
|---|---|---|
| 2002/0168367 A1 | 11/2002 | Larrick et al. |
| 2006/0015969 A1 | 1/2006 | Larrick et al. |
| 2007/0118934 A1 | 5/2007 | Yu et al. |

FOREIGN PATENT DOCUMENTS

| | | |
|---|---|---|
| EP | 0468257 A1 | 1/1992 |
| EP | 0480014 B1 | 4/1992 |
| EP | 0484148 A1 | 5/1992 |
| EP | 0371017 B1 | 9/1994 |
| WO | WO-87/00551 A1 | 1/1987 |
| WO | WO-88/06455 A1 | 9/1988 |
| WO | WO-90/14430 A1 | 11/1990 |
| WO | WO-91/06320 A1 | 5/1991 |
| WO | WO-91/16061 A1 | 10/1991 |
| WO | WO-9404690 A1 | 3/1994 |
| WO | WO-94/14467 A1 | 7/1994 |
| WO | WO-9621012 A1 | 7/1996 |
| WO | WO-99/49024 A2 | 9/1999 |
| WO | WO-00/36092 A2 | 6/2000 |
| WO | WO-01/64929 A1 | 9/2001 |
| WO | WO-01/83529 A2 | 11/2001 |
| WO | WO-02/46228 A2 | 6/2002 |
| WO | WO-03/064992 A2 | 8/2003 |
| WO | WO-2006/046072 A2 | 5/2006 |

OTHER PUBLICATIONS

Bardor et al. Trends in Plant Science, Sep. 1999, 4(9):376-380.*
Abdullah, R. et al. (Dec. 1986). "Efficient Plant Regeneration from Rice Protoplasts Through Somatic Embryogenesis," *Bio/Technology* 4:1087-1090.
Adelman, J. P. et al. (1983). "In Vitro Deletional Mutagenesis for Bacterial Production of the 20,000-Dalton Form of Human Pituitary Growth Hormone," *DNA* 2(3):183-193.
Altmann, F. et al. (1997). "More than Silk and Honey-or, Can Insect Cells Serve in the Production of Therapeutic Glycoproteins?," *Glycoconjugate Journal* 14:643-646.
Arruda, E. et al. (Jun. 1992). "In Vitro Studies of the Antirhinovirus Activity of Soluble Intercellular Adhesion Molecule-1," *Antimicrobial Agents and Chemotherapy* 36(6):1186-1191.
Arruda, E. et al. (May 1996). "Comparative Susceptibilities of Human Embryonic Fibroblasts and HeLa Cells for Isolation of Human Rhinoviruses," *Journal of Clinical Microbiology* 34(5):1277-1279.

(Continued)

*Primary Examiner* — Stacy B Chen
(74) *Attorney, Agent, or Firm* — Morrison & Foerster LLP

(57) ABSTRACT

The immunoadhesions of the present invention are useful in treating rhinovirus infections. The immunoadhesions contain a chimeric ICAM molecule and may optionally also contain J chain and secretory compounds. The chimeric ICAM molecule is a fusion protein that has a rhinovirus receptor protein linked to an immunoglobulin protein. This invention also includes the greatly increased and improved method of producing immunoadhesions in plants. Each of the components of an immunoadhesin is produced in a plant cell and thereby assembles within the plant cell. This method of producing the immunoadhesions of the present invention results in the efficient and economic production of these molecules. The present invention also contemplates the production of immunoadhesions in a variety of eukaryotic cells including plants and mammalian cells. The immunoadhesions of the present invention are useful as a therapeutic against the common cold in humans which is caused by rhinoviruses.

49 Claims, 70 Drawing Sheets

OTHER PUBLICATIONS

Aruffo, A. et al. (Dec. 1987). "Molecular Cloning of a CD28 cDNA by a High-Efficiency COS Cell Expression System," *Proceedings of the National Academy of Sciences* 84:8573-8577.

Bakos, M.-A. et al. (1994). "Expression and Purification of Biologically Active Domain I of the Human Polymeric Immunoglobulin Receptor," Molecular Immunology 31(2):165-168.

Banting, G. et al. (Aug. 1989). "Intracellular Targeting Signals of Polymeric Immunoglobulin Receptors are Highly Conserved Between Species," *FEBS Letters* 254:177-183.

Barnes, W. M. (Dec. 1990). "Variable Patterns of Expression of Luciferase in Transgenic Tobacco Leaves," *Proceedings of the National Academy of Sciences* 87:9183-9187.

Baumlein, H. et al. (1986). "The Legumin Gene Family: Structure of a B Type Gene of Vicia faba and a Possible Legumin Gene Specific Regulatory Element," Nucleic Acids Research 14(6): 2707-2720.

Becker, D. et al. (1992) "New Plant Binary Vectors with Selectable Markers Located Proximal to the Left T-DNA Border," *Plant Molecular Biology* 20:1195-1197.

Bella, J. et al. (1999). "Review: Rhinoviruses and Their ICAM Receptors," *Journal of Structural Biology* 128:69-74.

Benfey, P. N. et al. (Apr. 1989). "Regulated Genes in Transgenic Plants," *Science* 244:174-181.

Benfey, P. N. et al. (Nov. 1990). "The Cauliflower Mosaic Virus 35S Promoter: Combinatorial Regulation of Transcription in Plants," Science 250:959-966.

Bradley, K. A. et al. (Nov. 2001). "Identification of the Cellular Receptor for Anthrax Toxin," *Nature* 4:225-229.

Brandtzaeg, P. et al. (Sep. 1984). "Direct Evidence for an Integrated Function of J Chain and Secretory Component in Epithelial Transport of Immunoglobulins," *Nature* 311:71-73.

Breitfeld, P. P. et al. (Aug. 1990). "Deletions in the Cytoplasmic Domain of the Polymeric Immunoglobulin Receptor Differentially Affect Endocytotic Rate and Postendocytotic Traffic," *The Journal of Biological Chemistry* 265(23): 13750-13757.

Bytebier, B. et al. (Aug. 1987). "T-DNA Organization in Tumor Cultures and Transgenic Plants of the Monocotyledon Asparagus officinalis," *Proceedings of the National Academy of Sciences* 84:5345-5349.

Cabanes-Macheteau, M. et al. (1999). "N-Glycosylation of a Mouse IgG Expressed in Transgenic Tobacco Plants," *Glycobiology* 9(4):365-372.

Callis, J. et al. (1987). "Introns Increase Gene Expression in Cultured Maize Cells," *Genes and Development* 1:1183-1200.

Carayannopoulos, L. et al. (Aug. 1994). "Recombinant Human IgA Expressed in Insect Cells," *Proceedings of the National Academy of Sciences* 91:8348-8352.

Casasnovas, J. M. et al. (Apr. 1998). "A Dimeric Crystal Structure for the N-Terminal Two Domains of Intercellular Adhesion Molecule-I," *Proceedings of the National Academy of Sciences* 95:4134-4139.

Chamow, S. M. et al. (Feb. 1996). "Immunoadhesins: Principles and Applications," *Trends in Biotechnology* 14:52-60.

Chintalacharuvu, K. R. et al. (1994). "Divergence of Human Alpha-Chain Region Gene Sequences. A Novel Recombinant Alpha 2 Gene," *Journal of Immunology* 152:5299-5304.

Chintalacharuvu, K. R. et al. (1999). "Production and Characterization of Recombinant IgA," *Immunotechnology* 4:165-174.

Cocking, E. C. et al. (Jun. 1987). "Gene Transfer in Cereals," *Science* 236:1259-1262.

Colonno, R. J. et al. (Aug. 1988). "Evidence for the Direct Involvement of the Rhinovirus Canyon in Receptor Binding," *Proceedings of the National Academy of Sciences* 85:5449-5453.

Corthesy, B. (1997). "Recombinant Secretory IgA for Immune Intervention Against Mucosal Pathogens," *Biochemical Society Transactions* 25:471-475.

Corthesy, B. et al. (Feb. 1994). "Biochemical Characterization of Recombinant Secretory Component," *Experimentia* 50:Abstract S08-08.

Crago, S. S. et al. (1989). "Antisera to the Secretory Component Recognize the Murine Fc Receptor for IgA," *The Journal of Immunology* 142(11): 3909-3912.

Crump, C. E. et al. (1993). "Comparative Antirhinoviral Activities of Soluble Intercellular Adhesion Molecule-1 (sICAM-1) and Chimeric ICAM-1/Immunoglobulin A Molecule," *Antimicrobial Agents and Chemotherapy* 38(6):1425-1427.

Crump, C. E. et al. (1993). "In Vitro Inhibitory Activity of Soluble ICAM-1 for the Numbered Serotypes of Human Rhinovirus," *Antiviral Chemistry and Chemotherapy* 4(6):323-327.

De La Pena, A. et al. (Jan. 1987). "Transgenic Rye Plants Obtained by Injecting DNA into Young Floral Tillers," *Nature* 325:274-276.

Depicker, A. et al. (1982). "Nopaline Synthase: Transcript Mapping and DNA Sequence," *Journal of Molecular and Applied Genetics* pp. 561-573.

During, K. et al. (1988). "Wundinduzierbare Expression and Sekretion von T4 Lysozym and Monoklonalen Antikorpern in Nicotiana tabacum," Inaugural Dissertation zur Erlangung des Doktorgrades der Mathematisch-Naturwissenschaftlichen Fakultat der Universitat zu Koln, pp. 1-189. (English Translation attached, 68 pages).

During, K. et al. (1990). "Synthesis and Self-Assembly of a Functional Monoclonal Antibody in Transgenic Nicotiana Tabacum," *Plant Molecular Biology* 15:281-293.

Eliasson, M. et al. (Mar. 1988). "Chimeric IgG-Binding Receptors Engineered from *Staphylococcal* Protein A and *Streptococcal* Protein G," *Journal of Biological Chemistry* 23(9): 4323-4327.

Fraley, R. T. et al. (Aug. 1983). "Expression of Bacterial Genes in Plant Cells," *Proceedings of the National Academy of Sciences* 80:4803-4807.

Fraley, R. T. et al. (Jul. 1985). "The SEV System: A New Disarmed Ti Plasmid Vector System for Plant Transformation," *Biotechnology* 3:629-635.

Fromm, M. E. et al. (1986). "Stable Transformation of Maize after Gene Transfer by Elecfroporation," *Nature* 319:791-793.

Fujimura, T. et al. (1985). "Regeneration of Rice Plants from Protoplasts," *Plant Tissue Culture Letters* 2(2):74-75.

Gegenheimer, P. (1990). "Preparation of Extracts from Plants" Chapter 14 *In Methods in Enzymology*, vol. 182: Guide to Protein Purification. Deutscher, M. P. ed., Academic Press, Inc.: San Diego, pp. 174-193.

GenBank Accession No. X81371, located at <http://www.ncbi.nlm.nih.gov/entrez/viewer.fcgi?db=nuccore&val=563340> visited on Jun. 14, 2007. (3 pages).

Gielen, J. et al. (1984). "The Complete Nucleotide Sequence of the TL-DNA of the Agrobacterium tumefaciens Plasmid pTiAch5," *The EMBO Journal* 3(4):835-846.

Greve, J. M. et al. (1991). "Mechanisms of Receptor-Mediated Rhinovirus Neutralization Defined by Two Soluble Forms of ICAM-1," *Journal of Virology* 65(11):6015-6023.

Greve, J. M. et al. (Mar. 1989). "The Major Human Rhinovirus Receptor is ICAM-1," *Cell* 56:839-847.

Gwaltney Jr., J. M. et al. (1989). "Rhinovirus" Chapter 17 *In Diagnostic Procedures For Viral Rickettsial And Chlamydial Infections*. Schmidt, N. J. et al. eds., 6th Edition, American Public Health Association, Inc.: Washington, D.C., pp. 579-614.

Gwaltney, J. M. et al. (1992). "Updated Recommendations for Safety-Testing of Viral Inocula Used in Volunteer Experiments on Rhinovirus Colds," *Progress in Medical Virology* 39:256-263.

Harborne, J. B. et al. eds. (1975). *The Chemistry and Biochemistry of Plant Proteins*. Annual Proceedings of the Phytochemical Society No. 11, Academic Press Inc.: New York, NY, 7 pages (Table of Contents).

Harris II, J. M. et al. (Dec. 1996). "Incubation Periods of Experimental Rhinovirus Infection and Illness," *Clinical Infectious Diseases* 23:1287-1290.

Hein, M. B. et al. (1991). "Evaluation of Immunoglobulins from Plant Cells," *Biotechnlogy Progress* 7: 455-461.

Hess, D. (1987). "Pollen-Based Techniques in Genetic Manipulation," *International Review of Cytology* 107:367-395.

Hiatt, A. et al. (1993). "Characterization and Applications of Antibodies Produced in Plants," *International Reviews of Immunology* 10:139-152.

Hiatt, A. et al. (1994). "Structure, Function and Uses of Antibodies from Transgenic Plants and Animals" Chapter 12 *In The Pharmacology of Monoclonal Antibodies*. Rosenberg, M. et al. eds., Springer-Verlag: Berlin, pp. 317-330.

Hiatt, A. et al. (Jul. 1992). "Monoclonal Antibody Engineering in Plants," *FEBS Letters* 307(1):71-75.

Hiatt, A. et al. (Nov. 1989). "Production of Antibodies in Transgenic Plants," *Nature* 342:76-78.

Horsch, R. B. et al. (Mar. 1985). "A Simple and General Method for Transferring Genes into Plants," *Science* 227:1229-1231.

Huang, A. L. et al. (Dec. 1981). "Glucocorticoid Regulation of the Ha-MuSV p21 Gene Conferred by Sequences from Mouse Mammary Tumor Virus," *Cell* 27:245-255.

Huguenel, E. D. et al. (1997). "Prevention of Rhinovirus Infection in Chimpanzees by Soluble Intercellular Adhesion Molecule-1," *American Journal Respiratory and Critical Care Medicine* 155:1206-1210.

Huse, W. D. et al. (Dec. 1989). "Generation of a Large Combinatorial Library of the Immunoglobulin Repertoire in Phage Lambda," *Science* 246:1275-1281.

Ingelbrecht, I. et al. (1991). "Transcriptional Interference in Transgenic Plants," *Gene* 109:239-242.

International Search Report mailed Jun. 26, 2002, for PCT Application No. PCT/US01/13932 filed on Apr. 28, 2001, 4 pages.

Jorgensen, R. et al. (1987). "T-DNA is Organized Predominantly in Inverted Repeat Structures in Plants Transformed with Agrobacterium Tumifaciens C58 Derivatives," *Molecular and General Genetics* 207:471-477.

Klein, T. M. et al. (May 1987). "High-velocity Microprojectiles for Delivering Nucleic Acids into Living Cells," *Nature* 327:70-73.

Klein, T. M. et al. (Nov. 1988). "Stable Genetic Transformation of Intact Nicotiana Cells by the Particle Bombardment Process," *Proceedings of the National Academy of Sciences* 85:8502-8505.

Kobyashi, K. et al. (1973). "Studies on the Human Secretory IgA (II). Comparative Studies on a Fragment of Secretory Component Derived from Secretory IgA and Fragments Obtained by Enzymatic Digestion of Free Secretory Component," *Immunochemistry* 10:73-80.

Kornfeld, R. et al. (1985). "Assembly of Asparagine-Linked Oligosaccharides," *Annual Review of Biochemistry* 54:631-664.

Koshland, M. E. (1989). "The Immunoglobulin Helper: The J Chain" Chapter 18 *In Immunoglobulin Genes*. Honjo, T. et al. eds., Academic Press: San Diego, pp. 345-359.

Kozak, M. (Jan. 1986). "Point Mutations Define a Sequence Flanking the AUG Initiator Codon that Modulates Translation by Eukaryotic Ribosomes," *Cell* 44:283-292.

Kraehenbuhl, J.-P. et al. (1987). "Receptor-Mediated Transepithelial Transport of Secretory Antibodies and Engineering of Mucosal Antibodies," *Advances in Experimental Medicine and Biology*, pp. 1053-1060.

Kraehenbuhl, J.-P. et al. (Jun. 1992). "Transepithelial Transport and Mucosal Defense II: Secretion of IgA," *Trends in Cell Biology* 2:170-174.

Krajci, P. et al. (1992). "Molecular Cloning and Exon-Intron Mapping of the Gene Encoding Human Transmembrane Secretory Component (the Poly-Ig Receptor)," *European Journal of Immunology* 22:2309-2315.

Krajci, P. et al. (Feb. 1989). "Molecular Cloning of the Human Transmembrane Secretory Component (Poly-Ig Receptor) and its mRNA Expression in Human Tissues," *Biochemical and Biophysical Research Communications* 158(3):783-789.

Larrick, J. W. et al. (1994). "Recombinant Therapeutic Human Monoclonal Antibodies" Chapter 2 *In The Pharmacology of Monoclonal Antibodies*. Rosenberg, M. et al. eds., Springer-Verlag: Berlin, pp. 23-48.

Larrick, J. W. et al. (2001). "Production of Secretory IgA Antibodies in Plants," *Biomolecular Engineering* 18:87-94.

Lee, C. K. et al. (Mar. 1994). "Oral Administration of Polymeric Immunoglobulin A Prevents Colonization With Vibrio cholerae in Neonatal Mice," *Infection and Immunity* 62(3):887-891.

Lerouge, P. et al. (1998). "N-Glycoprotein Biosynthesis in Plants: Recent Developments and Future Trends," *Plant Molecular Biology* 38:31-48.

Lindh, E. (Jan. 1975). "Increased Resistance of Immunoglobulin A Dimers to Proteolytic Degradation After Binding of Secretory Component," *The Journal of Immunology* 114(1):284-286.

Loomis, W. D. (1974). "Overcoming Problems of Phenolics and Quinones in the Isolation of Plant Enzymes and Organelles" Chapter 54 *In Methods in Enzymology*, vol. XXXI: Biomembranes, Part A. Fleischer, S. et al. eds., Academic Press, Inc.: New York, pp. 528-544.

Lorz, H. et al. (1985). "Gene Transfer to Cereal Cells Mediated by Protoplast Transformation," *Molecular and General Genetics* 199:178-182.

Luo, Z. et al. (1988). "A Simple Method for the Transformation of Rice Via the Pollen-Tube Pathway," *Plant Molecular Biology Reporter* 6(3):165-174.

Ma, J. K.-C. et al. (1989). "Specificity of Monoclonal Antibodies in Local Passive Immunization Against *Streptococcus mutans*," *Clinical and Experimental Immunology* 77:331-337.

Ma, J. K.-C. et al. (1994). "Assembly of Monoclonal Antibodies with IgG1 and IGA Heavy Chain Domains in Transgenic Tobacco Plants," *European Journal of Immunology* 24:131-138.

Ma, J. K.-C. et al. (May 1995). "Generation and Assembly of Secretory Antibodies in Plants," *Science* 268:716-719.

MacDonald, M. H. et al. (1991). "Characterization of the Polyadenylation Signal from the T-DNA-Encoded Octopine Synthase Gene," *Nucleic Acids Research* 19(20):5575-5581.

Marcotte Jr., W. R. et al. (Sep. 1988). "Regulation of a Wheat Promoter by Abscisic Acid in Rice Protoplasts," *Nature* 335:454-457.

Mark, G. E. et al. (1994). "Humanization of Monoclonal Antibodies" Chapter 4 *In The Pharmacology of Monoclonal Antibodies*. Rosenberg, M. et al. eds., Springer-Verlag: Berlin, pp. 105-134.

Marlin, S. D. et al. (Mar. 1990). "A Soluble Form of Intercellular Adhesion Molecule-1 Inhibits Rhinovirus Infection," *Nature* 344:70-72.

Marshall, R. D. (1972). "Glycoproteins," *Annual Review of Biochemistry* 41:673-703.

Marshall, R. D. (1974). "The Nature and Metabolism of the Carbohydrate-Peptide Linkages of Glycoproteins," *Biochemical Society Symposium* 40:17-26.

Martin, S. et al. (Jun. 1993). "Efficient Neutralization and Disruption of Rhinovirus by Chimeric ICAM-1/Immunoglobulin Molecules," *Journal of Virology* 67(6):3561-3568.

Matsuuchi, L. et al. (Jan. 1986). "Immunoglobulin J Chain Gene from the Mouse," *Proceedings of the National Academy of Sciences* 83:456-460.

McCabe, D. E. et al. (Aug. 1988). "Stable Transformation of Soybean (Glycine Max) by Particle Acceleration," *Bio/Technology* 6:923-926.

McNabb, P. C. et al. (1981). "Host Defense Mechanisms at Mucosal Surfaces," *Annual Review of Microbiology* 35:477-496.

Michetti, P. et al. (1991). "Production and Use of Monoclonal IgA Antibodies Complexed with Recombinant Secretory Component for Passive Mucosal Protection" *In Immunology and the Neonate*. Mestecky, J. et al. eds., Plenum Press: New York, pp. 183-185.

Miller, J. et al. (Nov. 1995). "Intercellular Adhesion Molecule-1 Dimerization and its Consequences for Adhesion Mediated by Lymphocyte Function Associated-1," *The Journal of Experimental Medicine* 182:1231-1241.

Mogen, B. D. et al. (Dec. 1992). "Several Distinct Types of Sequence Elements are Required for Efficient mRNA 3' End Formation in a Pea rbcS Gene," *Molecular and Cellular Biology* 12(12):5406-5414.

Mostov, K. (1994). "Transepithelial Transport of Immunoglobulins," *Annual Review of Immunology* 12:63-84.

Mostov, K. E. et al. (Mar. 1984). "The Receptor for Transepithelial Transport of IgA and IgM Contains Multiple Immunoglobulin-Like Domains," *Nature* 308: 37-43.

Neuhaus, G. et al. (1987). "Transgenic Rapeseed Plants Obtained by the Microinjection of DNA into Microspore-Derived Embryoids," *Theoretical and Applied Genetics* 75:30-36.

Ni, M. et al. (1995). "Strength and Tissue Specificity of Chimeric Promoters Derived from the Octopine and Mannopine Synthase Genes," *The Plant Journal* 7(4):661-676.

Odell, J. T. et al. (Feb. 1985). "Identification of DNA Sequences Required for Activity of the Cauliflower Mosaic Virus 35S Promoter," *Nature* 313:810-812.

Ohlin, A. et al., (Jun. 1994). "Spectrum of Activity of Soluble Intercellular Adhesion Molecule-1 Against Rhinovirus Reference Strains and Field Isolates," *Antimicrobial Agents and Chemotherapy* 38(6):1413-1415.

Orlandi, R. et al. (May 1989). "Cloning Immunoglobulin Variable Domains for Expression by the Polymerase Chain Reaction," *Proceedings of the National Academy of Sciences* 86:3833-3837.

Paszkowski, J. et al. (1984). "Direct Gene Transfer to Plants," *The EMBO Journal* 3(12): 2717-2722.

Piskurich, J. F. et al. (Apr. 1993). "Molecular Cloning of Mouse Polymeric Ig Receptor cDNA," The Journal of Immunology 150(8):38A, Abstract 203.

Potrykus, I. et al. (1985). "Direct Gene Transfer to Cells of Graminaceous Monocot," *Molecular and General Genetics* 199:183-188.

Reilly, P. L. et al. (1995). "The Native Structure of Intercellular Adhesion Molecule-1 (ICAM-1) is a Dimer. Correlation with Binding to LFA-1," *Journal of Immunology* 155:529-532.

Roger, S. G. et al. (1987). "Pathways to Plant Genetic Manipulation Employing Agrobacterium" Chapter 7 *In Plant DNA Infectious Agents*. Hohn, T. et al. eds., Springer-Verlag/Wien: New York, pp. 179-203.

Rogers, S. G. et al. (1987). "Improved Vectors for Plant Transformation: Expression Cassette Vectors and New Selectable Markers" Chapter 15 *In Methods in Enzymology*, vol. 153: Recombinant DNA, Part D. Wu, R. et al. eds., Academic Press, Inc.: San Diego, pp. 253-277.

Rogers, S. G. et al. (1988). "Gene Transfer in Plants: Production of Transformed Plants Using Ti Plasmid Vectors" Chapter 26 *In Methods for Plant Molecular Biology*. Weissbach, A. et al. eds., Academic Press, Inc.: San Diego, pp. 423-436.

Rossman, M. G. et al. (Sep. 1985). "Structure of a Human Common Cold Virus and Functional Relationship to Other Picornaviruses," *Nature* 317:145-153.

Rueckert, R. R. (1990). "Picornaviridae and Their Replication" Chapter 20 In Virology, vol. 1. Fields, B. N. et al. eds., 2nd Edition, Reven Press, Ltd.: New York, pp. 507-548.

Sawant, S. V. et al. (Aug. 1999). "Conserved Nucleotide Sequences in Highly Expressed Genes in Plants," Journal of Genetics 78(2):123-130.

Schouten, A. et al. (1996). "The C-terminal KDEL Sequence Increases the Expression Level of a Single-Chain Antibody Designed to be Targeted to Both the Cytosol and the Secretory Pathway in Transgenic Tobacco," Plant Molecular Biology 30:781-793.

Silbart, L. K. et al. (Mar. 1989). "Reduction of Intestinal Carcinogen Absorption by Carcinogen-Specific Secretory Immunity," Science 243:1462-1464.

Smith, R. et al. (1989). "Characterization of Monoclonal Antibodies to Common Protein Epitopes on the Cell Surface of *Streptococcus mutants* and *Streptococcus sobrinus*," Oral Microbioogy and Immunology 4:153-158.

Solari, R. et al. (1989). "Cellular Location of the Clevage Event of the Polymeric Immunoglobulin Receptor and Fate of its Anchoring Domain in the Rat Hepatocyte," Biochemical Journal 257:759-768.

Sperber, S. J. et al. (Apr. 1988). "Minireview: Chemotherapy of Rhinovirus Colds," Antimicrobial Agents and Chemotherapy 32(4):409-419.

Spielmann, A. et al. (1986). "T-DNA Structure in Transgenic Tobacco Plants with Multiple Independent Integration Sites," Molecular and General Genetics 205:34-41.

Springer, T. A. (Jan. 1994). "Traffic Signals for Lymphocyte Recirculation and Leukocyte Emigration: The Multistep Paradigm," Cell 76:301-314.

St. Croix, B. et al. (Aug. 2000). "Genes Expressed in Human Tumor Endothelium," Science 289:1197-1202.

Staunton, D. E. et al. (Apr. 1990). "The Arrangement of the Immunoglobulin-like Domains of ICAM-1 and the Binding Sites for LFA-1 and Rhinovirus," Cell 61:243-254.

Staunton, D. E. et al. (Mar. 1988). "Primary Structure of ICAM-1 Demonstrates Interaction Between Members of the Immunoglobulin and Integrin Supergene Families," Cell 52:925-933.

Staunton, D. E. et al. (Mar. 1989). "A Cell Adhesion Molecule, ICAM-1, is the Major Surface Receptor for Rhinoviruses," Cell 56:849-853.

Supplemental Partial European Search Report mailed May 23, 2007, for European Application No. 02804821.3 filed Oct. 25, 2002, 5 pages.

Toriyama, K. et al. (1986). "Haploid and Diploid Plant Regeneration from Protoplasts of Another Callus in Rice," Theoretical and Applied Genetics 73:16-19.

Turner, R. B. et al. (May 1999). "Efficacy of Tremacamra, a Soluble Intercellular Adhesion Molecule 1, for Experimental Rhinovirus Infection: A Randomized Clinical Trial," The Journal of the American Medical Association 281(19):1797-1804.

Uchimiya, H. et al. (1986). "Expression of a Foreign Gene in Callus Derived from DNA-treated Protoplasts of Rice (*Oryza sativa* L.)," Molecular and General Genetics 204:204-207.

Vasil, I. K. (Apr. 1988). "Progress in the Regeneration and Genetic Manipulation of Cereal Crops," Bio/Technology 6:397-402.

Williams, A. F. et al. (1989). "The Immunoglobulin Superfamily" Chapter 19 In Immunoglobulin Genes. Honjo, T. et al. eds., Academic Press: San Diego, pp. 361-387.

Yamada, Y. et al. (1986). "Plant Regeneration from Protoplast-Derived Callus of Rice (*Oryza sativa* L.)," Plant Cell Reports 5:85-88.

Yamamoto, Y. Y. et al. (May 1995). "5'-Leader of a Photosystem I Gene in *Nicotiana sylvestris*, psaDb, Contains a Translational Enhancer," The Journal of Biological Chemistry 270(21):12466-12470.

Yoo, E. M. et al. (Nov. 1999). "Structural Requirements for Polymeric Immunoglobulin Assembly and Association with J Chain," *The Journal of Biological Chemistry* 274(47):33771-33777.

Zhou, G.-Y. et al. (1983). "Introduction of Exogenous DNA into Cotton Embryos," Chapter 29 *In Methods in Enzymology*, vol. 101: Recombinant DNA, Part C. Wu, R. et al. eds., Academic Press, Inc.: New York, pp. 433-481.

U.S. Appl. No. 08/367,395, filed Dec. 30, 1994 for Hiatt et al.

U.S. Appl. No. 11/605,720, filed Nov. 28, 2006 for Hiatt et al.

Benbrook, C. M. et al. (Apr. 29-May 1, 1986). "Herbicide Resistance: Environmental and Economic Issues," *Proceedings of Bio Expo 86: The American Commercial & Industrial Conference & Exposition in Biotechnology*, Boston, MA, pp. 27-54.

International Search Report and Written Opinion mailed Oct. 18, 2007, for PCT Application No. PCT/US2006/030325 filed Aug. 2, 2006, 16 pages.

International Search Report mailed on Jun. 4, 1996, for PCT Application No. PCT/US95/16889 filed on Dec. 27, 1995, 4 pages.

International Search Report mailed on Mar. 5, 2004, for PCT Application No. PCT/US02/34197 filed on Oct. 25, 2002, 3 pages.

Leroy, K. et al. (2007). "N-glycosylation Affects Substrate Specificity of Chicory Fructan 1-exohydrolase: Evidence for the Presence of an Inulin Binding Cleft," *The New Phytologist* 176(2):317-324.

Lu, L. et al. (2006). "Roles of O-fucose Glycans in Notch Signaling Revealed by Mutant Mice," *Methods in Enzymology* 417:127-136.

Notkins, A. (2004). "Polyreactivity of Antibody Molecules," *Trends in Immunology* 25(4):174-179.

Scobie, H. M. et al. (Apr. 29, 2003). "Human Capillary Morphogenesis Protein 2 Functions as an Anthrax Toxin Receptor," *Proceedings of the National Academy of Sciences* 100(9):5170-5174.

Supplementary Partial European Search Report mailed Sep. 19, 2007, for EP Application No. 02804821.3 filed on Oct. 25, 2002, 8 pages.

U.S. Office Action mailed Jan. 24, 2008, for U.S. Appl. No. 10/493,909, filed Jul. 21, 2005, 15 pages.

Wycoff, K. (Jun. 3-7, 2006). "Production of Biodefense-Related Proteins in Tobacco," Minneapolis, Minnesota, *Journal of the Society for In Vitro Biology*, 42:14-A.

Zhu, D. et al. (2002). "Acquisition of Potential N-glycosylation Sites in the Immunoglobulin Variable Region by Somatic Mutation is a Distinctive Feature of Follicular Lymphoma," *Blood* 99(7):2562-2568.

U.S. Office Action mailed on May 29, 2008, for U.S. Appl. No. 11/498,488, filed Aug. 2, 2006, 20 pages.

Bella, J. et al. (Apr. 1998). "The Structure of Two Amino-terminal Domains of Human ICAM-1 Suggests How It Functions as a Rhinovirus Receptor and as an LFA-1 Integrin Ligand," *Proceedings of the National Academy of Sciences* 95:4140-4145.

Berdoz, J. et al. (1999). "In vitro Comparison of the Antigen-binding and Stability Properties of the Various Molecular Forms of IgA Antibodies Assembled and Produced in CHO Cells," *Proceedings of the National Academy of Sciences* 96:3029-3034.

Casasnovas, J. (Jul. 1998). "The Domain Structure of ICAM-1 and the Kinetics of Binding to Rhinovirus," *Journal of Virology* 72(7):6244-6246.

Casasnovas, J. et al. (Jun. 1995). "Kinetics and Thermodynamics of Virus Binding to Receptor," *The Journal of Biological Chemistry* 270(22):13216-13224.

Chinese Office Action mailed on Sep. 10, 2008 for Chinese Application No. 018121381 filed on Apr. 28, 2001, 5 pages. (English translation attached, 7 pages).

Fiedler, Ulrike et al. (1995). "High-Level Production and Long-Term Storage of Engineered Antibodies in Transgenic Tobacco Seeds," *Bio/Technology* 13:1090-1093.

James, L. et al. (Feb. 28, 2003). "Antibody Multispecificity Mediated by Conformational Diversity," *Science* 299(5611):1362-1367.

Japanese Office Action mailed on Sep. 30, 2008 for Japanese Application No. 2001-580953 filed on Apr. 28, 2001, 5 pages. (English translation attached, 3 pages).

Jimenez, D. et al. (Feb. 2005). "Contribution of N-Linked Gkycans to the Conformation and Function of Intercellular Adhesion Molecules (ICAMS)," *The Journal of Biological Chemistry* 280(7):5854-5861.

Kolatkar, P. et al. (1999). "Structural Studies of Two Rhinovirus Serotypes Complexed with Fragment s of Their Cellular Receptor," *The EMBO Journal* 18(22):6249-6259.

Lineberger, D. (Jun. 1990). "Antibodies That Block Rhinovirus Attachment Map to Domain 1 of the Major Group Receptor," *Journal of Virology* 64(6):2582-2587.

Martin, S. et al. (1993). "Functional Studies of Truncated Soluble Intercellular Adhesion Molecule 1 Expressed in *Escherichia coli,*" *Antimicrobial Agents and Chemotherapy* 37(6):1278-1285.

McClelland, A. (Sep. 1991). "Identification of Monoclonal Antibody Epitopes and Critical Residues for Rhinovirus Binding in Domain 1 of Intercellular Adhesion Molecule 1," *Proceedings of the National Academy of Sciences* 88:7993-7997.

Mer, G. et al. (Jan. 1, 1996). "Stabilization of Proteins by Glycosylation Examined by NMR Analysis of a Fucosylated Proteinase Inhibitor," *Nature Structural Biology* 3(1):45-53.

U.S. Office Action mailed Jul. 17, 2008, for U.S. Appl. No. 10/493,909, filed Jul. 21, 2005, 15 pages.

Wang, G. et al. (1998). "Principles and Technologies of Genetic Engineering in Plants," *Science Press*, pp. 45-46.

Wyss, D. et al. (Sep. 1995). "Conformation and Function of the N-linked Glycan in the Adhesion Domain of Human CD2," *Science* 269:1273-1278.

Xing, Li. (2000). "Distinct Cellular Receptor Interactions in Poliovirus and Rhinoviruses," *The EMBO Journal* 19(6):1207-1216.

Burton, R. et al. (Jan. 6, 1992). "Human Antibody Effector Function," Advances in Immunology 51:1-84.

Edelman, G. et al. (May 3, 1962). "The Nature of Bence-Jones Proteins: Chemical Similarities to Polypeptide Chains of Myeloma Globulins and Normal γ-Globulins," The Journal of Experimental Medicine 116:207-227.

Norderhaug, I. et al. (1999). "Regulation of the Formation and External Transport of Secretory Immunoglobulins," Critical Reviews in Immunology 19:481-508.

U.S. Office Action mailed Mar. 5, 2009, for U.S. Appl. No. 11/498,488, filed Aug. 2, 2006, 7 pages.

U.S. Office Action mailed May 1, 2009, for U.S. Appl. No. 10/493,909, filed Jul. 21, 2005, 23 pages.

Scallon et al. (1995). "Functional comparisons of different tumour necrosis factor receptor/IgG fusion proteins," Cytokine 7(8):759-770.

Fischer et al. (1999). "Towards molecular farming in the future: moving from diagnostic protein and antibody production in microbes to plants," Biotechnology and Applied Biochemistry 30:101-108.

U.S. Office Action mailed Oct. 15, 2009, for U.S. Appl. No. 11/498,488, filed Aug. 2, 2006. 20 pages.

U.S. Office Action mailed Jan. 22, 2010, for U.S. Appl. No. 10/493,909, filed Jul. 21, 2005, 31 pages.

Arnold et al. (1976). "Naturally Occurring Secretory Immunoglobulin A Antibodies to *Streptococcus mutans* in Human Colostrum and Saliva," Infection and Immunity 14(2):355-362.

Rojas et al. (2002). "Immunoglobulin transport across polarized epithelial cells," Nature Reviews 3:944-956.

U.S. Office Action mailed Mar. 26, 2010, for U.S. Appl. No. 11/605,720, filed Nov. 28, 2006, 11 pages.

Ansley Scott '02 and Dawn Stancik '02 (Dec. 2001). "Anthrax Protective Antigen," Biology 363, Abstract.

Cha et al. (1999). "Hamster Diphtheria Toxin Receptor: A Naturally Occurring Chimera of Monkey and Mouse HB-EGF Precursors," Biochemical and Biophysical Research Communications 254:325-329.

"Dictionary of Immunology", Edited by Herbert et al., 3rd Edition, 1985, p. 107.

Hailman et al., "Stimulation of Macrophages and Neutrophils by Complexes of Lipopolysaccharide and Soluble CD14", The Journal of Immunology, vol. 156, 1996, pp. 4384-4390.

Potter (2001). "Snake toxins that bind specifically to individual subtypes of muscarinic receptors," Life Sciences 68:2541-2547.

Sorensen et al. (2000). "Structural requirements for incorporation of J chain into human IgM and IgA," International Immunology 12(1):19-27.

Sugita et al. (1999). "Neurexins Are Functional alpha-Latrotoxin Receptors," Neuron 22:489-496.

Final Office Action received for U.S. Appl. No. 11/498,488, mailed on Jul. 21, 2010, 35 pages.

Final Office Action received for U.S. Appl. No. 10/493,909, mailed on Sep. 30, 2010, 27 pages.

\* cited by examiner

FIGURE 2B

QTSVSPSKVILPRGGSVLVTCSTSCDQPKLLGIETPLPKKELLLPGNNRKVYELSNVQEDSQPMCYSNCPDGQSTAKTPLTVYWTPERVELAPLPSWQPVG
KNLTLRCQVEGGAPRANLTVVLLRGEKELKRPAVGEPAEVTTVLVRRDHHGANFSCRTELDLRPQGLELFENTSAPYQLQTFVLPATPPQLVSPRVLEV
DTQGTVVCSLDGLFPVSEAQVHLALQDQRLNPTVTYGNDSPSAKASVSVTABDEGTQRLTCAVILQNQSQETLQTVTIYSFPAPNVILTKPEVSEGTEVTV
KCEAHPRAKVTLNGVPAQPLGPRAQLLLKATPEDNGRSFSCSATLEVAGQLIHKNQTRELRVLYGPRLDERDCPGNMTWPENSQQTPMCQAWGNPLPELKC
LKDGTFPLPIGESVTVTRDLEGTYLCRARSTQGEVTREVTVNVTSGSSASPTSPKVFPLSLDSTPQDGNVVACLVQGFFPQEPLSVTWSESGQNVTARNF
PPSQDASGDLYTTSSQLTLPATQCPDGKSVTCHVKHYTNSSQDVTVPCRVPPPPCCHPRLSLHRPALEDLLLGSEANLTCLTGLRDASGATPTWTPSSG
KSAVQGPPERDLCGCYSVSRVLPGCAQPWNHGETPTCTAAHPBLKTPLTANITKSGNTFRPEVHLLPPPSEELALNELVTLTCLARGFSPKDVLVRWLQGS
QELPREKYLTWASRQEPSQGTTTYAVTSILRVAAEDWKKGETPSCMVGHEALPLAFTQKTIDRLAGKPTHINVSVMAEADGTCYRSEKDEL

[SEQUENCE ID NO:8]

FIGURE 3

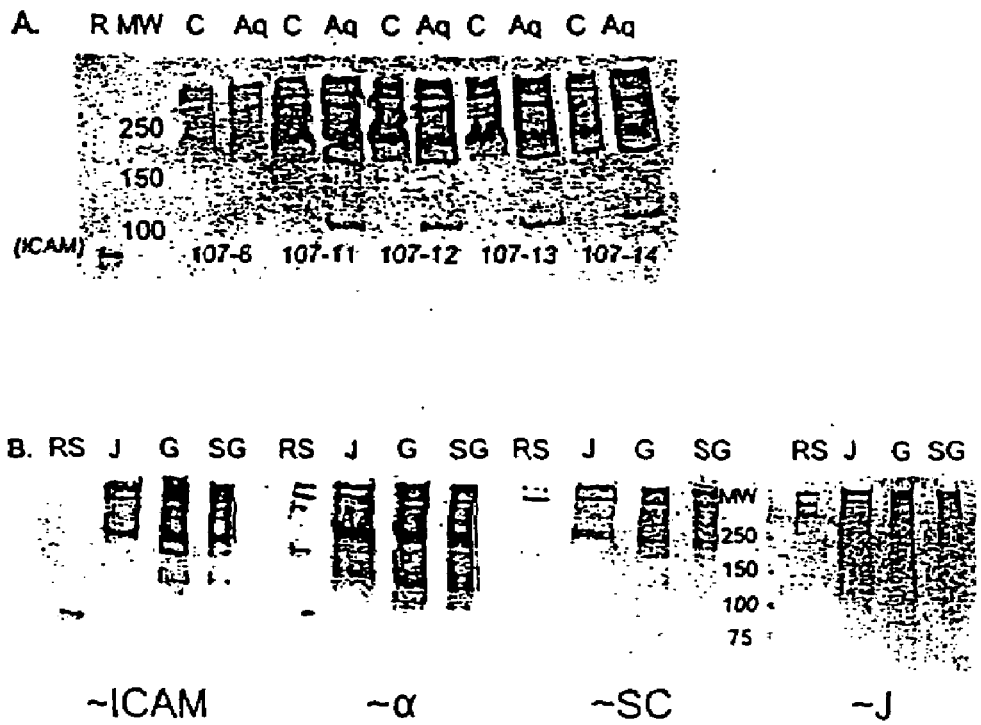

Expression of ICAM-1-SIgA in independently transformed tobacco calli. Immunoblots, of non-reducing SDS-polyacrylamide gels, of different calli (C), and aqueous extracts (Aq) derived from them, probed for the presence of human ICAM (A). The MW markers are indicated and the reference standard (R) was a mixture (~75 ng each) of human ICAM (~75 kD) and human SIgA (>>250 kD). The solubility of the plantibody assured us that extraction could be easily performed and the similarity of signals leads us to believe in the reproducibility of expression. B. Immuno-blots of non-reducing SDS-polyacrylamide gels containing various fractions of partially purified plantibody from callus Rhi107-11. J = juice, G = G-100 fraction, SG = sterile filtered G-100 fraction (used in CPE assay) and RS = a mixture of reference standards of human SIgA (75 ng) and human ICAM-1 (75 ng). Blots were probed with antibodies against: human ICAM (~ICAM), human IgA heavy chain (~α), human secretory component (~SC) and human J chain (~J). Secondary, enzyme-conjugated antibodies were employed as necessary to label immuno-positive bands with alkaline phosphatase. The specificity of immuno-blotting was further verified by a failure to detect immuno-positive bands in extracts of non-expresssing calli (not shown). The expected MW for dimerized ICAM-1-heavy-chain, without glycosylation, is 173,318; this form is likely present in the band migrating just below the 250kD marker since it is immuno-positive for ICAM-1 and heavy-chain. This band is also immuno-positive for SC (total expected MW of ~248 kD) but not for J chain which is somewhat unexpected given the canonical pathway for SIgA assembly, which involves 2 cell types (mammalian) and requires the presence of J chain prior to assembly of SC. A tetrameric ICAM-1-heavy-chain fusion, containing a single molecule of J chain and a single molecule of SC, has an expected MW of ~440 kD, prior to glycosylation. Several species with molecular weights well in excess of 200 kD, immuno-positive with all four probes, are readily apparent.

FIGURE 7A

I. HUMAN IG ALPHA-1 CHAIN C REGION - HOMO SAPIENS (HUMAN)

AMINO ACID SEQUENCE
>sp|P01876|ALC1_HUMAN IG ALPHA-1 CHAIN C REGION - Homo sapiens (Human)

```
          10         20         30         40         50         60
           |          |          |          |          |          |
     ASPTSPKVFP LSLCSTQPDG NVVIACLVQG FFPQEPLSVT WSESGQGVTA RNFPPSQDAS 70         80         90        100        110        120
           |          |          |          |          |          |
     GDLYTTSSQL TLPATQCLAG KSVTCHVKHY TNPSQDVTVP CPVPSTPPTP SPSTPPTPSP 130        140        150        160        170        180
           |          |          |          |          |          |
     SCCHPRLSLH RPALEDLLLG SEANLTCTLT GLRDASGVTF TWTPSSGKSA VQGPPERDLC 190        200        210        220        230        240
           |          |          |          |          |          |
     GCYSVSSVLP GCAEPWNHGK TFTCTAAYPE SKTPLTATLS KSGNTFRPEV HLLPPPSEEL 250        260        270        280        290        300
           |          |          |          |          |          |
     ALNELVTLTC LARGFSPKDV LVRWLQGSQE LPREKYLTWA SRQEPSQGTT TFAVTSILRV 310        320        330        340        350
           |          |          |          |          |
     AAEDWKKGDT FSCMVGHEAL PLAFTQKTID RLAGKPTHVN VSVVMAEVDG TCY
```
[SEQUENCE ID NO:16]

CODING SEQUENCE

```
                                                              g   -1
     catccccgac cagccccaag gtcttcccgc tgagcctctg cagcacccag ccagatggga    60
     acgtggtcat cgcctgcctg gtccagggct tcttcccccca ggagccactc agtgtgacct   120
     ggagcgaaag cggacagggc gtgaccgcca gaaacttccc acccagccag gatgcctccg   180
     gggacctgta caccacgagc agccagctga ccctgccggc cacacagtgc ctagccggca   240
     agtccgtgac atgccacgtg aagcactaca gaatcccag ccaggatgtg actgtgccct    300
     gcccagttcc ctcaactcca cctaccccat ctccctcaac tccacctacc ccatctccct   360
     catgctgcca cccccgactg tcactgcacc gacggccct cgaggacctg ctcttaggtt    420
     cagaagcgaa cctcacgtgc acactgaccg gcctgagaga tgcctcaggt gtcaccttca    480
     cctggacgcc ctcaagtggg aagagcgctg ttcaaggacc acctgagcgt gacctctgtg   540
     gctgctacag cgtgtccagt gtcctgccgg gctgtgccga gccatggaac catgggaaga   600
     ccttcacttg cactgctgcc taccccgagt ccaagacccc gctaaccgcc accctctcaa    660
     aatccggaaa cacattccgg cccgaggtcc acctgctgcc gccgccgtcg gaggagctgg    720
     ccctgaacga gctggtgacg ctgacgtgcc tggcacgcgg cttcagcccc aaggacgtgc    780
     tggttcgctg gctgcagggg tcacaggagc tgccccgcga gaagtacctg acttgggcat    840
     cccggcagga gcccagccag ggcaccacca cctttgctgt gaccagcata ctgcgcgtgg    900
     cagccgagga ctggaagaag gggacacct tctcctgcat ggtgggccac gaggccctgc     960
     cgctggcctt cacacagaag accatcgacc gcttggcggg taaacccacc catgtcaatg   1020
     tgcctgctgt catggcggag gtggacggca cctgctactg a                       1061
```
[SEQUENCE ID NO:15]

```
GenBank
J00220
LOCUS       HUMIGCC8    2533 bp    DNA             PRI    02-DEC-1998
DEFINITION  Homo sapiens immunoglobulin alpha-1 heavy chain constant region
            (IGHA1) gene, partial cds.
ACCESSION   J00220
VERSION     J00220.1 GI:184743
KEYWORDS
SOURCE      human.
  ORGANISM  Homo sapiens
```

FIGURE 7B

```
              Eukaryota; Metazoa; Chordata; Craniata; Vertebrata; Euteleostomi;
              Mammalia; Eutheria; Primates; Catarrhini; Hominidae; Homo.
REFERENCE     1  (bases 1 to 2533)
  AUTHORS     Takahashi,N., Ueda,S., Obata,M., Nikaido,T., Nakai,S. and Honjo,T.
  TITLE       Structure of human immunoglobulin gamma genes: Implications for
              evolution of a gene family
  JOURNAL     Cell 29, 671-679 (1982)
  MEDLINE     83001943
  COMMENT     This sequence is part of a multigene region containing the
              immunoglobulin heavy chain gamma-3, gamma-1, pseudo-epsilon, and
              alpha-1 genes.
FEATURES             Location/Qualifiers
     source          1..2533
                     /organism="Homo sapiens"
                     /db_xref="taxon:9606"
                     /chromosome="14"
                     /map="14q32.33"
                     /clone="cosmid Ig13; Ig-gamma3-122"
                     /tissue_type="placenta; liver"
                     /germline
     intron          <1..141
                     /note="alpha-1 intron J-C"
     exon            142..447
                     /gene="IGHA1"
     gene            <142..>1638
                     /gene="IGHA1"
     CDS             join(<142..447,662..1021,1244..1638)
                     /gene="IGHA1"
                     /codon_start=3
                     /product="immunoglobulin alpha-1 heavy chain constant
                     region"
                     /protein_id="AAC82528.1"
                     /db_xref="GI:184749"
                     /translation="SPTSPKVFPLSLCSTQPDGNVVIACLVQGFFPQEPLSVTWSESG
                     QGVTARNFPPSQDASGDLYTTSSQLTLPATQCLAGKSVTCHVKHYTNPSQDVTVPCPV
                     PSTPPTPSPSTPPTPSPSCCHPRLSLHRPALEDLLLGSEANLTCTLTGLRDASGVTFT
                     WTPSSGKSAVQGPPERDLCGCYSVSSVLPGCAEPWNHGKTFTCTAAYPESKTPLTATL
                     SKSGNTFRPEVHLLPPPSEELALNELVTLTCLARGFSPKDVLVRWLQGSQELPREKYL
                     TWASRQEPSQGTTTFAVTSILRVAAEDWKKGDTFSCMVGHEALPLAFTQKTIDRLAGK
                     PTHVNVSVVMAEVDGTCY"
     intron          448..661
                     /gene="IGHA1"
                     /note="A"
     exon            662..1021
                     /gene="IGHA1"
     intron          1022..1243
                     /gene="IGHA1"
                     /note="B"
     exon            1244..>1638
                     /gene="IGHA1"
BASE COUNT      490 a    866 c    753 g    424 t
ORIGIN
        1 ggtccaactg caggcctgtg gtgcaggagc tgtgtgacca tggggctgtc accaggcctc
       61 tctgtgctgg gtccctccag tatagaggag aggcagtata gaggagaggg ccgcgtcctc
      121 acagtgcatt ctgtgttcca gcatccccga ccagccccaa ggtcttcccg ctgagcctct
      181 gcagcaccca gccagatggg aacgtggtca tcgcctgcct ggtccagggc ttcttccccc
      241 aggagccact cagtgtgacc tggagcgaaa gcggacaggg cgtgaccgcc agaaacttcc
      301 cacccagcca ggatgcctcc ggggacctgt acaccacgag cagccagctg accctgccgg
      361 ccacacagtg cctagccggc aagtccgtga catgccacgt gaagcactac acgaatccca
      421 gccaggatgt gactgtgccc tgcccaggtc agagggcagg ctggggagtg gggcggggcc
      481 acccgtcgt gccctgacac tgcgcctgca cccgtgttcc ccacagggag ccgcccctc
      541 actcacacca gagtggaccc cgggccgagc cccaggaggt ggtggtggac aggccaggag
      601 gggcgaggcg ggggcatggg gaagtatgtg ccgaccagct caggccatct ctccactcca
      661 gttccctcaa ctccacctac cccatctccc tcaactccac ctacccctc tccctcatgc
      721 tgccacccc gactgtcact gcaccgaccg gccctcgagg acctgctctt aggttcagaa
      781 gcgaacctca cgtgcacact gaccggcctg agagatgcct caggtgtcac cttcacctgg
```

FIGURE 7C

```
 841 acgccctcaa gtgggaagag cgctgttcaa ggaccacctg agcgtgacct ctgtggctgc
 901 tacagcgtgt ccagtgtcct gccgggctgt gccgagccat ggaaccatgg gaagaccttc
 961 acttgcactg ctgcctaccc cgagtccaag accccgctaa ccgccaccct ctcaaaatcc
1021 ggtgggtcca gaccctgctc gggcccctgc tcagtgctct ggttcgcaaa gcatattcct
1081 ggcctgcctc ctccctccca atcctgggct ccagtgctca tgccaagtac acagggaaac
1141 tgaggcaggc tgaggggcca ggacacagcc cggggtgccc accagagcag aggggctctc
1201 tcatcccctg cccagccccc tgacctggct ctctaccctc caggaaacac atcccggccc
1261 gaggtccacc tgctgccgcc gccgtcggag gagctgccc tgaacgagct ggtgacgctg
1321 acgtgcctgg cacgcggctt cagccccaag gacgtgctgg ttcgctggct gcaggggtca
1381 caggagctgc cccgcgagaa gtacctgact tgggcatccc ggcaggagcc cagccagggc
1441 accaccacct tcgctgtgac cagcatactg cgcgtggcag ccgaggactg gaagaagggg
1501 gacaccttct cctgcatggt gggccacgag gccctgccgc tggccttcac acagaagacc
1561 atcgaccgct tggcgggtaa acccacccat gtcaatgtgt ctgtcgtcat ggcggaggtg
1621 gacggcacct gctactgagc cgcccgcctg tccccacccc tgaataaact ccatgctccc
1681 ccaagcagcc ccacgcttcc atccggcgcc tgtctgtcca tcctcagggt ctcagcactt
1741 gggaaagggc cagggcatgg acagggaaga ataccccctg ccctgagcct cggggggccc
1801 ctggcacccc catgagactt tccaccctgg tgtgagtgtg agtcgtgagt gtgagagtgt
1861 gtggtgcagg aggcctcgct ggtgtgagat cttaggtctg ccaaggcagg cacagcccag
1921 gatgggttct gagagacgca catgcccgg acagttctga gtgagcagtg gcatggccgt
1981 ttgtccctga gagagccgcc tctggctgta gctgggaggg aatagggagg gtaaagggag
2041 caggctagcc aagaaaggcg caggtagtgg caggagcggc gagggagtga ggggctggac
2101 tccagggccc cactgggagg acaagctcca ggagggcccc accaccctag tgggtgggcc
2161 tcaggacgtc ccactgacgc atgcaggaag gggcacctcc ccttaaccac actgctctgt
2221 acggggcacg tgggcacagg tgcacactca cactcacata tatgcctgag ccctgcagga
2281 gcggaaacgtt cacagcccag acccagttcc agaaaagcca gggagtccc ctcccaagcc
2341 cccaagctca gcctgctccc ctaggcccct ctggcttccc tgtgtttcca ctgtgcacag
2401 atcaggcacc aactccacag acccctccca ggcagccct gctccctgcc tggccaagtc
2461 tcccatcccc tcctaagccc aactaggacc caaagcatag acagggaggg gccacgtggg
2521 gtggcatcag aag
```
[SEQUENCE ID NO:52]

II. HUMAN IG ALPHA-2 CHAIN C REGION - HOMO SAPIENS (HUMAN).

AMINO ACID SEQUENCE
>sp|P01877|ALC2_HUMAN IG ALPHA-2 CHAIN C REGION - Homo sapiens (Human)

```
           10         20         30         40         50         60
            |          |          |          |          |          |
     ASPTSPKVFP LSLDSTPQDG NVVVACLVQG FFPQEPLSVT WSESGQNVTA RNFPPSQDAS 70         80         90        100        110        120
            |          |          |          |          |          |
     GDLYTTSSQL TLPATQCPDG KSVTCHVKHY TNPSQDVTVP CPVPPPPPCC HPRLSLHRPA 130        140        150        160        170        180
            |          |          |          |          |          |
     LEDLLLGSEA NLTCTLTGLR DASGATFTWT PSSGKSAVQG PPERDLCGCY SVSSVLPGCA 190        200        210        220        230        240
            |          |          |          |          |          |
     QPWNHGETFT CTAAHPELKT PLTANITKSG NTFRPEVHLL PPPSEELALN ELVTLTCLAR
```

FIGURE 7D

```
         250        260        270        280        290        300
          |          |          |          |          |          |
GFSPKDVLVR WLQGSQELPR EKYLTWASRQ EPSQGTTTFA VTSILRVAAE DWKKGDTFSC 310        320        330        340
          |          |          |          |
MVGHEALPLA FTQKTIDRLA GKPTHVNVSV VMAEVDGTCY
```

[SEQUENCE ID NO:18]

CODING SEQUENCE

```
                                                                  g    -1
     catccccgac cagccccaag gtcttcccgc tgagcctcga cagcaccccc caagatggga   60
     acgtggtcgt cgcatgcctg gtccagggct tcttccccca ggagccactc agtgtgacct  120
     ggagcgaaag cggacagaac gtgaccgcca gaaacttccc acctagccag gatgcctccg  180
     gggacctgta caccacgagc agccagctga ccctgccggc cacacagtgc ccagacggca  240
     agtccgtgac atgccacgtg aagcactaca cgaatcccag ccaggatgtg actgtgccct  300
     gcccagttcc cccacctccc ccatgctgcc acccccgact gtcgctgcac cgaccggccc  360
     tcgaggaccct gctcttaggt tcagaagcga acctcacgtg cacactgacc ggcctgagag  420
     atgcctctgg tgccaccttc acctggacgc cctcaagtgg gaagagcgct gttcaaggac  480
     cacctgagcg tgacctctgt ggctgctaca gcgtgtccag tgtcctgcct ggctgtgccc  540
     agccatggaa ccatggggag accttcacct gcactgctgc ccacccgag ttgaagaccc  600
     cactaaccgc caacatcaca aaatccggaa acacattccg gcccgaggtc cacctgctgc  660
     cgccgccgtc ggaggagctg gccctgaacg agctggtgac gctgacgtgc ctggcacgtg  720
     gcttcagccc caaggatgtg ctggttcgct ggctgcaggg gtcacaggag ctgccccgcg  780
     agaagtacct gacttgggca tcccggcagg agcccagcca gggcaccacc accttcgctg  840
     tgaccagcat actgcgcgtg gcagccgagg actggaagaa gggggacacc ttctcctgca  900
     tggtgggcca cgaggccctg ccgctggcct tcacacagaa gaccatcgac cgcttggcgg  960
     gtaaacccac ccatgtcaat gtgtctgttg tcatggcgga ggtggacggc acctgctact 1020
     ga                                                                1022
```

[SEQUENCE ID NO:17]

```
GenBank
J00221      Human Ig germline
LOCUS       HUMIGCD7    2516 bp    DNA              PRI      11-APR-2001
DEFINITION  Human Ig germline H-chain G-E-A region B: alpha-2 A2m(1) allele
            constant region, 3' end.
ACCESSION   J00221
VERSION     J00221.1  GI:184756
KEYWORDS    .
SOURCE      human.
  ORGANISM  Homo sapiens
            Eukaryota; Metazoa; Chordata; Craniata; Vertebrata; Euteleostomi
            Mammalia; Eutheria; Primates; Catarrhini; Hominidae; Homo.
REFERENCE   1  (bases 1 to 2516)
  AUTHORS   Ellison,J. and Hood,L.
  TITLE     Linkage and sequence homology of two human immunoglobulin gamma
            heavy chain constant region genes
  JOURNAL   Proc. Natl. Acad. Sci. U.S.A. 79 (6), 1984-1988 (1982)
  MEDLINE   82197621
   PUBMED   6804948
REFERENCE   2  (bases 737 to 1016)
  AUTHORS   Flanagan,J.G. and Rabbitts,T.H.
  TITLE     Arrangement of human immunoglobulin heavy chain constant region
            genes implies evolutionary duplication of a segment containing
            gamma, epsilon and alpha genes
  JOURNAL   Nature 300 (5894), 709-713 (1982)
  MEDLINE   83088998
   PUBMED   6817141
REFERENCE   3  (bases 49 to 229; 425 to 514)
  AUTHORS   Hisajima,H., Nishida,Y., Nakai,S., Takahashi,N., Ueda,S. and
            Honjo,T.
  TITLE     Structure of the human immunoglobulin C epsilon 2 gene, a truncated
            pseudogene: implications for its evolutionary origin
  JOURNAL   Proc. Natl. Acad. Sci. U.S.A. 80 (10), 2995-2999 (1983)
  MEDLINE   83221539
```

FIGURE 7E

```
PUBMED      6407005
REFERENCE   4  (bases 1 to 2516)
  AUTHORS   Flanagan,J.G., Lefranc,M.P. and Rabbitts,T.H.
  TITLE     Mechanisms of divergence and convergence of the human
            immunoglobulin alpha 1 and alpha 2 constant region gene sequences
  JOURNAL   Cell 36 (3), 681-688 (1984)
  MEDLINE   84130179
   PUBMED   6421489
  COMMENT   [3] also reports the complete alpha-1 gene and part of the A2m(2)
            alpha-2 allele (bases 737-2516; see Sites table). Comparison of the
            three sequences suggests that the A2m(1) alpha-2 allele might be a
            hybrid of the alpha-1 gene and A2m(2) alpha-2 allele. The hinge
            region in the alpha genes occurs at beginning of the CH2 domain.
            The alpha-1 hinge region is 13 amino acids longer than that in
            alpha-2. Both hinge regions consist of approximate tandem repeats
            of a 15 bp sequence. The first repeat occurs 5' to the mRNA splice
            site and is non-coding. The authors [3] suggest that this
            repetitive structure provides a possible mechanism for the large
            number of variations observed in hinge regions. There is a coupled
            30 bp insertion, 9 bp deletion in alpha-2 relative to alpha-1
            (starting at base 97).
            [1] also reports sequences for the epsilon-1 and epsilon-2
            (pseudogene) C-region genes. The authors [1] determined the
            physical linkage between epsilon-1 and alpha-2 and that between
            epsilon-2 and alpha-1. [2] also reports the alpha-1 CH2 domain and
            epsilon-2.
            This entry is part of a multigene region (region B), which includes
            the gamma-2, gamma-4, epsilon-1 and alpha-2 genes. See segment 1
            for more comments.
            Complete source information:
            Human genomic DNA, cosmid Ig10 [1],[3]; placenta DNA [2] clone
            H-Ig-alpha-25; genomic DNA from TOU II-5 library clone
            lambda-TOU-alpha2 (for A2m(2) allele) [3].
FEATURES             Location/Qualifiers
     source          1..2516
                     /organism="Homo sapiens"
                     /db_xref="taxon:9606"
                     /map="14q32.33"
                     /germline
     gene            <1..1621
                     /gene="IgH"
                     /note="IGHA2"
     intron          <1..163
                     /gene="IgH"
                     /note="alpha-2 intron J-C"
     CDS             join(<164..469,684..1004,1227..1621)
                     /gene="IgH"
                     /note="contains constant region"
                     /codon_start=3
                     /product="immunoglobulin alpha-2 heavy chain"
                     /protein_id="AAB59396.1"
                     /db_xref="GI:184761"
                     /translation="SPTSPKVFPLSLDSTPQDGNVVVACLVQGFFPQEPLSVTWSESG
                     QNVTARNFPPSQDASGDLYTTSSQLTLPATQCPDGKSVTCHVKHYTNPSQDVTVPCPV
                     PPPPPCCHPRLSLHRPALEDLLLGSEANLTCTLTGLRDASGATFTWTPSSGKSAVQGP
                     PERDLCGCYSVSSVLPGCAQPWNHGETFTCTAAHPELKTPLTANITKSGNTFRPEVHL
                     LPPPSEELALNELVTLTCLARGFSPKDVLVRWLQGSQELPREKYLTWASRQEPSQGTT
                     TFAVTSILRVAAEDWKKGDTFSCMVGHEALPLAFTQKTIDRLAGKPTHVNVSVVMAEV
                     DGTCY"
     exon            164..469
                     /gene="IgH"
                     /note="G00-119-333"
     intron          470..683
                     /gene="IgH"
                     /note="alpha-2 intron A"
     exon            684..1004
```

FIGURE 7F

```
                        /gene="IgH"
    intron              1005..1226
                        /gene="IgH"
                        /note="alpha
    exon                1227..1621
                        /gene="IgH"
    variation           1434
                        /gene="IgH"
                        /note="t in A2m(1); a in A2m(2)"
    variation           1444
                        /ge...
                        /note="g in A2m(1); a in A2m(2)"
    variation           1465
                        /gene="IgH"
                        /note="c in A2m(1); t in A2m(2)"
    variation           1486
                        /gene="IgH"
                        /note="c in A2m(1); g in A2m(2)"
    variation           1553
                        /gene="IgH"
                        /note="t in A2m(1); a in A2m(2)"
    variation           1573..1574
                        /gene="IgH"
                        /note="tg in A2m(1); ca in A2m(2)"
    variation           1602..1606
                        /gene="IgH"
                        /note="tggac in A2m(1); cggat in A2m(2)"
    variation           2060
                        /note="c in A2m(1); t in A2m(2)"
    variation           2384
                        /note="a in A2m(1); c in A2m(2)"
    variation           2390
                        /note="c in A2m(1); g in A2m(2)"
BASE COUNT     486 a     861 c     754 g     413 t
ORIGIN
    1 ggccaaccg caggcccatg gtgcaggagc tgtgtaacct atggggctgt caccaggcct
   61 ctctgtgctg ggttcctcca gtgtagagga gaggcaggta cagcctgtcc tcctggggac
  121 atggcatgag ggccgcgtcc tcacagcgca tcctgtgttc cagcatcccc gaccagcccc
  181 aaggtcttcc cgctgagcct cgacagcacc cccaagatg ggaacgtggt cgtcgcatgc
  241 ctggtccagg gcttcttccc tcaggagcca ctcagtgtga cctggagcga aagcggacag
  301 aacgtgaccg ccagaaactt cccacctagc caggatgcct ccggggacct gtacaccacg
  361 agcagccagc tgaccctgcc ggccacacag tgcccagacg gcaagtccgt gacatgccac
  421 gtgaagcact acacgaatcc cagccaggat gtgactgtgc cctgcccagg tcagagggca
  481 ggctggggag tggggcgggg ccaccccgtc ctgccctgac actgcgcctg caccegtgtt
  541 ccccacaggg agccgcccct tcactcacac cagagtggac cccgggccga gccccaggag
  601 gtggtggtgg acaggccagg aggggcgagg cggggcacg gggaagggcg ttctgaccag
  661 ctcaggccat ctctccactc cagttccccc acctccccca tgctgccacc cccgactgtc
  721 gctgcaccga ccggccctcg aggacctgct cttaggttca gaagcgaacc tcacgtgcac
  781 actgaccggc ctgagagatg cctctggtgc caccttcacc tggacgccct caagtgggaa
  841 gagcgctgtt caaggaccac ctgagcgtga cctctgtggc tgctacagcg tgccagtgt
  901 cctgcctggc tgtgcccagc catggaacca tggggagacc ttcaccctgca ctgctgccca
  961 ccccgagttg aagaccccac taaccgccaa catcacaaaa tccgtgggt ccagaccctg
 1021 ctcggggccc tgcctcagtgc tctggtttgc aaagcatatt cccggcctgc ctcctccctc
 1081 ccaatcctgg gctccagtgc tcatgccaag tacacaggga aactgaggca ggctgagggg
 1141 ccaggacaca gcccagggtg cccaccagag cagaggggct ctcctcatccc ctgcccagcc
 1201 ccctgacctg gctctctacc ctccaggaaa cacatccgg cccgaggtcc acctgctgcc
 1261 gccgccgtcg gaggagctgg ccctgaacga gctggtgacg ctgacgtgcc tggcacgtgg
 1321 cctcagcccc aaggatgtgc tggttcgctg gctgcagggg tcacaggagc tgccccgcga
 1381 gaagtacctg acttgggcat cccggcagga gcccagccag ggcaccacca cctcgctgt
 1441 gaccagcata ctgcgcgtgg cagccgagga ctggaagaag ggggacaccct tctcctgcat
 1501 ggtgggccac gaggccctgc cgctggcctt cacacagaag accatcgacc gctcggcggg
 1561 taaacccacc catgtcaatg tgtctgttgt catggcggag gtggacggca cctgctactg
 1621 agccgcccgc ctgtccccac ccctgaataa actccatgct cccccaagca gcccacgct
 1681 tccatccggc gcctgtcctgt ccatcctcag ggtctcagca cttgggaaag ggcagggca
 1741 tggacaggga agaataccc ctgccctgag cctcgggggg ccctggcac cccatgaga
 1801 ctttccaccc tggtgtgagt gtgagttgtg agtgtgagag tgtgtggtgc aggaggcccc
```

FIGURE 7G

```
1861 gctggtgtga gatcttaggt ctgccaaggc aggcacagcc caggatgggt tctgagagac
1921 gcacatgccc cggacagttc tgagtgagca gtggcatggc cgtttgtccc tgagagagcc
1981 gcctctggct gtagctggga gggaatagg agggtaaaag gagcaggcta gccaagaaag
2041 gcgcaggtag tggcaggagc ggcgagggag tgagggggctg gactccaggg ccccactggg
2101 aggacaagct ccaggagggc cccaccaccc tagtgggtgg gcctcaggac gtcccactga
2161 cgcatgcagg aaggggcacc tccccttaaa cacactgctc tgtacgggc acgtgggcac
2221 acatgcacac tcacactcac atatacgcct gagccctgca ggagtggaac gttcacagcc
2281 cagacccagt tccagaaaag ccaggggagt cccctcccaa gcccccaagc tcagcctgct
2341 cccccaggcc cctctggctt ccctgtgttt ccactgtgca cagatcaggc accaactcca
2401 cagaccccct ccaggcagcc cctgctccct gcctggccaa gtctcccatc cctcctaag
2461 cccaactagg acccaaagca tagacaggga ggggccgcgt ggggtggcat cagaag
```
[SEQUENCE ID NO:53]

III. HUMAN IG GAMMA-1 CHAIN C REGION - HOMO SAPIENS (HUMAN)

AMINO ACID SEQUENCE
>sp|P01857|GC1_HUMAN IG GAMMA-1 CHAIN C REGION - Homo sapiens (Human).

```
         10         20         30         40         50         60
          |          |          |          |          |          |
ASTKGPSVFP LAPSSKSTSG GTAALGCLVK DYFPEPVTVS WNSGALTSGV HTFPAVLQSS 70         80         90        100        110        120
          |          |          |          |          |          |
          GLYSLSSVVT VPSSSLGTQT YICNVNHKPS NTKVDKKVEP KSCDKTHTCP PCPAPELLGG 140        150        160        170        180
                    |          |          |          |          |
                    RTP EVTCVVVDVS HEDPEVKFNW YVDGVEVHNA KTKPREEQYN 200        210        220        230        240
          |          |          |          |          |
         NGK EYKCKVSNKA LPAPIEKTIS KAKGQPREPQ VYTLPPSRDE 260        270        280        290        300
          |          |          |          |          |
         SDI AVEWESNGQP ENNYKTTPPV LDSDGSFFLY SKLTVDKSRW 320        330
          |          |
         HYT QKSLSLSPGK
```
[SEQUENCE ID NO:20]

```
                                                        g         -1
       cccatcg gtcttccccc tggcaccctc ctccaagagc acctctgggg         60
       gggctgc ctggtcaagg actacttccc cgaaccggtg acggtgtcgt        120
       cctgacc agcggcgtgc acaccttccc ggctgtccta cagtcctcag        180
       cagcagc gtggtgaccg tgccctccag cagcttgggc acccagacct        240
       gaatcac aagcccagca acaccaaggt ggacaagaaa gttgagccca        300
       aactcac acatgcccac cgtgcccagc acctgaactc ctggggggac        360
       cctcccc ccaaaaccca aggacaccct catgatctcc cggacccctg        420
       ggtggtg gacgtgagcc acgaagaccc tgaggtcaag ttcaactggt        480
       ggaggtg cataatgcca agacaaagcc gcgggaggag cagtacaaca        540
       ggtcagc gtcctcaccg tcctgcacca ggactggctg aatggcaagg        600
       ggtcctc aacaaagccc tcccagcccc catcgagaaa accatctcca        660
       gccccga gaaccacagg tgtacaccct gcccccatcc cgggatgagc        720
       ggtcagc ctgacctgcc tggtcaaagg cttctatccc agcgacatcg        780
       gagcaat gggcagccgg agaacaacta caagaccacg cctcccgtgc        840
       ctccttc tccctctaca gcaagctcac cgtggacaag agcaggtggc        900
       cttctca cgctccgtga tgcatgaggc tctgcacaac cactacacgc        960
       ccctgtct ccgggtaaat ga                                    992
```

FIGURE 7H

[SEQUENCE ID NO:19]

```
GenBank
J00228.
LOCUS        HUMIGCC4      2009 bp    DNA              PRI       02-DEC-1998
DEFINITION   Homo sapiens immunoglobulin gamma-1 heavy chain constant region
             (IGHG1) gene, partial cds.
ACCESSION    J00228
VERSION      J00228.1  GI:184739
KEYWORDS
SOURCE       human.
  ORGANISM   Homo sapiens
             Eukaryota; Metazoa; Chordata; Craniata; Vertebrata; Euteleostomi;
             Mammalia; Eutheria; Primates; Catarrhini; Hominidae; Homo.
REFERENCE    1  (bases 1 to 2009)
  AUTHORS    Takahashi,N., Ueda,S., Obata,M., Nikaido,T., Nakai,S. and Honjo,T.
  TITLE      Structure of human immunoglobulin gamma genes: Implications for
             evolution of a gene family
  JOURNAL    Cell 29, 671-679 (1982)
  MEDLINE    83001943
COMMENT      This sequence is part of a multigene region containing the
             immunoglobulin heavy chain gamma-3, gamma-1, pseudo-epsilon, and
             alpha-1 genes.
FEATURES             Location/Qualifiers
     source          1..2009
                     /organism="Homo sapiens"
                     /db_xref="taxon:9606"
                     /chromosome="14"
                     /map="14q32.33"
                     /clone="cosmid Ig13; Ig-gamma3-122"
                     /tissue_type="placenta; liver"
                     /germline
     gene            <1..>1803
                     /gene="IGHG1"
     intron          <1..209
                     /gene="IGHG1"
     CDS             join(<210..503,892..936,1055..1384,1481..1803)
```

FIGURE 7I

```
                /replace=""
misc_difference 684
                /gene="IGHG1"
                /replace=""
misc_difference 692
                /gene="IGHG1"
                /replace=""
misc_difference 765..766
                /gene="IGHG1"
                /replace=""
misc_difference 1475
                /gene="IGHG1"
                /replace=""
misc_difference 1578
                /gene="IGHG1"
                /replace=""
BASE COUNT    418 a    698 c    566 g    327 t
ORIGIN
    1 agctttctgg ggcaggccag gcctgaccct ggctttgggg caggagggg gctaaggtga
   61 ggcaggtggc gccagcaggt gcacaccaa tgcccatgag cccagacact ggacgctgaa
  121 cctcgcggac agttaagaac caggggcct ctgcgcctgg gcccagctct gtcccacacc
  181 gcggtcacat ggcaccacct ctcttgcagc ctccaccaag ggcccatcgg tcttccccct
  241 ggcaccctcc tccaagagca ccctggggg cacagcggcc ctgggctgcc tggtcaagga
  301 ctacttcccc gaaccggtga cggtgtcgtg gaactcaggc gccctgacca gcggcgtgca
  361 caccttcccg gctgtcctac agtcctcagg actctactcc ctcagcagcg tggtgaccgt
  421 gccctccagc agcttgggca cccagaccta catctgcaac gtgaatcaca agcccagcaa
  481 caccaaggtg gacaagaaag ttggtgagag gccagcacag ggaggaggg tgtctgctgg
  541 aagcaggctc agcgctcctg cctggacgca tcccggctat gcagccccag tccagggcag
  601 caaggcaggc cccgtctgcc tcttcacccg gagcctctgc ccgccccact catgctcagg
  661 gagagggtct tctggctttt tccccaggctc tgggcaggca caggctaggt gccctaacc
  721 caggcctgc acacaaaggg gcaggtgctg ggctcagacc tgccaagagc catatccggg
  781 ggaccctgc ccctgaccta agcccaccc aaaggccaaa ctctccactc cctcagctcg
  841 gacacctcc ctcctcccag attccagtaa ctcccaatct tctctctgca gagcccaaat
  901 cttgtgacaa aactcacaca tgcccaccgt gcccaggtaa gccagcccag gcctcgccct
  961 ccagctcaag gcgggacagg tgccctagag tagcctgcat ccagggacag gccccagccg
 1021 ggtgctgaca cgtccacctc catctcttcc tcagcacctg aactcctggg gggaccgtca
 1081 gtcttcctct tccccccaaa acccaaggac acccctcatga tctcccggac ccctgaggtc
 1141 acatgcgtgg tggtggacgt gagccacgaa gaccctgagg tcaagttcaa ctggtacgtg
 1201 gacggcgtgg aggtgcataa tgccaagaca aagccgcggg aggagcagta caacagcacg
 1261 tacccgggtgg tcagcgtcct caccgtcctg caccaggact ggctgaatgg caaggagtac
 1321 aagtgcaagg tctccaacaa agccctccca gccccatcg agaaaaccat ctccaaagcc
 1381 aaaggtggga cccgtggggt gcgagggcca catggacaga ggccggctcg gcccaccctc
 1441 tgccctgaga gtgaccgctg taccaacctc tgtcctacag ggcagccccg agaaccacag
 1501 gtgtacaccc tgccccccatc ccgggatgag ctgaccaaga accaggtcag cctgacctgc
 1561 ctggtcaaag gcttctatcc cagcgacatc gccgtggagt gggagagcaa tgggcagccg
 1621 gagaacaact acaagaccac gcctcccgtg ctggactccg acggctcctt cttcctctac
 1681 agcaagctca ccgtggacaa gagcaggtgg cagcagggga acgtcttctc atgctccgtg
 1741 atgcatgagg ctctgcacaa ccactacacg cagaagagcc tctccctgtc tccgggtaaa
 1801 tgagtgcgac ggccggcaag ccccgctccc cgggctctcg cggtcgcacg aggatgcttg
 1861 gcacgtaccc cctgtacata ctcccggc gcccagcatg gaaataaagc acccagcgct
 1921 gccctgggcc cctgcgagac tgtgatggtt cttccacgg gtcaggccga gtctgaggcc
 1981 tgagtggcat gagggaggca gagcgggtc
                                              (SEQUENCE ID NO:54)
```

IV. HUMAN IG GAMMA-2 CHAIN C REGION - HOMO SAPIENS (HUMAN).

AMINO ACID SEQUENCE
>sp|P01859|GC2_HUMAN IG GAMMA-2 CHAIN C REGION - Homo sapiens (Human).

```
         10         20         30         40         50         60
          |          |          |          |          |          |
    ASTKGPSVFP LAPCSRSTSE STAALGCLVK DYFPEPVTVS WNSGALTSGV HTFPAVLQSS 70         80         90        100        110        120
```

FIGURE 7J

```
              |            |            |            |            |            |
GLYSLSSVVT   VPSSNFGTQT   YTCNVDHKPS   NTKVDKTVER   KCCVECPPCP   APPVAGPSVF 130          140          150          160          170          180
     |            |            |            |            |            |
LFPPKPKDTL   MISRTPEVTC   VVVDVSHEDP   EVQFNWYVDG   VEVHNAKTKP   REEQFNSTFR 190          200          210          220          230          240
     |            |            |            |            |            |
VVSVLTVVHQ   DWLNGKEYKC   KVSNKGLPAP   IEKTISKTKG   QPREPQVYTL   PPSREEMTKN 250          260          270          280          290          300
     |            |            |            |            |            |
QVSLTCLVKG   FYPSDIAVEW   ESNGQPENNY   KTTPPMLDSD   GSFFLYSKLT   VDKSRWQQGN 310          320          326
     |            |            |
VFSCSVMHEA   LHNHYTQKSL   SLSPGK
```
[SEQUENCE ID NO:22]

CODING SEQUENCE
```
gcctccacca  agggcccatc  ggtcttcccc  ctggcgccct  gtccaggag  cacctccgag    60
agcacagccg  ccctgggctg  cctggtcaag  gactacttcc  ccgaaccggt gacggtgtcg   120
tggaactcag  gcgctctgac  cagcggcgtg  cacaccttcc  cagctgtcct acagtcctca   180
ggactctact  ccctcagcag  cgtggtgacc  gtgccctcca  gcaacttcgg cacccagacc   240
tacacctgca  acgtagatca  caagcccagc  aacaccaagg  tggacaagac agttgagcgc   300
aaatgttgtg  tcgagtgccc  accgtgccca  gcaccacctg  tggcaggacc gtcagtcttc   360
ctcttccccc  caaaacccaa  ggacaccctc  atgatctccc  ggacccctga ggtcacgtgc   420
gtggtggtgg  acgtgagcca  cgaagacccc  gaggtccagt  tcaactggta cgtggacggc   480
gtggaggtgc  ataatgccaa  gacaaagcca  cgggaggagc  agttcaacag cacgttccgt   540
gtggtcagcg  tcctcaccgt  tgtgcaccag  gactggctga  acggcaagga gtacaagtgc   600
aaggtctcca  acaaaggcct  cccagccccc  atcgagaaaa  ccatctccaa aaccaaaggg   660
cagccccgag  aaccacaggt  gtacaccctg  cccccatccc  gggaggagat gaccaagaac   720
caggtcagcc  tgacctgcct  ggtcaaaggc  ttctaccccca gcgacatcgc cgtggagtgg   780
gagagcaatg  ggcagccgga  gaacaactac  aagaccacac  ctcccatgct ggactccgac   840
ggctccttct  tcctctacag  caagctcacc  gtggacaaga  gcaggtggca gcaggggaac   900
gtcctctcat  gctccgtgat  gcatgaggct  ctgcacaacc  actacacgca gaagagcctc   960
tccctgtctc  cgggtaaa                                                    978
```
[SEQUENCE ID NO:21]

```
GenBank
J00230. Human Ig germline ...
LOCUS        HUMIGCD1      2009 bp    DNA              PRI    11-APR-2001
DEFINITION   Human Ig germline H-chain G-E-A region B: gamma-2 constant region,
             3' end.
ACCESSION    J00230 V00554
VERSION      J00230.1  GI:184750
KEYWORDS
SOURCE       human.
  ORGANISM   Homo sapiens
             Eukaryota; Metazoa; Chordata; Craniata; Vertebrata; Euteleostomi;
             Mammalia; Eutheria; Primates; Catarrhini; Hominidae; Homo.
REFERENCE    1  (bases 1 to 2009)
  AUTHORS    Ellison,J. and Hood,L.
  TITLE      Linkage and sequence homology of two human immunoglobulin gamma
             heavy chain constant region genes
  JOURNAL    Proc. Natl. Acad. Sci. U.S.A. 79 (6), 1984-1988 (1982)
  MEDLINE    82197621
   PUBMED    6804948
REFERENCE    2  (bases 896 to 1256; 1749 to 1937)
  AUTHORS    Kravinkel,U. and Rabbitts,T.H.
  TITLE      Comparison of the hinge-coding segments in human immunoglobulin
             gamma heavy chain genes and the linkage of the gamma 2 and gamma 4
```

FIGURE 7K

```
                subclass genes JOURNAL   EMBO J. 1 (4), 403-407 (1982)
  MEDLINE       84235992    PUBMED    6329676
  REFERENCE     3 (bases 475 to 1071; 1179 to 1330; 1461 to 1524)
  AUTHORS       Takahashi,N., Ueda,S., Obata,M., Nikaido,T., Nakai,S. and Honjo,T.
  TITLE         Structure of human immunoglobulin gamma genes: implications for
                evolution of a gene family  JOURNAL   Cell 29 (2), 671-679 (1982)
  MEDLINE       83001943    PUBMED    6811139
  COMMENT       On Mar 2, 2000 this sequence version replaced gi:32759.
                [2] also reports sequences for gamma-3, gamma-4, and a gamma
                pseudogene. Most of this sequence is 95% homologous with gamma-4.
                The hinge exons are only 70% homologous. The authors estimate that
                gamma-2 and gamma-4 diverged 6.6 million years ago. The authors in
                [1] speculate that intron-mediated domain transfer played an
                important role in the evolution of human gamma genes. They also
                report the hinge regions of gamma-1, gamma-3, gamma-4, and a
                pseudo-gamma gene. [1] estimates the divergence of the human gamma
                genes to be between 7.7 and 4.4 million years ago. This entry is
                part of a multigene region containing the gamma-2, gamma-4,
                epsilon-1, and alpha-2 genes. The relative locations of the four
                genes were determined by Flanagan and Rabbitts (Nature 300, 709-713
                (1982)). They refer to this gene group as region B. The region A
                genes are gamma-3, gamma-1, pseudo-epsilon, alpha-1. Flanagan and
                Rabbitts also determined the general locations of the two regions.
                They place region A between the JH/mu/delta region and region B.
                Complete source information:
                Human fetal liver DNA, library of T. Maniatis [3] and Lawn et al
                [2],[1]; clones p-gamma-2RPA3 [2], 5A [3], and Ig-gamma-2-15 [1].
  FEATURES      Location/Qualifiers         source           1..2009
                /organism="Homo sapiens"
                /db_xref="taxon:9606"                        /map="14q32.33"
                /germline   intron          <1..215
                /gene="IgH"  gene           <1..2009
                /gene="IgH"                 /note="IGHG2"
        exon    216..509                    /gene="IgH"
                /note="G00-119-338"   C_region   216..508
                /gene="IgH"
                /note="immunoglobulin heavy chain constant region CH1"
        CDS     join(<216..509,902..937,1056..1382,1480..1802)
                /gene="IgH"                 /codon_start=3
                /product="immunoglobulin gamma-2 heavy chain"
                /protein_id="AAB59393.1"
                /db_xref="GI:184758"
                /translation="STKGPSVFPLAPCSRSTSESTAALGCLVKDYFPEPVTVSWNSGA
                LTSGVHTFPAVLQSSGLYSLSSVVTVPSSNFGTQTYTCNVDHKPSNTKVDKTVERKCC
                VECPPCPAPPVAGPSVFLFPPKPKDTLMISRTPEVTCVVVDVSHEDPEVQFNWYVDGV
                EVHNAKTKPREEQFNSTFRVVSVLTVVHQDWLNGKEYKCKVSNKGLPAPIEKTISKTK
                GQPREPQVYTLPPSREEMTKNQVSLTCLVKGFYPSDIAVEWESNGQPENNYKTTPPML
                DSDGSFFLYSKLTVDKSRWQQGNVFSCSVMHEALHNHYTQKSLSLSPGK"
        intron  510..901                    /gene="IgH"
      conflict  537                         /gene="IgH"
                /citation=[3]               /replace=""
      conflict  550..551                    /gene="IgH"
                /citation=[3]               /replace=""
      conflict  570                         /gene="IgH"
                /citation=[3]               /replace=""
      conflict  777..778                    /gene="IgH"
                /citation=[3]               /replace=""
      conflict  791                         /gene="IgH"
                /citation=[3]               /replace=""
      conflict  864                         /gene="IgH"
                /citation=[3]               /replace=""
      C_region  901..936                    /gene="IgH"
                /note="immunoglobulin heavy chain hinge"
        exon    902..937                    /gene="IgH"
                /note="G00-119-338"   intron       938..1055
                /gene="IgH"     C_region    1055..1381
```

FIGURE 7L

```
              /gene="IgH"
              /note="immunoglobulin heavy chain constant region CH2"
    exon      1056..1382
              /note="G00-119-338"     intron          1383..1479
              /gene="IgH"    C_region        1479..1799
              /gene="IgH"
              /note="immunoglobulin heavy chain constant region CH3"
    exon      1480..1802                      /gene="IgH"
              /note="G00-119-338"     conflict         1493
              /gene="IgH"                     /citation=(3)
              /replace=""    conflict         1802..1806
              /gene="IgH"                     /citation=(2)
              /replace=""    conflict         1814..1815
              /gene="IgH"                     /citation=(2)
              /replace=""    conflict         1825
              /gene="IgH"                     /citation=(2)
              /replace=""    conflict         1844..1853
              /gene="IgH"                     /citation=(2)
              /replace=""    conflict         1890
              /gene="IgH"                     /citation=(2)
              /replace=""    polyA_signal     1903..1908
              /gene="IgH"    conflict         1909..1918
              /gene="IgH"                     /citation=(2)
              /replace=""    conflict         1929..1932
              /gene="IgH"                     /citation=(2)
              /replace=""  BASE COUNT     410 a    700 c    568 g    331 t
ORIGIN
       1 agcttctgg ggcgagccgg gcccgactct ggctttgggg cagggagtgg gctaaggtga
      61 ggcaggtggc gccagccagg tgcacaccca atgcccgtga gcccagacac tggaccctgc
     121 ctggaccctc gtggatagac aagaaccgag gggcctctgc gcctgggccc agctctgtcc
     181 cacaccgcgg tcacatggca ccacctctct tgcagcctcc accaagggcc catcggtctt
     241 cccctggcg ccctgctcca ggagcacctc cgagagcaca gccgccctgg gctgcctggt
     301 caaggactac ttccccgaac cggtgacggt gtcgtggaac tcaggcgctc tgaccagcgg
     361 cgtgcacacc ttcccagctg tcctacagtc ctcaggactc tactccctca gcagcgtggt
     421 gaccgtgccc tccagcaact tcggcaccca gacctacacc tgcaacgtag atcacaagcc
     481 cagcaacacc aaggtggaca agacagttgg tgagaggcca gccagggag ggagggtgtc
     541 tgctggaagc caggctcagc cctcctgcct ggacgcaccc cggctgtgca gccccagccc
     601 agggcagcaa ggcaggcccc atctgtctcc tcacccggag gcctctgccc gccccactca
     661 tgctcaggga gagggtcttc tggctttttc caccaggctc caggcaggca caggctgggc
     721 gccctacc caggccctc acacacaggg gcaggtgctt ggctcagacc tgccaaaagc
     781 catatccggg aggacctgc ccctgaccta agccgacccc aaaggccaaa ctgtccactc
     841 cctcagctcg gacacctcct ctcctcccag atccgagtaa ctcccaatct tctctctgca
     901 gagcgcaaat gttgtgtcga gtgcccaccg tgcccaggta agccagccca ggcctcgccc
     961 tccagcctcaa ggcgggacag gtgccctaga gtagcctgca tccagggaca ggccccagct
    1021 gggtgctgac acgtccacct ccatctcttc ctcagcacca cctgtggcag gaccgtcagt
    1081 cttcctcttc cccccaaaac ccaaggacac cctcatgatc tcccggaccc ctgaggtcac
    1141 gtgcgtggtg gtggacgtga gccacgaaga ccccgaggtc cagttcaact ggtacgtgga
    1201 cggcgtggag gtgcataatg ccaagacaaa gccacgggga gagcagttca acagcacgtt
    1261 ccgtgtggtc agcgtcctca ccgttgtgca ccaggactgg ctgaacggca aggagtacaa
    1321 gtgcaaggtc tccaacaaag gcctcccagc ccccatcgag aaaaccatct ccaaaaccaa
    1381 aggtgggacc cgcggggtat gagggccaca tggacagagg ccggcctggc ccaccctctg
    1441 ccctgggagt gaccgctgtg ccaacctctg tccctacagg gcagccccga gaaccacagg
    1501 tgtacaccct gcccccatcc cgggaggaga tcaccaagaa ccaggtcagc ctgacctgcc
    1561 tggtcaaagg cttctacccc agcgacatcg ccgtggagtg ggagagcaat gggcagccgg
    1621 agaacaacta caagaccaca cctcccatgc tggactccga cggctccttc ttcctctaca
    1681 gcaagctcac cgtggacaag agcaggtggc agcaggggaa cgtcttctca tgctccgtga
    1741 tgcatgaggc tctgcacaac cactacacgc agaagagcct ctccctgtct ccgggtaaat
    1801 gagtgccacg gccggcaagc ccccgctccc caggctctcg gggtcgcgtg aggatgcttg
    1861 gcacgtaccc cgtgtacata cttcccaggc acccagcatg gaaataaagc accagcgct
    1921 gcccctgggcc cctgcgagac tgtgatggtt ctttccgtgg gtcaggccga gtctgaggcc
    1981 tgagtggcat gagggaggca gagtgggtc
                                              (SEQUENCE ID NO:55,
```

FIGURE 7M

V. HUMAN IG GAMMA-3 CHAIN C REGION - HOMO SAPIENS (HUMAN).

AMINO ACID SEQUENCE
CAA27268  C gamma 3 [Homo sapiens]

```
              10         20         30         40         50         60
               |          |          |          |          |          |
         ASTKGPSVFP LAPCSRSTSG GTAALGCLVK DYFPEPVTVS WNSGALTSGV HTFPAVLQSS 70         80         90        100        110        120
               |          |          |          |          |          |
         GLYSLSSVVT VPSSSLGTQT YTCNVNHKPS NTKVDKRVEL KTPLGDTTHT CPRCPEPKSC 130        140        150        160        170        180
               |          |          |          |          |          |
         DTPPPCPRCP EPKSCDTPPP CPRCPEPKSC DTPPPCPRCP APELLGGPSV FLFPPKPKDT 190        200        210        220        230        240
               |          |          |          |          |          |
         LMISRTPEVT CVVVDVSHED PEVQFKWYVD GVEVHNAKTK PREEQYNSTF RVVSVLTVLH 250        260        270        280        290        300
               |          |          |          |          |          |
         QDWLNGKEYK CKVSNKALPA PIEKTISKTK GQPREPQVYT LPPSREEMTK NQVSLTCLVK 310        320        330        340        350        360
               |          |          |          |          |          |
         GFYPSDIAVE WESSGQPENN YNTTPPMLDS DGSFFLYSKL TVDKSRWQQG NIFSCSVMHE 370        377
               |          |
         ALHNRFTQKS LSLSPGK
```

[SEQUENCE ID NO:24]

FIGURE 7N

CODING SEQUENCE
GCTTCCACCAAGGGCCCATCGGTCTTCCCCCTGGCGCCCTGCTCCAGGAGCACCTCTGGGGGCACAGCGGCCCTG
GGCTGCCTGGTCAAGGACTACTTCCCCGAACCGGTGACGGTGTCGTGGAACTCAGGCGCCCTGACCAGCGGCGTG
CACACCTTCCCGGCTGTCCTACAGTCCTCAGGACTCTACTCCCTCAGCAGCGTGGTGACCGTGCCCTCCAGCAGC
TTGGGCACCCAGACCTACACCTGCAACGTGAATCACAAGCCCAGCAACACCAAGGTGGACAAGAGAGTTGAGCTC
AAAACCCCACTTGGTGACACAACTCACACATGCCCACGGTGCCCAGAGCCCAAATCTTGTGACACACCTCCCCCG
TGCCCACGGTGCCCAGAGCCCAAATCTTGTGACACACCTCCCCCATGCCCACGGTGCCCAGAGCCCAAATCTTGT
GACACACCTCCCCCGTGCCCAAGGTGCCCAGCACCTGAACTCCTGGGAGGACCGTCAGTCTTCCTCTTCCCCCCA
AAACCCAAGGATACCCTTATGATTTCCCGGACCCCTGAGGTCACGTGCGTGGTGGTGGACGTGAGCCACGAAGAC
CCCGAGGTCCAGTTCAAGTGGTACGTGGACGGCGTGGAGGTGCATAATGCCAAGACAAAGCCGCGGGAGGAGCAG
TACAACAGCACGTTCCGTGTGGTCAGCGTCCTCACCGTCCTGCACCAGGACTGGCTGAACGGCAAGGAGTACAAG
TGCAAGGTCTCCAACAAAGCCCTCCCAGCCCCCATCGAGAAAACCATCTCCAAAACCAAAGGACAGCCCCGAGAA
CCACAGGTGTACACCCTGCCCCCATCCCGGGAGGAGATGACCAAGAACCAGGTCAGCCTGACCTGCCTGGTCAAA
GGCTTCTACCCCAGCGACATCGCCGTGGAGTGGGAGAGCAGCGGGCAGCCGGAGAACAACTACAACACCACGCCT
CCCATGCTGGACTCCGACGGCTCCTTCTTCCTCTACAGCAAGCTCACCGTGGACAAGAGCAGGTGGCAGCAGGGG
AACATCTTCTCATGCTCCGTGATGCATGAGGCTCTGCACAACCGCTTCACGCAGAAGAGCCTCTCCCTGTCTCCG
GGTAAATGA
[SEQUENCE ID NO:23]

GenBank
X03604 Human C gamma 3 gene for IgG G3m(b) heavy chain C-region from EZZ
(individual II-4 of TOU) PubMed, Protein, Related Sequences, Taxonomy,
OMIM, LinkOut

```
LOCUS        HSIGGC3     2590 bp     DNA           PRI       24-NOV-1998
DEFINITION   Human C gamma 3 gene for IgG G3m(b) heavy chain C-region from
EZZ
             (individual II-4 of TOU)
ACCESSION    X03604 M12958
VERSION      X03604.1  GI:33070
KEYWORDS     constant region; gamma-immunoglobulin; Ig heavy chain;
             immunoglobulin.
SOURCE       human.
  ORGANISM   Homo sapiens
             Eukaryota; Metazoa; Chordata; Craniata; Vertebrata;
Euteleostomi;
             Mammalia; Eutheria; Primates; Catarrhini; Hominidae; Homo.
REFERENCE    1  (bases 1 to 2590)
  AUTHORS    Huck,S., Fort,P., Crawford,D.H., Lefranc,M.P. and Lefranc,G.
  TITLE      Sequence of a human immunoglobulin gamma 3 heavy chain constant
             region gene: comparison with the other human C gamma genes
  JOURNAL    Nucleic Acids Res. 14 (4), 1779-1789 (1986)
  MEDLINE    86148507
REFERENCE    2  (bases 4 to 204; 2202 to 2236)
  AUTHORS    Takahashi,N., Ueda,S., Obata,M., Nikaido,T., Nakai,S. and
Honjo,T.
  TITLE      Structure of human immunoglobulin gamma genes: implications for
             evolution of a gene family
  JOURNAL    Cell 29 (2), 671-679 (1982)
  MEDLINE    83001943
FEATURES             Location/Qualifiers
     source          1..2590
                     /organism="Homo sapiens"
                     /db_xref="taxon:9606"
     conflict        28
                     /note="T is missing in [2]"
                     /citation=[2]
     conflict        80..82
                     /note="CGC is GCG in [2]"
```

FIGURE 70

```
              /citation=(2)
conflict      120
              /note="C is T in (2)"
              /citation=(2)
conflict      135
              /note="T is C in (2)"
              /citation=(2)
CDS           join(<215..509,901..951,1095..1139,1283..1327,
              1471..1515,1634..1963,2061..>2380)
              /codon_start=1
              /product="C gamma 3"
              /protein_id="CAA27268.1"
              /db_xref="GI:577056"
```

/translation="ASTKGPSVFPLAPCSRSTSGGTAALGCLVKDYFPEPVTVSWNSG

ALTSGVHTFPAVLQSSGLYSLSSVVTVPSSSLGTQTYTCNVNHKPSNTKVDKRVELKT

PLGDTTHTCPRCPEPKSCDTPPPCPRCPEPKSCDTPPPCPRCPEPKSCDTPPPCPRCP

APELLGGPSVFLFPPKPKDTLMISRTPEVTCVVVDVSHEDPEVQFKWYVDGVEVHNAK

TKPREEQYNSTFRVVSVLTVLHQDWLNGKEYKCKVSNKALPAPIEKTISKTKGQPREP

QVYTLPPSREEMTKNQVSLTCLVKGFYPSDIAVEWESSGQPENNYNTTPPMLDSDGSF

FLYSKLTVDKSRWQQGNIFSCSVMHEALHNRFTQKSLSLSPGK"

```
intron          510..900
                /note="intron I"
intron          952..1094
                /note="intron II"
intron          1140..1282
                /note="intron III"
intron          1328..1470
                /note="intron IV"
intron          1516..1633
                /note="intron V"
intron          1964..2060
                /note="intron VI"
misc_feature    2484..2489
                /note="pot. polyA signal"
BASE COUNT   541 a    925 c    703 g    421 t
ORIGIN
    1 agctttctgg ggcaggccag gcctgacttt ggctggggc agggaggggg ctaaggtgac
   61 gcaggtggcg ccagccaggc gcacacccaa tgcccgtgag cccagacact ggaccctgcc
  121 tggaccctcg tggatagaca agaaccgagg ggcctctgcg ccctgggccc agctctgtcc
  181 cacaccgcag tcacatggcg ccatctctct tgcagcttcc accaagggcc catcggtctt
  241 cccctggcg ccctgctcca ggagcacctc tgggggcaca gcggccctgg gctgcctggt
  301 caaggactac ttccccgaac cggtgacggt gtcgtggaac tcaggcgccc tgaccagcgg
  361 cgtgcacacc ttcccggctg tcctacagtc ctcaggactc tactccctca gcagcgtggt
  421 gaccgtgccc tccagcagct tgggcaccca gacctacacc tgcaacgtga atcacaagcc
  481 cagcaacaca aaggtggaca agagagttgg tgagaggcca gcgcagggag ggagggtgtc
  541 tgctggaagc caggctcagc cctcctgcct ggacgcatcc cggctgtgca gtcccagccc
  601 agggcagcaa ggcaggcccc gtctgactcc tcacccggag cctctgcccg ccccactcat
  661 gctcagggag agggtcttct ggcttttctcc accaggctcc gggcaggcac aggctggatg
  721 cccctacccc aggcccttca cacacagggg caggtgctgc gctcagagct gccaaaagcc
  781 atatccagga ggaccctgcc cctgacctaa gcccacccca aaggccaaac tctctactca
  841 etcagctcag acaccttctc tcttcccaga tctgagtaac tcccaatctt ctctctgcag
  901 agctcaaaac cccacttggt gacacaactc acacatgccc acggtgccca ggtaagccag
  961 cccaggactc gcccctccagc tcaaggcggg acaagagccc tagagtggcc tgagtccagg
```

FIGURE 7P

```
1021 gacaggcccc agcagggtgc tgacgcatcc acctccatcc cagatccccg taactcccaa
1081 tcttctctct gcagagccca aatcttgtga cacacctccc ccgtgcccac ggtgcccagg
1141 taagccagcc caggcctcac cctccagctc aaggcaggac aagagcccta gagtggcctg
1201 agtccaggga caggccccag cagggtgctg acgcgtccac ctccatccca gatcccgta
1261 actcccaatc ttctctctgc agagcccaaa tcttgtgaca cacctcccc.atgcccacgg
1321 tgcccaggta agccagccca ggcctcgccc tccagctcaa ggcgggacaa gagccctaga
1381 gtggcctgag tccagggaca ggccccagca gggtgctgac gcatccacct ccatcccaga
1441 tccccgtaac tcccaatctt ctctctgcag agcccaaatc ttgtgacaca cctcccccgt
1501 gcccaaggtg cccaggtaag ccagcccagg cctcgccctc cagctcaagg caggacaggt
1561 gccctagagt ggcctgcatc cagggacagg tcccagtcgg gtgctgacac atctgcctcc
1621 atctcttcct cagcacctga actcctggga ggaccgtcag tcttcctctt cccccaaaa
1681 cccaaggata cccttatgat ttcccggacc cctgaggtca cgtgcgtggt ggtggacgtg
1741 agccacgaag accccgaggt ccagttcaag tggtacgtgg acggcgtgga ggtgcataat
1801 gccaagacaa agccgcggga ggagcagtac aacagcacgt tccgtgtggt cagcgtcctc
1861 accgtcctgc accaggactg gctgaacggc aaggagtaca gtgcaaggt ctccaacaaa
1921 gccctccag cccccatcga gaaaaccatc tccaaaacca aaggtgggac ccgcggggta
1981 tgagggccac atggacagag gccagcttga cccaccctct gccctgggag tgaccgctgt
2041 gccaacctct gtccctacag gacagccccg agaaccacag gtgtacaccc tgccccatc
2101 ccgggaggag atgaccaaga accaggtcag cctgacctgc ctggtcaaag gcttctaccc
2161 cagcgacatc gccgtggagt gggagagcag cgggcagccg gagaacaact acaacaccac
2221 gcctcccatg ctggactccg acggctcctt cttcctctac agcaagctca ccgtggacaa
2281 gagcaggtgg cagcagggga acatcttctc atgctccgtg atgcatgagg ctctgcacaa
2341 ccgcttcacg cagaagagcc tctccctgtc tccgggtaaa tgagtgcgac agccggcaag
2401 cccccgctcc ccgggctctc ggggtcgcgc gaggatgctt ggcacgtacc ccgtgtacat
2461 acttccgg cacccagcat ggaaataaag cacccagcgc tgccctggc ccctgtgaga
2521 ctgtgatggt tctttccacg ggtcaggccg agtctgaggc ctgagtgaca tgagggaggc
2581 agagcgggtc
                                                                    [SEQUENCE ID NO:56]
```

VI. HUMAN IG GAMMA-4 CHAIN C REGION - HOMO SAPIENS (HUMAN).

AMINO ACID SEQUENCE.
>sp|P01861|GC4_HUMAN IG GAMMA-4 CHAIN C REGION - Homo sapiens (Human).

```
         10         20         30         40         50         60
          |          |          |          |          |          |
ASTKGPSVFP LAPCSRSTSE STAALGCLVK DYFPEPVTVS WNSGALTSGV HTFPAVLQSS 70         80         90        100        110        120
          |          |          |          |          |          |
GLYSLSSVVT VPSSSLGTKT YTCNVDHKPS NTKVDKRVES KYGPPCPSCP APEFLGGPSV 130        140        150        160        170        180
          |          |          |          |          |          |
FLFPPKPKDT LMISRTPEVT CVVVDVSQED PEVQFNWYVD GVEVHNAKTK PREEQFNSTY 190        200        210        220        230        240
          |          |          |          |          |          |
RVVSVLTVLH QDWLNGKEYK CKVSNKGLPS SIEKTISKAK GQPREPQVYT LPPSQEEMTK 250        260        270        280        290        300
          |          |          |          |          |          |
NQVSLTCLVK GFYPSDIAVE WESNGQPENN YKTTPPVLDS DGSFFLYSRL TVDKSRWQEG
```

FIGURE 7Q

```
            310        320       327
             |          |         |
NVFSCSVMHE ALHNHYTQKS LSLSLGK
```
[SEQUENCE ID NO:26]

CODING SEQUENCE

```
                                                                g      -1
           cttccaccaa gggcccatcc gtcttcccccc tggcgccctg ctccaggagc acctccgaga     60
           gcacagccgc cctgggctgc ctggtcaagg actacttccc cgaaccggtg acggtgtcgt    120
           ggaactcagg cgccctgacc agcggcgtgc acaccttccc ggctgtccta cagtcctcag    180
           gactctactc cctcagcagc gtggtgaccg tgccctccag cagcttgggc acgaagacct    240
           acacctgcaa cgtagatcac aagcccagca acaccaaggt ggacaagaga gttgagtcca    300
           aatatggtcc cccatgccca tcatgcccag cacctgagtt cctgggggga ccatcagtct    360
           tcctgttccc cccaaaaccc aaggacactc tcatgatctc ccggacccct gaggtcacgt    420
           gcgtggtggt ggacgtgagc caggaagacc ccgaggtcca gttcaactgg tacgtggatg    480
           gcgtggaggt gcataatgcc aagacaaagc cgcgggagga gcagttcaac agcacgtacc    540
           gtgtggtcag cgtcctcacc gtcctgcacc aggactggct gaacggcaag gagtacaagt    600
           gcaaggtctc caacaaaggc ctcccgtcct ccatcgagaa aaccatctcc aaagccaaag    660
           ggcagccccg agagccacag gtgtacaccc tgcccccatc ccaggaggag atgaccaaga    720
           accaggtcag cctgacctgc ctggtcaaag gcttctaccc cagcgacatc gccgtggagt    780
           gggagagcaa tgggcagccg gagaacaact acaagaccac gcctcccgtg ctggactccg    840
           acggctcctt cttcctctac agcaggctaa ccgtggacaa gagcaggtgg caggagggga    900
           atgtcttctc atgctccgtg atgcatgagg ctctgcacaa ccactacaca cagaagagcc    960
           tctccctgtc tctgggtaaa tga                                            983
```
[SEQUENCE ID NO:25]

```
GenBank
K01316. Human Ig germline
LOCUS       HUMIGCD2    2028 bp  DNA          PRI     11-APR-2001
DEFINITION  Human Ig germline H-chain G-E-A region B: gamma-4 constant region,
            3' end.
ACCESSION   K01316
VERSION     K01316.1  GI:184751
KEYWORDS
SOURCE      human.
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (bases 1 to 2028)
  AUTHORS   Ellison,J., Buxbaum,J. and Hood,L.
  TITLE     Nucleotide sequence of a human immunoglobulin C gamma 4 gene
  JOURNAL   DNA 1 (1), 11-18 (1981)
  MEDLINE   83157104
REFERENCE   2  (bases 475 to 1069; 1180 to 1331; 1432 to 1655)
  AUTHORS   Takahashi,N., Ueda,S., Obata,M., Nikaido,T., Nakai,S. and Honjo,T.
  TITLE     Structure of human immunoglobulin gamma genes: implications for
            evolution of a gene family
  JOURNAL   Cell 29 (2), 671-679 (1982)
  MEDLINE   83001943
   PUBMED   6811139
REFERENCE   3  (bases 894 to 1106)
  AUTHORS   Krawinkel,U. and Rabbitts,T.H.
  TITLE     Comparison of the hinge-coding segments in human immunoglobulin
            gamma heavy chain genes and the linkage of the gamma 2 and gamma 4
            subclass genes
  JOURNAL   EMBO J. 1 (4), 403-407 (1982)
  MEDLINE   84235992
   PUBMED   6329676
REFERENCE   4  (bases 1 to 2028)
  AUTHORS   Ellison,J. and Hood,L.
  TITLE     Linkage and sequence homology of two human immunoglobulin gamma
            heavy chain constant region genes
  JOURNAL   Proc. Natl. Acad. Sci. U.S.A. 79 (6), 1984-1988 (1982)
  MEDLINE   82197621
   PUBMED   6804948
```

FIGURE 7R

```
COMMENT      [1] reports that the human C-gamma-4 gene is equally homologous to
             the mouse gamma-1, gamma-2a, and gamma-2b genes (about 75%). [3]
             also reports partial sequences for human gamma-2, gamma-3, and a
             gamma pseudogene. [2] presents the gamma-1, gamma-2, gamma-3, and
             pseudo-gamma hinge regions.
             This entry is part of a multigene region (region B), which includes
             the gamma-2, gamma-4, epsilon-1, and alpha-2 genes. See segment 1
             for more comments.
             Complete source information:
             Human fetal liver DNA, library of T. Maniatis [3] and Lawn et al
             [1],[2]; clones 24B [1], lambda-HG4.1 [3], and Ig-gamma-4-2 [2].
FEATURES             Location/Qualifiers
     source          1..2028
                     /organism="Homo sapiens"
                     /db_xref="taxon:9606"
                     /map="14q32.33"
                     /germline
     gene            <1..2028
                     /gene="IgH"
                     /note="IGHG4"
     intron          <1..215
                     /gene="IgH"
                     /note="gamma-4 intron J-C"
     CDS             join(<216..509,900..935,1054..1383,1481..1803)
                     /gene="IgH"
                     /codon_start=3
                     /product="immunoglobulin gamma-4 heavy chain"
                     /protein_id="AAB59394.1"
                     /db_xref="GI:184759"
                     /translation="STKGPSVFPLAPCSRSTSESTAALGCLVKDYFPEPVTVSWNSGA
                     LTSGVHTFPAVLQSSGLYSLSSVVTVPSSSLGTKTYTCNVDHKPSNTKVDKRVESKYG
                     PPCPSCPAPEFLGGPSVFLFPPKPKDTLMISRTPEVTCVVVDVSQEDPEVQFNWYVDG
                     VEVHNAKTKPREEQFNSTYRVVSVLTVLHQDWLNGKEYKCKVSNKGLPSSIEKTISKA
                     KGQPREPQVYTLPPSQEEMTKNQVSLTCLVKGFYPSDIAVEWESNGQPENNYKTTPPV
                     LDSDGSFFLYSRLTVDKSRWQEGNVFSCSVMHEALHNHYTQKSLSLSLGK"
     exon            216..509
                     /gene="IgH"
                     /note="G00-119-340"
     intron          510..899
                     /gene="IgH"
     exon            900..935
                     /gene="IgH"
     intron          936..1053
                     /gene="IgH"
     exon            1054..1383
                     /gene="IgH"
     intron          1384..1480
                     /gene="IgH"
     exon            1481..1803
                     /gene="IgH"
BASE COUNT      421 a    709 c    567 g    331 t
ORIGIN
        1 agctttctgg ggcaggccgg gcctgacttt ggctgggggc agggaggggg ctaaggtgac
       61 gcaggtggcg ccagccaggt gcacacccaa tgcccatgag cccagacact ggaccctgca
      121 tggaccatcg cggatagaca agaaccgagg ggcctctgcg ccctgggccc agctctgtcc
      181 cacaccgcgg tcacatggca ccacctctct tgcagcttcc accaagggcc catccgtctt
      241 cccctggcg  ccctgctcca ggagcacctc cgagagcaca gccgccctgg gctgcctggt
      301 caaggactac ttccccgaac cggtgacggt gtcgtggaac tcaggcgccc tgaccagcgg
      361 cgtgcacacc ttcccggctg tcctacagtc ctcaggactc tactccctca gcagcgtggt
      421 gaccgtgccc tccagcagct tgggcacgaa gacctacacc tgcaacgtag atcacaagcc
      481 cagcaacacc aaggtggaca gagagttgg tgagaggcca gcacagggag ggagggtgtc
      541 tgctggaagc caggctcagc cctcctgcct ggacgcaccc cggctgtgca gccccagccc
      601 agggcagcaa ggcatgcccc atctgtctcc tcaccggag gcctctgacc accccactca
      661 tgctcaggga gagggtcttc tggatttttc caccaggctc ccggcaccac aggctggatg
      721 cccctacccc aggccctgcg catacagggc aggtgctgcg ctcagacctg caagagcca
      781 tatccgggag gaccctgccc ctgacctaag cccacccca aggccaaact ctccactccc
```

FIGURE 7S

```
 841 tcagctcaga caccttctct cctcccagat ctgagtaact cccaatcttc tctctgcaga
 901 gtccaaatat ggtcccccat gcccatcatg cccaggtaag ccaacccagg cctcgccctc
 961 cagctcaagg cgggacaggt gccctagagt agcctgcatc cagggacagg ccccagccgg
1021 gtgctgacgc atccacctcc atctcttcct cagcacctga gttcctgggg ggaccatcag
1081 tcttcctgtt cccccaaaa cccaaggaca ctctcatgat ctcccggacc cctgaggtca
1141 cgtgcgtggt ggtggacgtg agccaggaag accccgaggt ccagttcaac tggtacgtgg
1201 atggcgtgga ggtgcataat gccaagacaa agccgcggga ggagcagttc aacagcacgt
1261 accgtgtggt cagcgtcctc accgtcctgc accaggactg gctgaacggc aaggagtaca
1321 agtgcaaggt ctccaacaaa ggcctcccgt cctccatcga gaaaaccatc tccaaagcca
1381 aaggtgggac ccacggggtg cgagggccac acggacagag gccagctcgg cccaccctct
1441 gccctgggag tgaccgctgt gccaacctct gtccctacag ggcagccccg agagccacag
1501 gtgtacaccc tgcccccatc ccaggaggag atgaccaaga accaggtcag cctgacctgc
1561 ctggtcaaag gcttctaccc cagcgacatc gccgtggagt gggagagcaa tgggcagccg
1621 gagaacaact acaagaccac gcctcccgtg ctggactccg acggctcctt cttcctctac
1681 agcaggctaa ccgtggacaa gagcaggtgg caggagggga tgtcttctc atgctccgtg
1741 atgcatgagg ctctgcacaa ccactacaca cagaagagcc tctccctgtc tctgggtaaa
1801 tgagtgccag ggccggcaag ccccgctcc ccgggctctc ggggtcgcgc gaggatgctt
1861 ggcacgtacc ccgtctacat acttcccagg cacccagcat ggaaataaag cacccaccac
1921 tgccctgggc ccctgtgaga ctgtgatggt tcttccacg ggtcaggccg agcctgaggc
1981 ctgagtgaca tgagggaggc agagcgggtc ccactgtccc cacactgg
                                                 [SEQUENCE ID NO:57]
```

VII. HUMAN IG DELTA CHAIN C REGION - HOMO SAPIENS (HUMAN).

AMINO ACID SEQUENCE
>sp|P01880|DTC_HUMAN IG DELTA CHAIN C REGION - Homo sapiens (Human)

```
         10          20          30          40          50          60
          |           |           |           |           |           |
APTKAPDVFP IISGCRHPKD NSPVVLACLI TGYHPTSVTV TWYMGTQSQP QRTFPEIQRR 70          80          90         100         110         120
          |           |           |           |           |           |
DSYYMTSSQL STPLQQWRQG EYKCVVQHTA SKSKKEIFRW PESPKAQASS VPTAQPQAEG 130         140         150         160         170         180
          |           |           |           |           |           |
SLAKATTAPA TTRNTGRGGE EKKKEKEKEE QEERETKTPE CPSHTQPLGV YLLTPAVQDL 190         200         210         220         230         240
          |           |           |           |           |           |
WLRDKATFTC FVVGSDLKDA HLTWEVAGKV PTGGVEEGLL ERHSNGSQSQ HSRLTLPRSL 250         260         270         280         290         300
          |           |           |           |           |           |
WNAGTSVTCT LNHPSLPPQR LMALREPAAQ APVKLSLNLL ASSDPPEAAS WLLCEVSGFS 310         320         330         340         350         360
          |           |           |           |           |           |
PPNILLMWLE DQREVNTSGF APARPPPQPG STTFWAWSVL RVPAPPSPQP ATYTCVVSHE
```

FIGURE 7T

```
         370        380
          |          |
DSRTLLNASR SLEVSYVTDH GPM
                                                    (SEQUENCE ID NO:28)

GenBank
K02876. Human germline IgD...[gi:184766] PubMed. Protein. Related Sequences.
Taxonomy. OMIM. LinkOut LOCUS        HUMIGCH02      300 bp    DNA              PRI       08-NOV-1994
DEFINITION   Human germline IgD-chain gene, C-region, first hinge domain.
ACCESSION    K02876
VERSION      K02876.1  GI:184766
KEYWORDS     C-region; germline; hinge exon; immunoglobulin heavy chain;
             immunoglobulin-delta.
SOURCE       Homo sapiens (individual_isolate Chronic lymphocytic leukemia (CLL)
             patient) DNA.
  ORGANISM   Homo sapiens
             Eukaryota; Metazoa; Chordata; Craniata; Vertebrata; Euteleostomi;
             Mammalia; Eutheria; Primates; Catarrhini; Hominidae; Homo.
REFERENCE    1  (bases 1 to 300)
  AUTHORS    White,M.B., Shen,A.L., Word,C.J., Tucker,P.W. and Blattner,F.R.
  TITLE      Human immunoglobulin D: genomic sequence of the delta heavy chain
  JOURNAL    Science 228 (4700), 733-737 (1985)
  MEDLINE    85192522
COMMENT      See segment 1.
FEATURES             Location/Qualifiers
     source          1..300
                     /organism="Homo sapiens"
                     /isolate="Chronic lymphocytic leukemia (CLL) patient"
                     /db_xref="taxon:9606"
                     /map="14q32.33"
                     /cell_type="lymphocyte"
                     /germline
     intron          <1..151
                     /gene="IGHD"
                     /note="G00-120-084"
                     /number=1
     exon            101..202
                     /partial
                     /gene="IGHD"
                     /note="hinge-1 domain; G00-120-084"
                     /number=2
     intron          203..>300
                     /gene="IGHD"
                     /note="G00-120-084"
                     /number=2
     gene            join(K02875.1:1..495,1..300,K02877.1:1..300,
                     K02878.1:1..500,K02879.1:1..500,K02880.1:1..100,
                     K02881.1:1..200,K02882.1:1..52)
                     /gene="IGHD"
     CDS             join(K02875.1:101..403,101..202,K02877.1:101..172,
                     K02878.1:101..424,K02879.1:101..424,K02881.1:25..182,
                     K02882.1:44..52)
                     /partial
                     /gene="IGHD"
                     /note="membrane bound form"
                     /codon_start=3
                     /product="immunoglobulin delta-chain"
                     /protein_id="AAA52771.1"
                     /db_xref="GI:495872"
                     /db_xref="GDB:G00-120-084"
                     /translation="PTKAPDVFPIISGCRHPKDNSPVVLACLITGYHPTSVTVTWYMG
                     TQSQPQRTFPEIQRRDSYYMTSSQLSTPLQQWROGEYKCVVQHTASKSKKEIFRWPES
                     PKAQASSVPTAQPQAEGSLAKATTAPATTRNTGRGGEEKKKEKEKEEQEERETKTPEC
```

FIGURE 7U

```
                    PSHTQPLGVYLLTPAVQDLWLRDKATFTCFVVGSDLKDAHLTWEVAGKVPTGGVEEGL
                    LERHSNGSQSQHSRLTLPRSLWNAGTSVTCTLNHPSLPPQRLMALREPAAQAPVKLSL
                    NLLASSDPPEAASWLLCEVSGFSPPNILLMWLEDQREVNTSGFAPARPPPQPRSTTFW
                    AWSVLRVPAPPSPQPATYTCVVSHEDSRTLLNASRSLEVSYLAMTPLIPQSKDENSDD
                    YTTFDDVGSLWTTLSTFVALFILTLLYSGIVTFIKVK*
                                                              [SEQUENCE ID NO:30]
CDS                 join(K02875.1:101..403,101..202,K02877.1:101..172,
                    K02878.1:101..424,K02879.1:101..424,K02880.1:25..53)
                    /partial
                    /gene="IGHD"
                    /note="secreted form"
                    /codon_start=3
                    /product="immunoglobulin delta-chain"
                    /protein_id="AAA52770.1"
                    /db_xref="GI:495871"
                    /db_xref="GDB:G00-120-084"
                    /translation="PTKAPDVFPIISGCRHPKDNSPVVLACLITGYHPTSVTVTWYMG
                    TQSQPQRTFPEIQRRDSYYMTSSQLSTPLQQWRQGEYKCVVQHTASKSKKEIFRWPES
                    PKAQASSVPTAQPQAEGSLAKATTAPATTRNTGRGGEEKKKEKEKEEQEERETKTPEC
                    PSHTQPLGVYLLTPAVQDLWLRDKATFTCFVVGSDLKDAHLTWEVAGKVPTGGVEEGL
                    LERHSNGSQSQHSRLTLPRSLWNAGTSVTCTLNHPSLPPQRLMALREPAAQAPVKLSL
                    NLLASSDPPEAASWLLCEVSGFSPPNILLMWLEDQREVNTSGFAPARPPPQPRSTTFW
                    AWSVLRVPAPPSPQPATYTCVVSHEDSRTLLNASRSLEVSYVTDHGPMK*
BASE COUNT        59 a      133 c      52 g      56 t
ORIGIN       About 300 bp after segment 1; 118 bp upstream of StuI site.
        1 taggctgcct gtgcccccca cctgcctgtc cacaacccag cctctggtac atccatgccc
       61 tctgccctaa gcctcacctg cacttttcct tggatttcag agtctccaaa ggcacaggcc
      121 tcctccgtgc ccactgcaca acccaagca gagggcagcc tcgccaaggc aaccacagcc
      181 ccagccacca ccgtaacac aggtgagaag ccccttccct gcacactcca ccccaccca
      241 cctgctcatt cctcagccgc ctcctccagg cagcccttca taactccttg tctgagtctc
                                                              [SEQUENCE ID NO:27]
```

```
K02877. Human Ig germline ...[gi:184767] PubMed, Protein, Related Sequences,
Taxonomy, OMIM, LinkOut LOCUS           HUMIGCH03       300 bp    DNA             PRI       08-NOV-1994
DEFINITION      Human Ig germline delta H-chain C-region gene, second hinge domain
                (CLL lymphocyte)
ACCESSION       K02877
VERSION         K02877.1  GI:184767
KEYWORDS        C-region; germline; hinge exon; immunoglobulin heavy chain;
                immunoglobulin-delta.
SOURCE          Homo sapiens (individual_isolate Chronic lymphocytic leukemia (CLL)
                patient) DNA.
  ORGANISM      Homo sapiens
                Eukaryota; Metazoa; Chordata; Craniata; Vertebrata; Euteleostomi;
                Mammalia; Eutheria; Primates; Catarrhini; Hominidae; Homo.
REFERENCE       1  (bases 1 to 300)
  AUTHORS       White,M.B., Shen,A.L., Word,C.J., Tucker,P.W. and Blattner,F.R.
  TITLE         Human immunoglobulin D: genomic sequence of the delta heavy chain
  JOURNAL       Science 228 (4700), 733-737 (1985)
  MEDLINE       85192522
COMMENT         See segment 1.
FEATURES             Location/Qualifiers
     source          1..300
                     /organism="Homo sapiens"
                     /isolate="Chronic lymphocytic leukemia (CLL) patient"
                     /db_xref="taxon:9606"
                     /map="14q32.33"
                     /cell_type="lymphocyte"
                     /germline
     intron          <1..100
                     /gene="IGHD"
                     /note="G00-120-084"
                     /number=2
     exon            101..172
```

FIGURE 7V

```
                  /gene="IGHD"
                  /note="hinge-2 domain; G00-120-084; putative"
                  /number=3
    intron        173..>300
                  /gene="IGHD"
                  /note="G00-120-084"
                  /number=3
    gene          join(K02875.1:1..495,K02876.1:1..300,1..300,
                  K02878.1:1..560,K02879.1:1..500,K02880.1:1..100,
                  K02881.1:1..200,K02882.1:1..52)
                  /gene="IGHD"
    CDS           join(K02875.1:101..403,K02876.1:101..202,101..172,
                  K02878.1:101..424,K02879.1:101..424,K02881.1:25..182,
                  K02882.1:44..52)
                  /partial
                  /gene="IGHD"
                  /note="membrane bound form"
                  /codon_start=3
                  /product="immunoglobulin delta-chain"
                  /protein_id="AAA52771.1"
                  /db_xref="GI:495872"
                  /db_xref="GDB:G00-120-084"
                  /translation="PTKAPDVFPIISGCRHPKDNSPVVLACLITGYHPTSVTVTWYMG
                  TQSQPQRTFPEIQRRDSYYMTSSQLSTPLQQWRQGEYKCVVQHTASKSKKEIFRWPES
                  PKAQASSVPTAQPQAEGSLAKATTAPATTRNTGRGGEEKKKEKEKEEQEERETKTPEC
                  PSHTQPLGVYLLTPAVQDLWLRDKATFTCFVVGSDLKDAHLTWEVAGKVPTGGVEEGL
                  LERHSNGSQSQHSRLTLPRSLWNAGTSVTCTLNHPSLPPQRLMALREPAAQAPVKLSL
                  NLLASSDPPEAASWLLCEVSGFSPPNILLMWLEDQREVNTSGFAPARPPPQPRSTTFW
                  AWSVLRVPAPPSPQPATYTCVVSHEDSRTLLNASRSLEVSYLAMTPLIPQSKDENSDD
                  YTTFDDVGSLWTTLSTFVALFILTLLYSGIVTFIKVK"     [SEQUENCE ID NO: 30]
    CDS           join(K02875.1:101..403,K02876.1:101..202,101..172,
                  K02878.1:101..424,K02879.1:101..424,K02880.1:25..53)
                  /partial
                  /gene="IGHD"
                  /note="secreted form"
                  /codon_start=3
                  /product="immunoglobulin delta-chain"
                  /protein_id="AAA52770.1"
                  /db_xref="GI:495871"
                  /db_xref="GDB:G00-120-084"
                  /translation="PTKAPDVFPIISGCRHPKDNSPVVLACLITGYHPTSVTVTWYMG
                  TQSQPQRTFPEIQRRDSYYMTSSQLSTPLQQWRQGEYKCVVQHTASKSKKEIFRWPES
                  PKAQASSVPTAQPQAEGSLAKATTAPATTRNTGRGGEEKKKEKEKEEQEERETKTPEC
                  PSHTQPLGVYLLTPAVQDLWLRDKATFTCFVVGSDLKDAHLTWEVAGKVPTGGVEEGL
                  LERHSNGSQSQHSRLTLPRSLWNAGTSVTCTLNHPSLPPQRLMALREPAAQAPVKLSL
                  NLLASSDPPEAASWLLCEVSGFSPPNILLMWLEDQREVNTSGFAPARPPPQPRSTTFW
                  AWSVLRVPAPPSPQPATYTCVVSHEDSRTLLNASRSLEVSYVTDHGPHK"
    BASE COUNT         102 a     52 c     70 g     76 t
    ORIGIN        About 1.85 kb after segment 2.
         1 gtcattagct ggatttagcc attccacaat gtacacatat ttcaaacatt gtgttgtaca
        61 tgataaacat gtataattct tgtcaattaa aaattttcag gaagaggagg agaagagaag
       121 aagaaggaga aggagaaaga ggaacaagaa gagagagaga caaagacacc aggttttttc
       181 tgaccctgg gctatcaaaa cacctattgc ccaataacta gttggccgtt ggtgccctaa
       241 actattgaag cgattgctgt tatgtggatg ggccccggac actagaaaac tcgtgacccc
                                                              [SEQUENCE ID NO:29]
```

FIGURE 7W

K02878. Human germline IgD...[gi:184768] PubMed, Protein, Related Sequences, Taxonomy, OMIM, LinkOut

```
LOCUS       HUMIGCH04      500 bp    DNA             PRI       08-NOV-1994
DEFINITION  Human germline IgD chain gene, C-region, C-delta-2 domain.
ACCESSION   K02878
VERSION     K02878.1  GI:184768
KEYWORDS    C-region; germline; immunoglobulin heavy chain;
            immunoglobulin-delta.
SOURCE      Homo sapiens (individual_isolate Chronic lymphocytic leukemia (CLL)
            patient) DNA.
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (bases 1 to 500)
  AUTHORS   White,M.B., Shen,A.L., Word,C.J., Tucker,P.W. and Blattner,F.R.
  TITLE     Human immunoglobulin D: genomic sequence of the delta heavy chain
  JOURNAL   Science 228 (4700), 733-737 (1985)
  MEDLINE   85192522
COMMENT     See segment 1.
FEATURES             Location/Qualifiers
     source          1..500
                     /organism="Homo sapiens"
                     /isolate="Chronic lymphocytic leukemia (CLL) patient"
                     /db_xref="taxon:9606"
                     /map="14q32.33"
                     /cell_type="lymphocyte"
                     /germline
     intron          <1..100
                     /gene="IGHD"
                     /note="G00-120-084"
                     /number=3
     exon            101..424
                     /gene="IGHD"
                     /note="C-delta-2 domain; G00-120-084"
                     /number=4
     intron          425..>500
                     /gene="IGHD"
                     /note="G00-120-084"
                     /number=4
     intron          425..>500
                     /gene="IGHD"
                     /note="IgD-s intron D"
     gene            join(K02875.1:1..495,K02876.1:1..300,K02877.1:1..300,
                     1..500,K02879.1:1..500,K02880.1:1..100,K02881.1:1..200,
                     K02882.1:1..52)
                     /gene="IGHD"
     CDS             join(K02875.1:101..403,K02876.1:101..202,
                     K02877.1:101..172,101..424,K02879.1:101..424,
                     K02881.1:25..182,K02882.1:44..52)
                     /partial
                     /gene="IGHD"
                     /note="membrane bound form"
                     /codon_start=3
                     /product="immunoglobulin delta-chain"
                     /protein_id="AAA52771.1"
                     /db_xref="GI:495872"
                     /db_xref="GDB:G00-120-084"
                     /translation="PTKAPDVFPIISGCRHPKDNSPVVLACLITGYHPTSVTVTWYMG
                     TQSQPQRTFPEIQRRDSYYMTSSQLSTPLQQWRQGEYKCVVQHTASKSKKEIFRWPES
                     PKAQASSVPTAQPQAEGSLAKATTAPATTRNTGRGGEEKKKEKEKEEQEERETKTPEC
                     PSHTQPLGVYLLTPAVQDLWLRDKATFTCFVVGSDLKDAHLTWEVAGKVPTGGVEEGL
                     LERHSNGSQSQHSRLTLPRSLWNAGTSVTCTLNHPSLPPQRLMALREPAAQAPVKLSL
                     NLLASSDPPEAASWLLCEVSGFSPPMILLMWLEDQREVNTSGFAPARPPPQPRSTTFM
                     AMSVLRVPAPPSPQPATYTCVVSHEDSRTLLNASRSLEVSYLAMTPLIPQSKDENSDD
                     YTTFDDVGSLWTTLSTFVALFILTLLYSGIVTFIKVK"
```

FIGURE 7X

```
CDS             join(K02875.1:101..403,K02876.1:101..202,
                K02877.1:101..172,101..424,K02879.1:101..424,
                K02880.1:25..53)
                /partial
                /gene="IGHD"
                /note="secreted form"
                /codon_start=3
                /product="immunoglobulin delta-chain"
                /protein_id="AAA52770.1"
                /db_xref="GI:495871"
                /db_xref="GDB:G00-120-084"
                /translation="PTKAPDVFPIISGCRHPKDNSPVVLACLITGYHPTSVTVTWYMG
                TQSQPQRTFPEIQRRDSYYMTSSQLSTPLQQWRQGEYKCVVQHTASKSKKEIFRWPES
                PKAQASSVPTAQPQAEGSLAKATTAPATTRNTGRGGEEKKKEKEKEEQEERETKTPEC
                PSHTQPLGVYLLTPAVQDLWLRDKATFTCFVVGSDLKDAHLTWEVAGKVPTGGVEEGL
                LERHSNGSQSQHSRLTLPRSLWNAGTSVTCTLNHPSLPPQRLMALREPAAQAPVKLSL
                NLLASSDPPEAASWLLCEVSGFSPPNILLMWLEDQREVNTSGFAPARPPPQPRSTTFW
                AHSVLRVPAPPSPQPATYTCVVSHEDSRTLLNASRSLEVSYVTDHGPMK"
BASE COUNT          93 a    171 c    157 g    79 t          [SEQUENCE ID NO: 32]
ORIGIN      About 450 bp after segment 3; 131 bp upstream of AccI site.
        1 gaagctgggg agaggagagc acagtggtta agtcagtccc tgcagcccaa ctgctcccga
       61 aggtccggcc acagctgctc tcgtttgctc tcccctgcag agtgtccgag ccacacccag
      121 cctcttggcg tctacctgct aaccccctgca gtgcaggacc tgtggctccg ggacaaagcc
      181 acctccacct gcttcgtggt gggcagtgac ctgaaggatg ctcacctgac ctgggaggtg
      241 gctgggaagg tccccacagg gggcgtggag gaagggctgc tggagcggca cagcaacggc
      301 tcccagagcc agcacagccg tctgaccctg cccaggtcct tgtggaacgc ggggacctcc
      361 gtcacctgca cactgaacca tcccagcctc ccacccaga ggttgatggc gctgagagaa
      421 cccggtgagc ctggctccca ggtggggaga cgagggtgcc cacagcctgc tgaccctac
      481 gcccgcccca gggccatgac
                                                              [SEQUENCE ID NO: 31]

K02879. Human Ig germline ...(gi:184769) PubMed, Protein, Related Sequences,
Taxonomy, OMIM, LinkOut LOCUS       HUMIGCH05       500 bp    DNA           PRI       08-NOV-1994
DEFINITION  Human Ig germline delta H-chain C-region gene, C-delta-3 domain
            (CLL lymphocyte).
ACCESSION   K02879
VERSION     K02879.1  GI:184769
KEYWORDS    C-region; germline; immunoglobulin heavy chain;
            immunoglobulin-delta.
SOURCE      Homo sapiens (individual_isolate Chronic lymphocytic leukemia (CLL)
            patient) DNA.
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (bases 1 to 500)
  AUTHORS   White,M.B., Shen,A.L., Word,C.J., Tucker,P.W. and Blattner,F.R.
  TITLE     Human immunoglobulin D: genomic sequence of the delta heavy chain
  JOURNAL   Science 228 (4700), 733-737 (1985)
  MEDLINE   85192522
COMMENT     See segment 1.
FEATURES             Location/Qualifiers
     source          1..500
                     /organism="Homo sapiens"
                     /isolate="Chronic lymphocytic leukemia (CLL) patient"
                     /db_xref="taxon:9606"
                     /map="14q32.33"
                     /cell_type="lymphocyte"
                     /germline
     intron          <1..100
                     /gene="IGHD"
                     /note="G00-120-084"
                     /number=4
     exon            101..424
                     /gene="IGHD"
```

FIGURE 7Y

```
                    /note="C-delta-3 domain; G00-120-084; putative"
                    /number=5
    intron          425..>500
                    /gene="IGHD"
                    /note="G00-120-084"
                    /number=5
    gene            join(K02875.1:1..495,K02876.1:1..300,K02877.1:1..300,
                    K02878.1:1..500,1..500,K02880.1:1..100,K02881.1:1..200,
                    K02882.1:1..52)
                    /gene="IGHD"
    CDS             join(K02875.1:101..403,K02876.1:101..202,
                    K02877.1:101..172,K02878.1:101..424,101..424,
                    K02881.1:25..182,K02882.1:44..52)
                    /partial
                    /gene="IGHD"
                    /note="membrane bound form"
                    /codon_start=3
                    /product="immunoglobulin delta-chain"
                    /protein_id="AAA52771.1"
                    /db_xref="GI:495872"
                    /db_xref="GDB:G00-120-084"
                    /translation="PTKAPDVFPIISGCRHPKDNSPVVLACLITGYHPTSVTVTWYMG
                    TQSQPQRTFPEIQRRDSYYMTSSQLSTPLQQWRQGEYKCVVQHTASKSKKEIFRWPES
                    PKAQASSVPTAQPQAEGSLAKATTAPATTRNTGRGGEEKKKEKEKEEQEERETKTPEC
                    PSHTQPLGVYLLTPAVQDLWLRDKATFTCFVVGSDLKDAHLTWEVAGKVPTGGVEEGL
                    LERHSNGSQSQHSRLTLPRSLWNAGTSVTCTLNHPSLPPQRLMALREPAAQAPVKLSL
                    NLLASSDPPEAASWLLCEVSGFSPPNILLMWLEDQREVNTSGFAPARPPPQPRSTTFW
                    AWSVLRVPAPPSPQPATYTCVVSHEDSRTLLNASRSLEVSYLAMTPLIPQSKDENSDD
                    YTTFDDVGSLWTTLSTFVALFILTLLYSGIVTFIKVK"      [SEQUENCE ID NO: 34]
    CDS             join(K02875.1:101..403,K02876.1:101..202,
                    K02877.1:101..172,K02878.1:101..424,101..424,
                    K02880.1:25..53)
                    /partial
                    /gene="IGHD"
                    /note="secreted form"
                    /codon_start=3
                    /product="immunoglobulin delta-chain"
                    /protein_id="AAA52770.1"
                    /db_xref="GI:495871"
                    /db_xref="GDB:G00-120-084"
                    /translation="PTKAPDVFPIISGCRHPKDNSPVVLACLITGYHPTSVTVTWYMG
                    TQSQPQRTFPEIQRRDSYYMTSSQLSTPLQQWRQGEYKCVVQHTASKSKKEIFRWPES
                    PKAQASSVPTAQPQAEGSLAKATTAPATTRNTGRGGEEKKKEKEKEEQEERETKTPEC
                    PSHTQPLGVYLLTPAVQDLWLRDKATFTCFVVGSDLKDAHLTWEVAGKVPTGGVEEGL
                    LERHSNGSQSQHSRLTLPRSLWNAGTSVTCTLNHPSLPPQRLMALREPAAQAPVKLSL
                    NLLASSDPPEAASWLLCEVSGFSPPNILLMWLEDQREVNTSGFAPARPPPQPRSTTFW
                    AWSVLRVPAPPSPQPATYTCVVSHEDSRTLLNASRSLEVSYVTDHGPMK"
BASE COUNT          85 a    188 c    145 g    82 t
ORIGIN      About 150 bp after segment 4; 118 bp upstream of HindIII site.
        1 ccacaggaaa ggagaaggga ggcaccacac cctggccggc cccactcctc ccccagtgcc
       61 cccgtggcca gagcctgaca gcccccccac ctcccgcag ctgcgcaggc acccgtcaag
      121 ccttctctga acctgctggc ctcgtctgac cctcccgagg cggcctcgtg gctcctgtgt
      181 gaggtgtctg gcttcctcgcc cccaaacatc ctcctgatgt ggctggagga ccagcgtgag
      241 gtgaacactt ctgggttcgc cccgcacgc ccctcctccac agcccaggag caccacgttc
      301 tgggcctgga gtgtgctgcg tgtcccagcc ccgcccagcc ctcagccagc cacctacacg
```

FIGURE 7Z

```
361 tgtgtggtca gccacgagga ctcccggact ctgctcaacg ccagccggag cctagaagtc
421 agctgtgagt caccccagg ccagggttgg gacggggact ctgaggggg ccataaggag
481 ctggaatcca tactaggcag
```
(SEQUENCE ID NO:33)

```
K01311. Human IgD germline...[gi:184716] PubMed, Protein, Taxonomy, OMIM

LOCUS       HUMIGCB9       106 bp    DNA              PRI       12-APR-2001
DEFINITION  Human IgD germline chain J-delta region: C-delta CH1.
ACCESSION   K01311
VERSION     K01311.1  GI:184716
KEYWORDS    C-region; germline; immunoglobulin heavy chain;
            immunoglobulin-delta.
SOURCE      human.
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (bases 1 to 106)
  AUTHORS   Rabbitts,T.H., Forster,A. and Milstein,C.P.
  TITLE     Human immunoglobulin heavy chain genes: evolutionary comparisons of
            C mu, C delta and C gamma genes and associated switch sequences
  JOURNAL   Nucleic Acids Res. 9 (18), 4509-4524 (1981)
  MEDLINE   82059479
   PUBMED   6795593
  COMMENT   The deduced amino acid sequence is compared in [1] to the
            J/C-delta-1 junction of human ER1 protein. The delta gene occurs
            only 5 kb from the mu region. The authors [1] could not detect any
            switch-related sequences adjacent to the delta gene and state that
            this implies that the mu/delta switch cannot occur by the class
            switch recombination method. They speculate that the entire
            VH-(C-mu)-(C-delta) region is transcribed into one nuclear
            precursor molecule which is spliced later.
            This is part of a multigene region containing the J-region, switch
            region, C-mu-secreted, C-mu-membrane, and C-delta genes.
FEATURES             Location/Qualifiers
     source          1..106
                     /organism="Homo sapiens"
                     /db_xref="taxon:9606"
                     /map="14q32.33"
                     /cell_type="lymphocyte"
                     /tissue_type="placenta"
                     /tissue_type="liver"
                     /dev_stage="foetus"
                     /germline
                     /tissue_lib="of Lawn et al."
     gene            1..106
                     /gene="IGHD"
     intron          <1..26
                     /gene="IGHD"
                     /note="intron delta J-C; G00-120-084"
     CDS             <27..>106
                     /gene="IGHD"
                     /note="C-region CH1 domain"
                     /codon_start=3
                     /product="immunoglobulin delta-chain"
                     /protein_id="AAB59423.1"
                     /db_xref="GI:184735"
                     /translation="PTKAPDVFPIISGCRHPKDNSPVVLA"
BASE COUNT      24 a     38 c     24 g     20 t
ORIGIN
        1 tgccacccca ggactctgtc ttccagcacc caccaaggct ccggatgtgt tccccatcat
       61 atcagggtgc agacacccaa aggataacag ccctgtggtc ctggca
```
(SEQUENCE ID NO:58)

K02880. Human germline IgD...[gi:184770] PubMed, Protein, Related Sequences,
Taxonomy, OMIM, LinkOut

FIGURE 7AA

```
LOCUS       HUMIGCH06       100 bp    DNA              PRI       08-NOV-1994
DEFINITION  Human germline IgD chain gene, C-region, secreted terminus.
ACCESSION   K02880
VERSION     K02880.1  GI:184770
KEYWORDS    C-region; germline; immunoglobulin heavy chain;
            immunoglobulin-delta.
SOURCE      Homo sapiens (individual_isolate Chronic lymphocytic leukemia (CLL)
            patient) DNA.
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (bases 1 to 100)
  AUTHORS   White,M.B., Shen,A.L., Word,C.J., Tucker,P.W. and Blattner,F.R.
  TITLE     Human immunoglobulin D: genomic sequence of the delta heavy chain
  JOURNAL   Science 228 (4700), 733-737 (1985)
  MEDLINE   85192522
COMMENT     See segment 1.
FEATURES             Location/Qualifiers
     source          1..100
                     /organism="Homo sapiens"
                     /isolate="Chronic lymphocytic leukemia (CLL) patient"
                     /db_xref="taxon:9606"
                     /map="14q32.33"
                     /cell_type="lymphocyte"
                     /germline
     intron          <1..>100
                     /gene="IGHD"
                     /note="G00-120-084"
                     /number=5
     intron          <1..24
                     /gene="IGHD"
                     /note="G00-120-084"
                     /number=5
     exon            25..>53
                     /gene="IGHD"
                     /note="secreted terminus domain; G00-120-084"
                     /number=6
     gene            join(K02875.1:1..495,K02876.1:1..300,K02877.1:1..300,
                     K02878.1:1..500,K02879.1:1..500,1..100,K02881.1:1..200,
                     K02882.1:1..52)
                     /gene="IGHD"
     CDS             join(K02875.1:101..403,K02876.1:101..202,
                     K02877.1:101..172,K02878.1:101..424,K02879.1:101..424,
                     25..53)
                     /partial
                     /gene="IGHD"
                     /note="secreted form"
                     /codon_start=3
                     /product="immunoglobulin delta-chain"
                     /protein_id="AAA52770.1"
                     /db_xref="GI:495871"
                     /db_xref="GDB:G00-120-084"
                     /translation="PTKAPDVFPIISGCRHPKDNSPVVLACLITGYHPTSVTVTWYMG
                     TQSQPQRTFPEIQRRDSYYMTSSQLSTPLQQHRQGEYKCVVQHTASKSKKEIFRWPES
                     PKAQASSVPTAQPQAEGSLAKATTAPATTRNTGRGGEEKKKEKEKEEQEERETKTPEC
                     PSHTQPLGVYLLTPAVQDLWLRDKATFTCFVVGSDLKDAHLTWEVAGKVPTGGVEEGL
                     LERHSNGSQSQHSRLTLPRSLWNAGTSVTCTLNHPSLPPQRLMALREPAAQAPVKLSL
                     NLLASSDPPEAASWLLCEVSGFSPPNILLMWLEDQREVNTSGFAPARPPPQPRSTTFW
                     AWSVLRVPKPPSPQPATYTCVVSHEDSRTLLNASRSLEVSYVTDMGPMK"
BASE COUNT     24 a   33 c   22 g   21 t          [SEQUENCE ID NO: 37]
ORIGIN      About 1.8 kb after segment 5
        1 gacacgccga tttttgtta ttagatgtaa cagaccatgg ccccatgaaa tgatcccgga
       61 ccagatccgt ccgcacccgc cactcagcag ctctggccga
                                                      [SEQUENCE ID NO:36]
```

FIGURE 7BB

K02881. Human germline IgD...[gi:184771] PubMed, Protein, Related Sequences, Taxonomy, OMIM, LinkOut

```
LOCUS       HUMIGCH07    200 bp    DNA              PRI    08-NOV-1994
DEFINITION  Human germline IgD-chain gene, C-region, first domain of membrane
            terminus.
ACCESSION   K02881
VERSION     K02881.1  GI:184771
KEYWORDS    C-region; germline; immunoglobulin heavy chain;
            immunoglobulin-delta.
SOURCE      Homo sapiens (individual_isolate Chronic lymphocytic leukemia (CLL)
            patient) DNA.
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (bases 1 to 200)
  AUTHORS   White,M.B., Shen,A.L., Word,C.J., Tucker,P.W. and Blattner,F.R.
  TITLE     Human immunoglobulin D: genomic sequence of the delta heavy chain
  JOURNAL   Science 228 (4700), 733-737 (1985)
  MEDLINE   85192522
COMMENT     See segment 1.
FEATURES             Location/Qualifiers
     source          1..200
                     /organism="Homo sapiens"
                     /isolate="Chronic lymphocytic leukemia (CLL) patient"
                     /db_xref="taxon:9606"
                     /map="14q32.33"
                     /cell_type="lymphocyte"
                     /germline
     intron          <1..24
                     /gene="IGHD"
                     /note="G00-120-084"
                     /number=5
     exon            25..182
                     /gene="IGHD"
                     /note="first domain of membrane terminus; G00-120-084;
                     putative"
                     /number=6
     intron          183..>200
                     /gene="IGHD"
                     /note="G00-120-084"
                     /number=6
     gene            join(K02875.1:1..495,K02876.1:1..300,K02877.1:1..300,
                     K02878.1:1..500,K02879.1:1..500,K02880.1:1..100,1..200,
                     K02882.1:1..52)
                     /gene="IGHD"
     CDS             join(K02875.1:101..403,K02876.1:101..202,
                     K02877.1:101..172,K02878.1:101..424,K02879.1:101..424,
                     25..182,K02882.1:44..52)
                     /partial
                     /gene="IGHD"
                     /note="membrane bound form"
                     /codon_start=3
                     /product="immunoglobulin delta-chain"
                     /protein_id="AAA52771.1"
                     /db_xref="GI:495872"
                     /db_xref="GDB:G00-120-084"
                     /translation="PTKAPDVFPIISGCRHPKDNSPVVLACLITGYHPTSVTVTWYMG
                     TQSQPQRTFPEIQRRDSYYMTSSQLSTPLQQWROGEYKCVVQHTASKSKKEIFRWPES
                     PKAQASSVPTAQPQAEGSLAKATTAPATTRNTGRGGEEKKKEKEKEEQEERETKTPEC
                     PSHTQPLGVYLLTPAVQDLWLRDKATFTCFVVGSDLKDAHLTWEVAGKVPTGGVEEOL
                     LERHSNGSQSQHSRLTLPRSLWNAGTSVTCTLNHPSLPPQRLMALREPAAQAPVKLSL
                     NLLASSDPPEAASWLLCEVSGFSPPNILLMWLEDQREVNTSGFAPARPPPQPRSTTFW
                     AWSVLRVPAPPSPQPATYTCVVSHEDSRTLLNASRSLEVSYLAHTPLIPQSKDENSDD
                     YTTFDDVGSLWTTLSTFVALFILTLLYSGIVTFIKVK"
BASE COUNT        37 a     72 c    49 g    42 t
```

[SEQUENCE ID NO: 39]

FIGURE 7CC

ORIGIN   About 800 bp after segment 6.
```
   1 cgctcggccc ccgttcctcc ccagacctgg ccatgacccc cctgatccct cagagcaagg
  61 atgagaacag cgatgactac acgacctttg atgatgtggg cagcctgtgg accaccctgt
 121 ccacgtttgt ggccctcttc atcctcaccc tcctctacag cggcattgtc acttccatca
 181 aggtcagggg agcggccagg
```
                                                              (SEQUENCE ID NO:38)

K02882. Human germline IgD...[gi:184772] PubMed, Protein, Related Sequences, Taxonomy, OMIM, LinkOut

| | |
|---|---|
| LOCUS | HUMIGCH08    100 bp    DNA    PRI    08-NOV-1994 |
| DEFINITION | Human germline IgD-chain gene, C-region, second domain of membrane terminus. |
| ACCESSION | K02882 |
| VERSION | K02882.1  GI:184772 |
| KEYWORDS | C-region; germline; immunoglobulin heavy chain; immunoglobulin-delta.. |
| SOURCE | Homo sapiens (individual_isolate Chronic lymphocytic leukemia (CLL) patient) DNA. |
| ORGANISM | Homo sapiens<br>Eukaryota; Metazoa; Chordata; Craniata; Vertebrata; Euteleostomi; Mammalia; Eutheria; Primates; Catarrhini; Hominidae; Homo. |
| REFERENCE | 1 (bases 1 to 100) |
| AUTHORS | White,M.B., Shen,A.L., Word,C.J., Tucker,P.W. and Blattner,F.R. |
| TITLE | Human immunoglobulin D: genomic sequence of the delta heavy chain |
| JOURNAL | Science 228 (4700), 733-737 (1985) |
| MEDLINE | 85192522 |
| COMMENT | See segment 1. |
| FEATURES | Location/Qualifiers |
| source | 1..100<br>/organism="Homo sapiens"<br>/isolate="Chronic lymphocytic leukemia (CLL) patient"<br>/db_xref="taxon:9606"<br>/map="14q32.33"<br>/cell_type="lymphocyte"<br>/germline |
| intron | <1..43<br>/gene="IGHD"<br>/note="IgD-Mb"<br>/number=6 |
| exon | 44..>52<br>/gene="IGHD"<br>/note="membrane-bound form (second domain of membrane terminus); G00-120-084; putative"<br>/number=7 |
| gene | join(K02875.1:1..495,K02876.1:1..300,K02877.1:1..300, K02878.1:1..500,K02879.1:1..500,K02880.1:1..100, K02881.1:1..200,1..52)<br>/gene="IGHD" |
| CDS | join(K02875.1:101..403,K02876.1:101..202, K02877.1:101..172,K02878.1:101..424,K02879.1:101..424, K02881.1:25..182,44..52)<br>/partial<br>/gene="IGHD"<br>/note="membrane bound form"<br>/codon_start=3<br>/product="immunoglobulin delta-chain"<br>/protein_id="AAA52771.1"<br>/db_xref="GI:495872"<br>/db_xref="GDB:G00-120-084"<br>/translation="PTKAPDVFPIISGCRHPKDNSPVVLACLITGYHPTSVTVTWYHG TQSQPQRTFPEIQRRDSYYMTSSQLSTPLQQWRQGEYKCVVQHTASKSKKEIFRWPES PKAQASSVPTAQPQAEGSLAKATTAPATTRNTGRGGEEKKKEKEKEEQEERETKTPEC PSHTQPLGVYLLTPAVQDLWLRDKATFTCFVVGSDLKDAHLTWEVAGKVPTGGVEEGL LERMSHGSQSQHSRLTLPRSLWNAGTSVTCTLNHPSLPPQRLWALREPAAQAPVKLSL NLLASSDPPEAASWLLCEVSGFSPPNILLMWLEDQREVNTSGFAPARPPPQPRSTTFW" |

FIGURE 7DD

```
                    AWSVLRVPAPPSPQPATYTCVVSHEDSRTLLNASRSLEVSYLAMTPLIPQSKDENSDD
                    YTTFDDVGSLWTTLSTFVALFILTLLYSGIVTFIKVK"
BASE COUNT      22 a     30 c     30 g     18 t              [SEQUENCE ID NO: 41]
ORIGIN     About 1.3 kb after segment 7.
      1 tcaggcttct agccccntgtc tgaccccagg ggctgtcttt caggtgaagt agccccagaa
     61 gagcaggacg ccctgtacct gcagagaagg gaagcagcct
                                                              [SEQUENCE ID NO:40]

K02875. Human germline IgD...[gi:184765] PubMed, Related Sequences, Taxonomy, OMIM,
LinkOut LOCUS          HUMIGCH01        495 bp    DNA              PRI      08-NOV-1994
DEFINITION     Human germline IgD chain gene, C-region, C-delta-1 domain.
ACCESSION      K02875
VERSION        K02875.1  GI:184765
KEYWORDS       C-region; germline; immunoglobulin heavy chain;
               immunoglobulin-delta.
SOURCE         Homo sapiens (individual_isolate Chronic lymphocytic leukemia (CLL)
               patient) DNA.
  ORGANISM     Homo sapiens
               Eukaryota; Metazoa; Chordata; Craniata; Vertebrata; Euteleostomi;
               Mammalia; Eutheria; Primates; Catarrhini; Hominidae; Homo.
REFERENCE      1  (bases 1 to 495)
  AUTHORS      White,M.B., Shen,A.L., Word,C.J., Tucker,P.W. and Blattner,F.R.
  TITLE        Human immunoglobulin D: genomic sequence of the delta heavy chain
  JOURNAL      Science 228 (4700), 733-737 (1985)
  MEDLINE      85192522
COMMENT        Sequence in computer readable form and draft entry for [1] were
               kindly provided by M.B.White, 06-AUG-1985.
               The C-delta and delta-s exon boundaries were located by comparing
               the translated sequences with known AA sequences [1].
FEATURES             Location/Qualifiers
     source          1..495
                     /organism="Homo sapiens"
                     /isolate="Chronic lymphocytic leukemia (CLL) patient"
                     /db_xref="taxon:9606"
                     /map="14q32.33"
                     /cell_type="lymphocyte"
                     /germline
     gene            join(1..495,K02876.1:1..300,K02877.1:1..300,
                     K02878.1:1..500,K02879.1:1..500,K02880.1:1..100,
                     K02881.1:1..200,K02882.1:1..52)
                     /gene="IGHD"
     intron          <1..100
                     /gene="IGHD"
                     /note="J-C intron; G00-120-084"
     CDS             join(101..403,K02876.1:101..202,K02877.1:101..172,
                     K02878.1:101..424,K02879.1:101..424,K02880.1:25..53)
                     /partial
                     /gene="IGHD"
                     /note="secreted form"
                     /codon_start=3
                     /product="immunoglobulin delta-chain"
                     /protein_id="AAA52770.1"
                     /db_xref="GI:495871"
                     /db_xref="GDB:G00-120-084"
                     /translation="PTKAPDVFPIISGCRHPKDNSPVVLACLITGYHPTSVTVTWYMG
                     TQSQPQRTFPEIQRRDSYYMTSSQLSTPLQQWRQGEYKCVVQHTASKSKKEIFRWPES
                     PKAQASSVPTAQPQAEGSLAKATTAPATTRNTGRGGEEKKKEKEEQEERETKTPEC
                     PSHTQPLGVYLLTPAVQQLWLRDKATFTCFVVGSDLKDAHLTWEVAGKVPTGGVEEGL
                     LERHSNGSQSQHSRLTLPRSLWNAGTSVTCTLNHPSLPPQRLMALREPAAQAPVKLSL
                     NLLASSDPPEAASWLLCEVSGFSPPNILLMWLEDQREVNTSGFAPARPPPQPRSTTFW
                     AWSVLRVPAPPSPQPATYTCVVSHEDSRTLLNASRSLEVSYVTDHGPMK"
     exon            101..403                              [SEQUENCE ID NO: 43]
                     /gene="IGHD"
                     /note="C-delta-1 domain; G00-120-084; putative"
```

FIGURE 7EE

```
                /number=1
         CDS    join(101..403,K02876.1:101..202,K02877.1:101..172,
                K02878.1:101..424,K02879.1:101..424,K02881.1:25..182,
                K02882.1:44..52)
                /partial
                /gene="IGHD"
                /note="membrane bound form"
                /codon_start=1
                /product="immunoglobulin delta-chain"
                /protein_id="AAA52771.1"
                /db_xref="GI:495872"
                /db_xref="GDB:G00-120-084"
                /translation="PTKAPDVFPIISGCRHPKDNSPVVLACLITGYHPTSVTVTWYMG
                TQSOPQRTFPEIQRRDSYYMTSSQLSTPLQQWRQGEYKCVVQHTASKSKKEIFRWPES
                PKAQASSVPTAQPQAEGSLAKATTAPATTRNTGRGGEEKKKEKEKEEQEERETKTPEC
                PSHTQPLGVYLLTPAVQDLWLRDKATFTCFVVGSDLKDAHLTWEVAGKVPTGGVEEGL
                LERHSNGSQSQHSRLTLPRSLWNAGTSVTCTLNHPSLPPQRLMALREPAAQAPVKLSL
                NLLASSDPPEAASHLLCEVSGFSPPNILLMWLEDQREVNTSGFAPARPPPQPRSTTFW
                AWSVLRVPAPPSPQPATYTCVVSHEDSRTLLNASRSLEVSYLAMTPLIPQSKDENSDD
                YTTFDDVGSLWTTLSTFVALFILTLLYSGIVTFIKVK"
        intron  404..>495
                /gene="IGHD"
                /note="G00-120-084"
                /number=1
BASE COUNT     114 a    179 c    120 g    82 t
ORIGIN      182 bp upstream of SphI site; chromosome 14q32.3.
        1 tttccctgcc tcccgtcacc ctgccgccag ggcctctgcc ctgccctgcc ccctgtcctc
       61 aggttccaag cctcagactc ccactgtgtc tgtcttccag cacccaccaa ggctccggat
      121 gtgttcccca tcatatccagg gtgcagacac ccaaaggata acagccctgt ggtcctggca
      181 tgcttgataa ctgggtacca cccaacgtcc gtgactgtca cctggtacat ggggacacag
      241 agccagcccc agagaacctt ccctgagata caaagacggg acagctacta catgacaagc
      301 agccagctct ccacccccct ccagcagtgg cgccaaggcg agtacaaatg cgtggtccag
      361 cacaccgcca gcaagagtaa gaaggagatc ttccgctggc caggtaggtc gcaccggaga
      421 tcacccagaa gggcccccca ggacccccag caccttccac tcagggcctg accacaaaga
      481 cagaagcaag ggctg
```
[SEQUENCE ID NO:42]

VIII. HUMAN IG EPSILON CHAIN C REGION - HOMO SAPIENS (HUMAN).

AMINO ACID SEQUENCE
>sp|P01854|EPC_HUMAN IG EPSILON CHAIN C REGION - Homo sapiens (Human).

```
         10          20          30          40          50          60
          |           |           |           |           |           |
ASTQSPSVFP  LTRCCKNIPS  NATSVTLGCL  ATGYFPEPVM  VTWDTGSLNG  TTMTLPATTL 70          80          90         100         110         120
          |           |           |           |           |           |
TLSGHYATIS  LLTVSGAWAK  QMFTCRVAHT  PSSTDWVDNK  TFSVCSRDFT  PPTVKILQSS 130         140         150         160         170         180
          |           |           |           |           |           |
CDGGGHFPPT  IQLLCLVSGY  TPGTINITWL  EDGQVMDVDL  STASTTQEGE  LASTQSELTL 190         200         210         220         230         240
          |           |           |           |           |           |
SQKHWLSDRT  YTCQVTYQGH  TFEDSTKKCA  DSNPRGVSAY  LSRPSPFDLF  IRKSPTITCL 250         260         270         280         290         300
          |           |           |           |           |           |
VVDLAPSKGT  VNLTWSRASG  KPVNHSTRKE  EKQRNGTLTV  TSTLPVGTRD  WIEGETYQCR
```

FIGURE 7FF

```
         310        320        330        340        350        360
          |          |          |          |          |          |
VTHPHLPRAL MRSTTKTSGP RAAPEVYAFA TPEWPGSRDK RTLACLIQNF MPEDISVQWL 370        380        390        400        410        420
          |          |          |          |          |          |
HNEVQLPDAR HSTTQPRKTK GSGFFVFSRL EVTRAEWEQK DEFICRAVHE AASPSQTVQR

428
          |
AVSVNPGK
```

[SEQUENCE ID NO:49]

CODING SEQUENCE

```
atggactgga cctggatcct cttcttggtg gcagcagcca cgcgagtcca ctcccagacg    60
cagttggtgc agtctggggc tgaggtgagg aagcctgggg catcagtgag ggtctcctgc   120
aaggcttctg gatacacctt catcgactcc tatatccact ggatacgaca ggcccctggg   180
cacgggcttg agtgggtggg atggatcaac cctaacagtg gtggcacaaa ctatgctccg   240
agatttcagg gcagggtcac catgaccaga gacgcgtcct tcagtacagc ctacatggac   300
ctgagaagtc tgagatctga cgactcggcc gtgttttact gtgcgaaaag tgaccctttt   360
tggagtgatt attataactt tgactactcg tacactttgg acgtctgggg ccaagggacc   420
acggtcaccg tctcctcagc ctccacacag agcccatccg tcttcccctt gaccegctgc   480
tgcaaaaaca ttccctccaa tgccacctcc gtgactctgg gctgcctggc cacgggctac   540
ttcccggagc cggtgatggt gacctgggac acaggctccc tcaacgggac aactatgacc   600
ttaccagcca ccacccctcac gctctctggt cactatgcca ccatcagctt gctgaccgtc   660
tcgggtgcgt gggccaagca gatgttcacc tgccgtgtgg cacacactcc atcgtccaca   720
gactgggtcg acaacaaaac cttcagcgtc tgctccaggg actteacccc gccaccgtg   780
aagatcttac agtcgtcctg cgacggcggc gggcacttcc ccccgaccat ccagctcctg   840
tgcctcgtct ctgggtacac cccagggact atcaacatca cctggctgga ggacgggcag   900
gtcatggacg tggacttgtc caccgcctct accacgcagg agggtgagct ggcctccaca   960
caaagcgagc tcaccctcag ccagaagcac tggctgtcag accgcaccta cacctgccag  1020
gtcacctatc aaggtcacac ctttgaggac agcaccaaga agtgtgcaga ttccaacccg  1080
agaggggtga gcgcctacct aagccggccc agcccgttcg acctgttcat ccgcaagtcg  1140
cccacgatca cctgtctggt ggtggacctg gcacccagca aggggaccgt gaacctgacc  1200
tggtcccggg ccagtgggaa gcctgtgaac cactccacca gaaaggagga gaagcagcgc  1260
aatggcacgt taaccgtcac gtccacccctg ccggtgggca cccgagactg gatcgagggg  1320
gagacctacc agtgcagggt gacccacccc cacctgccca gggccctcat gcggtccacg  1380
accaagacca gcggcccgcg tgctgcccccg gaagtccatg cgtttgcgac gccggagtgg  1440
ccggggagcc gggacaagcg caccctcgcc tgcctgatcc agaacttcat gcctgaggac  1500
atctcggtgc agtggctgca caacgaggtg cagctcccgg acgcccggca cagcacgacg  1560
cagccccgca agaccaaggg ctccggcttc ttcgtcttca gccgcctgga ggtgaccagg  1620
gccgaatggg agcagaaaga tgagttcatc tgccgtgcag tccatgaggc agcgagcccc  1680
tcacagaccg tccagcgagc ggtgtctgta aatcccggta aatga                  1725
```

[SEQUENCE ID NO:44]

GenBank

```
L00022. Human Ig active he...
LOCUS       HUMIGHAE2    1920 bp    DNA             PRI       22-DEC-1994
DEFINITION  Human Ig active heavy chain epsilon-1 gene, constant region.
ACCESSION   L00022 J00227 V00555
VERSION     L00022.1  GI:185035
KEYWORDS    C-region; epsilon-immunoglobulin; immunoglobulin heavy chain;
            processed gene.
SOURCE      Human myeloma cell line 266B1 DNA and cDNA to mRNA, clones
            H-Ig-epsilon-11, lambda-epsilon-1.2, pJJ71, pGET2 and K85/A12 (see
            comment).
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (bases 1 to 1920)
  AUTHORS   Flanagan,J.G. and Rabbitts,T.H.
  TITLE     The sequence of a human immunoglobulin epsilon heavy chain constant
            region gene, and evidence for three non-allelic genes
  JOURNAL   EMBO J. 1 (5), 655-660 (1982)
```

FIGURE 7GG

```
MEDLINE      84236029
REFERENCE    2  (bases 528 to 736; 1044 to 1138)
  AUTHORS    Nishida,Y., Miki,T., Hisajima,H. and Honjo,T.
  TITLE      Cloning of human immunoglobulin epsilon chain genes: evidence for
             multiple C epsilon genes
  JOURNAL    Proc. Natl. Acad. Sci. U.S.A. 79 (12), 3833-3837 (1982)
  MEDLINE    82247945
REFERENCE    3  (bases 1 to 1920)
  AUTHORS    Kenten,J.H., Molgaard,H.V., Houghton,M., Derbyshire,R.B., Viney,J.,
             Bell,L.O. and Gould,H.J.
  TITLE      Cloning and sequence determination of the gene for the human
             immunoglobulin epsilon chain expressed in a myeloma cell line
  JOURNAL    Proc. Natl. Acad. Sci. U.S.A. 79 (21), 6661-6665 (1982)
  MEDLINE    83065234
REFERENCE    4  (bases 98 to 1884)
  AUTHORS    Seno,M., Kurokawa,T., Ono,Y., Onda,H., Sasada,R., Igarashi,K.,
             Kikuchi,M., Sugino,Y., Nishida,Y. and Honjo,T.
  TITLE      Molecular cloning and nucleotide sequencing of human immunoglobulin
             epsilon chain cDNA
  JOURNAL    Nucleic Acids Res. 11 (3), 719-726 (1983)
  MEDLINE    83168897
REFERENCE    5  (bases 691 to 807; 1571 to 1818; 1860 to 1885)
  AUTHORS    Liu,F.T., Albrandt,K.A., Bry,C.G. and Ishizaka,T.
  TITLE      Expression of a biologically active fragment of human IgE epsilon
             chain in Escherichia coli
  JOURNAL    Proc. Natl. Acad. Sci. U.S.A. 81 (17), 5369-5373 (1984)
  MEDLINE    84298140
  COMMENT    [2] and [1] report the isolation of two other epsilon genes,
             epsilon-2 and epsilon-3. The authors in [2] claim that epsilon-3 is
             a pseudogene. Compared in [4] with the germline C-region sequence
             by Max, et al (Cell 29, 691-699 (1982)), and there are three
             nucleotide differences. The deduced amino acid sequence in [4]
             differs somewhat from the published C-region sequence. [5] produced
             expression of IgE in E.coli by insertion into expression vector
             pUC7.
             Complete source information:
             Human myeloma cell line 266B1 DNA [2],[1],[5] and cDNA to mRNA [3],
             [4], clones H-Ig-epsilon-11 [2], lambda-epsilon-1.2 [1], pJJ71 [3],
             pGET2 [4] and K85/A12 [5].
FEATURES             Location/Qualifiers
     source          1..1920
                     /organism="Homo sapiens"
                     /db_xref="taxon:9606"
                     /map="14q32.33"
     prim_transcript <1..1886
                     /note="epsilon-1 mRNA"
     intron          <1..97
                     /gene="IGHE"
                     /note="epsilon-1 intron J-C"
     exon            98..406
                     /gene="IGHE"
                     /note="Ig heavy chain epsilon-1 (CH1 domain); G00-119-335"
     intron          407..613
                     /gene="IGHE"
                     /note="epsilon-1 intron A"
     exon            614..934
                     /gene="IGHE"
                     /note="Ig heavy chain epsilon-1 (CH2 domain)"
     conflict        735
                     /gene="IGHE"
                     /citation=[3]
                     /replace=""
     intron          935..1020
                     /gene="IGHE"
                     /note="epsilon-1 intron B"
     exon            1021..1344
```

FIGURE 7HH

```
              /gene="IGHE"
              /note="Ig heavy chain epsilon-1 (CH3 domain)"
conflict      1124
              /gene="IGHE"
              /citation=(3)
              /replace=""
conflict      1337
              /gene="IGHE"
              /citation=(3)
              /replace=""
intron        1345..1427
              /gene="IGHE"
              /note="epsilon-1 intron C"
exon          1428..>1759
              /note="Ig heavy chain epsilon-1 (CH4 domain)"
conflict      1444..1445
              /gene="IGHE"
              /citation=(3)
              /replace=""
conflict      1612
              /gene="IGHE"
              /citation=(3)
              /replace=""
conflict      1785
              /citation=(3)
              /replace=""
gene          join(L00021.1:57..495,1..1758)
              /gene="IGHE"
CDS           join(L00021.1:57..495,98..406,614..934,1021..1344,
              1428..1759)
              /partial
              /gene="IGHE"
              /note="Ig heavy chain epsilon-1 (V-D-J region)"
              /codon_start=1
              /protein_id="AAB59424.1"
              /db_xref="GI:386807"
              /db_xref="GDB:G00-119-335"
              /translation="MDWTWILFLVAAATRVHSQTQLVQSGAEVRKPGASVRVSCKASG
              YTFIDSYIHWIRQAPGHGLEWVGWINPNSGGTNYAPRFQGRVTMTRDASFSTAYMDLR
              SLRSDDSAVFYCAKSDPFWSDYYNFDYSYTLDVWGQGTTVTVSSASTQSPSVFPLTRC
              CKNIPSNATSVTLGCLATGYFPEPVMVTWDTGSLNGTTMTLPATTLTLSGHYATISLL
              TVSGAWAKQMFTCRVAHTPSSTDWVDNKTFSVCSRDFTPPTVKILQSSCDGGGHFPPT
              IQLLCLVSGYTPGTINITWLEDGQVMDVDLSTASTTQEGELASTQSELTLSQKHWLSD
              RTYTCQVTYQGHTFEDSTKKCADSNPRGVSAYLSRPSPFDLFIRKSPTITCLVVDLAP
              SKGTVNLTWSRASGKPVNHSTRKEEKQRNGTLTVTSTLPVGTRDWIEGETYQCRVTHP
              HLPRALMRSTTKTSGPRAAPEVYAFATPEWPGSRDKRTLACLIQNFMPEDISVQWLHN
              EVQLPDARHSTTQPRKTKGSGFFVFSRLEVTRAEWEQKDEFICRAVHEAASPSQTVQR
              AVSVNPGK"
                                                    (SEQUENCE ID NO:60)
BASE COUNT     387 a    658 c    576 g    299 t
ORIGIN    About 3 kb after ; 1 bp upstream of BamHI site.
    1 ggatccctgc cacggggtcc ccagctcccc catccaggcc cccaggctg atgggcgctg
   61 gcctgaggct ggcactgact agcttctgtc ctcacagcct ccacacagag cccatccgtc
  121 tcccccttga cccgctgctg caaaaacatt ccctccaatg ccacctccgt gactctgggc
  181 tgcctggcca cgggctactt cccggagccg gtgatggtga cctggacac aggctccctc
  241 aacgggacaa ctatgaccct accagccacc accctcacgc tctctggtca ctatgccacc
  301 atcagcttgc tgaccgtctc gggtgcgtgg gccaagcaga tgttcacctg ccgtgtggca
  361 cacactccat cgtccacaga ctgggtcgac aacaaaaccc tcagcggtaa gagagggcca
  421 agctcagaga ccacagttcc caggagtgcc aggctgaggg ctggcagagt gggcaggggt
  481 tgaggggggtg ggtgggctca aacgtgggaa cacccagcat gcctggggac ccgggccagg
  541 acgtggggc aagaggaggg cacacagagc tcagagaggc caacaacccc catgaccacc
  601 agctctcccc cagtcctgctc cagggaette accccgcccca ccgtgaagat cctacagtcg
  661 tcctgcgacg gcggcgggca cttccccccg accatccagc tcctgtgcct cgtctctggg
  721 tacaccccag ggactatcaa catcacctgg ctggaggacg ggcaggtcat ggacgtggac
  781 ttgtccaccg cctctaccac gcaggagggt gagctggcct ccacacaaag cgagctcacc
```

FIGURE 7II

```
 841 ctcagccaga agcactggct gtcagaccgc acctacacct gccaggtcac ctatcaaggt
 901 cacaccttty aggacagcac caagaagtgt gcaggtacgt ccccaccgc cctggtggcc
 961 gccacggagg ccagagaaga ggggcgggtg ggcctcacac agccctccgg tgtaccacag
1021 atcccaaccc gagaggggtg agcgcctacc taagccggcc cagcccgttc gacctgttca
1081 tccgcaagtc gcccacgatc acctgtctgg tggtggacct ggcacccagc aaggggaccg
1141 tgaacctgac ctggtcccgg gccagtggga agcctgtgaa ccactccacc agaaaggagg
1201 agaagcagcg caatggcacg ttaaccgtca cgtccaccct gccggtgggc acccgagact
1261 ggatcgaggg ggagacctac cagtgcaggg tgacccaccc ccacctgccc agggccctca
1321 tgcggtccac gaccaagacc agcggtgagc catgggcagg ccggggtcgt gggggaaggg
1381 agggagcgag tgagcggggc ccgggctgac cccacgtctg gccacaggcc cgcgtgctgc
1441 cccggaagtc tatgcgtttg cgacgccgga gtggccgggg agccgggaca agcgcaccct
1501 cgcctgcctg atccagaact tcatgcctga ggacatctcg gtgcagtggc tgcacaacga
1561 ggtgcagctc ccggacgccc ggcacagcac gacgcagccc cgcaagacca agggctccgg
1621 cctcttcgtc ttcagccgcc tggaggtgac cagggccgaa tgggagcaga aagatgagtt
1681 catctgccgt gcagtccatg aggcagcgag cccctcacag accgtccagc gagcggtgtc
1741 tgtaaatccc ggtaaatgac gtactcctgc ctccctcccc cccagggctc catccagctg
1801 tgcagtgggg aggactggcc agaccttctg tccactgttg caatgacccc aggaagctac
1861 ccccaataaa ctgtgcctgc tcagagcccc agtacaccca ttcttgggag cgggcagggc
```
[SEQUENCE ID NO:59]

IX. HUMAN IG MU CHAIN C REGION - HOMO SAPIENS (HUMAN).

AMINO ACID SEQUENCE
>sp|P01871|MUC_HUMAN IG MU CHAIN C REGION - Homo sapiens (Human).

```
         10         20         30         40         50         60
          |          |          |          |          |          |
GSASAPTLFP LVSCENSPSD TSSVAVGCLA QDFLPDSITF SWKYKNNSDI SSTRGFPSVL 70         80         90        100        110        120
          |          |          |          |          |          |
RGGKYAATSQ VLLPSKDVMQ GTDEHVVCKV QHPNGNKEKN VPLPVIAELP PKVSVFVPPR 130        140        150        160        170        180
          |          |          |          |          |          |
DGFFGNPRSK SKLICQATGF SPRQIQVSWL REGKQVGSGV TTDQVQAEAK ESGPTTYKVT 190        200        210        220        230        240
          |          |          |          |          |          |
STLTIKESDW LSQSMFTCRV DHRGLTFQQN ASSMCVPDQD TAIRVFAIPP SFASIFLTKS 250        260        270        280        290        300
          |          |          |          |          |          |
TKLTCLVTDL TTYDSVTISW TRQNGEAVKT HTNISESHPN ATFSAVGEAS ICEDDWNSGE 310        320        330        340        350        360
          |          |          |          |          |          |
RFTCTVTHTD LPSPLKQTIS RPKGVALHRP DVYLLPPARE QLNLRESATI TCLVTGFSPA 370        380        390        400        410        420
          |          |          |          |          |          |
DVFVQWMQRG QPLSPEKYVT SAPMPEPQAP GRYFAHSILT VSEEEWNTGE TYTCVVAHEA 430        440        450
          |          |          |
LPNRVTERTV DKSTGKPTLY NVSLVMSDTA GTCY
```
[SEQUENCE ID NO:47]

CODING SEQUENCE
```
atggactgga cctggaggtt cctctttgtg gtggcagcag ctacaggtgt ccagccccag   60
gtgcagctgg tgcagtctgg ggctgaggtg aagaagcctg ggtcctcggt gaaggtctcc  120
tgcaaggctt ctggaggcac cttcagcagc tatgctatca gctgggtgcg acaggcccct  180
ggacaagggc ttgagtggat gggagggatc atccctatcc ttggtacagc aaactacgca  240
cagaagttcc agggcagagt cacgattacc gcggacgaat ccacgagcac agcctacatg  300
```

FIGURE 7JJ

```
gagctgagca gcctgagatc tgaggacacg gccgtgtatt actgtgcgaa aaccgggatc      360
ctggggccgt atagcagtgg ctggtacccg aactcggact actactacta cggtatggac      420
gtctggggcc aagggaccac ggtcaccgtc tcctcaggga gtgcatccgc cccaaccctt      480
ttccccctcg tctcctgtga gaattccccg tcggatacga gcagcgtggc cgtcggctgc      540
ctcgcacagg acttcctctcc cgactccatc actttctcct ggaaatacaa gaacaactct     600
gacatcagca gcacccgggg cttcccatca gtcctgagag ggggcaagta cgcagccacc      660
tcacaggtgc tgctgccttc caaggacgtc atgcagggca cagacgaaca cgtggtgtgc      720
aaagtccagc accccaacgg caacaaagaa aagaacgtgc ctccttccagt gattgctgag     780
ctgcctccca aagtgagcgt cttcgtccca ccccgcgacg gcttcttcgg caaccccgc      840
agcaagtcca agctcatctg ccaggccacg ggtttcagtc cccggcagat tcaggtgtcc      900
tggctgcgcg aggggaagca ggtggggtct ggcgtcacca cggaccaggt gcaggctgag      960
gccaaagagt ctgggcccac gacctacaag gtgaccagca cactgaccat caaagagagc     1020
gactggctca gccagagcat gttcacctgc cgcgtggatc acagggcct gaccttccag      1080
cagaatgcgt cctccatgtg tgtccccgat caagacacag ccatccgggt cttcgccatc     1140
ccccatcct ttgccagcat cttcctcacc aagtccacca agttgacctg ccctggtcaca     1200
gacctgacca cctatgacag cgtgaccatc tcctggaccc gccagaatgg cgaagctgtg     1260
aaaacccaca ccaacatctc cgagagccac cccaatgcca cttccagcgc cgtgggtgag     1320
gccagcatct gcgaggatga ctggaattcc ggggagaggt tcacgtgcac cgtgacccac     1380
acagacctgc cctcgccact gaagcagacc atctcccggc ccaaggggt ggccctgcac     1440
aggcccgatg tctacttgct gccaccagcc cgggagcagc tgaacctgcg ggagtcggcc     1500
accatcacgt gcctggtgac gggcttctct cccgcggacg tcttcgtgca gtggatgcag    1560
aggggcagc ccttgtcccc ggagaagtat gtgaccagcg ccccaatgcc tgagcccag     1620
gcccaggcc ggtacttgc ccacagcatc ctgaccgtgt ccgaagagga atggaacacg      1680
ggggagacct acacctgcgt ggtggcccat gaggccctgc ccaacagggt caccgagagg    1740
accgtggaca agtccaccga gggggagggtg agcgccgacg aggagggctt tgagaacctg    1800
tgggccaccg cctccacctt catcgtcctc ttcctcctga gcctcttcta cagtaccacc    1860
gtcaccttgt tcaaggtgaa atga                                          1884
                                          [SEQUENCE ID NO:46]
```

```
GenBank
X17115. Human mRNA for IgM
LOCUS       HSIGM201     2213 bp   mRNA            PRI     03-APR-1995
DEFINITION  Human mRNA for IgM heavy chain complete sequence.
ACCESSION   X17115
VERSION     X17115.1  GI:33450
KEYWORDS    Ig heavy chain; IgM gene; IgM heavy chain; transmembrane protein.
SOURCE      human.
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (bases 1 to 2213)
  AUTHORS   Friedlander,R.M.
  TITLE     Direct Submission
  JOURNAL   Submitted (03-NOV-1989) Friedlander R. M., Harvard Medical School,
            Howard Hughes Medical Institute, Department of Genetics, 25
            Shattuck St, Boston, MA 02115, USA
REFERENCE   2  (bases 1 to 2213)
  AUTHORS   Friedlander,R.M., Nussenzweig,M.C. and Leder,P.
  TITLE     Complete nucleotide sequence of the membrane form of the human IgM
            heavy chain
  JOURNAL   Nucleic Acids Res. 18 (14), 4278 (1990)
  MEDLINE   90332450
REFERENCE   3  (bases 1 to 2213)
  AUTHORS   Kristensen,T., Lopez,R. and Prydz,H.
  TITLE     An estimate of the sequencing error frequency in the DNA sequence
            databases
  JOURNAL   DNA Seq. 2 (6), 343-346 (1992)
  MEDLINE   93075997
  REMARK    Erratum:[(published erratum appears in DNA Seq 1993;3(5):337)]
COMMENT     For genomic sequence see <K01306>,<X14939> and
            <X14940>. The author reports various conflicts with these
            sequences. Data kindly reviewed (30-MAY-1990) by Friedlander R.M.
FEATURES             Location/Qualifiers
     source          1..2213
                     /organism="Homo sapiens"
                     /db_xref="taxon:9606"
```

FIGURE 7KK

```
                    /clone="201-203"
                    /cell_line="lymphoma 201"
                    /cell_type="B"
                    /tissue_type="lymphoid"
     misc_feature   1..39
                    /note="putative VECTOR sequence Bluescript SK+"
                    /citation=[3]
     CDS            73..1956
                    /note="precursor (AA -15 to 612)"
                    /codon_start=1
                    /protein_id="CAA34971.1"
                    /db_xref="GI:33451"
                    /db_xref="SWISS-PROT:P01871"
                    /db_xref="SWISS-PROT:P20769"
                    /translation="MDWTWRFLFVVAAATGVQSQVQLVQSGAEVKKPGSSVKVSCKAS
                    GGTFSSYAISWVRQAPGQGLEWMGGIIPIFGTANYAQKFQGRVTITADESTSTAYMEL
                    SSLRSEDTAVYYCARTGILGPYSSGWYPNSDYYYYGMDVWGQGTTVTVSSGSASAPTL
                    FPLVSCENSPSDTSSVAVGCLAQDFLPDSITFSWKYKNNSDISSTRGFPSVLRGGKYA
                    ATSQVLLPSKDVMQGTDEHVVCKVQHPNGNKEKNVPLPVIAELPPKVSVFVPPRDGFF
                    GNPRSKSKLICQATGFSPRQIQVSWLREGKQVGSGVTTDQVQAEAKESGPTTYKVTST
                    LTIKESDWLSQSMFTCRVDHRGLTFQQNASSMCVPDQDTAIRVFAIPPSFASIFLTKS
                    TKLTCLVTDLTTYDSVTISWTRQNGEAVKTHTNISESHPNATFSAVGEASICEDDWNS
                    GERFTCTVTHTDLPSPLKQTISRPKGVALHRPDVYLLPPAREQLNLRESATITCLVTG
                    FSPADVFVQWMQRGQPLSPEKYVTSAPMPEPQAPGRYFAHSILTVSEEEWNTGETYTC
                    VVAHEALPNRVTERTVDKSTEGEVSADEEGFENLWATASTFIVLFLLSLFYSTTVTLF
                    KVK"
                                              [SEQUENCE ID NO:62]
     sig_peptide    73..117
     mat_peptide    118..1953
                    /product="IgM heavy chain (AA 1 to 612)"
     polyA_site     2213
                    /note="polyA site"
BASE COUNT      462 a    708 c    629 g    414 t
ORIGIN
        1 gctctagaac tagtggatcc cccgggctgc aggaattctc taaagaagcc cctgggagca
       61 cagctcatca ccatggactg gacctggagg ttcctctttg tggtggcagc agctacaggt
      121 gtccagtccc aggtgcagct ggtgcagtct ggggctgagg tgaagaagcc tgggtcctcg
      181 gtgaaggtct cctgcaaggc ttctggaggc acccttcagca gctatgctat cagctgggtg
      241 cgacaggccc ctggacaagg gcttgagtgg atgggaggga tcatccctat ctttggtaca
      301 gcaaactacg cacagaagtt ccagggcaga gtcacgatta ccgcggacga atccacgagc
      361 acagcctaca tggagctgag cagcctgaga tctgaggaca cggccgtgta ttactgtgcg
      421 aaaaccggga tcctggggcc gtatagcagt ggctggtacc cgaactcgga ctactactac
      481 tacggtatgg acgtctgggg ccaagggacc acggtcaccg tctcctcagg gagtgcatcc
      541 gccccaaccc ttttcccct cgtctcctgt gagaattccc cgtcggatac gagcagcgtg
      601 gccgtcggct gcctcgcaca ggacttcctt cccgactcca tcacttttctc ctggaaatac
      661 aagaacaact ctgacatcag cagcacccgg ggctcccat cagtcctgag aggggggcaag
      721 tacgcagcca cctcacaggt gctgctgcct tccaaggacg tcatgcaggg cacagacgaa
      781 cacgtggtgt gcaaagtcca gcaccccaac ggcaacaaag aaaagaacgt gcctcttcca
      841 gtgattgctg agctgcctcc caaagtgagc gtcttcgtcc cacccgcga cggcttcttc
      901 ggcaaccccc gcagcaagtc caagctcatc tgccaggcca cgggtttcag tcccgcag
      961 attcaggtgt cctggctgcg cgaggggaag caggtggggt ctggcgtcac cacggaccag
     1021 gtgcaggctg aggccaaaga gtctgggccc acgacctaca aggtgaccag cacactgacc
     1081 atcaaagaga gcgactggct cagccagagc atgttcacct gccgcgtgga tcacaggggc
     1141 ctgaccttcc agcagaatgc gtcctccatg tgtgtccccg atcaagacac agccatccgg
     1201 gtcttcgcca tcccccatc ctttgccagc atcttcctca ccaagtccac caagttgacc
     1261 tgcctggtca cagacctgac cacctatgac agcgtgacca tctcctggac ccgccagaat
     1321 ggcgaagctg tgaaaaccca caccaacatc tccgagagcc accccaatgc cactttcagc
     1381 gccgtgggtg aggccagcat ctgcgaggat gactgaatc ccggggagag gtcacgtgc
     1441 accgtgaccc acacagacct gccctcgcca ctgaagcaga ccatctcccg gcccaagggg
     1501 gtggccctgc acaggcccga tgtctacttg ctgccaccag cccgggagca gctgaacctg
     1561 cgggagtcgg ccaccatcac gtgcctggtg acgggcttct ctcccgcgga cgtcttcgtg
     1621 cagtggatgc agaggggggca gcccttgtcc ccggagaagt atgtgaccag cgccccaatg
     1681 cctgagcccc aggcccccagg ccggtacttc gcccacagca tcctgaccgt gtccgaagag
     1741 gaatggaaca cgggggagac ctacacctgc gtggtggccc atgaggccct gccaacagg
     1801 gtcaccgaga ggaccgtgga caagtccacc gagggggagg tgagcgccga cgaggggc
     1861 tttgagaacc tgtgggccac cgcctccacc ttcatcgtcc tcttcctcct gagcctcttc
```

FIGURE 7LL

```
1921 tacagtacca ccgtcacctt gttcaaggtg aaatgatccc aacagaagaa catcggagac
1981 cagagagagg aactcaaagg ggcgctgcct ccgggtctgg ggtcctggcc tgcgtggcct
2041 gttggcacgt gtttctcttc ccgcccggcc tccagttgtg tgctctcaca caggcttcct
2101 tctcgaccgg caggggctgg ctggcttgca ggccacgagg tgggctctac cccacactgc
2161 tttgctgtgt atacgcttgt tgccctgaaa taaatatgca catttatcc atg
```
(SEQUENCE ID NO:61)

[DNA sequence figure with rows numbered 3718 through 6278, showing nucleotide sequences. An NdeI restriction site is labeled within the sequence.]

[SEQUENCE ID NO:9]

FIGURE 8B

BEAN LEGUMIN SIGNAL PEPTIDE

MetSerLysProPheLeuSerLeuLeuSerLeuLeuLeuPheThrSerThrCysLeuAla

[SEQUENCE ID NO:10]

FIGURE 8C

NUCLEOTIDE AND AMINO ACID SEQUENCE OF PROTEIN CODING REGION OF pSHuJ

```
1141       AGGATCTATCGATTCCCGGGTACC ATG GAG AAC CAT CTT CTT TGG GGA GTC CTG GCG
                                    met glu asn his leu leu phe trp gly val leu ala
1201/13
GTT TTT ATT AAG GCT GTT CAT GTG AAA GCC CAA GAT GAA AGG ATT GTT CTT GAC
val phe ile lys ala val his val lys ala gln asp glu arg ile val leu asp
1261/33
AAC AAA TGT AAG TGT GCC CGG ATT ACT TCC AGG ATC CCT TCT GAA GAT CCT AAT
asn lys cys lys cys ala arg ile thr ser arg ile pro ser glu asp pro asn
1321/53
GAG GAC ATT GTC GAG AGA AAC ATC CGA ATT ATT GTT CCT CTG AAC AAC AGG GAG AAT ATC
glu asp ile val glu arg asn ile arg ile ile val pro leu asn asn arg glu asn ile
1381/73
TCT GAT CCC ACC TCA TTG AGA ACC CCA TTT GTG TAC CAT TTG GAC TCT TGT AAA
ser asp pro thr ser leu arg thr pro phe val tyr his leu asp ser cys lys
1441/93
AAA TGT GAT CCT ACA GAA GTG GAG CTG GTG CTG GAT AAT CAG ATA GTT ACT GCT ACC CAG AGC AAT
lys cys asp pro thr glu val glu leu asp asn gln ile val thr ala thr gln ser asn
1501/113
ATC TGT GAT GAA GAC AGT GCT GTA CTC ACT TAT GAC TAC ACT TAT GAT GAG AAC AAG TGC TAC
ile cys asp glu asp ser ala val leu thr tyr asp tyr thr tyr asp glu asn lys cys tyr
1561/133
ACA GCT GTG GTC CCA GTC TAT GGT GGT GGA ACC AAA ATG GTG GAA ACA GCC TTA ACC
thr ala val val pro leu val tyr gly gly thr lys met val glu thr ala leu thr
1621/153
CCA GAT GCC TGC TAT CCT GAC TGA ATTC
pro asp ala cys tyr pro asp
```

[SEQUENCE ID NO:111]

FIGURE 8D

NUCLEOTIDE AND AMINO ACID SEQUENCE OF PROTEIN CODING REGION OF pSHuSC

```
1137
                                   GTCGATTCCCGGGTACC ATG GTG CTC TTC GTG CTC ACC TGC
                                                     met val leu phe val leu thr cys
1178/9
CTG CTG GCG GTC TTC CCA GCC ATC TCC ACG AAG AGT CCC ATA TTT GGT CCC GAG GAG GTG
leu leu ala val phe pro ala ile ser thr lys ser pro ile phe gly pro glu glu val
1238/29
AAT AGT GTG GAA GGT AAC TCA GTG TCC ATC ACG TGC TAC TAC CCA CCC ACC TCT GTC AAC
asn ser val glu gly asn ser val ser ile thr cys tyr tyr pro pro thr ser val asn
1298/49
CGG CAC ACC CGG AAG TAC TGG TGC CGG CAG GGA GCT AGA GGT GGC TGC ATA ACC CTC ATC
arg his thr arg lys tyr trp cys arg gln gly ala arg gly gly cys ile thr leu ile
1358/69
TCC TCG GAG GGC TAC GTC TCC AGC AAA TAT GCA GGC AGG GCT AAC CTC ACC AAC TTC CCG
ser ser glu gly tyr val ser ser lys tyr ala gly arg ala asn leu thr asn phe pro
1418/89
GAG AAC GGC ACA TTT GTG GTG AAC ATT GCC CAG CTG AGC CAG GAT GAC TCC GGG CGC TAC
glu asn gly thr phe val val asn ile ala gln leu ser gln asp asp ser gly arg tyr
1478/109
AAG TGT GGC CTG GGC ATC AAT AGC CGA GGC CTG TCC TTT GAT GTC AGC CTG GAG GTC AGC
lys cys gly leu gly ile asn ser arg gly leu ser phe asp val ser leu glu val ser
1538/129
CAG GGT CCT GGG CTC CTA AAT GAC ACT AAA GTC TAC ACA GTG GAC CTG GGC AGA ACG GTG
gln gly pro gly leu leu asn asp thr lys val tyr thr val asp leu gly arg thr val
1598/149
ACC ATC AAC TGC CCT TTC AAG ACT GAG AAT GCT CAA AAG AGG AAG TCC TTG TAC AAG CAG
thr ile asn cys pro phe lys thr glu asn ala gln lys arg lys ser leu tyr lys gln
1658/169
ATA GGC CTG TAC CCT GTG CTG GTC ATC GAC TCC AGT GGT TAT GTG AAT CCC AAC TAT ACA
ile gly leu tyr pro val leu val ile asp ser ser gly tyr val asn pro asn tyr thr
1718/189
GGA AGA ATA CGC CTT GAT ATT CAG GGT ACT GGC CAG TTA CTG TTC AGC GTT GTC ATC AAC
gly arg ile arg leu asp ile gln gly thr gly gln leu leu phe ser val val ile asn
1778/209
CAA CTC AGG CTC AGC GAT GCT GGG CAG TAT CTC TGC CAG GCT GGG GAT GAT TCC AAT AGT
gln leu arg leu ser asp ala gly gln tyr leu cys gln ala gly asp asp ser asn ser
1838/229
AAT AAG AAG AAT GCT GAC CTC CAA GTG CTA AAG CCC GAG CCC GAG CTG GTT TAT GAA GAC
asn lys lys asn ala asp leu gln val leu lys pro glu pro glu leu val tyr glu asp
1898/249
CTG AGG GGC TCA GTG ACC TTC CAC TGT GCC CTG GGC CCT GAG GTG GCA AAC GTG GCC AAA
leu arg gly ser val thr phe his cys ala leu gly pro glu val ala asn val ala lys
1958/269
TTT CTG TGC CGA CAG AGC AGT GGG GAA AAC TGT GAC GTG GTC AAC ACC CTG GGG AAG
phe leu cys arg gln ser ser gly glu asn cys asp val val asn thr leu gly lys
2018/289
AGG GCC CCA GCC TTT GAG GGC AGG ATC CTC CTC AAC CCC CAG GAC AAG GAT GGC TCA TTC
arg ala pro ala phe glu gly arg ile leu leu asn pro gln asp lys asp gly ser phe
2078/309
AGT GTG GTG ATC ACA GGC CTG AGG AAG GAG GAT GCA GGG CGC TAC CTG TGT GGA GCC CAT
ser val val ile thr gly leu arg lys glu asp ala gly arg tyr leu cys gly ala his
2138/329
TCG GAT GGT CAG CTG CAG GAA GGC TCG CCT ATC CAG GCC TGG CAA CTC TTC GTC AAT GAG
ser asp gly gln leu gln glu gly ser pro ile gln ala trp gln leu phe val asn glu
2198/349
GAG TCC ACG ATT CCC CGC AGC CCC ACT GTG GTG AAG GGG GTG GCA GGA AGC TCT GTG GCC
glu ser thr ile pro arg ser pro thr val val lys gly val ala gly ser ser val ala
```

FIGURE 8D (Cont.)

```
2258/369
GTG CTC TGC CCC TAC AAC CGT AAG GAA AGC AAA AGC ATC AAG TAC TGG TGT CTC TGG GAA
val leu cys pro tyr asn arg lys glu ser lys ser ile lys tyr trp cys leu trp glu
2318/389
GGG GCC CAG AAT GGC CGC TGC CCC CTG CTG GTG GAC AGC GAG GGG TGG GTT AAG GCC CAG
gly ala gln asn gly arg cys pro leu leu val asp ser glu gly trp val lys ala gln
2378/409
TAC GAG GGC CGC CTC TCC CTG CTG GAG GAG CCA GGC AAC GGC ACC TTC ACT GTC ATC CTC
tyr glu gly arg leu ser leu leu glu glu pro gly asn gly thr phe thr val ile leu
2438/429
AAC CAG CTC ACC AGC CGG GAC GCC GGC TTC TAC TGG TGT CTG ACC AAC GGC GAT ACT CTC
asn gln leu thr ser arg asp ala gly phe tyr trp cys leu thr asn gly asp thr leu
2498/449
TGG AGG ACC ACC GTG GAG ATC AAG ATT ATC GAA GGA GAA CCA AAC CTC AAG GTT CCC GGG
trp arg thr thr val glu ile lys ile ile glu gly glu pro asn leu lys val pro gly
2558/469
AAT GTC ACG GCT GTG CTG GGA GAG ACT CTC AAG GTC CCC TGT CAC TTT CCA TGC AAA TTC
asn val thr ala val leu gly glu thr leu lys val pro cys his phe pro cys lys phe
2618/489
TCC TCG TAC GAG AAA TAC TGG TGC AAG TGG AAT AAC ACG GGC TGC CAG GCC CTG CCC AGC
ser ser tyr glu lys tyr trp cys lys trp asn asn thr gly cys gln ala leu pro ser
2678/509
CAA GAC GAA GGC CCC AGC AAG GCC TTC GTG AAC TGT GAC GAG AAC AGC CGG CTT GTC TCC
gln asp glu gly pro ser lys ala phe val asn cys asp glu asn ser arg leu val ser
2738/529
CTG ACC CTG AAC CTG GTG ACC AGG GCT GAT GAG GGC TGG TAC TGG TGT GGA GTG AAG CAG
leu thr leu asn leu val thr arg ala asp glu gly trp tyr trp cys gly val lys gln
2798/549
GGC CAC TTC TAT GGA GAG ACT GCA GCC GTC TAT GTG GCA GTT GAA GAG AGG AAG GCA GCG
gly his phe tyr gly glu thr ala ala val tyr val ala val glu glu arg lys ala ala
2858/569
GGG TCC CGC GAT GTC AGC CTA GCG AAG GCA GAC GCT GCT CCT GAT GAG AAG GTG CTA GAC
gly ser arg asp val ser leu ala lys ala asp ala ala pro asp glu lys val leu asp
2918/589
TCT GGT TTT CGG GAG ATT GAG AAC AAA GCC ATT CAG GAT CCC AGG CTT TTT GCA GAG TGA
ser gly phe arg glu ile glu asn lys ala ile gln asp pro arg leu phe ala glu
2978
ATTC
```

[SEQUENCE ID NO:12]

FIGURE 8E pBMSP-1

```
   1 CTGGCCGGCGCCAGATCTGGGGAACCTGTGGTTGGCATGCACATACAAATGGACGAACGGATAAACCTTTTCACGCCCTT
                                                                              PmeI
  81 TTAAATATCCGATTATTCTTAATAAACCTCTTTTTCTCTTAGTTTAAAAGCGGATAATATCCTGTCAAACACTGATAGTTT
 161 AAACTGAAGGCGGGAAACCACAATCTGATCATGAGCGGAGAATTAAGGGAGTCACGTTATGCACCCCCCGATGACGCGG
 241 GACAAGCCGTTTACGTTGAACTGACAGAACCCACAATCTTATCCTAGTTGCGCGCATCTAGTTTGTTTCTATCGGTATTAATG
 321 CTAGTAACCATAGATGACACCCCGCGGTATCTATTTCAATCATAATAACCATTCATGCATGCATCGTTAAGATTATTACATGCTTAAC
 401 TATAATTCGGGGACTCTAATCATAATGATAATCGCAAGACCGGCAACAGGATTCAATCTTAAGAAACTTTATTGCCAAATGT
 481 GTAATTCAACAGAAATTATATGATAATAATATTTAGAATATAATATATTCTATAGCTATTTGGTGTATCA
                                                                              XmaI
                                                                              SmaI
 561 TTGAACGATCGGGGAAATTCAGCTCCACGCGGTGGCGGCCGCCTCTAGAACTAGTGGATCCCCCGGGCTGCAGGAATTC
        SacI     NotI
              SalI XhoI                                                        KpnI
 641 GATCAGATCTGATCAAGCTTATCGATACCGTGCGATCCTGGACCTCGAGGGGGGCCCGGTACCCCCCTAGAGTCGATTTGGTGTATCGA
 721 GATTGGTTATGAAATTCAGATGCTAGTGATAATGTATTGGTAATTTGGGAAGATATAATAGGAAGCAAGGCTATTTATCCA
 801 TTTCTGAAAAGGCGAAATGGCAATGGCCTGCACCGCAGCGTCCGCGATCCGTTAATGCTCCGTCCCGGATCAAGAAAGTTGGAATAGAA
 881 TGACTAGCGAGCCTGGCGTGGAAATTCAGGCCCGGTTGCCATTCTATTCAAAAGTCCTAAAGAATCTCCCGTCGATCGAGAAGAGATCAATGTTGAGC
 961 ACAGAATACCCGCGAAATTCGGATACTTACGTCTCACGTCTTCGCGACACTTGAAAAATCTCCCCTGATCGAGAAGAGATCAATGTTGAGC
1041 ACTGACTCGATACTTACGTCGATTGACCAGTCGCGGATTCCCGGATCCTACAGGCTCTTAGCGTACTGCTCTTAGCGGTCTACAATATTACTCACCG
                                                                              BamHI
1121 TGCTTCAAAAGCTACAGGGATTGACCAGTCGCGGATTCCCGGATCCTACAGGCTCTTAGCGTACAATAATCAGCTACCAGTTT
1201 GTGCGATACCCCCATCGTAGGTGAAGCGCTTACGTACAATCCATCTTGAACCAGGCCCACACAGCCAATTTGTAGATGTTAACATCCAAC
1281 CCTCAAGGGTCCACCAAAACGTAAGCGCTTACGTACAATCCATCTTGAACCAGGCCCACACAGCCAATTTGTAGATGTTAACATCCAAC
                                                                              BamHI
1361 GTCGCTTACGTACAGGATCCTACAGGCGAAATTCGCTCTTAGCCGTACAATAATAATTACTCACCGGTGCATGCCCCCATCGTAG
1441 GTGAAGCGTGGAAATTGGAAATTTACTCCATCTTGAACCAGCCACACAGCTACCAGTTTCCTCAAGGGTTCCACCAAAAC
1521 GTAAGCGCTTACGTACAGGATCCTCATAGGAAAAGGCAATTTGTAGATGTTAACATCCAACGTCCTTCAGGGATCCTACA
1601 GGCCAAATTCGCTCTTAGCCGTACAATATTACTCACCGGTGCATGCCCCCATCGTAGGTGAAGGGTGGAAATTAATGAT
1681 CCATCTTGAGACCAACAGCCCACACAGTTACCAGTTTCCTCAAGGGTTCCAAAAACGTAAGCCTTACGTACATGGT
1761 CGATAAGCAAAGGCAATTTGTAGATGTTAACATCCAACGTCCGTCTTCAGGGATCCTCGAGCTTATCGCGATACGTCGAA
1841 TATAATTAATAATTATATTGTAAGAATATTATTATATATAAATATATATATAATATATATTCTATAGCCTTAGACTCCTCATCAATAGACTAGCTA
1921 AATTATTAATAATAATATTAATCATTTAGATATATAAATATATATATAATATATATTCTATAGCCTTAGACTCCTCATCAATAGAAGCTACGTA
```

```
4001 TCGACCCCAAAAAACTTGATTTGGGTGATGGTTCAGGTAGTGGGCCATCGCCCTGATAGACGGTTTTTCGCCCTTTGACG
4081 TTGGAGTCCACGTTCTTAATAGTGGACTCTTGTTCCAAACTGGAACACACTCAACCTATCTCGGGCTATTCTTTTGA
4161 TTTATAAGGATTTTGCCGATTTCGGAACCACCATCAAACAGGATTTCGCCTCGCCTGGGCAAACAGCGTGGACCGCTT
4241 GCTGCAACTCTCTCAGGGCCAGGCCAATCAGCTGTTGCCCGTCTTCACTGGTGAAAAGAAAACCACCCAG
4321 TACATTAAAACGTCCGCAATGTGTTATTAAGTTGTCTAAGCGTCAAATTGTTTACACCACAATATATCCTGCCACCAG
4401 CAGCCAACAGCTCCCCGACCGGCAGCTCGGCACAAAATCACCACTCGATACAGGCAGGCCCATCAG
```

[SEQUENCE ID NO:13]

FIGURE 8F pBMSP-1spJSC

```
   1 CTGATGGGCTGCCTGCCTTGTATCGAGTGGTGATTTTGTCCAGTGGTGTCGGGGAGCTGTTGGCTGGTGGTGGCAGGATA
  81 TATTGTGTGTAAACAAATTGACGCTTAGACGCTTAATAACACATTGCGACCCGGTAGAGAGTTGCAGCAAGCGGTCCACGCTG
 161 TTTTCACCAGTGAGACGGGCAACAGTGATTGCCCTTCACCGCCTGGCCTGGTTCGGAAATCGGCAAATCCTTATAAATCAAAGATAGCCC
 241 GTTTGCCCAGCAGGCGAAAATCCTGTCTTTGATGGTGGTCGAGACAGAGTCCACTATTAAAGAACGTGGACTCCAACGTCAAGCGTCAAGGCCAAA
 321 GAGATAGGGTTGAGTGTTGTTCCAGTTTGGAACAGAGTCCAAGTCATCACCCAAATCAAGTTTTTGGGTCGAAGTCCGTAAGCAC
 401 AACCCTTATCAGGCGATGGCCACTACGTAGAGCTTGACGGGAAAGCCGGCAACGTTGACGGCGAACGTGCGAAGAAAGGAAG
 481 TAAATCGGAACCCTAAAGGGAGCCCCGATTTAGAGCTTGACGGGTAACGCCCAGTCAGCGGTTGTAAACG
 561 AAAGCGAAGGAGGAGCGGCCCATTCAGCTCGCAACTGTTGGGAGGGCGATGGTGCGGGCCCTCTTCGCTATTACGCC
 641 AGCTTGGCGAAAGGGGGAATGTGCTGCAAGGCGATTAAGTTGGGTAACGCCCAGGGTTTCCCAGTCACGACGTTGTAAAACG
        Xmn I
 721 ACGGCCAGTGAATTAATTCCCATCTTGAAAGAATATTCAATAATCGAATGTTTATTGAATAAAATAACAAGTCAGTATTATAG
                                                          Xmn I
 801 TCCAAGCAAAAACATAAATTTATTGATGCGAAGTTTAAATTCAGAAATATTTCAATAACTGATTTATATCAGCTGGTACATT
                  ...PhePheGluAspPheArgSerHisProGlyLeuGluGlyLeuAlaIleAspArgThrAlaLeuAlaIleAspArgIleAsnTyrArg
 881 GCCGTAGATGAAAGACTGAGTGCGATTCAGAAAACGGCATGATCAATCCAGAAAACGGCCATTTCCACCATGATATTCGGCAAGCAGGCAT
     euValLeuPheArgAspAlaTrpGlnGlyLeuGlnLeuAlaIleAspArgThrAlaLeuAlaIleAspArgIleAsnTyrArg
 961 CTCAGATGTCCCCGCTCAGAGAACTCGTCAGAAGGCGATAGAAGGCGATGCGCTGCGAATCGGGAGCGGCGATACCGTAA
     ...PhePheGluAspPheArgSerHisProGlyLeuGluGlyLeuAlaIleAspArgIleAsnProLeuCysAlaAla
1041 AGCACGAGGAAGCCGGTCAGCCGATTCCGCCGCAAGCTCTTCAGCAATATCACGGTAGCCAACGCTATGTCCTGATAGCG
     euValLeuPheArgAspAlaTrpGlnGlyLeuGlnLeuAlaIleAspArgThrAlaLeuAlaIleAspArgIleAsnTyrArg
1121 GTCCCGCCACACCCAGCCGGCCACAGTCGATGAATCCAGAAAAGCGGCCATTTTCCACCATGATATTCGGCAAGCAGGCAT
     AspAlaValGlyLeuArgGlyCysAspIleAspAlaValLeuAlaAspSerGlnIleAspValLeuAlaGluMetArgThrArgAlaArgHisLysAla
1201 CGGCATGGGTCACAGACGCAGATCATCCGTCGGCAGCGGCGAATCATCGCCTGCGAACCAGTTGCCGGTCAGCGATACGGCATGG
     AspAlaValGlyLeuArgGlyCysAspIleAspAlaValLeuAlaAspSerGlnIleAspValLeuAlaGluMetArgThrArgAlaArgHisLysAla
1281 TGATCCTCTCGCTGAATGGGAACCTTGATCCTGAATCGGCGAATCAGCGAGTACAGAACCGGCTTCCAGCCGGACGAGTACCAGACTTCTCCG
     AspAlaValGlyLeuArgGlyCysAspIleAspAlaValLeuAlaAspSerGlnIleAspValLeuAlaGluMetArgThrArgAlaArgHisLysAla
1361 TTGGTGGTGCGAATCGACCAGGGTAGCCGCGGATCAAGCCTATGCAGCCCGCCATTGCATCGCGCCGCCCATCGATCACCATCGACTACCTTCTCGG
     GlnHisAspPheProCysThrAlaProAspLeuThrHisLeuArgArgMetAlaAspAlaMetIleSerValLysGluAl
```

```
5443 GCCGTCTATGTGGCAGTTGAAGAGAGAAGGCAGCGGGGTCCCCGATGTCAGCCTAGCG
     AlaValTyrValAlaValGluGluArgLysAlaAlaGlySerArgAspValSerLeuAla
5503 AAGGCAGACCGTCTCCTGATAGAGAAGTGCTAGACTCTGGTTTCGGAGATTGAGAAC
     LysAlaAspAlaAlaProAspGluLysValLeuAspSerGlyPheArgGluIleGluAsn
                              EcoRI
5563 AAAGCCATTCAGGATCCCAGGCTTTTTCAGAGTGAATTCCCGATCGTTCAAACATTTGGCAATAAAG
     LysAlaIleGlnAspProArgLeuPheAlaGlu
5631 TTTCTTAAGATGAATCGTTCTGCCGGTCTGGATGATTATCATATAATTCTGTGAATTAGCTTAAGCATGTAATAA
5711 TTAACATGTAATGCATGACGTTATTTATGAGATGGTTTTTATGATTAGAGTCCCGCAATTATACCATTTAATACCGATA
5791 GAAAACAAAATATAGCGCGCAAACTAGGATAAATTATCCGCGCGTCATCTATGTTACTAGATCGGGATCCGTCGA
             ClaI
5871 CGGTATCGATAAGGATCCCTGAAAGCGACTTGGATGTTAACATCTACAAATTGCCTTTTCTTATCGACCATGTACGTAA
5951 GCGCTTACGTTTTGGTGGACCCTTGAGGAAACTGGTAGCTGTTGTGGCCTTGGTCTCAAGATGGATCATTAATTTCC
6031 ACCTTCACCTACGATGGGGCATGCACCGGTGAGTATATATTGGCCTAAGACGAATTTGGCTGTAGGATCCCTG
6111 AAAGCGACGTTGGATGTTAACATCTACAAATTGCCTTTTCTTATCGACCATGATCATTAATTTCCACCTTTGGTGGAC
6191 CCTTGAGGAAACTGGTAGCTGTTGTGGGGCCTGTAAGAGACGAATTTGGCCTTACGTTTTCACCTTCACCTACGATGGGGG
6271 CATGCACCGGTGAGTATATTCTATCGACCATGATCATTAATTCCACCTTCACCTACGTTTTGGTGGACAAACTGGTAGCTG
6351 ATCTACAAATTGCCTTGGTCTCAAGATGGATCATTAATTTCCACCTTGGTGGACCATGGGGCATCGCACGGTGAGTAATAT
6431 TGTGGCCTGAGACGAATTTGGCCTAAGCGAATTGCCTTTATGGGTCAATCGTAGATCCGCAGCTCAACATTGAT
6511 TGTACGGCTAAGACGAATTTGGCCTGTCAATCGTAGATGCGCAAGACGTAAGTATCCGAGTCAGTTTTTATTTTCTACTAA
6591 CTCTTTCTGGAGGGAGATTTTCAAATCAGTGCGGCAAGACCGGCCTGAAATTCGCGGGTATTCGTTCGTTCTATTCCAACTTTT
6671 TTTGGTCGTTTTATTTCGCGTGTAGGATGTGCGTGCAACCGGGCTGACACGTCCGCCGAGTCAGTTGCAAAGTGTACCAAACAAC
6751 CTTGATCCCAGCCATTTACGACTTTTGATAGATACGTCCGGTGACGTCCGGTGACCGCCATTCGCCTTTCAGAAATGGATAAATAGCCTTGC
6831 GCTTTACAGCAAGAGCGGAATGGCCGGTAGACCAATTACCAATTACCATTACCATTAACCAATTCTCGATACACCAAATCGA
6911 TTCCTATTATATCTTTCCCAAATTACCAAATTACCAGCATCGAAATTTCATAACCAATTCGATACACCAAATCGA
         XbaI
6991 CTCTAGAGGATCTAACCATGGATCTAAACCTTTTTGTCTCTTTCATTGTTCATTGCTT
                 MetGlySerLysProPheLeuLeuSerLeuLeuSerLeuLeu
                 SpeI
7053 TTGTTTACATCTACTAGTTGGCACAAGAAGATAAAGGATTGTTCTTGTGACAACAAA
     LeuPheThrSerThrSerLeuAlaGlnGluAspLysGlyLeuValLeuValAspAsnLys
```

FIGURE 8F (Cont.)

```
7113 TGTAAGTGTGCCCGGATTACTTCCAGGATCATCCTTCTTCCGAAGATCCTAATGAGGAC
     CysLysCysAlaArgIleThrSerArgIleIleArgSerSerArgGluAspProAsnGluAsp
7173 ATTGTGGAGAGAAACATCCGAATTATTGTTCCTCTGAACACACGGAGAATATCTCTGAT
     IleValGluArgAsnIleArgIleIleValProLeuAsnAsnArgGluAsnIleSerAsp
7233 CCCACCTCACCATTGAGACCAGACCAGATTGTGTGACCTCTGTAAAAATGT
     ProThrSerProLeuArgThrArgPheValTyrHisLeuSerAspLeuCysLysLysCys
7293 GATCCTACAGAAGTGGAGCTGGATAATCAGATAGTTACTGCTACCAGAGCAATATCTGT
     AspProThrGluValGluLeuAspAsnGlnIleValThrAlaThrGlnSerAsnIleCys
7353 GATGAAGACAGTGCTACAGAGACCTGCTACACTTATGACAGAAACAAGTGCTACACAGCT
     AspGluAspSerAlaThrGluThrCysTyrThrTyrAspArgAsnLysCysTyrThrAla
7413 GTGGTCCACTCGTATATGGTAGACCAAATGGTGGAACAAGCCTTAACCCAGAT
     ValValProLeuValTyrGlyValGlyMetValGluThrAlaLeuThrProAsp
                                                 Sae I
7473 GCCTGCTATCCTGACTGAGCTCGAATTCCCGATCGTTCAAACATTGGCAATACCTTAAGGAATACCTTAAGGATACATGTAATCAT
     AlaCysTyrProAsp***
7547 CCTGTTGCCGGTCTGGATGATTATCATTATAATTCTGTTGAATTGGTTAAGGCATGTAATAATACGCGATAGAAACAAAATATAGC
7627 GACGTTATTTATGAGATGGTTTATCGCGGCATCATATAGATTAGAGTCCCGCAATTATACATTTAATACGCGATAATCGGCTGAGTGGCT
7707 GCGCAAACTAGGATAAATTATCGCGCGCGGTTCAAGCGCGTGCATCTATGTTACTAGATCGGGAATTAATTCGATCGGGGGTCATAACGTGACTC
7767 CCTTCAATCGTTGCGTTCTGTCAGTTGCAAACGTAAAACGCCTTGTCGGTCATCGGCTGTCCCGCCTTAAACTATCAGTGTTTGACTGGTGATGGCG
7867 CCTTAATTCTCCGCTCATGATCAGATTGTCGTTTCCCCGCCTTAATAATCGGATATATTAAAAGGGCGTGAAAGGTTTATCGCGTTCGTCCAT
7947 GGTAAACCTAAGAGAAAAGAGCGTTTATTAGAATAATCGGATATATTAAAAGGGCGTGAAAGGTTTATCGCGTTCGTCCAT
                                      Bgl II Sto I
8027 TTGTATGTGCATGCCAACCAGGTTCCCCAGATCTGGCCGCGGCCAG
```

[SEQUENCE ID NO:14]

FIGURE 9

SEQUENCE LISTING

<110> PLANET BIOTECHNOLOGY, INCORPORATED
    Larrick, James William
    Wycoff, Keith Lynn

<120> NOVEL IMMUNOADHESION FOR THE PREVENTION
    OF RHINOVIRUS INFECTION

<130> 030905.0003.WO

<140> To be assigned
<141> 2001-04-27

<150> 60/200,298
<151> 2000-04-27

<160> 8

<170> FastSEQ for Windows Version 4.0

<210> 1
<211> 1596
<212> DNA
<213> Homo Sapien

<220>
<221> CDS
<222> (1)...(1596)
<223> ICAM-1

<400> 1
```
atg gct ccc agc agc ccc cgg ccc gcg ctg ccc gca ctc ctg gtc ctg        48
Met Ala Pro Ser Ser Pro Arg Pro Ala Leu Pro Ala Leu Leu Val Leu
 1               5                  10                  15 ctc ggg gct ctg ttc cca gga cct ggc aat gcc cag aca tct gtg tcc        96
Leu Gly Ala Leu Phe Pro Gly Pro Gly Asn Ala Gln Thr Ser Val Ser
                20                  25                  30 ccc tca aaa gtc atc ctg ccc cgg gga ggc tcc gtg ctg gtg aca tgc       144
Pro Ser Lys Val Ile Leu Pro Arg Gly Gly Ser Val Leu Val Thr Cys
            35                  40                  45 agc acc tcc tgt gac cag ccc aag ttg ttg ggc ata gag acc ccg ttg       192
Ser Thr Ser Cys Asp Gln Pro Lys Leu Leu Gly Ile Glu Thr Pro Leu
        50                  55                  60 cct aaa aag gag ttg ctc ctg cct ggg aac aac cgg aag gtg tat gaa       240
Pro Lys Lys Glu Leu Leu Leu Pro Gly Asn Asn Arg Lys Val Tyr Glu
65                  70                  75                  80
```

FIGURE 9 (Cont.)

```
ctg agc aat gtg caa gaa gat agc caa cca atg tgc tat tca aac tgc        288
Leu Ser Asn Val Gln Glu Asp Ser Gln Pro Met Cys Tyr Ser Asn Cys
             85                  90                  95 cct gat ggg cag tca aca gct aaa acc ttc ctc acc gtg tac tgg act        336
Pro Asp Gly Gln Ser Thr Ala Lys Thr Phe Leu Thr Val Tyr Trp Thr
            100                 105                 110 cca gaa cgg gtg gaa ctg gca ccc ctc ccc tct tgg cag cca gtg ggc        384
Pro Glu Arg Val Glu Leu Ala Pro Leu Pro Ser Trp Gln Pro Val Gly
            115                 120                 125 aag aac ctt acc cta cgc tgc cag gtg gag ggt ggg gca ccc cgg gcc        432
Lys Asn Leu Thr Leu Arg Cys Gln Val Glu Gly Gly Ala Pro Arg Ala
        130                 135                 140 aac ctc acc gtg gtg ctg ctc cgt ggg gag aag gag ctg aaa cgg gag        480
Asn Leu Thr Val Val Leu Leu Arg Gly Glu Lys Glu Leu Lys Arg Glu
145                 150                 155                 160 cca gct gtg ggg gag ccc gct gag gtc acg acc acg gtg ctg gtg agg        528
Pro Ala Val Gly Glu Pro Ala Glu Val Thr Thr Thr Val Leu Val Arg
                165                 170                 175 aga gat cac cat gga gcc aat ttc tcg tgc cgc act gaa ctg gac ctg        576
Arg Asp His His Gly Ala Asn Phe Ser Cys Arg Thr Glu Leu Asp Leu
                180                 185                 190 cgg ccc caa ggg ctg gag ctg ttt gag aac acc tcg gcc ccc tac cag        624
Arg Pro Gln Gly Leu Glu Leu Phe Glu Asn Thr Ser Ala Pro Tyr Gln
            195                 200                 205 ctc cag acc ttc gtc ctg cca gcg act ccc cca caa ctt gtc agc ccc        672
Leu Gln Thr Phe Val Leu Pro Ala Thr Pro Pro Gln Leu Val Ser Pro
        210                 215                 220 cgg gtc cta gag gtg gac acg cag ggg acc gtg gtc tgt tcc ctg gac        720
Arg Val Leu Glu Val Asp Thr Gln Gly Thr Val Val Cys Ser Leu Asp
225                 230                 235                 240 ggg ctg ttc cca gtc tcg gag gcc cag gtc cac ctg gca ctg ggg gac        768
Gly Leu Phe Pro Val Ser Glu Ala Gln Val His Leu Ala Leu Gly Asp
                245                 250                 255 cag agg ctg aac ccc aca gtc acc tat ggc aac gac tcc ttc tcg gcc        816
Gln Arg Leu Asn Pro Thr Val Thr Tyr Gly Asn Asp Ser Phe Ser Ala
            260                 265                 270 aag gcc tca gtc agt gtg acc gca gag gac gag ggc acc cag cgg ctg        864
Lys Ala Ser Val Ser Val Thr Ala Glu Asp Glu Gly Thr Gln Arg Leu
        275                 280                 285 acg tgt gca gta ata ctg ggg aac cag agc cag gag aca ctg cag aca        912
Thr Cys Ala Val Ile Leu Gly Asn Gln Ser Gln Glu Thr Leu Gln Thr
        290                 295                 300 gtg acc atc tac agc ttc ccg gcg ccc aac gtg atc ctg acg aag cca        960
Val Thr Ile Tyr Ser Phe Pro Ala Pro Asn Val Ile Leu Thr Lys Pro
305                 310                 315                 320
```

FIGURE 9 (Cont.)

```
gag gtc tca gaa ggg acc gag gtg aca gtg aag tgt gag gcc cac cct      1008
Glu Val Ser Glu Gly Thr Glu Val Thr Val Lys Cys Glu Ala His Pro
            325                 330                 335 aga gcc aag gtg acg ctg aat ggg gtt cca gcc cag cca ctg ggc ccg      1056
Arg Ala Lys Val Thr Leu Asn Gly Val Pro Ala Gln Pro Leu Gly Pro
            340                 345                 350 agg gcc cag ctc ctg ctg aag gcc acc cca gag gac aac ggg cgc agc      1104
Arg Ala Gln Leu Leu Leu Lys Ala Thr Pro Glu Asp Asn Gly Arg Ser
            355                 360                 365 ttc tcc tgc tct gca acc ctg gag gtg gcc ggc cag ctt ata cac aag      1152
Phe Ser Cys Ser Ala Thr Leu Glu Val Ala Gly Gln Leu Ile His Lys
        370                 375                 380 aac cag acc cgg gag ctt cgt gtc ctg tat ggc ccc cga ctg gac gag      1200
Asn Gln Thr Arg Glu Leu Arg Val Leu Tyr Gly Pro Arg Leu Asp Glu
385                 390                 395                 400 agg gat tgt ccg gga aac tgg acg tgg cca gaa aat tcc cag cag act      1248
Arg Asp Cys Pro Gly Asn Trp Thr Trp Pro Glu Asn Ser Gln Gln Thr
            405                 410                 415 cca atg tgc cag gct tgg ggg aac cca ctg ccc gag ctc aag tgt cta      1296
Pro Met Cys Gln Ala Trp Gly Asn Pro Leu Pro Glu Leu Lys Cys Leu
            420                 425                 430 aag gat ggc act ttc cca ctg ccc atc ggg gaa tca gtg act gtc act      1344
Lys Asp Gly Thr Phe Pro Leu Pro Ile Gly Glu Ser Val Thr Val Thr
            435                 440                 445 cga gat ctt gag ggc acc tac ctc tgt cgg gcc agg agc act caa ggg      1392
Arg Asp Leu Glu Gly Thr Tyr Leu Cys Arg Ala Arg Ser Thr Gln Gly
            450                 455                 460 gag gtc acc cgc aag gtg acc gtg aat gtg ctc tcc ccc cgg tat gag      1440
Glu Val Thr Arg Lys Val Thr Val Asn Val Leu Ser Pro Arg Tyr Glu
465                 470                 475                 480 att gtc atc atc act gtg gta gca gcc gca gtc ata atg ggc act gca      1488
Ile Val Ile Ile Thr Val Val Ala Ala Ala Val Ile Met Gly Thr Ala
            485                 490                 495 ggc ctc agc acg tac ctc tat aac cgc cag cgg aag atc aag aaa tac      1536
Gly Leu Ser Thr Tyr Leu Tyr Asn Arg Gln Arg Lys Ile Lys Lys Tyr
            500                 505                 510 aga cta caa cag gcc caa aaa ggg acc ccc atg aaa ccg aac aca caa      1584
Arg Leu Gln Gln Ala Gln Lys Gly Thr Pro Met Lys Pro Asn Thr Gln
            515                 520                 525 gcc acg cct ccc                                                      1596
Ala Thr Pro Pro
        530
```

[DNA Sequence is SEQUENCE ID NO:1]
[Protein Sequence is SEQUENCE ID NO:2]

FIGURE 9 (Cont.)

<210> 2
<211> 532
<212> PRT
<213> Homo Sapien

<400> 2
Met Ala Pro Ser Ser Pro Arg Pro Ala Leu Pro Ala Leu Leu Val Leu
1               5                   10                  15
Leu Gly Ala Leu Phe Pro Gly Pro Gly Asn Ala Gln Thr Ser Val Ser
            20                  25                  30
Pro Ser Lys Val Ile Leu Pro Arg Gly Gly Ser Val Leu Val Thr Cys
        35                  40                  45
Ser Thr Ser Cys Asp Gln Pro Lys Leu Leu Gly Ile Glu Thr Pro Leu
    50                  55                  60
Pro Lys Lys Glu Leu Leu Pro Gly Asn Asn Arg Lys Val Tyr Glu
65                  70                  75                  80
Leu Ser Asn Val Gln Glu Asp Ser Gln Pro Met Cys Tyr Ser Asn Cys
                85                  90                  95
Pro Asp Gly Gln Ser Thr Ala Lys Thr Phe Leu Thr Val Tyr Trp Thr
            100                 105                 110
Pro Glu Arg Val Glu Leu Ala Pro Leu Pro Ser Trp Gln Pro Val Gly
        115                 120                 125
Lys Asn Leu Thr Leu Arg Cys Gln Val Glu Gly Gly Ala Pro Arg Ala
    130                 135                 140
Asn Leu Thr Val Val Leu Leu Arg Gly Glu Lys Glu Leu Lys Arg Glu
145                 150                 155                 160
Pro Ala Val Gly Glu Pro Ala Glu Val Thr Thr Thr Val Leu Val Arg
                165                 170                 175
Arg Asp His His Gly Ala Asn Phe Ser Cys Arg Thr Glu Leu Asp Leu
            180                 185                 190
Arg Pro Gln Gly Leu Glu Leu Phe Glu Asn Thr Ser Ala Pro Tyr Gln
        195                 200                 205
Leu Gln Thr Phe Val Leu Pro Ala Thr Pro Pro Gln Leu Val Ser Pro
    210                 215                 220
Arg Val Leu Glu Val Asp Thr Gln Gly Thr Val Val Cys Ser Leu Asp
225                 230                 235                 240
Gly Leu Phe Pro Val Ser Glu Ala Gln Val His Leu Ala Leu Gly Asp
                245                 250                 255
Gln Arg Leu Asn Pro Thr Val Thr Tyr Gly Asn Asp Ser Phe Ser Ala
            260                 265                 270
Lys Ala Ser Val Ser Val Thr Ala Glu Asp Glu Gly Thr Gln Arg Leu
        275                 280                 285
Thr Cys Ala Val Ile Leu Gly Asn Gln Ser Gln Glu Thr Leu Gln Thr
    290                 295                 300
Val Thr Ile Tyr Ser Phe Pro Ala Pro Asn Val Ile Leu Thr Lys Pro
305                 310                 315                 320
Glu Val Ser Glu Gly Thr Glu Val Thr Val Lys Cys Glu Ala His Pro
                325                 330                 335
Arg Ala Lys Val Thr Leu Asn Gly Val Pro Ala Gln Pro Leu Gly Pro
            340                 345                 350
Arg Ala Gln Leu Leu Leu Lys Ala Thr Pro Glu Asp Asn Gly Arg Ser
        355                 360                 365
Phe Ser Cys Ser Ala Thr Leu Glu Val Ala Gly Gln Leu Ile His Lys
    370                 375                 380
Asn Gln Thr Arg Glu Leu Arg Val Leu Tyr Gly Pro Arg Leu Asp Glu
385                 390                 395                 400
Arg Asp Cys Pro Gly Asn Trp Thr Trp Pro Glu Asn Ser Gln Gln Thr
                405                 410                 415

FIGURE 9 (Cont.)

```
Pro Met Cys Gln Ala Trp Gly Asn Pro Leu Pro Glu Leu Lys Cys Leu
            420                 425                 430
Lys Asp Gly Thr Phe Pro Leu Pro Ile Gly Glu Ser Val Thr Val Thr
            435                 440                 445
Arg Asp Leu Glu Gly Thr Tyr Leu Cys Arg Ala Arg Ser Thr Gln Gly
450                 455                 460
Glu Val Thr Arg Lys Val Thr Val Asn Val Leu Ser Pro Arg Tyr Glu
465                 470                 475                 480
Ile Val Ile Ile Thr Val Val Ala Ala Ala Val Ile Met Gly Thr Ala
                485                 490                 495
Gly Leu Ser Thr Tyr Leu Tyr Asn Arg Gln Arg Lys Ile Lys Lys Tyr
            500                 505                 510
Arg Leu Gln Gln Ala Gln Lys Gly Thr Pro Met Lys Pro Asn Thr Gln
            515                 520                 525
Ala Thr Pro Pro
            530
```

[SEQUENCE ID NO:2]

```
<210> 3
<211> 3003
<212> DNA
<213> Homo Sapien

<400> 3
gctataagga tcacgcgccc cagtcgacgc tgagctcctc tgctactcag agttgcaacc    60
tcagcctcgc tatggctccc agcagccccc ggcccgcgct gcccgcactc ctggtcctgc   120
tcggggctct gttcccagga cctggcaatg cccagacatc tgtgtccccc tcaaaagtca   180
tcctgccccg gggaggctcc gtgctggtga catgcagcac ctcctgtgac cagcccaagt   240
tgttgggcat agagaccccg ttgcctaaaa aggagttgct cctgcctggg aacaaccgga   300
aggtgtatga actgagcaat gtgcaagaag atagccaacc aatgtgctat tcaaactgcc   360
ctgatgggca gtcaacagct aaaaccttcc tcaccgtgta ctggactcca gaacgggtgg   420
aactggcacc cctcccctct tggcagccag tgggcaagaa ccttacccca cgctgccagg   480
tggagggtgg ggcacccegg gccaacctca ccgtggtgct gctccgtggg gagaaggagc   540
tgaaacggga gccagctgtg ggggagcccg ctgaggtcac gaccacggtg ctggtgagga   600
gagatcacca tggagccaat ttctcgtgcc gcactgaact ggacctgcgg ccccaagggc   660
tggagctgtt tgagaacacc tcggcccct accagctcca gacctttgtc ctgccagcga   720
ctcccccaca acttgtcagc ccccgggtcc tagaggtgga cacgcagggg accgtggtct   780
gttccctgga cgggctgttc ccagtctcgg aggcccaggt ccacctggca ctggggggacc   840
agaggttgaa ccccacagtc acctatggca acgactcctt ctcggccaag gcctcagtca   900
gtgtgaccgc agaggacgag ggcacccagc ggctgacgtg tgcagtaata ctggggaacc   960
agagccagga gacactgcag acagtgacca tctacagctt tccggcgccc aacgtgattc  1020
tgacgaagcc agaggtctca gaagggaccg aggtgacagt gaagtgtgag gcccacccta  1080
gagccaaggt gacgctgaat gggttccag cccagccact gggccgagg gcccagctcc   1140
tgctgaaggc cacccagag gacaacgggc gcagcttctc ctgctctgca accctggagg  1200
tggccggcca gcttatacac aagaaccaga cccgggagct tcgtgtcctg tatggccccc  1260
gactggacga gagggattgt ccgggaaact ggacgtggcc agaaaattcc cagcagactc  1320
caatgtgcca ggcttggggg aacccattgc ccgagctcaa gtgtccaaag gatggcactt  1380
tcccactgcc catcggggaa tcagtgactg tcactcgaga tcttgagggc acctacctct  1440
gtcgggccag gagcactcaa gggaggtca cccgcaaggt gaccgtgaat gtgctctccc  1500
cccggtatga gattgtcatc atcactgtgg tagcagccgc agtcataatg ggcactgcag  1560
gcctcagcac gtacctctat aaccgccagc ggaagatcaa gaaatacaga ctacaacagg  1620
cccaaaaagg gacccccatg aaaccgaaca cacaagccac gcctccctga acctatcccg  1680
ggacagggcc tcttcctcgg ccttcccata ttggtggcaca ctgaacagag  1740
tggaagacat atgccatgca gctacaccta ccggccctgg gacgccggag gacagggcat  1800
tgtcctcagt cagatacaac agcatttggg gccatggtac ctgcacacct aaaacactag  1860
gccacgcatc tgatctgtag tcacatgact aagcaagag gaaggagcaa gactcaagac  1920
atgattgatg gatgttaaag tctagcctga tgagagggga agtggtgggg gagacatagc  1980
cccaccatga ggacatacaa ctgggaaata ctgaaactcg ctgcctattg ggtatgctga  2040
```

FIGURE 9 (Cont.)

```
ggccccacag acttacagaa gaagtggccc tccatagaca tgtgtagcat caaaacacaa    2100
aggcccacac ttcctgacgg atgccagctt gggcactgct gtctactgac cccaaccctt    2160
gatgatatgt atttattcat ttgttatttt accagctatt tattgagtgt cttttatgta    2220
ggctaaatga acataggtct ctggcctcac ggagctccca gtccatgtca cattcaaggt    2280
caccaggtac agttgtacag gttgtacact gcaggagagt gcctggcaaa aagatcaaat    2340
ggggctggga cttctcattg gccaacctgc cttteeccag aaggagtgat ttttctatcg    2400
gcacaaaagc actatatgga ctggtaatgg ttcacaggtt cagagattac ccagtgaggc    2460
cttattcctc cctteeeece aaaactgaca cctttgttag ccacctcccc acccacatac    2520
atttctgcca gtgttcacaa tgacactcag cggtcatgtc tggacatgag tgcccaggga    2580
atatgcccaa gctatgcctt gtcctcttgt cctgtttgca tttcactggg agcttgcact    2640
attgcagctc cagtttcctg cagtgatcag ggtcctgcaa gcagtgggga aggggccaa     2700
ggtattggag gactccctcc cagctttgga agcctcatcc gcgtgtgtgt gtgtgtgtgt    2760
atgtgtagac aagctctcgc tctgtcaccc aggctggagt gcagtggtgc aatcatggtt    2820
cactgcagtc ttgacctttt gggctcaagt gatcctccca cctcagcctc ctgagtagct    2880
gggaccatag gctcacaaca ccacacctgg caaatttgat tttttttttt ttttcagag     2940
acggggtctc gcaacattgc ccagacttcc tttgtgttag ttaataaagc ttcctcaact    3000
gcc                                                                 3003
```
[SEQUENCE ID NO:3]

```
<210> 4
<211> 6
<212> PRT
<213> Homo Sapien

<400> 4
Ser Glu Lys Asp Glu Leu
 1               5
```
[SEQUENCE ID NO:4]

```
<210> 5
<211> 7
<212> PRT
<213> Homo Sapien

<400> 5
Arg Ser Glu Lys Asp Glu Leu
 1               5
```
[SEQUENCE ID NO:5]

```
<210> 6
<211> 52
<212> DNA
<213> Homo Sapien

<400> 6
tctgttccca ggaactagtt tggcacagac atctgtgtcc ccctcaaaag tc             52
```
[SEQUENCE ID NO:6]

```
<210> 7
<211> 38
<212> DNA
<213> Homo Sapien

<400> 7
cataccgggg actagtcaca ttcacggtca cctcgcgg                            38
```
[SEQUENCE ID NO:7]

FIGURE 9 (Cont.)

<210> 8
<211> 799
<212> PRT
<213> Homo Sapien
<220>
<221> CDS
<222> (1)...(448)
<223> ICAM-1 Extracellular Domains <220>
<221> CDS
<222> (453)...(799)
<223> Human IgA2m(2)

<400> 8
```
Gln Thr Ser Val Ser Pro Ser Lys Val Ile Leu Pro Arg Gly Gly Ser
1               5                   10                  15
Val Leu Val Thr Cys Ser Thr Ser Cys Asp Gln Pro Lys Leu Leu Gly
            20                  25                  30
Ile Glu Thr Pro Leu Pro Lys Lys Glu Leu Leu Leu Pro Gly Asn Asn
        35                  40                  45
Arg Lys Val Tyr Glu Leu Ser Asn Val Gln Glu Asp Ser Gln Pro Met
    50                  55                  60
Cys Tyr Ser Asn Cys Pro Asp Gly Gln Ser Thr Ala Lys Thr Phe Leu
65                  70                  75                  80
Thr Val Tyr Trp Thr Pro Glu Arg Val Glu Leu Ala Pro Leu Pro Ser
                85                  90                  95
Trp Gln Pro Val Gly Lys Asn Leu Thr Leu Arg Cys Gln Val Glu Gly
            100                 105                 110
Gly Ala Pro Arg Ala Asn Leu Thr Val Val Leu Leu Arg Gly Glu Lys
        115                 120                 125
Glu Leu Lys Arg Glu Pro Ala Val Gly Glu Pro Ala Glu Val Thr Thr
    130                 135                 140
Thr Val Leu Val Arg Arg Asp His His Gly Ala Asn Phe Ser Cys Arg
145                 150                 155                 160
Thr Glu Leu Asp Leu Arg Pro Gln Gly Leu Glu Leu Phe Glu Asn Thr
                165                 170                 175
Ser Ala Pro Tyr Gln Leu Gln Thr Phe Val Leu Pro Ala Thr Pro Pro
            180                 185                 190
Gln Leu Val Ser Pro Arg Val Leu Glu Val Asp Thr Gln Gly Thr Val
    195                 200                 205
Val Cys Ser Leu Asp Gly Leu Phe Pro Val Ser Glu Ala Gln Val His
210                 215                 220
Leu Ala Leu Gly Asp Gln Arg Leu Asn Pro Thr Val Thr Tyr Gly Asn
225                 230                 235                 240
Asp Ser Phe Ser Ala Lys Ala Ser Val Ser Val Thr Ala Glu Asp Glu
                245                 250                 255
Gly Thr Gln Arg Leu Thr Cys Ala Val Ile Leu Gly Asn Gln Ser Gln
            260                 265                 270
Glu Thr Leu Gln Thr Val Thr Ile Tyr Ser Phe Pro Ala Pro Asn Val
    275                 280                 285
Ile Leu Thr Lys Pro Glu Val Ser Glu Gly Thr Glu Val Thr Val Lys
290                 295                 300
Cys Glu Ala His Pro Arg Ala Lys Val Thr Leu Asn Gly Val Pro Ala
305                 310                 315                 320
Gln Pro Leu Gly Pro Arg Ala Gln Leu Leu Leu Lys Ala Thr Pro Glu
                325                 330                 335
Asp Asn Gly Arg Ser Phe Ser Cys Ser Ala Thr Leu Glu Val Ala Gly
            340                 345                 350
```

FIGURE 9 (Cont.)

```
Gln Leu Ile His Lys Asn Gln Thr Arg Glu Leu Arg Val Leu Tyr Gly
            355                 360                 365
Pro Arg Leu Asp Glu Arg Asp Cys Pro Gly Asn Trp Thr Trp Pro Glu
        370                 375                 380
Asn Ser Gln Gln Thr Pro Met Cys Gln Ala Trp Gly Asn Pro Leu Pro
385                 390                 395                 400
Glu Leu Lys Cys Leu Lys Asp Gly Thr Phe Pro Leu Pro Ile Gly Glu
                405                 410                 415
Ser Val Thr Val Thr Arg Asp Leu Glu Gly Thr Tyr Leu Cys Arg Ala
                420                 425                 430
Arg Ser Thr Gln Gly Glu Val Thr Arg Glu Val Thr Val Asn Val Thr
            435                 440                 445
Ser Gly Ser Ser Ala Ser Pro Thr Ser Pro Lys Val Phe Pro Leu Ser
    450                 455                 460
Leu Asp Ser Thr Pro Gln Asp Gly Asn Val Val Val Ala Cys Leu Val
465                 470                 475                 480
Gln Gly Phe Phe Pro Gln Glu Pro Leu Ser Val Thr Trp Ser Glu Ser
                485                 490                 495
Gly Gln Asn Val Thr Ala Arg Asn Phe Pro Pro Ser Gln Asp Ala Ser
                500                 505                 510
Gly Asp Leu Tyr Thr Thr Ser Ser Gln Leu Thr Leu Pro Ala Thr Gln
            515                 520                 525
Cys Pro Asp Gly Lys Ser Val Thr Cys His Val Lys His Tyr Thr Asn
    530                 535                 540
Ser Ser Gln Asp Val Thr Val Pro Cys Arg Val Pro Pro Pro Pro Pro
545                 550                 555                 560
Cys Cys His Pro Arg Leu Ser Leu His Arg Pro Ala Leu Glu Asp Leu
                565                 570                 575
Leu Leu Gly Ser Glu Ala Asn Leu Thr Cys Thr Leu Thr Gly Leu Arg
                580                 585                 590
Asp Ala Ser Gly Ala Thr Phe Thr Trp Thr Pro Ser Ser Gly Lys Ser
            595                 600                 605
Ala Val Gln Gly Pro Pro Glu Arg Asp Leu Cys Gly Cys Tyr Ser Val
    610                 615                 620
Ser Arg Val Leu Pro Gly Cys Ala Gln Pro Trp Asn His Gly Glu Thr
625                 630                 635                 640
Phe Thr Cys Thr Ala Ala His Pro Glu Leu Lys Thr Pro Leu Thr Ala
                645                 650                 655
Asn Ile Thr Lys Ser Gly Asn Thr Phe Arg Pro Glu Val His Leu Leu
                660                 665                 670
Pro Pro Pro Ser Glu Glu Leu Ala Leu Asn Glu Leu Val Thr Leu Thr
            675                 680                 685
Cys Leu Ala Arg Gly Phe Ser Pro Lys Asp Val Leu Val Arg Trp Leu
    690                 695                 700
Gln Gly Ser Gln Glu Leu Pro Arg Glu Lys Tyr Leu Thr Trp Ala Ser
705                 710                 715                 720
Arg Gln Glu Pro Ser Gln Gly Thr Thr Thr Tyr Ala Val Thr Ser Ile
                725                 730                 735
Leu Arg Val Ala Ala Glu Asp Trp Lys Lys Gly Glu Thr Phe Ser Cys
                740                 745                 750
Met Val Gly His Glu Ala Leu Pro Leu Ala Phe Thr Gln Lys Thr Ile
            755                 760                 765
Asp Arg Leu Ala Gly Lys Pro Thr His Ile Asn Val Ser Val Val Met
    770                 775                 780
Ala Glu Ala Asp Gly Thr Cys Tyr Arg Ser Glu Lys Asp Glu Leu
785                 790                 795
```

[SEQUENCE ID NO:8]

IMMUNOADHESIN COMPRISING A CHIMERIC ICAM-1 MOLECULE PRODUCED IN A PLANT

STATEMENT REGARDING FEDERALLY SPONSORED RESEARCH OR DEVELOPMENT

Federal research support was provided in the form of an SBIR Phase I grant (R43 AI43122) and SBIR Phase II grant (2R44AI43122-02).

PRIORITY

This application claims benefit under §119(e) of U.S. Provisional Patent Application No. 60/200,298, filed Apr. 28, 2000, entitled NOVEL IMMUNOADHESIN FOR THE PREVENTION OF RHINOVIRUS INFECTION, and naming J. W. Larrick and K. L. Wycoff as inventors. This application is incorporated herein by reference in its entirety and for all purposes.

FIELD OF THE INVENTION

The present invention relates to immunoadhesins, fusions of the human rhinovirus receptor protein and immunoglobin, and the expression of immunoadhesins in plants. The therapeutic use of immunoadhesins for the prevention and treatment of human rhinovirus infection is also contemplated.

BACKGROUND TO THE INVENTION

The common cold is generally a relatively mild disease, however significant, complications resulting from colds, such as otitis media, sinusitis and asthma exacerbations are common. Human rhinoviruses (HRV) cause up to 50% of all adult colds and 25% of colds in children (Bella and Rossmann, *J Struct Biol.* 128:69-74, 1999, and Sperber and Hayden, *Antimicrob Agents Chemother.* 32:409-19, 1988). The cost to society runs into billions of dollar per year. These small, nonenveloped RNA viruses represent a subgroup of picornavirus (Rueckert, *Virology, pp.* 507-548, eds. Fields, et al., Raven Press, Ltd. New York, 1990) X-ray crystallography of rhinovirus identified a capsid 360 Å in diameter (1 Å=0.1 nm) with icosahedral symmetry, constructed from sixty copies each of the viral coat proteins VP1, VP2, and VP3 (Rossmann, *Nature* 317:145-153, 1985). A surface depression or "canyon" on HRV was suggested as the receptor binding site (Colonno, et al., *Proc Natl Acad Sci USA.* 85:5449-5453, 1985; Rossmann, et al. *Nature* 317:145-153, 1985). Of the 102 characterized HRV serotypes, 91 (known as the major group) share as their receptor a cell surface glycoprotein known as intercellular adhesion molecule-1 (ICAM-1) (Greve, et al., *Cell* 56:839-847, 1989; Staunton, et al., *Cell* 56:849-853, 1989); the binding site is located within N-terminal domain 1 (Greve, et al., *J Virol.* 65:6015-6023, 1991; Staunton, et al., *Cell* 61:243-254, 1990).

ICAM-1 is a membrane protein with five extracellular domains, a hydrophobic transmembrane domain, and a short cytoplasmic domain. ICAM-1 is expressed on many cells important in immune and inflammatory responses, and is inducible on others (Casasnovas, et al. *Proc Natl Acad Sci USA.* 95:4134-9, 1998). ICAM-1 functions as a ligand for the leukocyte integrins LFA-1 and Mac-1 (Springer, *Cell.* 76:301-14, 1994; Staunton et al., *Cell* 61:243-254, 1990). On the cell surface, ICAM-1 is primarily a diner due to association of the transmembrane domains (Miller, et al., *J Exp Med.* 182:1231-41, 1995; Reilly, et al *J Immunol.* 155:529-32, 1995).

Recombinant, soluble forms of ICAM-1 (sICAM-1) consisting of the five extracellular domains were shown to be effective in blocking rhinovirus infection of human cells in vitro (Greve, et al., *J Virol.* 65:6015-6023, 1991; Marlin, et al., *Nature.* 344:70-2, 1990). Evaluation of sICAM-1 activity against a spectrum of laboratory strains and field isolates showed that all major strains of HRV are sensitive to sICAM-1. Minor strains, which do not use ICAM as a receptor, were unaffected by sICAM-1 (Crump et al., *Antiviral Chem. Chemother.* 4:323-327, 1993; Ohlin, et al., *Antimicrob Agents Chemother.* 38:1413-5, 1994).

The anti-viral activity of soluble ICAM-1 in vitro appears to be mediated by more than one mechanism. These mechanisms include competition with cell-surface ICAM-1 for binding sites, interference with virus entry or uncoating, and direct inactivation by premature release of viral RNA and formation of empty capsids (Arruda, et al., *Antimicrob Agents Chemother.* 36:1186-1191, 1992; Greve, et al., *J Virol.* 65:6015-6023, 1991; Marlin, et al., *Nature* 344:70-2, 1990; Martin et al., *J Virol.* 67:3561-8, 1993).

The host range of HRV is restricted to primates. A recent study showed that soluble ICAM-1 was effective in preventing rhinovirus infection in chimpanzees (Huguenel, et al., *Am J Respir Crit Care Med.* 155:1206-10, 1997). Although chimpanzees do not show clinical symptoms, infection was demonstrated by measuring seroconversion and virus shedding. A single dose of 10 mg of soluble ICAM-1 as an intranasal spray was effective at preventing infection by HRV-16 when co-administered with HRV, or when the virus was administered ten minutes later.

A human clinical trial with soluble ICAM-1 showed that it reduced the severity of experimental HRV colds (Turner, et al., *JAMA* 281:1797-804, 1999). In this trial a total of 196 subjects received either soluble ICAM-1 or placebo in various formulations. Some subjects were given soluble ICAM-1 or placebo starting seven hours before inoculation with HRV 39 and others were started twelve hours after virus inoculation. Medications were administered as either an intranasal solution or powder, given in six daily doses for seven days (a total of 4.4 mg per day). In this study, soluble ICAM-1 did not prevent infection, as measured by either virus isolation or seroconversion (infection rate of 92% for placebo-treated vs. 85% of soluble ICAM-1 treated). However, soluble ICAM-1 did have an impact on all measures of illness. The total symptom score was reduced by 45%, the proportion of subjects with clinical colds was reduced 23% and nasal mucus weight was reduced by 56%. There was not a significant difference between the use of powder or solution formulations, or between pre- and post-inoculation groups. Treatment with soluble ICAM-1 did not result in any adverse effects or evidence of absorption through the nasal mucosa. Also, there was no inhibition of the development of anti-HRV type-specific antibodies.

As discussed, ICAM-1 is dimeric on the cell surface. Martin et al., in *J Virol.* 67:3561-8, (1993) first proposed that multivalent binding to HRV by a multimeric soluble ICAM might result in a higher effective affinity, termed avidity, and thus facilitate uncoating of the virus. They constructed multivalent, ICAM-1/immunoglobulin molecules, postulating that these would be more effective than monovalent soluble ICAM-1 in neutralizing HRV and thus would have increased therapeutic utility. These ICAM-1/immunoglobulin molecules included ICAM-1 amino-terminal domains 1 and 2 fused to the hinge and constant domains of the heavy chains of IgA1 (IC1-2D/IgA), IgM (IC1-2D/IgM) and IgG1 (IC1-2D/IgG). In addition, five extracellular domains were fused to IgA1 (IC1-5D/IgA). These ICAM-1/immunoglobulin molecules were compared with soluble forms of ICAM-1 having two (sIC1-2D) and five (sIC1-5D) domains in assays of HRV binding, infectivity and conformation. The ICAM-1/IgA immunoglobulin (IC1-5D/IgA) was 200 times, and the ICAM-1/IgM immunoglobulin (IC1-2D/IgM) and ICAM-1/IgG immunoglobulin molecules (IC1-2D/IgG) were 25 and 10 times, more effective than soluble ICAM-1. These molecules were highly effective in inhibiting rhinovirus binding to cells and disrupting the conformation of the virus capsid. The ICAM-1/IgA immunoglobulin molecules were effective in the nanomolar concentration range. Comparison of IC1-2D/IgA and IC1-2D/IgG showed that the class of Ig constant region used had a large impact on efficacy.

A subsequent study compared the inhibitory activities of soluble ICAM-1 and IC1-5D/IgA against nine major HRV serotypes and a variant of HRV-39 selected for moderate resistance to soluble ICAM-1 (Crump, et al., *Antimicrob Agents Chemother.* 38:1425-7, 1993). IC1-5D/IgA was more potent than monomeric soluble ICAM-1 by 50 to 143 times on a weight basis and by 60 to 170 times on a molar basis against the standard serotypes. The HRV-39 variant was 38-fold more resistant to soluble ICAM-1 than the wild-type, and it was only 5-fold more resistant to IC1-5D/IgA. This is consistent with the hypothesis that virus escape from inhibition by multivalent molecules would be expected to occur at lower frequency than virus escape from inhibition by monomeric soluble receptor (Martin, et al., *J Virol.* 67:3561-8, 1993). An assay designed to measure viral inactivation showed that HRV-39 and HRV-13 were not directly inactivated to a significant extent by soluble ICAM-1 (<0.5 $\log_{10}$ reduction in infectivity). However, incubation with IC1-5D/IgA resulted in a reduction of infectivity of these same viruses by about 1.0 $\log_{10}$ (Crump, et al., *Antimicrob Agents Chemother.* 38:1425-7, 1994). Results by Martin et al. (*J Virol.* 67:3561-8, 1993) suggest that the greater the valence, the greater the effectiveness of the molecules. Dimeric and decameric forms of IC1-2/IgM were separable by sucrose gradient sedimentation. The decameric form was five times more effective than the dimeric form at blocking binding of HRV to HeLa cells.

The ICAM-1/immunoglobulin molecules that have been described suffer from several drawbacks, including the laborious production techniques and high costs associated with those production methods. In addition, the previously described ICAM-1/immunoglobulin molecules have limited stability as multimers in the harsh environment in which the molecule must inactivate rhinoviruses.

The immunoadhesins of the present invention have significant advantages over what has been described in the art. The immunoadhesins of the present invention that are, expressed in plants would be tetrameric, rather than only dimeric. Immunoadhesins having multiple binding sites have a higher effective affinity for the virus, thereby increasing the effectiveness of the immunoadhesin. In addition, the association of secretory component and immunoglobin, J chain with the immunoadhesin of the present invention increases the stability of the immunoadhesin in the mucosal environment (Corthesy, *Biochem Soc Trans.* 25:471-475, 1997). Secretory IgA, which is associated with secretory component, is the antibody isotype normally found in mucosal secretions, including milk and colostrum. Unlike other antibody isotypes, SIgA can pass through the gut with very little proteolytic degradation. It also is very stable in crude plant preparations at room temperature. A function of the secretory component appears to be to protect the antibody from the harsh environment of the mucosa (Paul, *Fundamental Immunology*, Raven Press, NY, Third Edition, pp. 303-304, 1993). Furthermore, the immunoadhesin of the present invention are significantly less expensive to produce in plants than in animal cell culture, and production in plants would make it safer for human use, since plants are not known to harbor any animal viruses.

SUMMARY OF THE INVENTION

The present invention contemplates an immunoadhesin comprising a chimeric ICAM-1 molecule having a rhinovirus receptor protein linked to at least a portion of an immunoglobulin heavy chain, wherein J chain and secretory component are associated with the chimeric ICAM-1 molecule.

In preferred embodiments, the immunoadhesin of the present invention is comprised of a rhinovirus receptor protein made of any combination of extracellular domains 1, 2, 3, 4 and 5 of the rhinovirus receptor protein, ICAM-1, linked to an immunoglobulin heavy chain. Also contemplated by the present invention are immunoadhesins of the present invention in which the immunoglobulin is IgA, $IgA_1$, $IgA_2$, $IgG_1$, $IgG_2$, $IgG_3$, $IgG_4$, IgM, IgD, IgE or a chimeric immunoglobulin heavy chain made up of domains or segments from different immunoglobulin isotypes.

In other preferred embodiments of the present invention, the immunoadhesin comprises multiple chimeric ICAM-1 molecules associated with J chain and secretory component. The increase in valency results in a higher effective affinity for the rhinovirus, thereby increasing the effectiveness of the immunoadhesin.

In a preferred embodiment of the present invention, all proteins used to make, the immunoadhesin of the present invention are human proteins. In addition to production in plants or plant cells, the present invention contemplates an immunoadhesin expressed in mammalian cells, hairy root cultures, plant cells in tissue culture, and heterologous cells derived from plants, vertebrates or invertebrates.

In preferred embodiments of the present invention, the immunoadhesins are expressed, in plants, including monocotyledonous plants and dicotyledonous plants as a part of the plants genome. Expression in plants, as opposed to expression in cultured cells, allows for a significant reduction in the cost of producing the immunoadhesin.

The present invention contemplates an immunoadhesin having plant-specific glycosylation. A gene coding for a polypeptide having within its amino acid sequence, the glycosylation signal asparagine-X-serine/threonine, where X can be any amino acid residue, is glycosylated via oligosaccharides linked to the asparagine residue of the sequence when expressed in a plant cell. See Marshall, *Ann. Rev. Biochem.*, 41:673 (1972) and Marshall, *Biochem. Soc. Symp.*, 40:17 (1974) for a general review of the polypeptide sequences that function as glycosylation signals. These signals are recognized in both mammalian and in plant cells. At the end of their maturation, proteins expressed in plants or plant cells have a different pattern of glycosylation than do proteins expressed in other types of cells, including mammalian cells and insect cells. Detailed studies characterizing plant-specific glycosylation and comparing it with glycosylation in other cell types have been performed, for example, in studies described by Cabanes-Macheteau et al., *Glycobiology* 9(4):365-372 (1999), and Altmann, *Glycoconjugate J.* 14:643-646 (1997). These groups and others have shown that plant-specific-glycosylation generates glycans that have xylose linked $\beta(1,2)$ to mannose, but xylose is not linked $\beta(1,2)$ to mannose as a result of glycosylation in mammalian and insect cells. Plant-specific glycosylation results in a fucose linked β(1,3) to the proximal GlcNAc, while glycosylation in mammalian cells results in a fucose linked α(1,6) to the proximal GlcNAc. Furthermore, plant-specific glycosylation does not result in the addition of a sialic acid to the terminus of the protein glycan, whereas in glycosylation in mammalian cells, sialic acid is added.

In other embodiments, the immunoadhesin of the present invention is part of a composition comprising plant material and the immunoadhesin, associated with J chain and secretory component. The plant material present may be plant cell walls, plant organelles, plant cytoplasms, intact plant cells, viable plants, and the like. The particular plant materials or plant macromolecules that may be present include ribulose bisphosphate carboxylase, light harvesting complex, pigments, secondary metabolites or chlorophyll. Compositions of the present invention may have an immunoadhesin concentration of between 0.001% and 99.9% mass excluding-water. In other embodiments, the immunoadhesin is present in a concentration of 0.01% to 99% mass excluding water. In other embodiments, the compositions of the present invention have plant material or plant macromolecules present at a concentration of 0.01% to 99% mass excluding water.

The present invention also contemplates methods for the treatment or prevention of human rhinovirus infection in a subject, including reducing the infection by human rhinovirus of host cells susceptible to infection by the virus, or reducing the initiation or spread of the common cold due to human rhinovirus, by a method comprising contacting the virus with an immunoadhesin of the present invention, wherein the immunoadhesin binds to the human rhinovirus and reduces infectivity. The immunoadhesin could mediate infection by competition with cell-surface ICAM-1 for binding sites, interference with virus entry or uncoating, and/or direct inactivation by premature release of viral RNA and formation of empty capsids (Arruda, et al., *Antimicrob. Agents Chemother.* 36:1186-1191; 1992; Greve, et al., *J. Virol.* 65:6015-6023, 1991; Martin, et al., *Nature* 344:70-2, 1990; Martin et al, *J Virol* 67:3561-8, 1993). In another embodiment, human rhinovirus infection in a subject is treated by a method comprising intranasally administering to the subject an effective amount of an immunoadhesin of the present invention, wherein the immunoadhesin reduces human rhinovirus infectivity.

BRIEF DESCRIPTION OF THE DRAWINGS

FIG. 3 illustrates the expression of the immunoadhesin in independently transformed tobacco calli. 3A shows immunoblots of non-reducing SDS-polyacrylamide gels on which samples containing different transformed tobacco calli (C) and aqueous extracts (Aq) were run and probed for the presence of human ICAM. The molecular weight markers are indicated, and the reference standard (R) was a mixture (~75 ng each) of human ICAM (~75 kD) and human SigA (>>250 kD). 3B shows immunoblots of nonreducing SDS-polyacrylamide gels containing various fractions of partially purified immunoadhesin from callus Rhi107-11. The purification fractions analyzed were juice (J), G-100 fraction (G), sterile filtered G-100 fraction (SG), and a mixture of reference standards of human SigA (75 ng) and human ICAM-1 (75 ng) (RS).

Blots were probed with antibodies against human ICAM (~ICAM), human IgA heavy chain (~α), human secretory component (~SC) and human J chain (~J), Secondary, enzyme-conjugated antibodies were employed as necessary to label immuno-positive bands with alkaline phosphatase.

Figure 4:
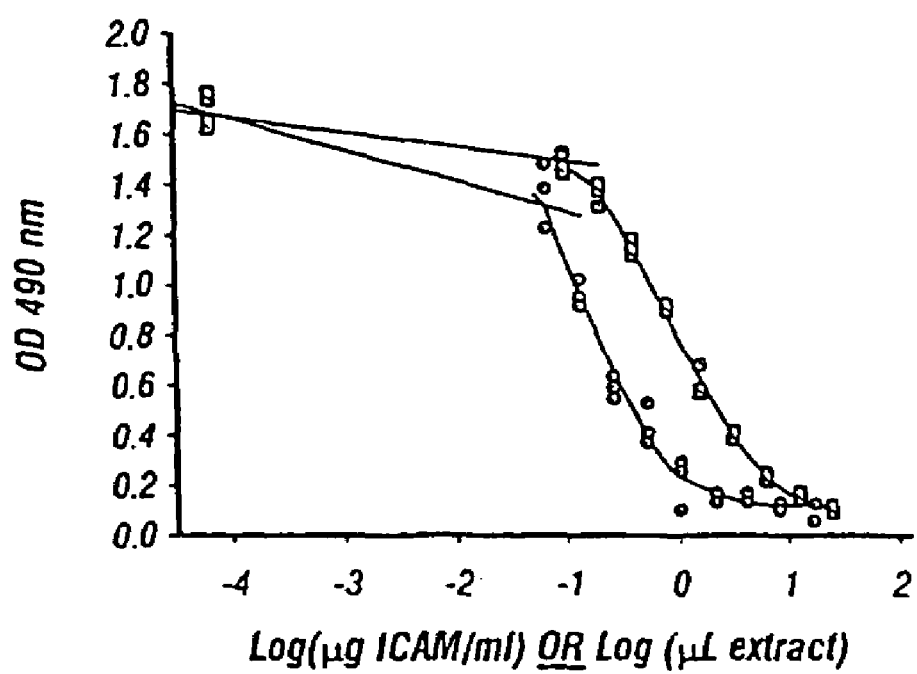

FIG. 4 illustrates the results of an enzyme-linked immunosorbent assay (ELISA) showing competition between plant extract and soluble ICAM-1 for binding to an anti-ICAM mAb. For the assay, 96-well plates were coated with 0.25 μg soluble ICAM-1/ml. The squares represent the increasing concentrations of sICAM and the circles represent the increasing amounts of callus extract (sterile filtered fraction from G-100) used to compete with the adhered ICAM for a constant amount of a mouse (anti-human ICAM) antibody.

Figure 5A:
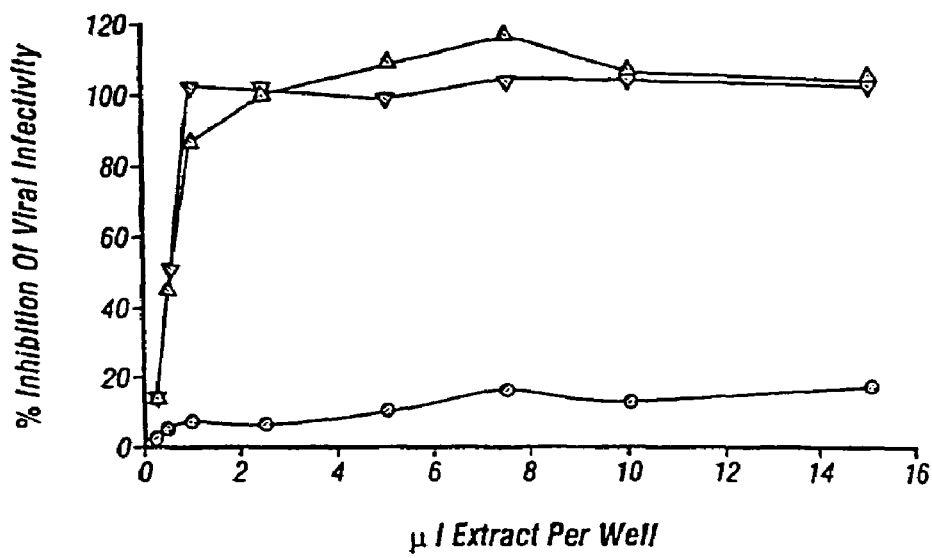

FIG. 5 illustrates the results of an assay showing the ability of an immunoadhesin to inhibit human rhinovirus killing of HeLa cells (cytopathic effect, or CPE, assay). 5A shows the results of an assay comparing the CPE of human rhinovirus on HeLa cells in the presence of partially purified extracts containing either the immunoadhesinin the ICAM-Fc fusion (IC1-5D/IgA) or containing an antibody against doxorubicin. (The right side-up and upside-down triangles represent two extracts derived from Rhi107-11, containing the immunoadhesin.) 5B shows the results of an assay comparing the CPE of human rhinovirus on HeLa cells in the presence of soluble human ICAM-1 or an extract from the immunoadhesin in the ICAM-Fc fusion (IC1-5D/IgA). The Inset shows scale expansion in the range of the IC50 for soluble ICAM (1.35 μg/ml) and for IC1-5D/IgA (0.12 μg/ml; 11.3 fold-less).

Figure 6:
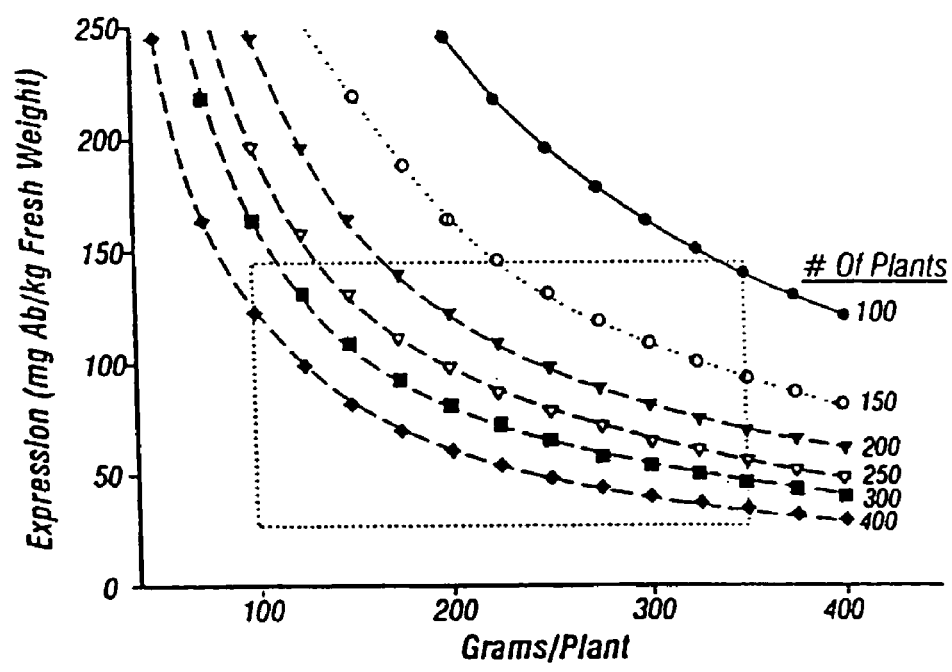

FIG. 6 shows an evaluation of the production necessities for making 1 gram of finished immunoadhesin. In this diagram, the number of plants needed for 1 g of immunoadhesin, at 20% yield, at expected levels of expression and plant weight is illustrated. At different levels of immunoadhesin expression (mg/kg fresh weight) and overall recovery (set at 20%), the weight of each plant, and so the total number of plants, may be determined for a specified production target (1 g/harvest) within a window (dotted square) of reasonable possibilities. The number of required plants decreases, inversely, with the number of specified growth and re-growth periods. The expected biomass production, a function of time and growth conditions, influences the time to harvest and the time between harvests. These growth periods can be adjusted to the realities of the purification schedule by staggering planting and harvesting dates.

FIG. 7 shows the coding and amino acid sequences of each of the immunoglobulin genes and proteins listed in Table 2 [SEQ ID NO:15 through 47 and SEQ ID NO:52 through 62].

Figure 8A:
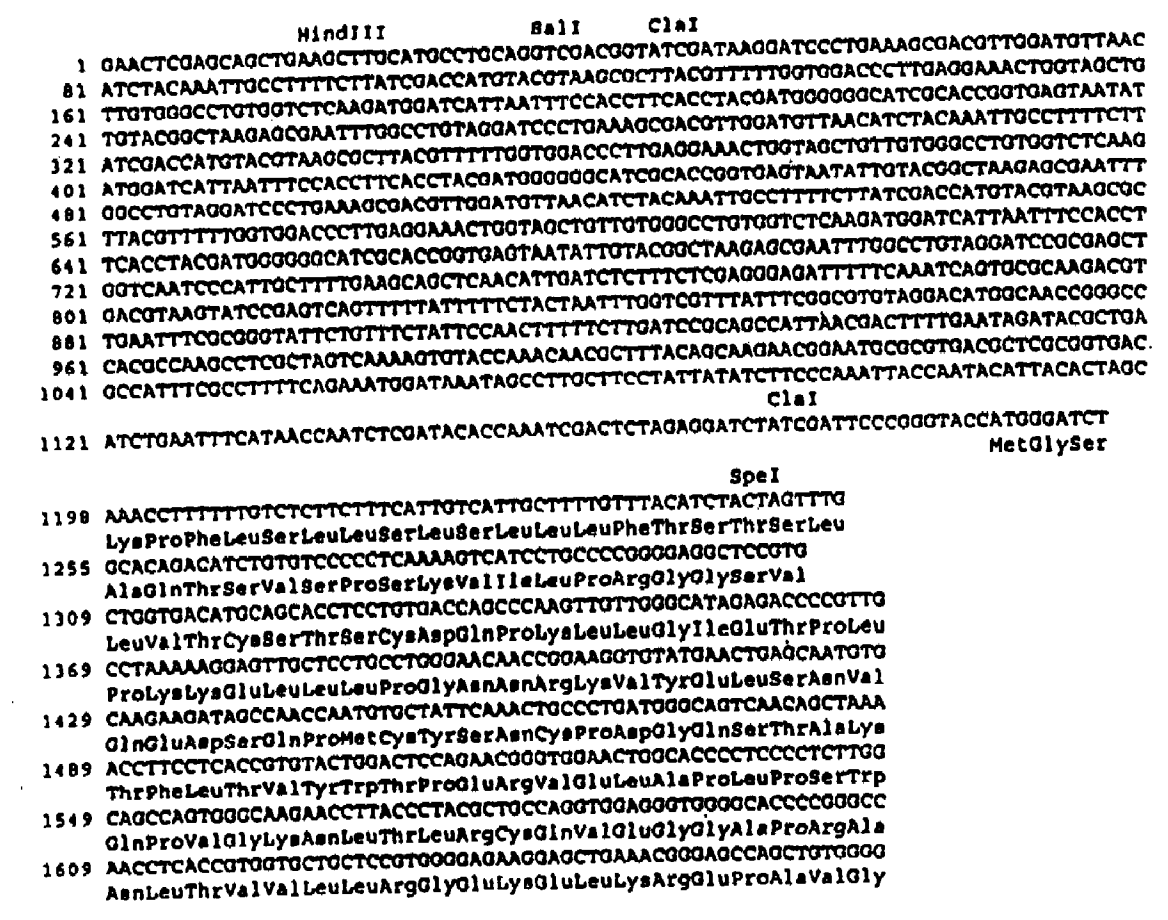
Figure 8A:
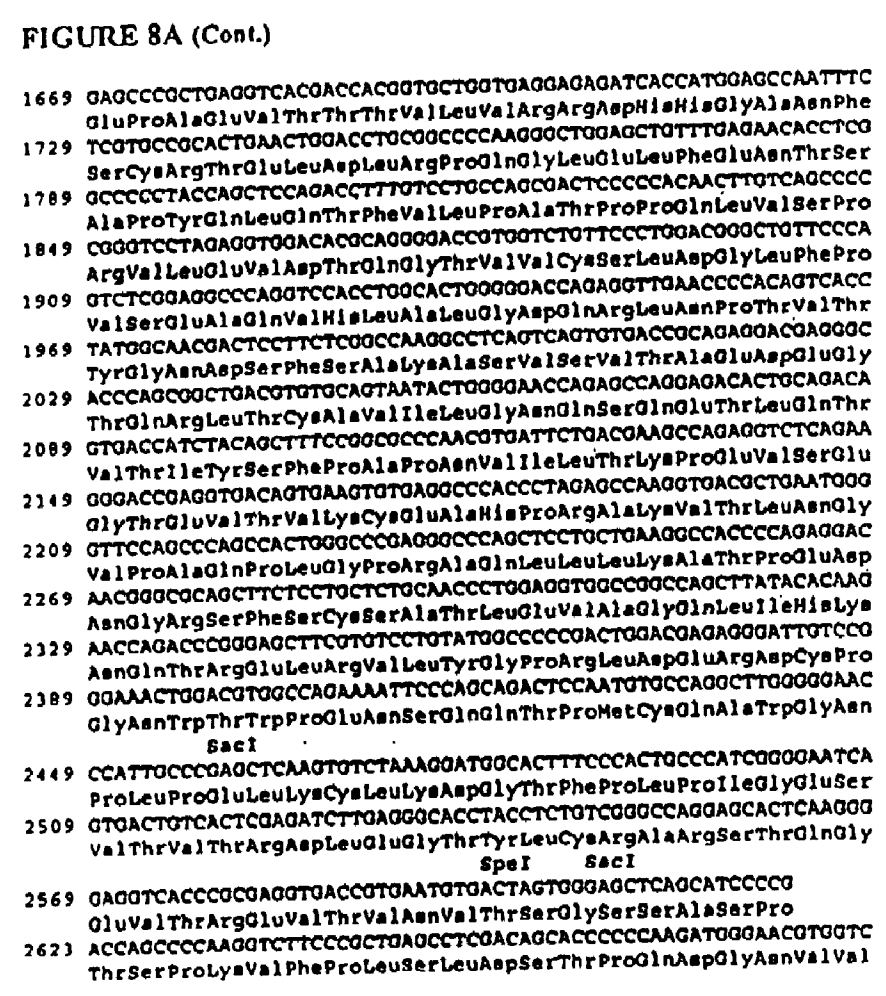
Figure 8A:
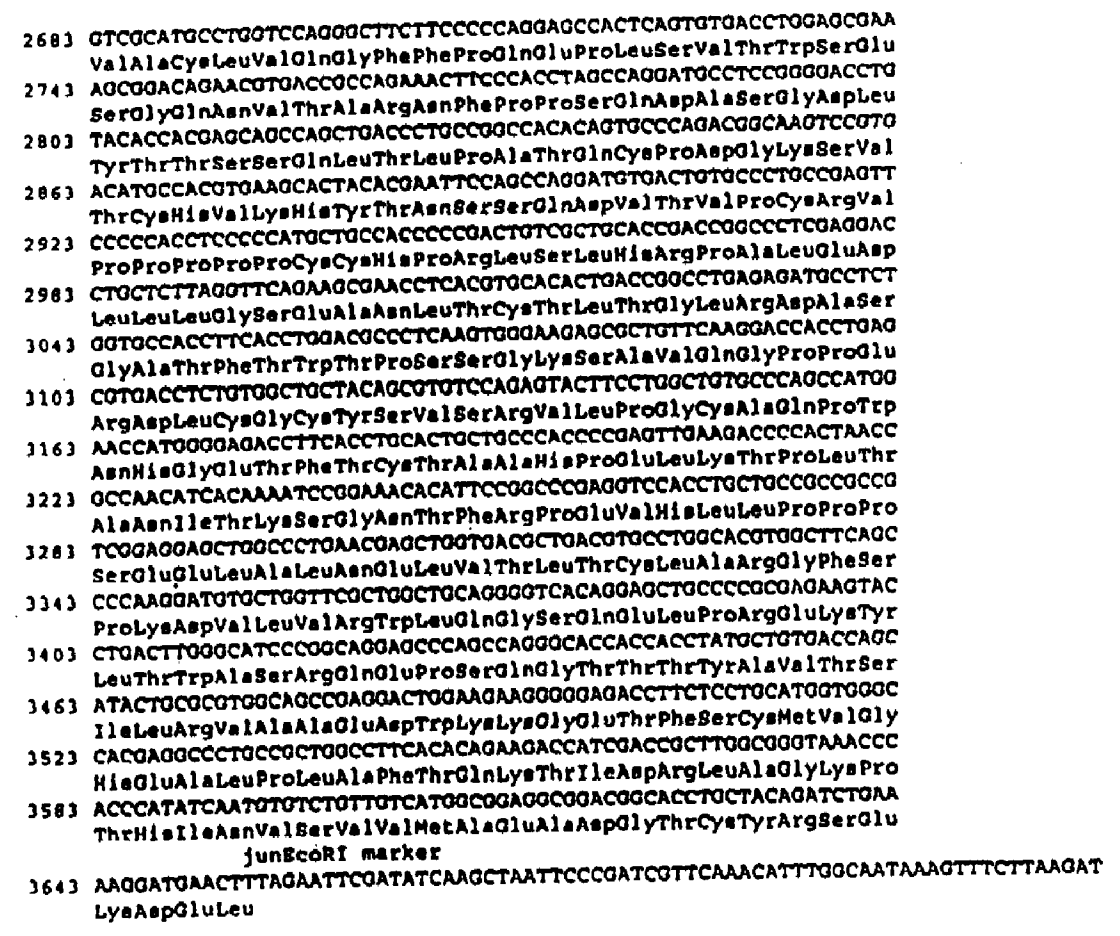
Figure 8E:
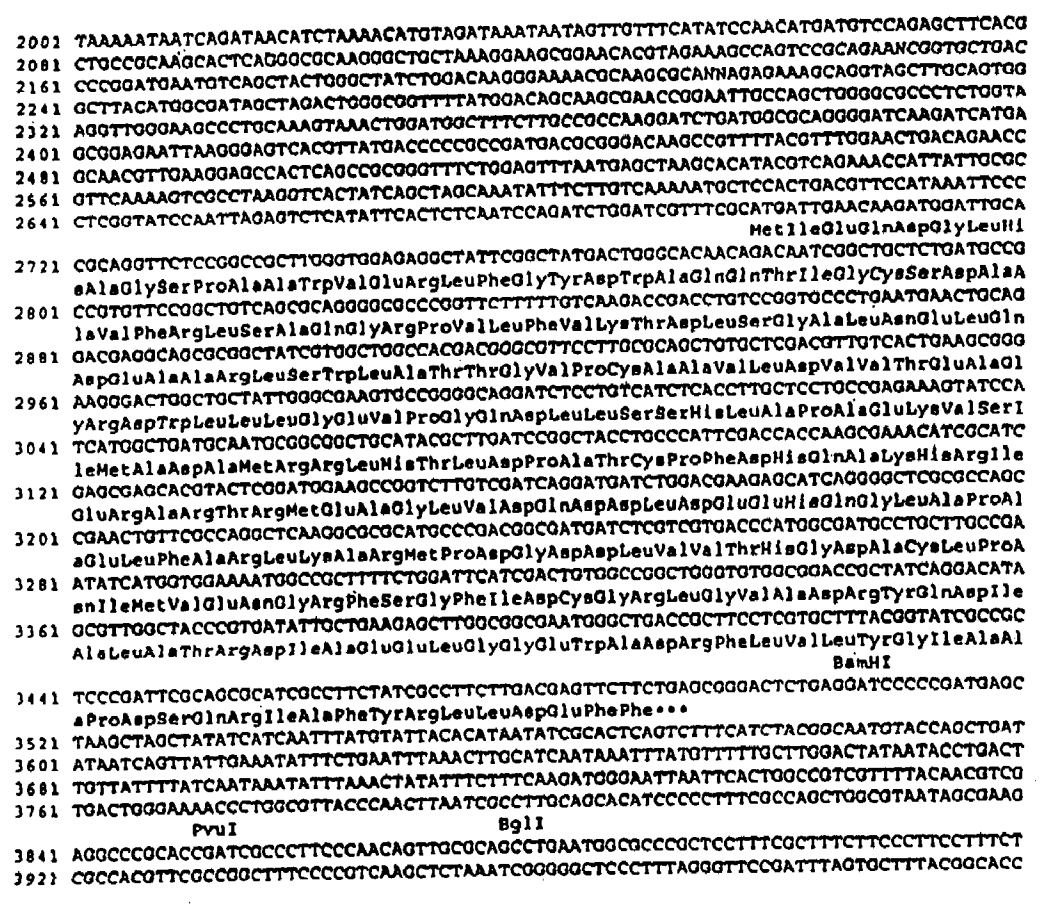
Figure 8F:
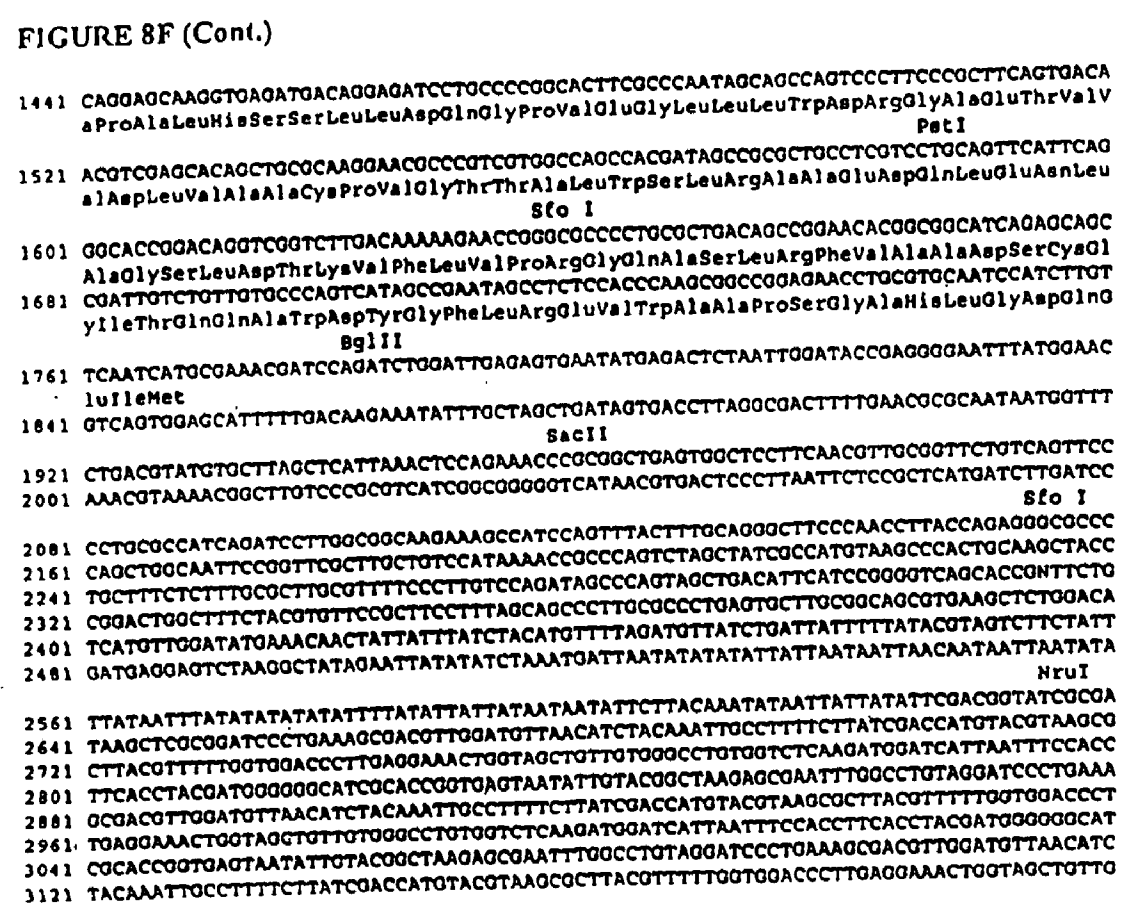
Figure 8F:
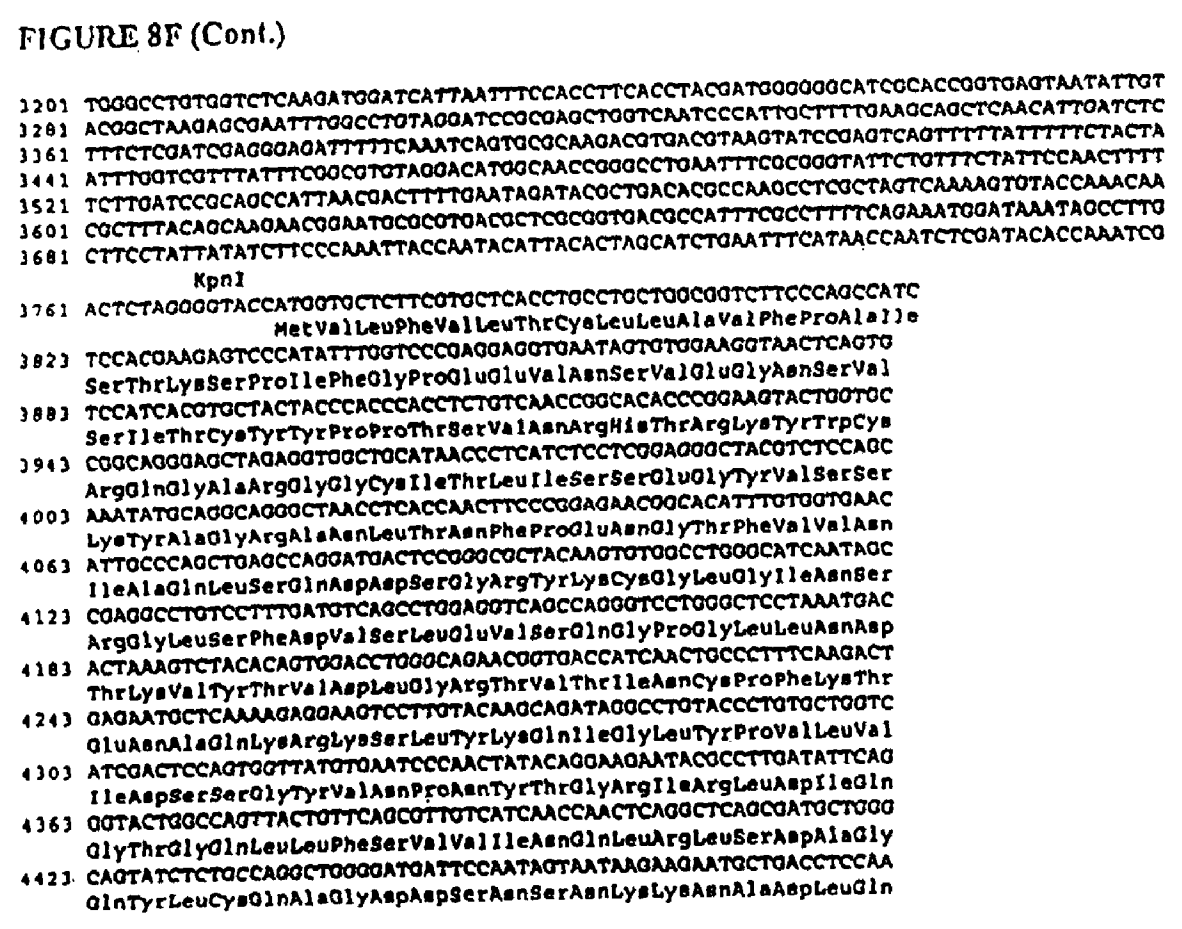
Figure 8F:
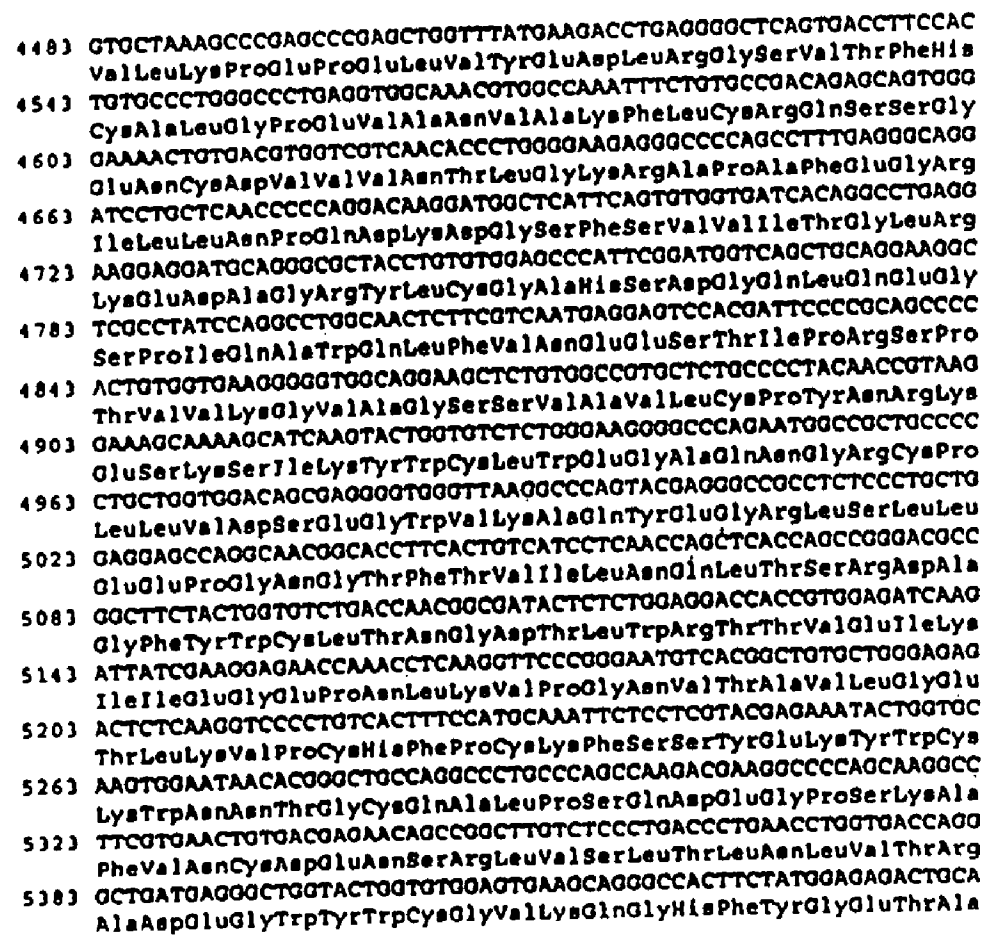

FIG. 8 shows the sequences of plasmids used to transform plants, as described in Example 2, for use in studies of the expression of immunoadhesins of the present invention.

FIG. 8 A shows the nucleotide [SEQ ID NO:9] and protein [SEQ ID NO:48] sequences for plasmids PSSpICAMHuA2.

FIG. 8 B shows the nucleotide and protein [SEQ ID NO:10] sequence for the bean legumin signal peptide.

FIG. 8 C shows the nucleotide [SEQ ID NO:11] and amino acid [SEQ ID NO:50] sequence of the protein coding region of pSHuJ.

FIG. 8 D shows the nucleotide [SEQ ID NO:12] and amino acid [SEQ ID NO:51] sequence of protein coding region of pSHuSC.

FIG. 8 E shows the nucleotide sequence [SEQ ID NO:13] of plasmid pBMSP-1.

FIG. 8 F shows the nucleotide sequence [SEQ ID NO:14] of plasmid pBMSP-1spJSC.

FIG. 9 contains nucleotide and protein sequences SEQ ID NO:1; SEQ ID NO:2; SEQ ID NO:3; SEQ ID NO:4; SEQ ID NO:5; SEQ ID NO:6; SEQ ID NO:7; SEQ ID NO:8, for ICAM-1, and human IgA2 and other nucleotide sequences.

DETAILED DESCRIPTION OF THE INVENTION

A. Definitions

As used herein, the following abbreviations and terms include, but are not necessarily limited to, the following definitions.

The practice of the present invention will employ, unless otherwise indicated, conventional techniques of immunology; molecular biology, microbiology, cell biology and recombinant DNA, which are within the skill of the art. See, e.g., Sambrook, et al., *Molecular Cloning: A Laboratory Manual*, 2nd edition (1989); *Current Protocols In Molecular Biology* (F. M. Ausubel, et al. eds., (1987)); the series *Methods In Enzymology* (Academic Press, Inc.); M. J. MacPherson, et al., eds. *Pcr 2: A Practical Approach* (1995); Harlow and Lane, eds, *Antibodies: A Laboratory Manual* (1988), and H. Jones, *Methods In Molecular Biology* vol. 49, "Plant Gene Transfer And Expression Protocols" (1995).

Immunoglobulin molecule or Antibody. A polypeptide or multimeric protein containing the immunologically active portions of an immunoglobulin heavy chain and immunoglobulin light chain covalently coupled together and capable of specifically combining with antigen. The immunoglobulins or antibody molecules are a large family of molecules that include several types of molecules such as IgD, IgG, IgA, secretory IgA (SIgA), IgM, and IgE.

Construct or Vector. An artificially assembled DNA segment to be transferred into a target plant tissue or cell. Typically, the construct will include the gene or genes of a particular interest, a marker gene and appropriate control sequences. The term "plasmid" refers to an autonomous, self-replicating extrachromosomal DNA molecule. In a preferred embodiment, the plasmid constructs of the present invention contain sequences coding for heavy and light chains of an antibody. Plasmid constructs containing suitable regulatory elements are also referred to as "expression cassettes." In a preferred embodiment, a plasmid construct can also contain a screening or selectable marker, for example an antibiotic resistance gene.

Selectable marker. A gene that encodes a product that allows the growth of transgenic tissue on a selective medium. Non-limiting examples of selectable markers include genes encoding for antibiotic resistance, e.g., ampicillin, kanamycin, or the like. Other selectable markers will be known to those of skill in the art.

Transgenic plant. Genetically engineered plant or progeny of genetically engineered plants. The transgenic plant usually contains material from at least one unrelated organism, such as a virus, another plant or animal.

Chimeric ICAM-1 molecule: The fusion of any combination of the extracellular domains 1, 2, 3, 4 and 5 of ICAM-1 with at least a part of an immunoglobulin heavy chain protein, made by linking ICAM-1 sequence upstream of an immunoglobulin heavy chain gene sequence and expressing the encoded protein from the construct.

Chimeric immunoglobulin heavy chain: An immunoglobulin derived heavy chain having at least a portion of its amino acid sequence derived from an immunoglobulin heavy chain of a different isotype or subtype or some other peptide, polypeptide or protein. Typically, a chimeric immunoglobulin heavy chain has its amino acid residue sequence derived from at least two different isotypes or subtypes of immunoglobulin heavy chain.

Dicotyledonous plants (dicots): Flowering plants whose embryos have two seed halves or cotyledons. Examples of dicots are: tobacco; tomato, the legumes including alfalfa; oaks; maples; roses; mints; squashes; daisies, walnuts; cacti; violets and buttercups.

Effective amount: An effective amount of an immunoadhesin of the present invention is sufficient to detectably inhibit rhinovirus infection, cytotoxicity or replication; or to reduce the severity or length of rhinovirus infection.

Human rhinovirus (HRV): A nonenveloped RNA virus representing a subgroup of picornavirus, that is a major cause of the common cold in humans. Rhinoviruses are described in Rhinoviruses, Reoviruses, and Parvoviruses, pp. 1057-1059, *Zinsser Microbiology*, Joklik et al., eds. Appleton and Lange (1992).

Immunoadhesin: A complex containing a chimeric ICAM-1 molecule, and optionally containing secretory component, and J chain.

Immunoglobulin heavy chain: A polypeptide that contains at least a portion of the antigen binding-domain of an immunoglobulin and at least a portion of a variable region of an immunoglobulin heavy chain or at least a portion of a constant region of an immunoglobulin heavy chain. Thus, the immunoglobulin derived heavy chain has significant regions of amino acid sequence homology with a member of the immunoglobulin gene superfamily. For example, the heavy chain in an Fab fragment is an immunoglobulin-derived heavy chain.

Immunoglobulin light chain: A polypeptide that contains at least a portion of the antigen binding domain of an immunoglobulin and at least a portion of the variable region or at least a portion of a constant region of an immunoglobulin light chain. Thus, the immunoglobulin-derived light chain has significant regions of amino acid homology with a member of the immunoglobulin gene superfamily.

Immunoglobulin molecule: A protein containing the immunologically-active portions of an immunoglobulin heavy chain and immunoglobulin light chain covalently coupled together and capable of specifically combining with antigen.

ICAM-1: Intercellular adhesion molecule-1. In humans, ICAM-1 functions as the receptor for human rhinovirus.

J chain: A polypeptide that is involved in the polymerization of immunoglobulins and transport of polymerized immunoglobulins through epithelial cells. See, *The Immunoglobulin Helper: The J Chain in Immunoglobulin Genes*, at pg. 345, Academic Press (1989). J chain is found in pentameric IgM and dimeric IgA and typically attached via disulphide bonds; J chain has been studied in both mouse and human.

Monocotyledonous plants (monocots): Flowering plants whose embryos have one cotyledon or seed leaf. Examples of monocots are: lilies; grasses; corn; grains, including oats, wheat and barley, orchids; irises; onions and palms.

Glycosylation: The modification of a protein by oligosaccharides. See, Marshall, *Ann. Rev. Biochem.*, 41:673 (1972) and Marshall, *Biochem. Soc. Symp.*, 40:17 (1974) for a general review of the polypeptide sequences that function as glycosylation signals. These signals are recognized in both mammalian and in plant cells.

Plant-specific glycosylation: The glycosylation pattern found on plant-expressed proteins, which is different from that found in proteins made in mammalian or insect cells. Proteins expressed in plants or plant cells have a different pattern of glycosylation than do proteins expressed in other types of cells, including mammalian cells and insect cells. Detailed studies characterizing plant-specific glycosylation and comparing it with glycosylation in other cell types have been performed by Cabanes-Macheteau et al., *Glycobiology* 9(4):365-372 (1999), Lerouge et al., *Plant Molecular Biology* 38:31-48 (1998) and Altmann, *Glycoconjugate J.* 14:643-646 (1997). Plant-specific glycosylation generates glycans that have xylose linked $\beta(1,2)$ to mannose. Neither mammalian nor insect glycosylation generate xylose linked $\beta(1,2)$ to mannose. Plants do not have a sialic acid linked to the terminus of the glycan, whereas mammalian cells do. In addition, plant-specific glycosylation results in a fucose linked $\alpha(1,3)$ to the proximal GlcNAc, while glycosylation in mammalian cells results in a fucose linked $\alpha(1,6)$ to the proximal GlcNAc.

Secretory component (SC): A component of secretory immunoglobulins that helps to protect the immunoglobulin against inactivating agents thereby increasing the biological effectiveness of secretory immunoglobulin. The secretory component may be from any mammal or rodent including mouse or human.

sICAM: A naturally-occurring soluble truncated form of ICAM-1 lacking both the hydrophobic transmembrane domain and the carboxy-terminal cytoplasmic domain of ICAM.

The articles, patents and patent applications cited in this document are incorporated into this document as if set forth in full.

B. Immunoadhesins Containing Chimeric ICAM Molecules

The present invention provides novel methods for producing immunoadhesin molecules containing chimeric ICAM molecules. The immunoadhesins of the present, invention contain chimeric ICAM-1 molecules made up of a rhinovirus receptor protein linked to a portion of an immunoglobulin heavy chain molecule in association with J chain and secretory component. The chimeric ICAM-1 molecules of the present invention contain two molecules derived from different sources: a rhinovirus receptor protein portion and an immunoglobulin chain portion. The rhinovirus receptor protein of the present invention is derived from the intercellular adhesion molecule 1 (ICAM-1). The nucleotide sequence for the human rhinovirus receptor ICAM-1 has been determined and characterized by Staunton, et al., *Cell* 52:925-933 (1988); Greve, et al. *Cell* 56:839-847 (1989); Greve, et al. *J. Virology* 65:6015-6023 (1991); Staunton, et al., *Cell*, 61:243-254 (1990) and described in Sequence ID No. 3 and GenBank accession no. M24283.

The ICAM-1 molecule is a membrane protein (SEQ ID NOS: 1 and 2) that has 5 extracellular domains, a hydrophobic transmembrane domain and a short cytoplasmic domain. These features have been described by Casasnovas, et al., *Proc. Natl. Acad. Sci. U.S.A.*, 95:413-44139 (1998) and Staunton, et al. *Cell* 52:925-933 (1988). Of particular use in the present invention are the domains of the ICAM-1 molecule that are responsible for the binding of human rhinoviruses which have been localized to the N-terminal domains 1 and 2 (Greve, et al., *J. Virol.*, 65:6015-6023 1991, and Staunton, et al., *Cell*, 61:243-245 1990. The present invention also contemplates rhinovirus receptor protein portions which include any combination of extracellular domains 1, 2, 3, 4, and 5 of the ICAM-1 molecule. In particular preferred embodiments, the rhinovirus receptor protein portion includes domains 1 and 2 of the ICAM-1 molecule and in other preferred embodiments domains 1, 2, 3; 4 and 5 of the ICAM-1 molecule are present.

The boundaries of the 5 extracellular domains are well known in the art and described in Staunton, et al., *Cell* 52:925-933 (1988). The approximated domain boundaries are shown in Table 1 below.

TABLE 1

| ICAM-1 Domains | Amino Acids |
|---|---|
| 1 | 1-88 |
| 2 | 89-105 |
| 3 | 106-284 |
| 4 | 285-385 |
| 5 | 386-453 |

As used in the present invention, the ICAM-1 domain 1 is from about residue 1 to about residue 88; domain 2 is from about residue 89 to about residue 105; domain 3 is from about residue 106 to about residue 284; domain 4 is from about residue 285 to about 385; and domain 5 is from about residue 386 to 453. One of skill in the art will understand that the exact boundaries of these domains may vary.

The chimeric ICAM-1 molecules of the present invention preferably contain at least a portion of an IgM or IgA heavy chain which allows that immunoglobulin heavy chain to bind to immunoglobulin J chain and thereby binds to the secretory component. It is contemplated that the portion of the chimeric ICAM-1 molecule derived from the immunoglobulin heavy chain of the present invention may be comprised of individual domains selected from the IgA heavy chain or the IgM heavy chain or from some other isotype of heavy chain. It is also contemplated that an immunoglobulin domain derived from an immunoglobin heavy chain other than IgA or IgM or from an immunoglobulin light chain may be molecularly engineered to bind immunoglobulin J chain and thus may be used to produce immunoglobulins of the present invention.

One skilled in the art will understand that immunoglobulins consist of domains which are approximately 100-110 amino acid residues. These various domains are well known in the art and have known boundaries. The removal of a single domain and its replacement with a domain of another antibody molecule is easily achieved with modern molecular biology. The domains are globular structures which are stabilized by intrachain disulfide bonds. This confers a discrete shape and makes the domains a self-contained unit that can be replaced or interchanged with other similarly shaped domains. The heavy chain constant region domains of the immunoglobulins confer various properties known as antibody effector functions on a particular molecule containing that domain. Example effector functions include complement fixation, placental transfer, binding to staphylococcal protein, binding to streptococcal protein G, binding to mononuclear cells, neutrophils or mast cells and basophils. The association of particular domains and particular immunoglobulin isotypes with these effector functions is well known and for example, described in Immunology, Roitt et al., *Mosby St. Louis, Mo.* (1993 3rd Ed.)

One of skill in the art will be able to identify immunoglobulin heavy chain constant region sequences. For example, a number of immunoglobulin DNA and protein sequences are available through GenBank. Table 2 shows the GenBank Accession numbers of immunoglobulin heavy chain genes and the proteins encoded by the genes. The sequences listed in Table 2 are shown in FIG. 7.

TABLE 2

| GENBANK ACCESSION NO. | HUMAN IMMUNOGLOBULIN SEQUENCE NAME | SEQ ID NO. |
| --- | --- | --- |
| J00220 | $Ig_{\alpha 1}$ Heavy Chain Constant Region Coding Sequence | 15 |
| J00220 | $Ig_{\alpha 1}$ Heavy Chain Constant Region Amino Acid Sequence | 16 |
| J00221 | $IgA_2$ Heavy Chain Constant Region Coding Sequence | 17 |
| J00221 | $IgA_2$ Chain Constant Region Amino Acid Sequence | 18 |
| J00228 | $Ig_{\gamma 1}$ Heavy Chain Constant Region Coding Sequence | 19 |
| J00228 | $Ig_{\gamma 1}$ Heavy Chain Constant Region Amino Acid Sequence | 20 |
| J00230 V00554 | $IgG_2$ Heavy Chain Constant Region Coding Sequence | 21 |
| J00230 V00554 | $IgG_2$ Heavy Chain Constant Region Amino Acid Sequence | 22 |
| X03604 M12958 | $IgG_3$ Heavy Chain Constant Region Coding Sequence | 23 |
| X03604 M12958 | $IgG_3$ Heavy Chain Constant Region Amino Acid Sequence | 24 |
| K01316 | $IgG_4$ Heavy Chain Constant Region Coding Sequence | 25 |
| K01316 | $IgG_4$ Heavy Chain Constant Region Amino Acid Sequence | 26 |
| K02876 | IgD Heavy Chain Constant Region Coding Sequence | 27 |
| K02876 | IgD Heavy Chain Constant Region Acid Sequence | 28 |
| K02877 | IgD Heavy Chain Constant Region Coding Sequence | 29 |
| K02877 | IgD Heavy Chain Constant Region Amino Acid Sequence | 30 |
| K02878 | Germline IgD Heavy Chain Coding Sequence | 31 |
| K02878 | Germline IgD Heavy Chain Amino Acid Sequence | 32 |
| K02879 | Germline IgD Heavy Chain C-δ-3 Domain Coding Sequence | 33 |
| K02879 | Germline IgD Heavy Chain C-δ-3 Amino Acid Sequence | 34 |
| K01311 | Germline IgD Heavy Chain J-δ Region: C-δ CH1 Amino Acid Sequence. | 35 |
| K02880 | Germline IgD Heavy Chain Gene, C-Region, Secreted Terminus Coding Sequence | 36 |
| K02880 | Germline IgD Heavy Chain Gene, C-Region, Secreted Terminus Amino Acid Sequence | 37 |
| K02881 | Germline IgD-Heavy Chain Gene, C-Region, First Domain of Membrane Terminus Coding Sequence | 38 |
| K02881 | Germline IgD-Heavy Chain Gene, C-Region, First Domain of Membrane Terminus Amino Acid Sequence | 39 |
| K02882 | Germline IgD Heavy Chain Coding Sequence | 40 |
| K02882 | Germline IgD Heavy Chain Amino Acid Sequence | 41 |
| K02875 | Germline IgD Heavy Chain Gene, C-Region, C-δ-1 Domain Coding Sequence | 42 |

TABLE 2-continued

| GENBANK ACCESSION NO. | HUMAN IMMUNOGLOBULIN SEQUENCE NAME | SEQ ID NO. |
|---|---|---|
| K02875 | Germline IgD Heavy Chain Gene, C-Region, C-δ-1 Domain Amino Acid Sequence | 43 |
| L00022 J00227 V00555 | IgE Heavy Chain Constant Region Coding Sequence | 44 |
| L00022 J00227 V00555 | IgE Heavy Chain Constant Region Amino Acid Sequence | 45 |
| X17115 | IgM Heavy Chain Complete Sequence Coding Sequence | 46 |
| X17115 | IgM Heavy Chain Complete Sequence mRNA | 47 |

The immunoadhesins of the present invention may, in addition to the chimeric ICAM-1 molecule, contain immunoglobulin light chains, or immunoglobulin 3 chain bound to the immunoglobulin derived heavy chains. In preferred embodiments, the immunoadhesin of the present invention comprises two or four chimeric ICAM-1 molecules and an immunoglobulin J chain bound to at least one of the chimeric ICAM-1 molecules. The J chain is described and known in the art. See, for example, M. Koshland, The Immunoglobulin Helper: The J Chain, in Immunoglobulin Genes, Academic. Press, London, pg. 345, (1989) and Matsuuchi et al., *Proc. Natl. Acad. Sci. U.S.A.*, 83:456-460 (1986). The sequence of the immunoglobulin J chain is available on various databases in the United States.

The immunoadhesin of the present invention may have a secretory component associated with the chimeric ICAM-1 molecule. This association may occur by hydrogen bonds, disulfide bonds, covalent bonds, ionic interactions or combinations of these various bonds. Typically, chimeric ICAM-1 molecules are held together by disulfide bonds between the molecules. The interaction of the chimeric ICAM-1 molecules may be non-covalent or disulfide bonding. The present invention contemplates the use of secretory component from a number of different species, including human, rat, rabbit, bovine and the like. The nucleotide sequences for these molecules are well known in the art. For example, U.S. Pat. No. 6,046,037 contains many of the sequences and this patent is incorporated herein by reference.

The immunoadhesins of the present invention containing the secretory component, the chimeric ICAM-1 molecule and J chain are typically bonded together by one of the following: hydrogen bonds, disulfide bonds, covalent bonds, ionic interactions or combinations of these bonds.

The present invention also contemplates immunoadhesins which comprise more than one chimeric ICAM-1 molecule. The immunoadhesin may contain chimeric ICAM-1 molecules that are monomeric units and not disulfide bonded to other chimeric ICAM-1 molecules. In preferred embodiments, the immunoadhesin does contain chimeric ICAM-1 molecules that are in association with other chimeric ICAM-1 molecules to form dimers and other multivalent molecules. Typically the chimeric ICAM-1 molecule is present as a dimer because of the association of the immunoglobulin portion of the chimeric molecule. The immunoglobulin portion of the chimeric ICAM-1 molecule allows the association of two chimeric ICAM-1 molecules to form a dimeric molecule having two active binding portions made up of the rhinovirus receptor protein portion. In preferred embodiments, dimerization occurs via the disulfide bonding regions that normally occur between the immunoglobulin domains as part of a naturally-occurring immunoglobulin molecule and the native immunoglobulin protein. One of skill in the art will understand that these disulfide bonds that are normally present in the native immunoglobulin molecule can be modified, moved and removed while still maintaining the ability to form a dimer of the chimeric ICAM-1 molecules.

In other preferred embodiments, the immunoadhesin contains multimeric forms of the chimeric ICAM-1 molecule due to the association of J chain with the immunoglobulin portion of the chimeric ICAM molecule. The association of J chain with the dimer of two chimeric ICAM-1 molecules allows the formation of tetrameric forms of the immunoadhesin in a preferred embodiment, the immunoglobulin portion of the chimeric ICAM-1 molecule is derived from the IgA molecule, and the addition of J chain allows the formation of a tetrameric complex containing four chimeric ICAM-1 molecules and four binding sites. In other preferred embodiments, the immunoglobulin heavy-chain portion of the chimeric molecule is derived from IgM and multivalent complexes containing ten or twelve molecules may be formed. In other preferred embodiments, in which the chimeric ICAM-1 molecule uses a chimeric immunoglobulin heavy-chain, the chimeric ICAM-1 molecule may form dimers or other higher order multivalent complexes through the domains from either IgA or IgM that are responsible for J chain binding. In other chimeric immunoglobulin molecules the portions of the immunoglobulin responsible for the disulfide bonding between the two immunoglobulin heavy-chains and/or the disulfide bonding between an immunoglobulin light-chain and heavy-chain may be placed in the chimeric immunoglobulin molecule to allow the formation of dimers or other high order multivalent complexes.

The present invention contemplates immunoadhesins containing a chimeric ICAM-1 molecule in which the immunoglobulin domains comprising the heavy chain are derived from different isotypes of either heavy or light chain immunoglobulins. One skilled in the art will understand that using molecular techniques, these domains can be substituted for a similar domain and thus produce an immunoglobulin that is a hybrid between two different immunoglobulin molecules. These chimeric immunoglobulins allow immunoadhesins containing secretory component to be constructed that contain a variety of different and desirable properties that are conferred by different immunoglobulin domains.

The present invention also contemplates chimeric ICAM-1 molecules in which the portion of the chimeric molecule derived from immunoglobulin, heavy or light J chain may contain less than an entire domain derived from a different immunoglobulin molecule. The same molecular techniques may be employed to produce such chimeric ICAM-1 molecules.

In preferred embodiments, the chimeric ICAM-1 molecules of the present invention contain at least the $C_H1$, $C_H2$, $C_H3$, domain of mouse or human $IgA_1$, $IgA_2$ or IgM. Other preferred embodiments of the present invention contain immunoglobulin domains that include at least the Cμ1, Cμ2, Cμ3, or Cμ4 domains of IgM.

Preferred chimeric ICAM-1 molecules contain domains from two different isotypes of human immunoglobulin. Preferred chimeric ICAM-1 molecules that include immunoglobulins that contain immunoglobulin domains including at least the $C_H1$, $C_H2$, or $C_H3$ of human IgG, IgG1, IgG2, IgG3, IgG4, IgA1, IgA2, IgE, or IgD. Other preferred immunoglobulins for use as part of chimeric ICAM-1 molecules include immunoglobulins that contain domains from at least the $C_H1$, $C_H2$, $C_H3$, or $C_H4$ domain of IgM or IgE. The present invention also contemplates chimeric ICAM-1 molecules that contain immunoglobulin domains derived from at least two different isotypes of mammalian immunoglobulins. Generally, any of the mammalian immunoglobulins can be used in the preferred embodiments, such as the following isotypes: any isotype of IgG, any isotype of IgA, IgE, IgD or IgM. The present invention also contemplates chimeric ICAM-1 molecules derived from a species such as human, mouse or other mammals. In preferred embodiments, the chimeric ICAM-1 molecule contains the portion of IgA or IgM responsible for the association of J chain with the IgA and IgM. Thus, by using a chimeric immunoglobulin in the chimeric ICAM-1 molecule, the J chain may associate with a chimeric immunoglobulin that is predominantly of an isotype that does not bind J chain or secretory component.

The present invention also contemplates chimeric ICAM-1 molecules that contain immunoglobulin domains derived from two different isotypes of rodent or primate immunoglobulin. The isotypes of rodent or primate immunoglobulin are well known in the art. The chimeric ICAM-1 molecules of the present invention may contain immunoglobulin derived heavy chains that include at least one of the following immunoglobulin domains: the $C_H1$, $C_H2$, or $C_H3$ domains of a mouse IgG, IgG1, IgG2a, IgG2b, IgG3, IgA, IgE, or IgD; the $C_H1$, $C_H2$, $C_H3$ or $C_H4$ domain of mouse IgE or IgM; the $C_H1$ domain of a human IgG, IgG1, IgG2, IgG3, IgG4, IgA1, IgA2, or IgD; the $C_H1$, $C_H2$, $C_H3$, $C_H4$ domain of human IgM or IgE; the $C_H1$, $C_H2$, or $C_H3$ domain of an isotype of mammalian IgG, an isotype of IgA, IgE, or IgD; the $C_H1$, $C_H2$, $C_H3$ or $C_H4$ domain of a mammalian IgE or IgM; the $C_H1$, $C_H2$, or $C_H3$ domain of an isotype of rodent IgG, IgA, IgE, or IgD; the $C_H1$, $C_H2$, $C_H3$ or $C_H4$ domain of a rodent IgE or IgM; the $C_H1$, $C_H2$, or $C_H3$ domain of an isotype of animal IgG, an isotype of IgA, IgE, or IgD; and the $C_H1$, $C_H2$, $C_H3$, or $C_H4$ domain of an animal IgE or IgM. The present invention also contemplates the replacement or addition of protein domains derived from molecules that are members of the immunoglobulin superfamily into the chimeric ICAM-1 molecules. The molecules that belong to the immunoglobulin superfamily have amino acid residue sequence and nucleic acid sequence homology to immunoglobulins. The molecules that are part of the immunoglobulin superfamily can be identified by amino acid or nucleic acid sequence homology. See, for example, p. 361 of Immunoglobulin Genes, Academic Press (1989).

In preferred embodiments of the present invention, the immunoadhesin is expressed by methods that generate an immunoadhesin having plant-specific glycosylation. It is well-known in the art that glycosylation is a major modification of proteins in plant cells (Lerouge et al., *Plant Molecular Biology* 38:31-48, 1998). Glycosylation of proteins also occurs in other cell types, including mammalian and insect cells. The glycosylation process starts in the endoplasmic reticulum by the co-translational transfer of a precursor oligosaccharide to specific residues of the nascent polypeptide chain. Processing of this oligosaccharide into different types of glycans, which differ in the types of residues present and the nature of the linkages between the residues, occurs in the secretory pathway as the glycoprotein moves from the endoplasmic reticulum to its final destination. One of skill in the art will understand that at the end of their maturation, proteins expressed in plants or plant cells have a different pattern of glycosylation than do proteins expressed in other types of cells, including mammalian cells and insect cells. Detailed studies characterizing plant-specific glycosylation and comparing it with glycosylation in other cell types have been performed, for example, in studies described by Cabanes-Macheteau et al., *Glycobiology* 9(4):365-372 (1999), and Altmann, *Glycoconjugate J.* 14:643-646 (1997). These groups and others have shown that plant-specific glycosylation generates glycans that have xylose linked β(1,2) to mannose, but xylose is not linked β(1,2) to mannose as a result of glycosylation in mammalian and insect cells. Plant-specific glycosylation results in a fucose linked α(1,3) to the proximal GlcNAc, while glycosylation in mammalian cells results in a fucose linked α(1,6) to the proximal GlcNAc. Furthermore, plant-specific glycosylation does not result in the addition of a sialic acid to the terminus of the protein glycan, whereas in glycosylation in mammalian cells, sialic acid is added.

The immunoadhesin of the present invention that is glycosylated in a plant-specific manner can contain a chimeric ICAM-1 molecule that includes any combination of extracellular domains 1, 2, 3, 4, and 5 of the ICAM-1 molecule. FIG. 2B shows the amino acid sequence of the chimeric ICAM-1/IgA2 molecule (SEQ ID NO: 8) of the present invention, that contains all five domains of ICAM-1. The bolded N's represent asparagine residues to which oligosaccharide moieties are linked during glycosylation in plant cells, as well as mammalian and insect cells. One of skill in the art will know that the glycosylation sites are the tripeptide Asn-X-Ser/Thr where X can be any amino acid except proline and aspartic acid (Kornfeld and Kornfeld, *Annu Rev Biochem* 54:631-664, 1985). It will therefore be known to one of skill in the art that which amino acids of the protein having plant-specific glycosylation would depend on which domains of ICAM-1 are present. Because the sequence and domain boundaries of ICAM-1 are known (see Staunton et. al., *Cell* 52:925-933, 1988), it would be evident to one of skill in the art how to determine the plant-specific glycosylation sites on any potential combination of any of the five ICAM-1 domains.

In other preferred embodiments of the present invention, the immunoadhesin having plant-specific glycosylation and containing a chimeric ICAM-1 molecule having any combination of ICAM-1 extracellular domains 1, 2, 3, 4 and 5 further comprises a J chain and secretory component associated with said chimeric ICAM-1 molecule. As was true, with respect to the chimeric ICAM-1 molecule, one of skill in the art will be able to identify the sites for plant-specific glycosylation in the J chain and secretory component sequences.

The present invention contemplates immunoadhesins having plant-specific glycosylation, that contain a chimeric ICAM-1 molecule in which the immunoglobulin heavy chain is selected from the group of IgA (SEQ ID NOS: 15-18), $IgA_1$ (SEQ ID NOS: 15-16), $IgA_2$ (SEQ ID NO: 17), $IgG_1$ (SEQ ID NOS: 19-20), $IgG_2$ (SEQ ID NOS: 21-22), $IgG_3$ (SEQ ID NOS: 23-24), $IgG_4$ (SEQ ID NOS: 25-26), IgM (SEQ ID NOS: 46-47), IgD (SEQ ID NO: 27-32 and 36-41-43), IgE (SEQ ID NOS: 44-45), and a chimeric immunoglobulin heavy chain. One of skill in the art will know that which of these heavy chain sequences, or which combination of immunoglobulin heavy chain sequences are combined in a chimeric immunoglobulin heavy chain, will have an effect on the number and location of glycosylation sites in the chimeric ICAM-1 molecule of the immunoadhesin. As was true with respect to the chimeric ICAM-1 molecule, one of skill in the art will be able to identify the sites for plant-specific glycosylation in the immunoglobulin heavy chain sequences, including the various chimeric immunoglobulin heavy chain sequences that can be constructed.

Also provided herein are immunoadhesin functional derivatives. By "functional derivative" is meant a "chemical derivative," "fragment," or "variant," of the polypeptide or nucleic acid of the invention which retains at least a portion of the function of the protein, for example reactivity with an antibody specific for the protein, enzymatic activity or binding activity, which permits its utility in accordance with the present invention. It is well known in the art that due to the degeneracy of the genetic code numerous different nucleic acid sequences can code for the same amino acid sequence. It is also well known in the art that conservative changes in amino acid can be made to arrive at a protein or polypeptide that retains the functionality of the original. In both cases, all permutations are intended to be covered by this disclosure.

The derivatives may also be engineered according to routine methods to include an affinity purification tag such that large quantities and/or relatively pure or isolated quantities of immunoadhesin may be produced. Many different versions of tag exist that can be incorporated into one or more components of the immunoadhesin, preferably not destroying the desired binding activity of the immunoadhesin in the absence of tag. Such tags can be engineered as expressible encoded nucleic acid sequence fused with nucleic acid sequences encoding the immunoadhesins of the invention. The tags may further be engineered to be removable, e.g., with a commercially available enzyme.

Further, it is possible to delete codons or to substitute one or more codons with codons other than degenerate codons to produce a structurally modified polypeptide, but one which has substantially the same utility activity as the polypeptide produced by the unmodified nucleic acid molecule. As recognized in the art, the two polypeptides can be functionally equivalent, as are the two nucleic acid molecules that give rise to their production, even though the differences between the nucleic acid molecules are not related to the degeneracy of the genetic code.

Manipulations of this sort, and post-production chemical derivatization may be implemented, e.g., to improve stability, solubility, absorption, biological or therapeutic effect, and/or biological half-life. Moieties capable of mediating such effects are disclosed, for example, in Remington's Pharmaceutical Sciences, 18th ed., Mack Publishing Co., Easton, Pa. (1990). A functional derivative intended to be within the scope of the present invention is a "variant" polypeptide which either lacks one or more amino acids or contains additional or substituted amino acids relative to the native polypeptide. The variant may be derived from a naturally occurring complex component by appropriately modifying the protein DNA coding sequence to add, remove, and/or to modify codons for one or more amino acids at one or more sites of the C-terminus, N-terminus, and/or within the native sequence. It is understood that such variants having added, substituted and/or additional amino acids retain one or more characterizing portions of the native protein, as described above.

A functional derivative of a protein with deleted, inserted and/or substituted amino acid residues may be prepared using standard techniques well-known to those of ordinary skill in the art. For example, the modified components of the functional derivatives may be produced using site-directed mutagenesis techniques (as exemplified by Adelman et. al., 1983, DNA 2.183) wherein nucleotides in the DNA coding sequence are modified such that a modified coding sequence is produced, and thereafter expressing this recombinant DNA in a prokaryotic or eukaryotic host cell, using techniques such as those described above. Alternatively, proteins with amino acid deletions, insertions and/or substitutions may be conveniently prepared by direct chemical synthesis, using methods well-known in the art. The functional derivatives of the proteins typically exhibit the same qualitative biological activity as the native proteins.

In addition, the immunoadhesins of the invention may be not just modified ICAM-1/Ig immunoadhesins, but may also embrace other native ICAM family members, isotypes, and/or other homologous amino acid sequences, e.g. human, primate, rodent, canine, feline, bovine, avian, etc. Furthermore, the Ig type used in the immunoadhesins can vary, e.g., may assume a different Ig family member identity, within or without a given species. ICAMs and Igs are diverse and have well-known sequences that one of ordinary skill can exploit to create different immunoadhesins having more or less different utility in a given organism to undergo treatment. An illustrative, nonexhaustive list of examples of molecules having ICAM-1 homology that can be used to create other immunoadhesins include those in the following table.

TABLE 3

| ACCESSION NO. | ICAM NAME | SPECIES |
|---|---|---|
| NP 000192 | Intercellular Adhesion Molecule-1 (CD54) | Homo sapiens |
| AAH03097 | Intercellular Adhesion Molecule ICAM-2 | Homo sapiens |
| NP 002153 | Intercellular Adhesion Molecule 3 Precursor | Homo sapiens |
| BAB20325 | TCAM-1 | Homo sapiens |
| NP 003250 | Intercellular Adhesion Molecule 5 (Telencephalin) | Homo sapiens |
| NM 007164 | Mucosal Vascular Address in Cell Adhesion Molecule (MADCAM1) | Homo sapiens |
| NM 001078 | Vascular Cell Adhesion Molecule 1 (VCAM1) | Homo sapiens |
| AAA37875 | MALA-2 | Mus musculus |
| AAA37876 | Intercellular Adhesion Molecule-1 Precursor | Mus musculus |
| AAG30280 | Intracellular Adhesion Molecule 1 | Cricetulus griseus |
| AAB39264 | Intercellular Adhesion Molecule-3 | Bos taurus |
| AAF80287 | Intercellular Adhesion Molecule-1 Precursor | Sus scrofa |
| AAA18478 | Telecephalin | Oryctolagus cuniculus |
| NP 032345 | Intercellular Adhesion Molecule 5, telencephalin | Mus musculus |
| BAB41106 | Cell adhesion molecule TCAM-1 | Mus musculus |

TABLE 3-continued

| ACCESSION NO. | ICAM NAME | SPECIES |
| --- | --- | --- |
| NP 067705 | Testicular Cell Adhesion Molecule 1 | *Rattus norvegicus* |
| AAG35584 | Nectin-Like Protein 1 | *Mus musculus* |
| AAC18956 | CD22 Protein | *Homo sapiens* |
| AAA35415 | Intercellular Adhesion Molecule 1 | *Pan troglodytes* |
| AAA83206 | 89 kDa Protein | *Mus musculus* |
| AAA92551 | Intercellular Adhesion Molecule-1 | *Canis familiaris* |
| AAB06749 | Intercellular Adhesion Molecule-1 | *Bos taurus* |
| AAD13617 | Intercellular Adhesion Molecule-1 Precursor | *Ovis aries* |
| NP 037099 | Intercellular Adhesion Molecule-1 | *Rattus norvegicus* |
| AAE22202 | ICAM-4 | *Rattus norvegicus* |
| AAA60392 | cell surface glycoprotein | *Homo sapiens* |
| AAF91086 | nephrin | *Rattus norvegicus* |
| AAF91087 | nephrin | *Mus musculus* |

Likewise, numerous heavy chain constant regions of different Ig molecules, both in humans and other species, are known that can be substituted in for those specific Ig regions of the chimeras described herein.

C. Vectors, Cells and Plants Containing Immunoadhesins

The present invention also contemplates expression and cloning vectors, cells and plants containing the immunoadhesins of the present invention. Technology for isolating the genes encoding the various portions of the immunoadhesins are well-known to one of skill in the art and can be applied to insert the various required genes into expression vectors and cloning vectors such as those vectors can be introduced into cells and into transgenic plants.

The present invention contemplates a method of assembling an immunoadhesin comprising the steps of: introducing into an organism a DNA segment encoding a chimeric ICAM-1 molecule, immunoglobulin J chain, and introducing into the same organism a DNA encoding a secretory component. The preferred secretory component contains at least a segment of the amino acid residues 1 to residue about 606 of the human polyimmunoglobulin receptor (pIgR) amino acid residue sequence or analogous amino acid residues from other species (Mostov, *Ann Dev. Immu.* 12:63-84-1994).

The present invention contemplates eukaryotic cells, including plant cells, containing immunoadhesins of the present invention. The present invention also contemplates plant cells that contain nucleotide sequences encoding the various components of the immunoadhesin of the present invention. One skilled in the art will understand that the nucleotide sequences that encode the secretory component protection protein and the chimeric ICAM-1 molecule and J chain will typically be operably linked to a promoter and present as part of an expression vector or cassette. Typically, if the eukaryotic cell used is a plant cell than the promoter used will be a promoter that is able to operate in a plant cell. After the chimeric ICAM-1 genes, secretory component genes and J chain genes are isolated, they are typically operatively linked to a transcriptional promoter in an expression vector. The present invention also contemplates expression vectors containing a nucleotide sequence encoding a chimeric ICAM-1 molecule which has been operatively linked to a regulatory sequence for expression. These expression vectors place the nucleotide sequence to be expressed in a particular cell 3' of a promoter sequence which causes the nucleotide sequence to be transcribed and expressed. The expression vector may also contain various enhancer sequences which improve the efficiency of this transcription.

In addition, such sequences as terminators, polyadenylation (poly A) sites and other 3' end processing signals may be included to enhance the amount of nucleotide sequence transcribed within a particular cell.

Expression of the components in the organism of choice can be derived from an independently replicating plasmid, or from a permanent component of the chromosome, or from any piece of DNA which may transiently give rise to transcripts encoding the components. Organisms suitable for transformation can be either prokaryotic or eukaryotic. Introduction of the components of the complex can be by direct DNA transformation, by biolistic delivery into the organism, or mediated by another organism as for example by the action of recombinant *Agrobacterium* on plant cells. Expression of proteins in transgenic organisms usually requires co-introduction of an appropriate promoter element and polyadenylation signal. In one embodiment of the invention, the promoter element potentially results in the constitutive expression of the components in all of the cells of a plant. Constitutive expression occurring in most or all of the cells will ensure that precursors can occupy the same cellular endomembrane system as might be required for assembly to occur.

Expression vectors compatible with the host cells, preferably those compatible with plant cells are used to express the genes of the present invention. Typical expression vectors useful for expression of genes in plants are well known in the art and include vectors derived from the tumor-inducing (Ti) plasmid of *Agrobacterium tumefaciens* described by Rogers et al., *Meth. in Enzymol.*, 153:253-277 (1987). However, several other expression vector systems are known to function in plants. See for example, Verma et al., PCT Publication No. WO87/00551; and Cocking and Davey, *Science,* 236:1259-1262 (1987).

The expression vectors described above contain expression control elements including the promoter. The genes to be expressed are operatively linked to the expression vector to allow the promoter sequence to direct RNA polymerase binding and synthesis of the desired polypeptide coding gene. Useful in expressing the genes are promoters which are inducible, viral, synthetic, constitutive, and regulated. The choice of which expression vector is used and ultimately to which promoter a nucleotide sequence encoding part of the immunoadhesin of the present invention is operatively linked depends directly, as is well known in the art, on the functional properties desired, e.g. the location and timing of protein expression, and the host cell to be transformed, these being limitations inherent in the art of constructing recombinant DNA molecules. However, an expression vector useful in practicing the present invention is at least capable of directing the replication, and preferably also the expression of the polypeptide coding gene included in the DNA segment to which it is operatively linked.

In preferred embodiments, the expression vector used to express the genes includes a selection marker that is effective in a plant cell, preferably a drug resistance selection marker. A preferred drug resistance marker is the gene whose expression results in kanamycin resistance, i.e., the chimeric gene containing the nopaline synthase promoter, Tn5 neomycin phosphotransferase II and nopaline synthase 3' nontranslated region described by Rogers et al., in *Methods For Plant Molecular Biology*, a Weissbach and H. Weissbach, eds., Academic Press Inc., San Diego, Calif. (1988). A useful plant expression vector is commercially available from Pharmacia, Piscataway, N.J. Expression vectors and promoters for expressing foreign proteins in plants have been described in U.S. Pat. Nos. 5,188,642; 5,349,124; 5,352,605, and 5,034,322 which are hereby incorporated by reference.

A variety of methods have been developed to operatively link DNA to vectors via complementary cohesive termini. For instance, complementary homopolymer tracks can be added to the DNA segment to be inserted into the vector DNA. The vector and DNA segment are then joined by hydrogen bonding between the complementary homopolymeric tails to form recombinant DNA molecules. Alternatively, synthetic linkers containing one or more restriction endonuclease sites can be used to join the DNA segment to the expression vector. The synthetic linkers are attached to blunt-ended DNA segments by incubating the blunt-ended DNA segments with a large excess of synthetic linker molecules in the presence of an enzyme that is able to catalyze the ligation of blunt-ended DNA molecules, such as bacteriophage T4 DNA ligase. Thus, the products, of the reaction are DNA segments carrying synthetic, liner sequences at their ends. These DNA segments are then cleaved with the appropriate restriction endonuclease and ligated into an expression vector that has been cleaved with an enzyme that produces term compatible with those of the synthetic linker. Synthetic linkers containing a variety of restriction endonuclease sites are commercially available from a number of sources including New England BioLabs, Beverly, Mass.

The nucleotide sequences encoding the secretory component, 3 chain, the chimeric ICAM-1 molecules of the present invention are introduced into the same plant cell either directly or by introducing each of the components into a plant cell and regenerating a plant and cross-hybridizing, the various components to produce the final plant cell containing all the required components.

Any method may be used to introduce the nucleotide sequences encoding the components of the immunoadhesins of the present invention into a eukaryotic cell. For example, methods for introducing genes into plants include *Agrobacterium*-mediated transformation, protoplast transformation; gene transfer into pollen, injection into reproductive organs and injection into immature embryos. Each of these methods has distinct advantages and disadvantages. Thus, one particular method of introducing genes into a particular eukaryotic cell or plant species may not necessarily be the most effective for another eukaryotic cell or plant species.

*Agrobacterium* tumefaciens-mediated transfer is a widely applicable system for introducing genes into plant cells because the DNA can be introduced into whole plant tissues, bypassing the need for regeneration of an intact plant from a protoplast. The use of *Agrobacterium*-mediated expression vectors to introduce DNA into plant cells is well known in the art. See, for example, the methods described by Fraley et al., *Biotechnology,* 3:629 (1985) and Rogers et al., *Methods in Enzymology,* 153:253-277 (1987). Further, the integration of the Ti-DNA is a relatively precise process resulting in few rearrangements. The region of DNA to be transferred is defined by the border sequences and intervening DNA is usually inserted into the plant genome as described by Spielmann et al., *Mol. Gen. Genet.,* 205:34 (1986) and Jorgensen et al., *Mol. Gen. Genet.,* 207:471 (1987). Modern *Agrobacterium* transformation vectors are capable of replication in *Escherichia coli* as well as *Agrobacterium*, allowing for convenient manipulations as described by Klee et al., in *Plant DNA Infectious Agents*, T. Hohn and J. Schell, eds., Springer-Verlag, New York, pp. 179-203 (1985). Further recent technological advances in vectors for *Agrobacterium*-mediated gene transfer have improved the arrangement of genes and restriction sites in the vectors to facilitate construction of vectors capable of expressing various polypeptide coding genes. The vectors described by Rogers et al., *Methods in Enzymology,* 153:253 (1987), have convenient multi-linker regions flanked by a promoter and a polyadenylation site for direct expression of inserted polypeptide coding genes and are suitable for present purposes.

In those plant species where *Agrobacterium*-mediated transformation is efficient, it is the method of choice because of the facile and defined nature of the gene transfer. *Agrobacterium*-mediated transformation of leaf disks and other tissues appears to be limited to plant species that *Agrobacterium tumefaciens* naturally infects. Thus, *Agrobacterium*-mediated transformation is most efficient in dicotyledonous plants.

Few monocots appear to be natural hosts for *Agrobacterium*, although transgenic, plants have been produced in asparagus using *Agrobacterium* vectors as described by Bytebier et al., *Proc. Natl. Acad. Sci. U.S.A.,* 84:5345 (1987). Therefore, commercially important cereal grains such as rice, corn, and wheat must be transformed using alternative methods. Transformation of plant protoplasts can be achieved using methods based on calcium phosphate precipitation, polyethylene glycol treatment, electroporation, and combinations of these treatments. See, for example, Potrykus et al., *Mol. Gen. Genet.,* 199:183 (1985); Lorz et al., *Mol. Gen. Genet.,* 199:178 (1985); Fromm et al., *Nature,* 319:791 (1986); Uchimiya et al., *Mol. Gen. Genet.,* 204:204 (1986); Callis et al., *Genes and Development,* 1:1183 (1987); and Marcotte et al., *Nature,* 335:454 (1988).

Application of these methods to different plant species depends upon the ability to regenerate that particular plant species from protoplasts. Illustrative methods for the regeneration of cereals from protoplasts are described in Fujimura et al., *Plant Tissue Culture Letters,* 2:74 (1985); Toriyama et al., *Theor Appl. Genet.,* 73:16 (1986); Yamada et al., *Plant Cell Rep.,* 4:85 (1986); Abdullah et al., *Biotechnology,* 4:1087 (1986).

To transform plant species that cannot be successfully regenerated from protoplasts, other ways to introduce DNA into intact cells or tissues can be utilized. For example, regeneration of cereals from immature embryos or explants can be effected as described by Vasil, *Biotechnology,* 6:397 (1988). In addition, "particle gun" or high-velocity microprojectile technology can be utilized. Using such technology, DNA is carried through the cell wall and into the cytoplasm on the surface of small (0.525 μm) metal particles that have been accelerated to speeds of one to several hundred meters per second as described in Klein et al., *Nature,* 327:70 (1987); Klein et al., *Proc. Natl. Acad. Sci. USA.,* 85:8502 (1988); and McCabe et al., *Biotechnology,* 6:923 (1988). The metal particles penetrate through several layers of cells and thus allow the transformation of cells within tissue explants. Metal particles have been used to successfully transform corn cells and to produce fertile, stably transformed tobacco and soybean plants. Transformation of tissue explants eliminates the need for passage through a protoplast stage and thus speeds the production of transgenic plants.

DNA can also be introduced into plants by direct DNA transfer into pollen as described by Zhou et al., *Methods in Enzymology*, 101:433 (1983); D. Hess, *Intern Rev. Cytol.*, 107:367 (1987); Luo et al., *Plant Mol. Biol. Reporter*, 6:165 (1988). Expression of polypeptide coding genes can be obtained by injection of the DNA into reproductive organs of a plant as described by Pena et al., *Nature*, 325:274 (1987). DNA can also be injected directly into the cells of immature embryos and the rehydration of desiccated embryos as described by Neuhaus et al., *Theor. Appl. Genet.*, 75:30 (1987); and Benbrook et al., in *Proceedings Bio Expo 1986*, Butterworth, Stoneham, Mass., pp. 27-54 (1986).

The regeneration of plants from either single plant protoplasts or various explants is well known in the art. See, for example, Methods for Plant Molecular Biology, A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil.

The regeneration of plants containing the foreign gene introduced by *Agrobacterium* tumefaciens from leaf explants can be achieved as described by Horsch et al., *Science*, 227: 1229-1231 (1985). In this procedure, transformants are grown in the presence of a selection agent and in a medium that induces the regeneration of shoots in the plant species being transformed as described by Fraley et al., *Proc. Natl. Acad. Sci. U.S.A.*, 80:4803 (1983). This procedure typically produces shoots within two to four weeks and these transformant shoots are then transferred to an appropriate root-inducing medium containing the selective agent and an antibiotic to prevent bacterial growth. Transformant shoots that rooted in the presence of the selective agent to form plantlets are then transplanted to soil to allow the production of roots. These procedures will vary depending upon the particular plant species employed, such variations being well known in the art.

The immunoadhesins of the present invention may be produced in any plant cell including plant cells derived from plants that are dicotyledonous or monocotyledonous, solanaceous, alfalfa, legumes, or tobacco.

Transgenic plants of the present invention can be produced from any sexually crossable plant species that can be transformed using any method known to those skilled in the art. Useful plant species are dicotyledons including tobacco, tomato, the legumes, alfalfa, oaks, and maples; monocotyledons including grasses, corn, grains, oats, wheat, and barley; and lower plants including gymnosperms, conifers, horsetails, club mosses, liverworts, hornworts, mosses, algaes, gametophytes, sporophytes or pteridophytes.

The present invention also contemplates expressing the immunoadhesins within eukaryotic cells including mammalian cells. One of skill in the art will understand the various systems available for expression of the immunoadhesin in mammalian cells and can readily modify those system to express the immunoadhesins and chimeric ICAM-1 molecules of the present invention in those cells. In preferred embodiments, the chimeric ICAM-1, J chain and secretory component molecules of the present invention are placed in a vector pCDM8 which has been previously described by Aruffo, et al, *Proc. Natl. Acad. Sci. U.S.A.*, 84:8573-8577 (1987). The use of the PCDM8 construct is by no means unique and numerous other systems are available that do not utilize the cog cell expression-system. For example, the following United States Patents describe useful eukaryotic expression systems that may be used with the chimeric ICAM-1 and other molecules of the immunoadhesin.

D. Compositions Containing Immunoadhesins

The present invention also contemplates compositions containing an immunoadhesin of the present invention together with plant macromolecules or material. Typically these plant macromolecules or plant materials are derived from any plant useful in the present invention. The plant macromolecules are present together with an immunoadhesin of the present invention for example, in a plant cell, in an extract of a plant cell, or in a plant. Typical plant macromolecules associated with the immunoadhesin of the present invention in a composition are ribulose bisphosphate carboxylase, light harvesting complex pigments (LHCP), secondary metabolites or chlorophyll. The compositions of the present invention have plant material or plant macromolecules in a concentration of between 0.01% and 99% mass excluding water. Other compositions include compositions having the immunoadhesins of the present invention present at a concentration of between 1% and 99% mass excluding water. Other compositions include immunoadhesins at a concentration of 50% to 90% mass excluding water.

The compositions of the present invention may contain plant macromolecules at a concentration of between 0.1% and 5% mass excluding water. Typically the mass present in the composition will consist of plant macromolecules and immunoadhesins of the present invention. When the immunoadhesins of the present invention are present at a higher or lower concentration the concentration of plant macromolecules present in the composition will vary inversely. In other embodiments the composition of plant macromolecules are present in a concentration of between 0.12% and 1% mass excluding water.

The present invention contemplates a composition of matter comprising all or part of the following: a chimeric ICAM-1 molecule, a J chain or a secretory component. These components form a complex and are associated as was previously described. Typically, the composition also contains molecules derived from a plant. This composition may also be obtained after an extraction process yielding functional immunoadhesin and plant-derived molecules.

The extraction method comprises the steps of applying a force to a plant containing the complex whereby the apoplastic compartment of the plant is ruptured releasing said complex. The force involves shearing as the primary method of releasing the apoplastic liquid.

The whole plant or plant extract contains an admixture of immunoadhesin and various other macromolecules of the plant. Among the macromolecules contained in the admixture is ribulose bisphosphate carboxylase (RuBisCo) or fragments of RuBisCo. Another macromolecule is LHCP. Another molecule is chlorophyll.

Other useful methods for preparing compositions containing immunoadhesins having chimeric ICAM-1 molecule include extraction with various solvents and application of vacuum to the plant material. The compositions of the present invention may contain plant macromolecules in a concentration of between about 0.1% and 5% mass excluding water.

The present invention also contemplates therapeutic compositions which may be used in the treatment of a patient or animal. Administration of the therapeutic composition can be before or after extraction from the plant or other transgenic organism. Once extracted the immunoadhesins may also be further purified by conventional techniques such as size exclusion, ion exchange, or affinity chromatography. Plant molecules may be co-administered with the complex.

The present invention also contemplates that the relative proportion of plant-derived molecules and animal-derived molecules can vary. Quantities of specific plant proteins, such as RuBisCo or chlorophyll may be as little as 0.01% of the mass or as much as 99.9% of the mass of the extract, excluding water.

The present invention also contemplates the direct use of the therapeutic plant extract containing immunoadhesins without any further purification of the specific therapeutic component. Administration may be by topical application, oral ingestion, nasal spray or any other method appropriate for delivering the antibody to the mucosal target pathogen.

E. Pharmaceutical Compositions, Formulations, and Routes of Administration

The immunoadhesins described herein can be administered to a patient, preferably in the form of a suitable pharmaceutical composition. Such composition may include components in addition to, or in lieu of, those described above. The composition preferably exhibits either or both of a therapeutic and prophylactic property when administered. The preparation of such compositions can be done according to routine methodologies in the art, and may assume any of a variety of forms, e.g., liquid solutions, suspensions or emulsifications, and solid forms suitable for inclusion in a liquid prior to ingestion. Techniques for the formulation and administration of polypeptides and proteins may be found in *Remington's Pharmaceutical Sciences*, Mack Publishing Co., Easton, Pa., latest edition. Using these procedures, one of ordinary skill can utilize the immunoadhesins of the invention to achieve success without undue experimentation.

1. Administration Routes

Suitable routes of administration for the invention include, e.g., oral, nasal, inhalation, intraocular, phanyngeal, bronchial, transmucosal, or intestinal administration. Alternatively, one may administer the compound in a local manner, e.g., via injection or other application of the compound to a preferred site of action.

2. Formulations

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes. One or more physiologically acceptable carriers comprising excipients and/or other auxiliaries can be used to facilitate processing of the active compounds into pharmaceutical preparations. Proper formulation is dependent upon the particular route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Suitable carriers include excipients such as, e.g., fillers such as sugars, including lactose, sucrose, mannitol, and/or sorbitol; cellulose preparations such as, e.g., maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentations from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Alternatively, the active ingredient may be in powder form for constitution with a suitable vehicle, e.g. sterile pyrogen-free water, before use.

In addition, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutically compatible salts may be formed with many acids, including but not limited to hydrochloric, sulfuric, acetic, lactic, tartaric, malic, succinic, citric, etc. Salts tend to be more soluble in aqueous or other protonic solvents that are the corresponding free base forms. In solutions, manipulation of pH is also routinely employed for optimizing desired properties.

3. Determining Effective Dosages and Dosage Regimens

Pharmaceutical compositions suitable for use in the present invention include compositions where the active ingredients are contained in an amount effective to achieve an intended purpose, e.g., a therapeutic and/or prophylactic use. A pharmaceutically effective amount means an amount of compound effective to prevent, alleviate or ameliorate symptoms of disease or prolong the survival of the subject being treated. Determination of a pharmaceutically effective amount is well within the capability of those skilled in the art, and will typically assume an amount of between about 0.5 tag/kg/day and about 500 g/kg/day, with individual dosages typically comprising between about 1 nanogram and several grams of immunoadhesin.

For any compound used in the methods of the invention, the therapeutically effective dose can be estimated initially from cell culture assays. For example, varying dosages can be administered to different animals or cell cultures and compared for effect. In this way, one can identify a desired concentration range, and prepare and administer such amount accordingly. Optimization is routine for one of ordinary skill in the art.

The person of skill, in addition to considering pharmaceutical efficacy, also considers toxicity according to standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio between LD50 and ED50. Compounds which exhibit high therapeutic indices are preferred. The data obtained from these cell culture assays and animal studies can be used in formulating a range of dosage for use in humans. The dosage of such compounds lies preferably within a range of concentrations that include the ED50 with little or no toxicity. The dosage may vary within this range depending upon the dosage form employed and the route of administration utilized. The exact formulation, route of administration and dosage can be chosen by the individual physician in view of the patient's condition. (See e.g., Fingl et al., 1975, in "*The Pharmacological Basis of Therapeutics*," Ch. 1 p. 1).

Dosage amount and frequency may be adjusted to provide mucosal levels of immunoadhesin sufficient to maintain or provide a pharmaceutical effect, e.g., therapeutic and/or prophylactic. The minimal effective concentration (MEC) will vary for each immunoadhesin and immunoadhesin formulation, but can be estimated from in vitro and/or in vivo data. Dosages necessary to achieve MEC will depend on individual characteristics and route of administration. However, assays as described herein can be used to determine mucosal concentrations, which can then be further optimized in amount and precise formulation.

Dosage intervals can also be determined using MEC value. Compounds can be administered using a regimen which maintains mucosal levels above the MEC for 10-90% of the time, 30-90% of the time, or, most preferably, 50-90% of the time.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the immunoadhesin for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition, e.g. treatment or prophylaxis of a disease mediated by host organism/patient ICAM molecules.

F. Methods of Treatment and Prevention of ICAM-mediated Afflictions

A patient in need of therapeutic and/or prophylactic immunoadhesin chimeras of the invention, e.g., to counter rhinovirus infection and/or symptoms such as occur with colds, can be administered a pharmaceutically effective amount of desired immunoadhesin, preferably as part of a pharmaceutical composition determined, produced, and administered as described above. These formulations and delivery modalities can vary widely. Described following are preliminary procedures that can be used to deduce effective amounts and toxicity, and which can then be conveniently used to determine treatment and prophylaxis parameters and regimens, both in humans and other animals. These procedures are illustrative only and are not intended to be limiting of the invention. Further, these procedures are routine for one of ordinary skill in the art.

1. Ability of the Immunoadhesin to Reduce Rhinovirus Infectivity in Humans: Dose Escalation Tolerance Study Immunoadhesins of the invention may be tested, e.g., using randomized controlled trials to determine the effect of administration, e.g., intranasal, of immunoadhesin on infection. Other administration routes can be used. Various assays exist that can be used to monitor effect, e.g., IL-8 response assays that evaluate illness symptoms, e.g., cold symptoms caused by rhinovirus infection. These studies can evaluate the extent to which an immunoadhesin taken by a patient subjects can prevent or treat rhinovirus infection. For example, healthy or unhealthy subjects can be administered the immunoadhesin and evaluated over a time course, e.g., in tandem with rhinovirus inoculation and/or illness progression. The clinical protocols used may be based on protocols previously used in evaluation of a recombinant soluble ICAM-1 molecule for efficacy against rhinovirus infection, or modifications thereto (Turner, et. al., *JAMA* 281:1797-804, 1999).

Male and female subjects of any species, age, health, or disease state can be evaluated The subjects may exhibit a serum neutralizing antibody titer in advance of study, which titer may fluctuate in response to infection and immunoadhesin administration.

The immunoadhesin of the present invention may be formulated as a buffered saline with varying amounts of immunoadhesin within and administered at various intervals to a patient. Single ascending dose and multiple ascending dose studies can be used to evaluate the safety of the immunoadhesin. In each case, one or more subjects may be evaluated at each dosage level, some receiving the immunoadhesin, and one or more optionally receiving placebo. In either study, multiple-dosage levels may be evaluated. Dosage levels can vary, but are typically in the nanogram to gram range.

Dosages may be administered over seconds, minutes, hours, weeks, and months, and evaluated for toxicity and/or pharmaceutical effect.

Safety and toxicity may be assessed, e.g., by visual examination of the nasal mucosa for signs of irritation or inflammation. Blood safety evaluations can also be employed according to routine methods and using sensitive assays such as ELISA to determine various blood components, including circulating immunoadhesin and rhinovirus quantities. Naval lavage testing may similarly be done according to routine methodologies.

Routine statistical analyses and calculations may be employed to determine efficacy and toxicity predicted over time courses for single patients and/or for populations of patient recipients.

Challenge studies as well known in the art can be used to demonstrate that treatment protects against clinical colds and/or reduces cold symptoms after viral challenge, and using commercially available starting materials such virus, cells, and animals. See, e.g., Gwaltney, et. al., *Prog. Med. Virol.* 39:256-263, 1992.

The following examples illustrate the disclosed invention. These examples in no way limit the scope of the claimed invention.

EXAMPLES

1. Construction of Immunoadhesin Expression Cassettes

A cassette encoding ICAM-1 extracellular domains D1 through D5 was prepared by PCR cloning. Specifically, a fragment containing all five extracellular Ig-like domains of ICAM-1 was amplified from plasmid pCDIC1-5D/IgA (insert Martin, et al. reference) using the following oligonucleotide primers:

```
                                          (SEQ ID NO: 6)
5'-TCTGTTCCCAGGAACTAGTTTGGCACAGACATCTGTGTCCCCCTCAA

AAGTC-3'

(SEQ ID NO: 7)
5'-CATACCGGGGACTAGTCACATTCACGGTCACCTCGCGG-3'
```

These two primers were designed to introduce SpeI sites at the 5' and 3' ends of the PCR fragment (underlined nucleotides). PCR was performed with Pfu polymerase (Stratagene) to reduce accumulation of errors. The PCR fragment was cloned into the vector PCRScript (Stratagene), and sequenced before fusing to the human IgA2 cassettes (with and without SEKDEL at the carboxy-terminus).

Figure 1:
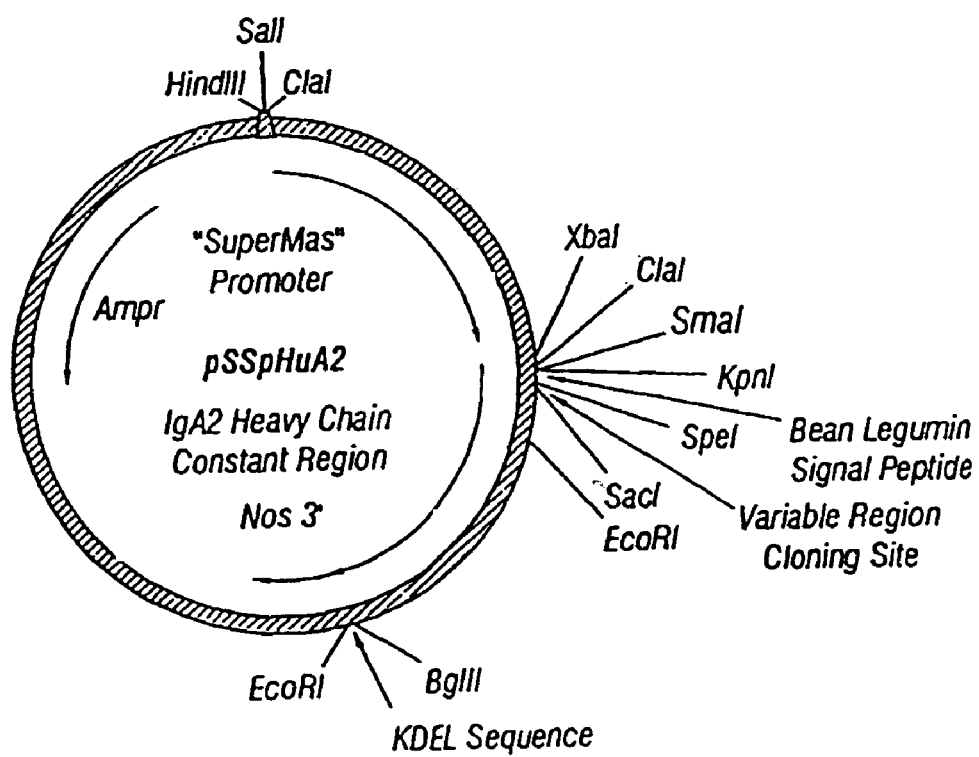
FIG. 1 illustrates pSSPHuA2, vector in which DNAs encoding a chimeric ICAM-1 molecule containing the first five domains of human ICAM-1 and the Fc region of human IgA2m(2) were fused [SEQ ID NO:9, 48]. This vector contains the SuperMas promoter for driving the expression of a signal peptide and the constant regions of the human IgA2m (2) heavy-chain. Sequences encoding ICAM domains 1-5 were amplified, by PCR, to contain convenient restriction sites (5' SpeI and 3' Spe I) for insertion between the signal peptide and the Cα1 domain. DNA encoding an ER retention signal (RSEKDEL) [SEQ ID NO:5] was appended to the 3' end of the heavy-chain in order to boost the expression level of the construct.

Constructs for the expression in plants of human J chain and secretory component, as well as a human IgA2 heavy chain, were developed. A heavy chain expression cassette vector was made and called pSSpHuA2 (See FIG. 1). It contains sequence encoding a bean legumin signal peptide (Baumlein et al., *Nucleic Acids Res.* 14 (6), 2707-2720, 1986). The sequence of bean legumin is provided as GenBank Accession No. X03677, and the sequence of the bean legumin signal peptide is SEQ ID NO: 10 (also see FIG. 8) and the IgA2m(2) constant region with SpeI and SacI sites in between, and the SuperMas promoter for driving the expression of a signal peptide and the constant regions of the human IgA2m(2) heavy-chain.

Figure 2A:
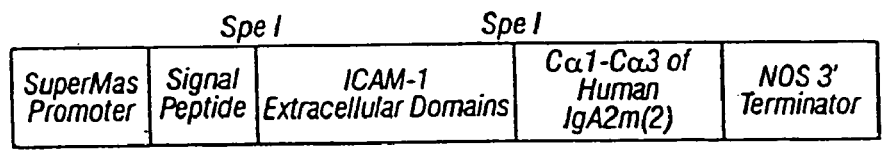
FIG. 2 illustrates a chimeric ICAM molecule. 2A shows the DNA expression cassette from which the chimeric ICAM-1 molecule was produced. 2B shows the amino acid sequence, after signal peptide cleavage, of the mature form of the fusion protein [SEQ ID NO:8]. Amino acids introduced by the cloning procedure are underlined and mark the junction between the five extracellular domains of ICAM-1 and the Cα1-Cα3 domains of the IgA2m(2) heavy chain. The bolded N's indicate the fifteen potential glycosylation sites.

The amplified DNAs encoding the first five domains of human ICAM-1, and the Fe region of human IgA2m(2) were fused in a plant-expression cassette to make a chimeric ICAM-1 molecule expression construct, shown in FIG. 2A. This was done by cloning the fragment encoding the five-extracellular domains of ICAM-1 into vector pSSPHuA2 to generate pSSPICAMHuA2. The convenient restriction sites (5' SpeI and 3' Spe I) allowed the amplified fragment to be inserted between the signal peptide and the Cα1 domain. In the resulting construct, expression of the chimeric ICAM-1 molecule is under the control of the constitutive promoter "superMAS" (Ni et. al., 1995) and the nos 3' terminator region.

The resulting chimeric ICAM-1 molecule construct contains no variable region. Upon translation of the mRNA, signal peptide cleavage is predicted to deposit the ICAM-1-heavy chain fusion into the plant cell's endoplasmic reticulum (ER). DNA encoding an ER retention signal (RSEKDEL, SEQ ID NO: 5 was appended to the 3' end of the heavy-chain in order to boost the expression level of the construct. The amino acid sequence SEKDEL (SEQ ID NO: 4) is the consensus signal sequence for retention of proteins in the endoplasmic reticulum in plant cells. This sequence has been shown to enhance accumulation levels of antibodies in plants (Schouten et al, *Plant Molecular Biology* 30:781-793, 1996). The amino acid sequence of the chimeric ICAM-1 molecule construct is shown in FIG. 2B. The DNA sequence and translational frame of the construct was verified before it was used for particle bombardment.

It has been shown recently that assembly of J chain with IgA takes place in the Golgi apparatus (Yoo et al., *J. Biol. Chem.* 274:33771-33777, 1999), and so constructions of heavy; chain without SEKDEL have been made as well. The ICAM-1 fragment was cloned into an expression cassette containing the IgA2m(2) constant region without SEKDEL.

2. Expression of Assembled Immunoadhesin in Plants

A. Immunoadhesin Expression Vectors

The plasmid pSSPICAMHuA2 (SEQ ID NO:9 and FIG. 8) is 6313 bp in length. Nucleotides 49-1165 represent the Superpromoter (Ni et al., *Plant Journal* 7:661-676, 1995). Nucleotides 1166-3662 comprise a sequence encoding a human ICAM-1/human IgA2m(2) constant hybrid with linker sequences. A consensus Kozak sequence (Kozak, *Cell* 44(2):283-92, 1986) is included (nt 1186-1192) to enhance translation initiation, as well as the signal peptide from *V. faba* legumin (nt 1189-1257; Bäumlein et al., *Nucleic Acids Reg.* 14(6):2707-2720 (1986). The sequence of the human IgA2m (2) constant region (nt 3663-3633) has been previously published (Chintalacharuvu, et al., *J. Imm.* 152: 5299-5304, 1994). A sequence encoding the endoplasmic reticulum retention signal SEKDEL is appended to the end of the heavy Chain (nt 3634-3654). Nucleotides 3663-3933 derive from the nopaline synthase 3' end (transcription termination and polyadenylation signal; Depicker et al., 1982). The remainder of the plasmid derives from the vector pSP72 (Promega).

The plasmid pSHuJ (SEQ ID NO: 11 and FIG. 8) is 4283 bp in length. Nucleotides 14-1136 represent the Superpromoter (Ni et al., *Plant Journal* 7:661-676, 1995) and nucleotides 1137-1648 are shown in FIG. 8 and comprise a sequence encoding the human J Chain including the native signal peptide (Max and Korsmeyer, *J Imm.* 152:5299-5304, 1985) along with linker sequences. A consensus Kozak sequence (Kozak, *Cell* 44(2):283-92, 1986) is included (nt 1162-1168) to enhance translation initiation. Nucleotides 1649-1902 derive from the nopaline synthase 3' end (transcription termination and polyadenylation signal; Depicker et al., *J Mol Appl Genet* 1(6):561-73, 1982). The remainder of the plasmid derives from the vector pSP72 (Promega).

The plasmid pSHuSC (SEQ ID NO:12 and FIG. 8) is 5650 bp in length. Nucleotides 13-1136 are derived from the Super-promoter (Ni et al., *Plant Journal* 7:661-676, 1995), and nucleotides 1137-2981 comprise a sequence encoding the human Secretory Component including the native signal peptide (Krajci, et al., *Biochem. and Biophys. Res. Comm* 158: 783, 1994) along with linker sequences. A consensus Kozak sequence (Kozak, *Cell* 44(2):283-92, 1986) is included (nt 1151-1157) to enhance translation initiation. Nucleotides 2982-3236 derive from the nopaline synthase 3' end, providing a transcription termination and polyadenylation signal, described in Depicker et al., *J Mol Appl Genet* 1(6):561-73 (1982). The remainder of the plasmid derives from the vector pSP72 (Promega).

The plasmid pBMSP-1 (SEQ ID NO:13 and FIG. 8) is derived from pGPTV-KAN. Becker et al., in Plant Molecular Biology 20, 1195-1197, (1992), describe new plant binary vectors with selectable markers located proximal to the left T-DNA border, and the sequences outside of the left and right borders. Nucleotides 18-187 of pBMSP-1 represent the right T-DNA border, and nucleotides 1811-775 represent the superMAS promoter. Nucleotides 2393-2663 represent the NOS promoter (Depicker et al., *J Mol Appl Genet* 1(6):561-73, 1982), nucleotides 2698-3492 encode the NPTII gene (conferring resistance to kanamycin), and nucleotides 3511-3733 are the polyadenylation signal from *A. tumefaciens* gene 7 (Gielen et al., *Embo J* 3:835-46, 1984). Nucleotides 1768-976 encode the NPTII gene, and nucleotides 4317-4464 represent the left T-DNA border.

The plasmid pBMSP-1spJSC (SEQ ID NO:14 and FIG. 8) is a derivative of pBMSP, containing both J and SC under control of superpromoter. In this plasmid, nucleotides 1-149 represent the left T-DNA border. Nucleotides 955-733 are the polyadenylation signal from *A. tumefaciens* gene, nucleotides 1768-976 encode the NPTII gene (conferring resistance to kanamycin), and nucleotides 2073-1803 represent the NOS promoter. Nucleotides 2635-3768 represent the superMAS promoter, nucleotides 3774-5595 encode the Human Secretory component, and nucleotides 5603-5857 represent the NOS polyadenylation signal. Nucleotides 5880-6991 represent the superMAS promoter, nucleotides 7007-7490 encode the Human Joining Chain, and nucleotides 7504-7757 represent the NOS polyadenylation signal. Nucleotides 7886-8057 represent the right T-DNA border.

The plasmid pGPTV-HPT, encoding the enzyme conferring hygromycin resistance, is available commercially from the Max-Planck-Institut für Züchtungsforschung (Germany). It is described by Becker in Plant Molecular Biology 20, 1195-1197 (1992).

B. Plant Transformation and Immunoadhesin Expression in Plants

The expression cassettes described above were used to produce the assembled immunoadhesin in plants. Plasmids pSSPICAMHuA2, pSHuJ, pSHuSC and pBMSP-1 were co-bombarded into tobacco leaf tissue (*N. tabacum* cultivar Xanthi) and transformed microcalli were selected on nutrient agar in the presence of kanamycin. Individual microcalli, indicative of independent transformation events, were dissected from the parent tissue and propagated on nutrient agar with kanamycin.

The callus tissues were screened for transgene expression. Callus #7132 was shown to express a chimeric ICAM-1 immunoadhesin and J chain by immunoblotting and PCR (data not shown). This callus did not possess DNA encoding the SC. The callus grew well in culture and, upon accumulation of sufficient mass, #7132 was bombarded again, this time with two of the plasmids described above, PBMSP-1 SpJSC, containing expression cassettes for both the J chain and SC and pGPTV-HPT, containing an expression cassette for the hpt I gene which confers hygromycin resistance. After a period of selection and growth on nutrient agar, several independent transformants were identified, by immunoblotting, that expressed the chimeric ICAM-1 molecule, the J chain and SC in several states of assembly.

FIG. 3 illustrates the expression of the chimeric ICAM-1 molecule in independently transformed tobacco calli. FIG. 3A shows immunoblots of non-reducing SDS-polyacrylamide gels on which samples containing different transformed tobacco calli (C) and aqueous extracts (Aq) were run and probed for the presence of human ICAM. The solubility of the immunoadhesin assured us that extraction could be easily performed, and the similarity of signals leads us to believe in the reproducibility of expression. FIG. 3B shows immunoblots of nonreducing SDS-polyacrylamide gels containing various fractions of partially purified immunoadhesin from callus Rhi107-11. The blots were probed with antibodies against human ICAM (~ICAM), human IgA heavy chain (~α), human secretory component (~SC) and human J chain (~J). Secondary, enzyme-conjugated antibodies were employed as necessary to label immuno-positive bands with alkaline phosphatase. The specificity of immuno-blotting was further verified by a failure to detect immuno-positive bands in extracts of non-expressing calm (not shown). The expected MW for a dimerized chimeric ICAM-1 molecule, without-glycosylation, is 173,318; this form is likely present in the band migrating just below the 250 kD marker, since it is immuno-positive for ICAM-1 and heavy-chain. This band is also immuno-positive for SC (total expected MW of ~248 kD) but not for J chain which is somewhat unexpected given the canonical pathway for SIgA assembly, which involves 2 cell types (in mammalian) and requires the presence of J chain prior to assembly of SC. A tetrameric immunoadhesin, containing a single molecule of J chain and a single molecule of SC, has an expected MW of ~440 kD, prior to glycosylation. Several species with molecular weights well in excess of 200 kD, immuno-positive with all four probes, are readily apparent.

Bombardment with DNA-coated microprojectiles is used to produce stable transformants in both plants and animals (reviewed by Sanford et al., *Meth. Enz.* 217:483-509, 1993. Particle-mediated transformation with the vectors encoding the immunoadhesin of the present invention was performed using the PDS-1000/He particle acceleration device; manufactured by Bio-Rad. The PDS-1000/He particle acceleration device system uses Helium pressure to accelerate DNA-coated microparticles toward target cells. The physical nature of the technique makes it extremely versatile and easy to use. We have successfully transformed tobacco with all four components of a secretory IgA simultaneously.

The basic biolistic procedure was performed as follows: A stock suspension of microprojectiles was prepared by mixing 60 mg of particles in 1 ml of absolute ethanol. This suspension was vortexed and 25-50 µl was removed and added to a sterile microcentrifuge tube. After microcentrifuging for 30 seconds the ethanol was removed and the pellet resuspended in 1 ml sterile water and centrifuged for 5 minutes. The water was then removed and the pellet resuspended in 25-50 µl of DNA solution containing a mixture of plasmid DNAs, usually, but not always in equimolar amounts. The amount of plasmid added varied between 0.5 ng and 1 µg per preparation. The following were added sequentially: 220 µl of sterile water, 250 µL of 2.5M CaCl2, and 50 µl of 0.1M spermidine. This mixture was vortexed for at least 10 min and then centrifuged for 5 min. The supernatant was removed and the DNA/microprojectile precipitated in 600 µl of absolute ethanol, mixed and centrifuged 1 min. The ethanol was removed and the pellet resuspended in 36 µl of ethanol. Ten µl of the suspension was applied as evenly as possible onto the center of a macrocarrier sheet made of Kapton (DuPont) and the ethanol was evaporated. The macrocarrier sheet and a rupture disk were placed in the unit. A petri dish containing surface-sterilized tobacco leaves was placed below the stopping screen. The chamber was evacuated to 28-29 mm Hg and the target was bombarded once. The protocol has been optimized for tobacco, but is optimized for other plants as well by varying parameters such as He pressure, quantity of coated particles, distance between the macrocarrier and the stopping screen and flying distance from the stopping screen to the tissue.

Figure 5B:
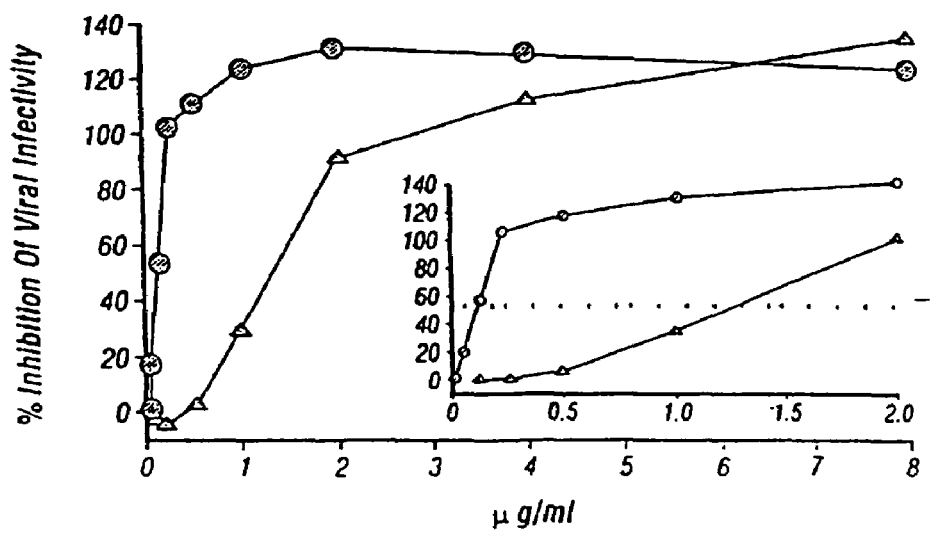

Expression cassettes for chimeric ICAM-1 molecules were also assembled in binary vectors for use in *Agrobacterium*-mediated transformation. An *Agrobacterium* binary vector designed for expression of both human J chain and human secretory component, as well as kanamycin resistance, was introduced into *A. tumefaciens* strain LBA4404. The chimeric ICAM/IgA molecule in another binary vector was also used to transform LBA4404. Overnight cultures of both strains were used for simultaneous "co-cultivation" with leaf pieces of tobacco, according to a standard protocol (Horsch et al., *Science* 227:1229-1231, 1985).

A standard protocol for regeneration of both bombarded and *Agrobacterium*-transformed tobacco leaf disks was used (Horsch et al., *Science* 227:1229-1231, 1985. Because transformed plants, regenerated from bombarded tissue, frequently undergo gene-silencing upon maturation, transgenic tobacco plants were prepared via *Agrobacterium* mediated transformation, which gives a higher yield of expressing, mature plants.

3. Purification of Assembled Immunoadhesin

The immunoadhesin expressed according to Examples 3 was purified. Calli were grown in large amounts to facilitate the development of extraction procedures. A partial purification schedule provided a stable concentrate, available in a variety of buffer conditions, for investigation of subsequent chromatographic techniques for the further purification of the immunoadhesin (See FIG. 3). Calli were extracted in a juicer, which crushes tissue between two stainless-steel gears, while bathed in a buffer containing sodium citrate (0.6 M, pH 7.4) and urea (final concentration of 2 M). The juice (~1 ml/g fresh weight) was precipitated, after coarse filtration through cheesecloth, with 0.67 volumes of saturated ammonium sulfate. A green pellet was collected after centrifugation and thoroughly extracted, in a small volume of 50 mM sodium citrate (pH 6.6), with a Dounce homogenizer. After additional centrifugation, a clear brown supernatant was collected and partially purified, during buffer exchange in a de-salting mode, by passage through a Sephadex G-100 column. The desalting/buffer exchange step has allowed preparation of a partially purified concentrate (~0.2 ml/g fresh weight callus) in a desirable buffer, the G-100 column was eluted with 0.25× phosphate buffered saline. This eluate appeared to be stable for at least 10 days at 2-8° C.

4. The Immunoadhesin Inhibits Human Rhinovirus Infectivity

The infectivity of cells by human rhinovirus was demonstrated to be inhibited by the immunoadhesin prepared according to Example 3. Callus extract prepared according to Example 3 successfully competed for binding of an anti-ICAM monoclonal antibody to soluble ICAM-1. FIG. 4 shows the data from an enzyme-linked immunosorbent assay (ELISA). For the assay, 96-well plates were coated with 0.25 μg soluble ICAM-1/ml. The squares represent the increasing concentrations of sICAM and the circles represent the increasing amounts of callus extract (sterile filtered fraction from G-100 used to compete with the adhered ICAM for a constant amount of a mouse (anti-human ICAM) antibody. After washing the wells, adherent mouse antibody was detected with an anti-mouse antibody conjugated to horseradish peroxidase. Adherent-enzyme activity was measured at 490 nm, with ortho-phenylene diamine as a substrate. The data (squares, sICAM; circles, Extract) are well described by sigmoids of the form $OD490=y=y_0+a/[1+e\hat{}-\{(x-x_0)/b\}]$, where a=y max, $y_0$=y min, b=the slope of the rapidly changing portion of the curve and $x_0$=the value of x at the 50% response level. Relative to soluble ICAM-1, the immunoadhesin extract tested here contains the equivalent of ~250 μg ICAM/ml; this is an overestimate due to expected avidity effects of the dimeric and tetrameric assemblies of the ICAM-1-heavy-chain fusions. Thus, this ELISA demonstrated that the immunoadhesin competes with soluble ICAM-1 for binding to an anti-ICAM mAb.

The competitive ELISA allows for quantitative assessment of the recovery of activity by comparing the normalized amounts of various fractions required to give a 50% response. Upon purification, the titer of a immunoadhesin preparation may be expressed as a reciprocal dilution, or the number of milliliters to which a milligram of immunoadhesin must be diluted in order to give a 50% response. This ELISA will facilitate the development of a purification process for the immunoadhesin.

A cytopathic effect assay (CPE) demonstrated the specific ability of the partially purified immunoadhesin to inhibit the infectivity of human cells by human rhinovirus (FIG. 5). Rhinovirus serotype HRV-39 was pre-incubated with human ICAM-1, an ICAM/IgA fusion (gift of Dr. Tim Springer), or with extracts from calli either expressing our ICAM-1/SIgA immunoadhesin or another, different, antibody before plating each of the mixtures with HeLa S3 cells at 33° C. After 3 days, viable cells were fixed and stained with a methanolic solution of Crystal Violet; the optical density at 570 nm provides a proportional measure of cell viability.

Two extracts derived from Rhi107-11, containing the immunoadhesin, clearly inhibited the virus' ability to infect and kill HeLa S3 cells (FIG. 5A; right side-up and upside-down triangles). Because the extracts were only partially purified, we also assayed a similarly prepared extract that contained a human IgA2m(2) directed against Doxorubicin, a chemotherapeutic agent. That extract, containing a similar immunoglobulin with an unrelated binding specificity, was unable to inhibit the infectivity of the rhinovirus and demonstrates that expression of the ICAM-1-heavy-chain fusion confers specificity to the inhibition. The CPE assay demonstrated, as expected, the differential ability of soluble ICAM-1 and an (IC1-5/IgA; Martin, et al., 1993) to inhibit viral infectivity (FIG. 5B). The insert in FIG. 5B is the scale expansion in the range of the IC50 for soluble ICAM-1 (1.35 μg/ml) and for the IC1-5/IgA (0.12 μg/ml; 11.3 fold less).

5. Production and Purification of Immunoadhesins for Clinical and Toxicological Studies Production of sufficient immunoadhesin for the proposed clinical and toxicological needs is performed by making transgenic tobacco plants. The transgenic plants which express the immunoadhesin (without an ER retention signal) are generated by *Agrobacterium*-mediated transformation. The absence of an ER retention signal is anticipated to enhance assembly since the nascent SIgA is processed through the entire Golgi apparatus, including, in particular, the trans-Golgi, where SC is covalently linked to dIgA as suggested by pulse-chase experiments (Chintalacharuvu & Morrison, *Immunotechnology* 4:165-174, 1999). Because *Agrobacterium*-mediated transformation is much more likely to generate plants with consistent levels of transgene expression, it is likely that progeny of these plants will be used for the production of clinical grade immunoadhesin.

In order to maximize expression levels, and create a true-breeding line, it is desirable to create homozygous plants. The highest producing plants (generation $T_0$) can self-fertilize in the greenhouse before seed is collected. One quarter of the $T_1$ plants are expected to be homozygous. These are grown in the greenhouse and seed samples from several plants are separately germinated on medium containing kanamycin. All the progeny ($T_2$) from homozygous positive plants are expected to be green. Some of the progeny of heterozygous plants are expected to be white or yellowish Homozygosity is confirmed by back-crossing to wild-type and immunoblotting extracts of the progeny.

Harvesting and processing may be continuously meshed during a production campaign, especially since multiple harvests may be obtained from a single planting, i.e. plants cut to soil level for one harvest are regrown for subsequent-harvests. In developing a sense of scale for the production of immunoadhesin it is necessary to decide on the required amount of finished immunoadhesin, account for expression levels (mg immunoadhesin present/kg fresh weight tobacco), know the growth rate of the plants and the expected weight of the average plant, and the overall yield of the purification schedule (set at 20%). Setting the overall need at 3 g of finished immunoadhesin requires preparing for 4 harvests, each with an expected yield of 1 g of finished immunoadhesin.

Given these targets and parameters, the necessary number of plants and hence the space requirements for plant growth is determined. FIG. 6 shows an evaluation of the production necessities for making 1 gram of finished Immunoadhesin. In this diagram, the number of plants needed for 1 g of immunoadhesin, at 20% yield, at expected levels of expression and plant weight is illustrated. At different levels of immunoadhesin expression (mg/kg fresh weight) and overall recovery (set at 20%), the weight of each plant, and so the total number of plants, may be determined for a specified production target (1 g/harvest) within a window (dotted square) of reasonable possibilities. The number of required plants decreases, inversely, with the number of specified growth and re-growth periods. The expected biomass production, a function of time and growth conditions, influences the time to harvest and the time between harvests. These growth periods can be adjusted to the realities of the purification schedule by staggering planting and harvesting dates. From our experience, production requires x number of plants. For example, 1 g of finished immunoadhesin from plants with a reasonable expression level of 100 mg of immunoadhesin/kg fresh weight, require 250 plants when harvested at a weight of 200 g/plant (~80 days post germination). At this scale, these plants require about 10 m² of growing space and are harvested twice over 150 days.

Processing 50+ kg of biomass at a time requires several moderately large-scale operations which all have counterparts in the food-processing industry. These include bulk materials handling, size reduction, juicing and filtration. A Vincent Press and a Durco filtration system are used to efficiently process these quantities. The juicing step employs a proven and simple buffer of sodium citrate and urea. These components buffer the extract, help prevent the oxidation of phenolics and their association with proteins (Gegenheimer, *Methods in Enzymology* 182:174-193, 1990; Loomis, *Methods in Enzymology*, 31:528-5444, 1974; Van Sumere, et al., *The Chemistry and Biochemistry of Plant Proteins*, 1975) and ensure the solubility of the immunoadhesin during a subsequent acid precipitation.

Filtration of acid-insoluble lipid and protein (~90% of the total) is followed by tangential flow ultrafiltration to concentrate the immunoadhesin and to remove small proteins, especially phenolics. Diafiltration enhances the removal of small molecules and exchanges the buffer in preparation for short-term storage and subsequent chromatography. Either SP-Sepharose (binding at pH 5.0 or below) or Q-Sepharose (binding at pH 5.5 or above) are among the ion-exchanges that can be used for filtering immunoadhesin. They are readily available, scalable, robust and have high capacities. In particular, they are available for expanded-bed formats, which reduce the stringency of prior filtration steps. Cation-exchange chromatography, which can be more selective than anion-exchange chromatography, is used first. The immunoadhesin is purified from the several species of protein potentially present, to the point where at least 95% of the protein is in the form of ICAM-1/IgA, ICAM-1/dIgA or ICAM-1/SIgA, as the presence of di- and tetra-valent ICAM-1 domains are critical for potent anti-viral activity. Purified immunoadhesin is then tested for acceptable levels of endotoxin, alkaloids such as nicotine and for bio-burden. In addition, potency levels (defined by ELISA and CPE assays), protein concentration, pH and appearance are monitored. Subsequently, the stability of the clinical lots of immunoadhesin is determined, to ensure that patients receive fully potent immunoadhesin. Even partially purified extracts have been found to be stable for 10 days when refrigerated. The titer and potency of clinically formulated immunoadhesin (in phosphate-buffered saline), when stored at −20° C., 2-8° C., and at 37° C., over a period of 3 to 6 months, is also tested.

6. The Immunoadhesins Have Plant-Specific Glycosylation

The immunoadhesins produced are analyzed to determine the pattern of glycosylation, present. Cabanes-Macheteau et al., Glycobiology 9(4):365-372 (1999), demonstrated the presence of several glycosyl moieties, typical of plants, on a plant-expressed antibody construct. Their methods are used to demonstrate that the immunoadhesins produced according to Example 1, 2 and 3 have a plant-specific glycosylation pattern. We anticipate that this diversity will also be a source of variability for immunoadhesin. Since crude extracts have been shown to have anti-viral activity in vitro (data not shown), glycosylation, as such, does not appear to affect potency. N-linked glycosylation (FIG. 2 shows that there are fifteen potential sites on the chimeric ICAM-1 molecule alone) probably contributes to the diversity of bands seen in immuno-blots. Immunoadhesin preparations are digested with N-Glycosidase A, before blotting, showing that the difference in banding patterns collapse into fewer, discrete bands. In this way, glycoforms are initially characterized with reducing and non-reducing polyacrylamide gels. In addition, digested and mock-digested fractions are tested in the CPE assay and competition ELISA, demonstrating the effect of N-linked glycosylation on potency and titer in vitro.

7. The Immunoadhesin Inactivates Human Rhinovirus

The immunoadhesin prepared according to Examples 1, 2 and 3 is assayed for its ability and to inactivate HRV by binding to the virus, blocking virus entry, and inducing the formation of empty virus capsids. To measure binding of the immunoadhesin to HRV, the immunoadhesin is incubated with [$^3$H]leucine-labeled HRV-39 for 30 min and then added to HeLa cells for 1 hr. After washing, cells and bound virus are detached with Triton X-100 and [$^3$H] measured in a scintillation-counter.

Inactivation of HRV-39 by incubation with the immunoadhesin is compared with HRV inactivation by sICAM-1. HRV-39 is not directly inactivated to a significant extent (<0.5 $\log_{10}$ reduction in infectivity) by incubation with monomeric sICAM-1, while incubation with IC1-5D/IgA reduced infectivity approximately 1.0 $\log_{10}$ (Arruda et al., *Antimicrob. Agents Chemother.* 36:1186-1191, 1992; Crump, et al., *Antimicrob. Agents Chemother.* 38:1425-7, 1994). In order to test the ability of the immunoadhesin to inactivate HRV-39, $10^6$ 50% tissue culture infective doses ($TCID_{50}$) of HRV-39 are incubated in medium containing a concentration of sICAM-1 or immunoadhesin equal to ten times the $IC_{50}$ of each molecule for that virus, or in plain medium, for 1 hr at 33° C. on a rocker platform. Each virus-immunoadhesin or virus-medium mixture are then diluted serially in ten-fold dilutions, and the titer determined on HeLa cells in 96-well plates.

The effect of the immunoadhesin on HRV attachment to host cells is tested by inoculating HeLa cells with HRV-39 at a MOI of 0.3 in the presence or absence of the immunoadhesin. Absorbance proceeds for one hour at 4° C., the cells are washed, and media is replaced plus or minus the immunoadhesin. Cells are incubated for ten hours at 33° C. (to allow one round of replication), and virus are harvested by freeze/thawing the cells. The virus is titered on HeLa cells.

ICAM-IgA (IC1-5D/IgA) is more efficient than sICAM-1 at inducing conformational changes in HRV, leading to the formation of empty, non-infectious viral particles (Martin, et al. *J. Virol* 67:3561-8, 1993). To examine the ability of the immunoadhesin produced according to Examples 1, 2 and 3 to induce conformational changes in HRV, causing release of viral RNA, purified immunoadhesin is incubated with [$^3$H] leucine-labeled HRV-39 for 30 min and then the virus is overlayed onto a 5 to 30% sucrose gradient. Following centrifugation for 90 min at 40,000 rpm, fractions are collected, [$^3$H] measured and fractions assessed for infectivity. (Intact HRV sediments at 149S on a sucrose gradient while empty capsids lacking RNA sediments at 75S (Martin, et al. *J. Virol.* 67:3561-8, 1993)). Due to its increased valence, we expect the ICAM/SIgA immunoadhesin is more efficient at inducing empty non-infectious particles than ICAM-IgA.

The inhibitory effect of purified immunoadhesin on a panel of both major and minor (that do not use ICAM-1 as a receptor) HRV serotypes will be examined using the CPE assay. The ability of ICAM-1 to inhibit HRV infection varies among viral isolates. It has been shown (Crump, et al. *Antimicrob. Agents Chemother.* 38:1425-7, 1994) that the $EC_{50}$ for sICAM-1 varies from 0.6 µg/ml to >32 µg/ml when tested on a panel of HRV major receptor serotypes assay using HeLa cells. Our panel includes nine major serotypes (HRV-3, -13, -14, -16, -23, -39, -68, -73, and -80) and the minor receptor serotype HRV-1A.

8. Clinical Studies Demonstrating the Ability of the Immunoadhesin to Reduce Infectivity in Humans: Dose Escalation Tolerance Study The immunoadhesin of the present invention is tested in two randomized controlled trials to determine the effect of intranasal administration of the immunoadhesin on infection, IL-8 response, and illness in experimental rhinovirus colds. These two studies evaluate the immunoadhesin taken by subjects before or after rhinovirus inoculation. The clinical protocols used here are based on protocols previously used by in evaluation of a recombinant soluble ICAM-1 molecule for efficacy against rhinovirus infection (Turner, et al., *JAMA* 281:1797-804, 1999).

A. Subjects.

Subjects are recruited from university communities at the University of Virginia, Charlottesville. Subjects are required to be in good health, non-smokers, and between the ages of 18 and 60 years. Subjects are excluded if they have a history of allergic disease or nonallergic rhinitis, abnormal nasal anatomy or mucosa, or a respiratory tract infection in the previous 2 weeks. Pregnant or lactating women or women not taking medically approved birth control are also excluded. In the experimental virus challenge study (Phase I/II, see below), subjects are required to be susceptible to the study virus as evidenced by a serum neutralizing antibody titer of 1:4 or less to the virus, determined within 90 days of the start of the trial.

B. Study Medication.

The immunoadhesin of the present invention is formulated as a phosphate-buffered saline (PBS) spray solution containing 2.6 mg/ml. The placebo consists of PBS and is identical in appearance to the active preparation. The solutions are administered using a medication bottle equipped with a metered nasal spray pump. The pump delivers 70 µl of solution containing 183 µg of the immunoadhesin with each spray. The medication is administered as two sprays per nostril, six times daily (at 3-hour intervals) for a total daily dose of 4.4 mg. This is the same dose, in mg protein/day, as was used for soluble ICAM-1 in the tremacamra study infection (Turner, et al., *JAMA* 281:1797-804, 1999). A mole of the immunoadhesin has about twice the mass as a mole of sICAM-1. However, given the differences in in vitro activity between sICAM-1 and ICAM/IgA fusions, the immunoadhesin is many fold more effective on a molar basis than sICAM-1. Thus, this amount is a conservative calculation of what is necessary. This amount is used, except in the event that the dose escalation study reveals problems at this dose.

C. Study Design

Single ascending dose and multiple ascending dose studies are used to evaluate the safety of the immunoadhesin. In each case, three subjects are evaluated at each dosage level, two receiving the immunoadhesin and one receiving placebo. In the single ascending dose study, four dosage levels are evaluated. The lowest individual dose is half the anticipated dose to be used in the challenge study, and the highest individual dose is twice the anticipated challenge study dose. The dosage levels are as follows: one spray in each nostril (366 µg total), two sprays in each nostril (732 µg total), three sprays in each nostril (1098 µg total), four sprays in each nostril (1464 µg total).

The same dosage levels are used in the multiple ascending dose study. Subjects receive doses every three hours (six times per day) for five days. In both studies subjects are evaluated at each dosage level, staggering the start of each subsequent level until it is clear that there is no acute toxicity at the previous level. All subjects return for a single dose 21 days after the first dose, and then for a follow-up at six weeks (for determination of serum antibody against the immunoadhesin).

A separate group of twelve subjects is given one dose of two sprays in each nostril (732 µg total), and nasal lavage is done at 1, 2, 4, 8 and 16 hours (two subjects at each time point). Washings are assayed at Panorama Research by ELISA for the immunoadhesin in order to calculate its in vivo half-life. The total amount of the immunoadhesin to be used in the dose escalation and half-life determination studies (on a total of 28 subjects) will be approximately 270 mg.

D. Safety Evaluations.

In addition to routine adverse event recording, the safety of the immunoadhesin is assessed in three ways. First, prior to the first dose and after the last dose the investigators perform a visual examination of the nasal mucosa, in particular looking for signs of irritation or inflammation. Any visible changes are noted Second, standard blood safety evaluations are done on samples collected prior to treatment and after the last dose on study days 1, 4, and 8 (and 21 in the multiple ascending dose study). Third, serum samples are saved, frozen, and used to determine if the immunoadhesin is able to pass through the nasal mucosa into the blood. This is accomplished in two ways. First, the presence the immunoadhesin in serum samples is measured by ELISA. In this assay, anti-human IgA antibodies adsorbed to microtiter plates capture any the immunoadhesin in the serum, which are detected by an anti-ICAM antibody. The sensitivity of the assay is determined using normal human serum samples spiked with known concentrations of the immunoadhesin. Alternatively, anti-ICAM antibodies can be adsorbed to plates to capture the immunoadhesin in the serum, that would be detected by anti-IgA. Second, the presence of an immune response to the immunoadhesin is assayed with an ELISA method that uses the immunoadhesin adsorbed to microtiter plates. Any anti-immunoadhesin antibodies in the serum bind, and are detected with anti-human IgG or anti-human IgM. Pre-treatment and post-treatment serum samples are compared, and any change in titer is considered evidence of uptake of the immunoadhesin. If there is any positive evidence of anti-immunoadhesin antibodies, additional assays will be done to distinguish between anti-ICAM-1 and anti-IgA activity.

Patients are screened for the development of an allergic reaction to the immunoadhesin. (In previous studies, there were no episodes of adverse reactions with soluble ICAM applied topically in the nose or plantibodies applied topically in the oral cavity.) Individuals exhibiting symptoms of nasal allergy are tested for anti-immunoadhesin-specific IgE antibodies in nasal lavage fluids using a sensitive two-step ELISA (R & D Systems).

E. Statistical Analysis.

The sample size for these studies is based on previous studies using the rhinovirus challenge model. The sample size planned for the protection studies should be adequate to detect a reduction in the incidence of clinical colds from 75% in the placebo groups to 25% in the active treatment groups at I-sided levels of $\alpha=0.05$ and $1-\beta=0.80$. In addition, the sample size should be adequate to detect a change in the total symptom score of 5 units assuming an SD of 5.8 units.

9. Clinical Studies Demonstrating the Ability of the Immunoadhesin to Reduce Infectivity in Humans: Challenge Studies Challenge studies are used to demonstrate that treatment with the immunoadhesin of the present invention protect against clinical colds or reduce cold symptoms after viral challenge.

A. Challenge Virus.

The challenge virus used for this study is rhinovirus 39 (HRV-39). Rhinovirus type 39 is a major group of rhinovirus that requires ICAM-1 for attachment to cells. The challenge virus pool is safety-tested according to consensus guidelines (Gwaltney, et al., *Prog. Med. Virol.* 39:256-263, 1992). AU subjects are inoculated with approximately 200 median tissue culture infective dose ($TCID_{50}$). The virus are administered as drops in two inocula of 250 µl per nostril given approximately 15 minutes apart while the subjects are supine.

TABLE 1

| | Day | | | | | | | |
|---|---|---|---|---|---|---|---|---|
| | 0 | 1 | 2 | 3 | 4 | 5 | 6 | 7-14 | 21 |
| Pre-inoculation study timetable | | | | | | | | |
| Medications | | 6 doses | 6 doses | 6 doses | 6 doses | 6 doses | | | |
| Inoculation | | hour 4 | | | | | | | |
| Symptom scores | | m/e | m/e | m/e | m/e | m/e | m/e | e | |
| Nasal lavage | | m | m | m | m | m | m | | |
| Serum sample | X | | | | | | | | X |
| Post-inoculation study timetable | | | | | | | | |
| Medications | | 6 doses | 6 doses | 6 doses | 6 doses | 6 doses | | | |
| Inoculation | hour 0 | | | | | | | | |
| Symptom scores | | m/e | m/e | m/e | m/e | m/e | m/e | e | |
| Nasal lavage | | m | m | m | m | m | m | | |
| Serum sample | X | | | | | | | | X |

Note:
In both studies on days 1-5, doses are given at hours 0, 3, 6, 9, 12, and 15 m = morning e = evening

B. Study Design.

Two randomized rhinovirus challenge studies are performed (see Table 1). The same formulation of the immunoadhesin of the present invention is evaluated in pre-inoculation and post-inoculation studies. In both studies, medication is administered as six doses each day for five days. Subjects are randomly assigned to receive either the immunoadhesin or matching placebo at the time of enrollment into each study. The study is blinded and all clinical trial personnel, subjects, and employees of Panorama Research remain blinded until all data are collected.

In the pre-inoculation study, medications are started four hours (two doses) prior to viral challenge. The virus challenge is administered one hour after the second dose of the immunoadhesin (or placebo) and the four remaining doses of study medication for the first day are given as scheduled. In this study eighteen subjects receive the active treatment and eighteen subjects receive placebo.

In the post-inoculation study, medications begin 24 hours after virus challenge. This timepoint was chosen because it has been used in other studies of protection from virus challenge, and because cold symptoms are clearly present (Harris & Gwaltney, *Clin. Infect. Dis.* 23:1287-90, 1996). Virus challenge in this study is administered in the morning of study day 0 approximately 24 hours prior to the first dose of study medication on the morning of study day 1. In this study, 36 subjects receive the active treatment and 18 subjects receive placebo.

Subjects are isolated in individual hotel rooms from study day 0 (the day of virus challenge) to study day 6. On each of these days a symptom score and a nasal lavage for virus isolation are done in the morning prior to the first dose of medication and a second symptom score is done each evening. On study day 6, subjects are released from isolation but continue to record symptom scores each evening through day 14. The subjects return to the study site on study day 21, when a final serum sample for detection of anti-immunoadhesin antibodies will be collected. The total amount of immunoadhesin to be used in the two virus challenge studies (on a total of 54 subjects) is approximately 1200 mg.

C. Viral Isolation.

Virus shedding is detected by virus isolation in cell culture. Nasal wash specimens are collected by instillation of 5 ml of 0.9% saline into each nostril. This wash is then expelled into a plastic cup and kept chilled for one to two hours until it is processed for viral cultures. Immunoadhesin is removed from the specimens by treatment with anti-ICAM-1 antibody adsorbed to an agarose support (Affi-Gel 10, Bio-Rad Laboratories, Hercules, Calif.). A portion of each processed specimen is stored at −80° C., and another portion is inoculated into two tubes of HeLa-1 cells, a HeLa cell line enriched for the production of ICAM-1 Arruda, et al., *J. Clin. Microb.* 34:1277-1279, 1996). Rhinovirus are identified by the development of typical cytopathic effect. Subjects with a positive viral culture on any of the postchallenge study days are considered infected. Viral titers in the specimens stored at −80° C. are determined by culturing serial ten-fold dilutions in microtiter plates of HeLa-1 cells.

Antibody to the challenge virus are detected by serum neutralizing titers done using standard methods Gwaltney, et al, *Diagnostic Procedures for Viral Rickettsial and Chlamydial Infections*, p. 579-614, American Public Health Association). Serum specimens for antibody testing are collected during screening, immediately prior to virus challenge (acute), and again 21 days later (convalescent). Subjects with at least a four-fold rise in antibody titer to the challenge, virus when the convalescent serum, sample, is compared with the acute serum sample are considered infected.

D. Evaluation of Illness Severity

Illness severity is assessed as previously described (Turner, et al, *JAMA* 281:1797-804, 1999). Symptom scores are recorded prior to virus challenge (baseline) and twice each day at approximately twelve-hour intervals for the next 6 days. On study days 7 through 14 each subject records his/her symptom score once per day in the evening. At each evaluation, subjects are asked to judge the maximum severity of the following eight symptoms in the interval since the last-symptoms evaluation: sneezing, rhinorrhea, nasal obstruction, sore throat, cough, headache, malaise, and chilliness. Each symptom is assigned a severity score of 0 to 3 corresponding to a report of symptom severity of absent, mild, moderate, or severe. If symptoms are present at baseline, the baseline symptom score will be subtracted from the reported symptom score. The higher of the two daily evaluations are taken as the daily symptom score for each symptom. The daily symptom scores for the eight, individual symptoms are summed to yield the total daily symptom score. The total daily symptom scores for the first 5 days after virus challenge (study days 1-5) are summed and on the evening of study day 5, all subjects are asked, "Do you feel you have had a cold?" Subjects who had a total symptom score of at least 6 and either at least three days of rhinorrhea or the subjective impression that they had a cold are defined as having a clinical cold.

The weight of expelled nasal secretions is determined on days 1-7 by providing all subjects with packets of preweighed nasal tissues. After the tissues are used they are stored in an airtight plastic bag. Each morning the used tissues, together with any unused tissues from the original packet, are collected and weighed.

E. IL-8 Assay.

Recent studies have suggested that the host inflammatory response, particularly interleukin 8 (IL-8), may play a role in the pathogenesis of common cold symptoms due to rhinovirus infection. Concentrations of IL-8 in nasal lavage are determined with a commercially available ELISA (R&D Systems, Minneapolis, Minn.) as previously described (Turner, et al., *JAMA* 281:1797-804, 1999).

F. Safety Evaluations.

The same evaluations are done in the challenge study as in the dose escalation study described in Example 8.

G. Statistical Analysis.

Statistical analysis is performed similarly as to that described for the dose escalation study described in Example 8.

SEQUENCE LISTING

<160> NUMBER OF SEQ ID NOS: 62

<210> SEQ ID NO 1
<211> LENGTH: 1596
<212> TYPE: DNA
<213> ORGANISM: Homo sapiens

<400> SEQUENCE: 1

```
atggctccca gcagccccg gcccgcgctg cccgcactcc tggtcctgct cggggctctg      60
ttcccaggac ctggcaatgc ccagacatct gtgtccccct caaaagtcat cctgccccgg    120
ggaggctccg tgctggtgac atgcagcacc tcctgtgacc agcccaagtt gttgggcata    180
gagaccccgt tgcctaaaaa ggagttgctc ctgcctggga caaccggaa ggtgtatgaa     240
ctgagcaatg tgcaagaaga tagccaacca atgtgctatt caaactgccc tgatgggcag    300
tcaacagcta aaaccttcct caccgtgtac tggactccag aacgggtgga actggcaccc    360
ctcccctctt ggcagccagt gggcaagaac cttaccctac gctgccaggt ggagggtggg    420
gcacccggg ccaacctcac cgtggtgctg ctccgtgggg agaaggagct gaaacgggag     480
ccagctgtgg gggagcccgc tgaggtcacg accacggtgc tggtgaggag agatcaccat    540
ggagccaatt tctcgtgccg cactgaactg gacctgcggc ccaagggct ggagctgttt     600
gagaacacct cggccccta ccagctccag acctttgtcc tgccagcgac tccccacaa     660
cttgtcagcc cccgggtcct agaggtggac acgcagggga ccgtggtctg ttccctggac    720
gggctgttcc cagtctcgga ggcccaggtc cacctggcac tggggaccca gaggttgaac    780
cccacagtca cctatggcaa cgactccttc tcggccaagg cctcagtcag tgtgaccgca    840
gaggacgagg gcacccagcg gctgacgtgt gcagtaatac tggggaacca gagccaggag    900
acactgcaga cagtgaccat ctacagcttt ccggcgccca cgtgattct gacgaagcca     960
gaggtctcag aagggaccga ggtgacagtg aagtgtgagg cccacccta g agccaaggtg   1020
acgctgaatg gggttccagc ccagccactg gcccgaggg ccagctcct gctgaaggcc     1080
accccagagg acaacgggcg cagcttctcc tgctctgcaa ccctggaggt ggccggccag    1140
cttatacaca gaaccagac ccgggagctt cgtgtcctgt atggccccg actggacgag      1200
agggattgtc cgggaaactg gacgtggcca gaaaattccc agcagactcc aatgtgccag    1260
gcttgggga acccattgcc cgagctcaag tgtctaaagg atggcacttt cccactgccc    1320
atcggggaat cagtgactgt cactcgagat cttgagggca cctacctctg tcgggccagg    1380
agcactcaag gggaggtcac ccgcaaggtg accgtgaatg tgctctcccc ccggtatgag    1440
attgtcatca tcactgtggt agcagccgca gtcataatgg gcactgcagg cctcagcacg    1500
tacctctata accgccagcg gaagatcaag aaatacagac tacaacaggc ccaaaaaggg    1560
accccccatga aaccgaacac acaagccacg cctccc                             1596
```

<210> SEQ ID NO 2
<211> LENGTH: 532
<212> TYPE: PRT
<213> ORGANISM: Homo sapiens

<400> SEQUENCE: 2

```
Met Ala Pro Ser Ser Pro Arg Pro Ala Leu Pro Ala Leu Leu Val Leu
  1               5                  10                  15

Leu Gly Ala Leu Phe Pro Gly Pro Gly Asn Ala Gln Thr Ser Val Ser
                 20                  25                  30

Pro Ser Lys Val Ile Leu Pro Arg Gly Gly Ser Val Leu Val Thr Cys
         35                  40                  45

Ser Thr Ser Cys Asp Gln Pro Lys Leu Leu Gly Ile Glu Thr Pro Leu
     50                  55                  60

Pro Lys Lys Glu Leu Leu Leu Pro Gly Asn Asn Arg Lys Val Tyr Glu
 65                  70                  75                  80
```

```
Leu Ser Asn Val Gln Glu Asp Ser Gln Pro Met Cys Tyr Ser Asn Cys
                85                  90                  95
Pro Asp Gly Gln Ser Thr Ala Lys Thr Phe Leu Thr Val Tyr Trp Thr
            100                 105                 110
Pro Glu Arg Val Glu Leu Ala Pro Leu Pro Ser Trp Gln Pro Val Gly
            115                 120                 125
Lys Asn Leu Thr Leu Arg Cys Gln Val Glu Gly Gly Ala Pro Arg Ala
            130                 135                 140
Asn Leu Thr Val Val Leu Leu Arg Gly Glu Lys Glu Leu Lys Arg Glu
145                 150                 155                 160
Pro Ala Val Gly Glu Pro Ala Glu Val Thr Thr Thr Val Leu Val Arg
                165                 170                 175
Arg Asp His His Gly Ala Asn Phe Ser Cys Arg Thr Glu Leu Asp Leu
                180                 185                 190
Arg Pro Gln Gly Leu Glu Leu Phe Glu Asn Thr Ser Ala Pro Tyr Gln
            195                 200                 205
Leu Gln Thr Phe Val Leu Pro Ala Thr Pro Pro Gln Leu Val Ser Pro
            210                 215                 220
Arg Val Leu Glu Val Asp Thr Gln Gly Thr Val Val Cys Ser Leu Asp
225                 230                 235                 240
Gly Leu Phe Pro Val Ser Glu Ala Gln Val His Leu Ala Leu Gly Asp
                245                 250                 255
Gln Arg Leu Asn Pro Thr Val Thr Tyr Gly Asn Asp Ser Phe Ser Ala
                260                 265                 270
Lys Ala Ser Val Ser Val Thr Ala Glu Asp Glu Gly Thr Gln Arg Leu
            275                 280                 285
Thr Cys Ala Val Ile Leu Gly Asn Gln Ser Gln Glu Thr Leu Gln Thr
290                 295                 300
Val Thr Ile Tyr Ser Phe Pro Ala Pro Asn Val Ile Leu Thr Lys Pro
305                 310                 315                 320
Glu Val Ser Glu Gly Thr Glu Val Thr Val Lys Cys Glu Ala His Pro
                325                 330                 335
Arg Ala Lys Val Thr Leu Asn Gly Val Pro Ala Gln Pro Leu Gly Pro
            340                 345                 350
Arg Ala Gln Leu Leu Leu Lys Ala Thr Pro Glu Asp Asn Gly Arg Ser
            355                 360                 365
Phe Ser Cys Ser Ala Thr Leu Glu Val Ala Gly Gln Leu Ile His Lys
370                 375                 380
Asn Gln Thr Arg Glu Leu Arg Val Leu Tyr Gly Pro Arg Leu Asp Glu
385                 390                 395                 400
Arg Asp Cys Pro Gly Asn Trp Thr Trp Pro Glu Asn Ser Gln Gln Thr
                405                 410                 415
Pro Met Cys Gln Ala Trp Gly Asn Pro Leu Pro Glu Leu Lys Cys Leu
            420                 425                 430
Lys Asp Gly Thr Phe Pro Leu Pro Ile Gly Glu Ser Val Thr Val Thr
            435                 440                 445
Arg Asp Leu Glu Gly Thr Tyr Leu Cys Arg Ala Arg Ser Thr Gln Gly
450                 455                 460
Glu Val Thr Arg Lys Val Thr Val Asn Val Leu Ser Pro Arg Tyr Glu
465                 470                 475                 480
Ile Val Ile Ile Thr Val Val Ala Ala Val Ile Met Gly Thr Ala
                485                 490                 495
Gly Leu Ser Thr Tyr Leu Tyr Asn Arg Gln Arg Lys Ile Lys Lys Tyr
            500                 505                 510
```

Arg Leu Gln Gln Ala Gln Lys Gly Thr Pro Met Lys Pro Asn Thr Gln
        515                 520                 525

Ala Thr Pro Pro
    530

<210> SEQ ID NO 3
<211> LENGTH: 3003
<212> TYPE: DNA
<213> ORGANISM: Homo sapiens

<400> SEQUENCE: 3

```
gctataagga tcacgcgccc cagtcgacgc tgagctcctc tgctactcag agttgcaacc      60
tcagcctcgc tatggctccc agcagccccc ggcccgcgct gcccgcactc ctggtcctgc     120
tcggggctct gttcccagga cctggcaatg cccagacatc tgtgtccccc tcaaaagtca     180
tcctgccccg gggaggctcc gtgctggtga catgcagcac ctcctgtgac cagcccaagt     240
tgtttgggcat agagacccccg ttgcctaaaa aggagttgct cctgcctggg aacaaccgga     300
aggtgtatga actgagcaat gtgcaagaag atagccaacc aatgtgctat tcaaactgcc     360
ctgatgggca gtcaacagct aaaaccttcc tcaccgtgta ctggactcca gaacgggtgg     420
aactggcacc cctcccctct tggcagccag tgggcaagaa ccttacccta cgctgccagg     480
tggagggtgg ggcaccccgg ccaacctca ccgtggtgct gctccgtggg gagaaggagc     540
tgaaacggga gccagctgtg ggggagcccg ctgaggtcac gaccacggtg ctggtgagga     600
gagatcacca tggagccaat ttctcgtgcc gcactgaact ggacctgcgg ccccaagggc     660
tggagctgtt tgagaacacc tcggccccct accagctcca gacctttgtc ctgccagcga     720
ctccccccaca acttgtcagc ccccgggtcc tagaggtgga cacgcagggg accgtggtct     780
gttccctgga cgggctgttc ccagtctcgg aggcccaggt ccacctggca ctggggaccc     840
agaggttgaa ccccacagtc acctatggca acgactcctt ctcggccaag gcctcagtca     900
gtgtgaccgc agaggacgag ggcacccagc ggctgacgtg tgcagtaata ctggggaacc     960
agagccagga gacactgcag acagtgacca tctacagctt ccggcgccc aacgtgattc    1020
tgacgaagcc agaggtctca aagggaccg aggtgacagt gaagtgtgag gcccacccta    1080
gagccaaggt gacgctgaat ggggttccag cccagccact gggcccgagg gccagctcc    1140
tgctgaaggc caccccagag gacaacgggc gcagcttctc ctgctctgca accctggagg    1200
tggccggcca gcttatacac aagaaccaga ccccgggagct tcgtgtcctg tatggccccc    1260
gactggacga gagggattgt ccgggaaact ggacgtggcc agaaaattcc cagcagactc    1320
caatgtgcca ggcttggggg aacccattgc ccgagctcaa gtgtctaaag gatggcactt    1380
tcccactgcc catcggggaa tcagtgactg tcactcgaga tcttgagggc acctacctct    1440
gtcgggccag gagcactcaa ggggaggtca cccgcaaggt gaccgtgaat gtgctctccc    1500
cccggtatga gattgtcatc atcactgtgg tagcagccgc agtcataatg ggcactgcag    1560
gcctcagcac gtacctctat aaccgccagc ggaagatcaa gaaatacaga ctacaacagg    1620
cccaaaaagg gaccccccatg aaaccgaaca cacaagccac gcctccctga acctatcccg    1680
ggacagggcc tcttcctcgg ccttcccata ttggtggcag tggtgccaca ctgaacagag    1740
tggaagacat atgccatgca gctacaccta ccggccctgg gacgccggag acagggcat    1800
tgtcctcagt cagatacaac agcatttggg ccatggtac ctgcacacct aaaacactag    1860
gccacgcatc tgatctgtag tcacatgact aagccaagag gaaggagcaa gactcaagac    1920
atgattgatg gatgttaaag tctagcctga tgagagggga agtggtgggg gagacatagc    1980
```

```
cccaccatga ggacatacaa ctgggaaata ctgaaacttg ctgcctattg ggtatgctga    2040
ggccccacag acttacagaa gaagtggccc tccatagaca tgtgtagcat caaaacacaa    2100
aggcccacac ttcctgacgg atgccagctt gggcactgct gtctactgac cccaacccct    2160
gatgatatgt atttattcat ttgttatttt accagctatt tattgagtgt cttttatgta    2220
ggctaaatga acataggtct ctggcctcac ggagctccca gtccatgtca cattcaaggt    2280
caccaggtac agttgtacag gttgtacact gcaggagagt gcctggcaaa aagatcaaat    2340
ggggctggga cttctcattg gccaacctgc ctttccccag aaggagtgat ttttctatcg    2400
gcacaaaagc actatatgga ctggtaatgg ttcacaggtt cagagattac ccagtgaggc    2460
cttattcctc ccttcccccc aaaactgaca cctttgttag ccacctcccc acccacatac    2520
atttctgcca gtgttcacaa tgacactcag cggtcatgtc tggacatgag tgcccaggga    2580
atatgcccaa gctatgcctt gtcctcttgt cctgtttgca tttcactggg agcttgcact    2640
attgcagctc cagtttcctg cagtgatcag ggtcctgcaa gcagtgggga aggggccaa     2700 ggtattggag gactccctcc cagctttgga agcctcatcc gcgtgtgtgt gtgtgtgtgt    2760
atgtgtagac aagctctcgc tctgtcaccc aggctggagt gcagtggtgc aatcatggtt    2820
cactgcagtc ttgaccttt ggctcaagt gatcctccca cctcagcctc ctgagtagct      2880
gggaccatag gctcacaaca ccacacctgg caaatttgat tttttttttt ttttcagag     2940 acggggtctc gcaacattgc ccagacttcc tttgtgttag ttaataaagc tttctcaact    3000
gcc                                                                  3003
```

<210> SEQ ID NO 4
<211> LENGTH: 6
<212> TYPE: PRT
<213> ORGANISM: Homo sapiens

<400> SEQUENCE: 4

Ser Glu Lys Asp Glu Leu
  1               5

<210> SEQ ID NO 5
<211> LENGTH: 7
<212> TYPE: PRT
<213> ORGANISM: Homo sapiens

<400> SEQUENCE: 5

Arg Ser Glu Lys Asp Glu Leu
  1               5

<210> SEQ ID NO 6
<211> LENGTH: 52
<212> TYPE: DNA
<213> ORGANISM: Artificial Sequence
<220> FEATURE:
<223> OTHER INFORMATION: Description of Artificial Sequence: Cloning
      primer

<400> SEQUENCE: 6
tctgttccca ggaactagtt tggcacagac atctgtgtcc ccctcaaaag tc            52

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: Cloning
      primer

<400> SEQUENCE: 7
cataccgggg actagtcaca ttcacggtca cctcgcgg                                    38

<210> SEQ ID NO 8
<211> LENGTH: 799
<212> TYPE: PRT
<213> ORGANISM: Homo sapiens

<400> SEQUENCE: 8

```
Gln Thr Ser Val Ser Pro Ser Lys Val Ile Leu Pro Arg Gly Gly Ser
  1               5                  10                  15

Val Leu Val Thr Cys Ser Thr Ser Cys Asp Gln Pro Lys Leu Leu Gly
             20                  25                  30

Ile Glu Thr Pro Leu Pro Lys Lys Glu Leu Leu Leu Pro Gly Asn Asn
         35                  40                  45

Arg Lys Val Tyr Glu Leu Ser Asn Val Gln Glu Asp Ser Gln Pro Met
     50                  55                  60

Cys Tyr Ser Asn Cys Pro Asp Gly Gln Ser Thr Ala Lys Thr Phe Leu
 65                  70                  75                  80

Thr Val Tyr Trp Thr Pro Glu Arg Val Glu Leu Ala Pro Leu Pro Ser
                 85                  90                  95

Trp Gln Pro Val Gly Lys Asn Leu Thr Leu Arg Cys Gln Val Glu Gly
            100                 105                 110

Gly Ala Pro Arg Ala Asn Leu Thr Val Val Leu Leu Arg Gly Glu Lys
        115                 120                 125

Glu Leu Lys Arg Glu Pro Ala Val Gly Glu Pro Ala Glu Val Thr Thr
    130                 135                 140

Thr Val Leu Val Arg Arg Asp His His Gly Ala Asn Phe Ser Cys Arg
145                 150                 155                 160

Thr Glu Leu Asp Leu Arg Pro Gln Gly Leu Glu Leu Phe Glu Asn Thr
                165                 170                 175

Ser Ala Pro Tyr Gln Leu Gln Thr Phe Val Leu Pro Ala Thr Pro Pro
            180                 185                 190

Gln Leu Val Ser Pro Arg Val Leu Glu Val Asp Thr Gln Gly Thr Val
        195                 200                 205

Val Cys Ser Leu Asp Gly Leu Phe Pro Val Ser Glu Ala Gln Val His
    210                 215                 220

Leu Ala Leu Gly Asp Gln Arg Leu Asn Pro Thr Val Thr Tyr Gly Asn
225                 230                 235                 240

Asp Ser Phe Ser Ala Lys Ala Ser Val Ser Val Thr Ala Glu Asp Glu
                245                 250                 255

Gly Thr Gln Arg Leu Thr Cys Ala Val Ile Leu Gly Asn Gln Ser Gln
            260                 265                 270

Glu Thr Leu Gln Thr Val Thr Ile Tyr Ser Phe Pro Ala Pro Asn Val
        275                 280                 285

Ile Leu Thr Lys Pro Glu Val Ser Glu Gly Thr Glu Val Thr Val Lys
    290                 295                 300

Cys Glu Ala His Pro Arg Ala Lys Val Thr Leu Asn Gly Val Pro Ala
305                 310                 315                 320

Gln Pro Leu Gly Pro Arg Ala Gln Leu Leu Lys Ala Thr Pro Glu
                325                 330                 335

Asp Asn Gly Arg Ser Phe Ser Cys Ser Ala Thr Leu Glu Val Ala Gly
            340                 345                 350

Gln Leu Ile His Lys Asn Gln Thr Arg Glu Leu Arg Val Leu Tyr Gly
```

```
                355                 360                 365
Pro Arg Leu Asp Glu Arg Asp Cys Pro Gly Asn Trp Thr Trp Pro Glu
    370                 375                 380

Asn Ser Gln Gln Thr Pro Met Cys Gln Ala Trp Gly Asn Pro Leu Pro
385                 390                 395                 400

Glu Leu Lys Cys Leu Lys Asp Gly Thr Phe Pro Leu Pro Ile Gly Glu
            405                 410                 415

Ser Val Thr Val Thr Arg Asp Leu Glu Gly Thr Tyr Leu Cys Arg Ala
        420                 425                 430

Arg Ser Thr Gln Gly Glu Val Thr Arg Glu Val Thr Val Asn Val Thr
    435                 440                 445

Ser Gly Ser Ser Ala Ser Pro Thr Ser Pro Lys Val Phe Pro Leu Ser
    450                 455                 460

Leu Asp Ser Thr Pro Gln Asp Gly Asn Val Val Ala Cys Leu Val
465                 470                 475                 480

Gln Gly Phe Phe Pro Gln Glu Pro Leu Ser Val Thr Trp Ser Glu Ser
            485                 490                 495

Gly Gln Asn Val Thr Ala Arg Asn Phe Pro Pro Ser Gln Asp Ala Ser
        500                 505                 510

Gly Asp Leu Tyr Thr Thr Ser Ser Gln Leu Thr Leu Pro Ala Thr Gln
    515                 520                 525

Cys Pro Asp Gly Lys Ser Val Thr Cys His Val Lys His Tyr Thr Asn
    530                 535                 540

Ser Ser Gln Asp Val Thr Val Pro Cys Arg Val Pro Pro Pro Pro
545                 550                 555                 560

Cys Cys His Pro Arg Leu Ser Leu His Arg Pro Ala Leu Glu Asp Leu
            565                 570                 575

Leu Leu Gly Ser Glu Ala Asn Leu Thr Cys Thr Leu Thr Gly Leu Arg
        580                 585                 590

Asp Ala Ser Gly Ala Thr Phe Thr Trp Thr Pro Ser Ser Gly Lys Ser
    595                 600                 605

Ala Val Gln Gly Pro Pro Glu Arg Asp Leu Cys Gly Cys Tyr Ser Val
    610                 615                 620

Ser Arg Val Leu Pro Gly Cys Ala Gln Pro Trp Asn His Gly Glu Thr
625                 630                 635                 640

Phe Thr Cys Thr Ala Ala His Pro Glu Leu Lys Thr Pro Leu Thr Ala
            645                 650                 655

Asn Ile Thr Lys Ser Gly Asn Thr Phe Arg Pro Glu Val His Leu Leu
        660                 665                 670

Pro Pro Pro Ser Glu Glu Leu Ala Leu Asn Glu Leu Val Thr Leu Thr
    675                 680                 685

Cys Leu Ala Arg Gly Phe Ser Pro Lys Asp Val Leu Val Arg Trp Leu
    690                 695                 700

Gln Gly Ser Gln Glu Leu Pro Arg Glu Lys Tyr Leu Thr Trp Ala Ser
705                 710                 715                 720

Arg Gln Glu Pro Ser Gln Gly Thr Thr Thr Tyr Ala Val Thr Ser Ile
            725                 730                 735

Leu Arg Val Ala Ala Glu Asp Trp Lys Lys Gly Glu Thr Phe Ser Cys
        740                 745                 750

Met Val Gly His Glu Ala Leu Pro Leu Ala Phe Thr Gln Lys Thr Ile
    755                 760                 765

Asp Arg Leu Ala Gly Lys Pro Thr His Ile Asn Val Ser Val Val Met
    770                 775                 780
```

Ala Glu Ala Asp Gly Thr Cys Tyr Arg Ser Glu Lys Asp Glu Leu
785                 790                 795

<210> SEQ ID NO 9
<211> LENGTH: 6313
<212> TYPE: DNA
<213> ORGANISM: Artificial Sequence
<220> FEATURE:
<223> OTHER INFORMATION: Description of Artificial Sequence:
      Expression-type plasmid pSSPICAMHuA2

<400> SEQUENCE: 9

| | | | | | |
|---|---|---|---|---|---|
| gaactcgagc | agctgaagct | tgcatgcctg | caggtcgacg | gtatcgataa | ggatccctga | 60 |
| aagcgacgtt | ggatgttaac | atctacaaat | tgccttttct | tatcgaccat | gtacgtaagc | 120 |
| gcttacgttt | ttggtggacc | cttgaggaaa | ctggtagctg | ttgtgggcct | gtggtctcaa | 180 |
| gatggatcat | taatttccac | cttcacctac | gatgggggc | atcgcaccgg | tgagtaatat | 240 |
| tgtacggcta | agagcgaatt | tggcctgtag | gatccctgaa | agcgacgttg | gatgttaaca | 300 |
| tctacaaatt | gccttttctt | atcgaccatg | tacgtaagcg | cttacgtttt | tggtggaccc | 360 |
| ttgaggaaac | tggtagctgt | tgtgggcctg | tggtctcaag | atggatcatt | aatttccacc | 420 |
| ttcacctacg | atgggggca | tcgcaccggt | gagtaatatt | gtacggctaa | gagcgaattt | 480 |
| ggcctgtagg | atccctgaaa | gcgacgttgg | atgttaacat | ctacaaattg | ccttttctta | 540 |
| tcgaccatgt | acgtaagcgc | ttacgttttt | ggtggaccct | tgaggaaact | ggtagctgtt | 600 |
| gtgggcctgt | ggtctcaaga | tggatcatta | atttccacct | tcacctacga | tgggggcat | 660 |
| cgcaccggtg | agtaatattg | tacggctaag | agcgaatttg | gcctgtagga | tccgcgagct | 720 |
| ggtcaatccc | attgcttttg | aagcagctca | acattgatct | ctttctcgag | ggagattttt | 780 |
| caaatcagtg | cgcaagacgt | gacgtaagta | tccgagtcag | tttttatttt | tctactaatt | 840 |
| tggtcgttta | tttcggcgtg | taggacatgg | caacccgggc | tgaatttcgc | gggtattctg | 900 |
| tttctattcc | aacttttctc | tgatccgcag | ccattaacga | cttttgaata | gatacgctga | 960 |
| cacgccaagc | ctcgctagtc | aaaagtgtac | caaacaacgc | tttacagcaa | gaacggaatg | 1020 |
| cgcgtgacgc | tcgcggtgac | gccatttcgc | cttttcagaa | atggataaat | agccttgctt | 1080 |
| cctattatat | cttcccaaat | taccaataca | ttacactagc | atctgaattt | cataaccaat | 1140 |
| ctcgatacac | caaatcgact | ctagaggatc | tatcgattcc | cgggtaccat | gggatctaaa | 1200 |
| ccttttttgt | ctcttctttc | attgtcattg | cttttgttta | catctactag | tttggcacag | 1260 |
| acatctgtgt | cccctcaaa | agtcatcctg | ccccggggag | ctccgtgct | ggtgacatgc | 1320 |
| agcacctcct | gtgaccagcc | caagttgttg | ggcatagaga | ccccgttgcc | taaaaggag | 1380 |
| ttgctcctgc | ctgggaacaa | ccggaaggt | tatgaactga | gcaatgtgca | agaagatagc | 1440 |
| caaccaatgt | gctattcaaa | ctgccctgat | gggcagtcaa | cagctaaaac | cttcctcacc | 1500 |
| gtgtactgga | ctccagaacg | ggtggaactg | gcaccctcc | cctcttggca | gccagtgggc | 1560 |
| aagaaccta | ccctacgctg | ccaggtggag | ggtgggcac | cccgggccaa | cctcaccgtg | 1620 |
| gtgctgctcc | gtgggagaa | ggagctgaaa | cgggagccag | ctgtgggga | gcccgctgag | 1680 |
| gtcacgacca | cggtgctggt | gaggagagat | caccatggag | ccaatttctc | gtgccgcact | 1740 |
| gaactggacc | tgcggcccca | agggctgag | ctgtttgaga | acacctcggc | ccctaccag | 1800 |
| ctccagacct | tgtcctgcc | agcgactccc | ccacaacttg | tcagccccg | ggtcctagag | 1860 |
| gtggacacgc | aggggaccgt | ggtctgttcc | ctggacgggc | tgttcccagt | ctcggaggcc | 1920 |
| caggtccacc | tggcactggg | ggaccagagg | ttgaacccca | cagtcaccta | tggcaacgac | 1980 |

```
tccttctcgg ccaaggcctc agtcagtgtg accgcagagg acgagggcac ccagcggctg      2040
acgtgtgcag taatactggg gaaccagagc caggagacac tgcagacagt gaccatctac      2100
agctttccgg cgcccaacgt gattctgacg aagccagagg tctcagaagg gaccgaggtg      2160
acagtgaagt gtgaggccca ccctagagcc aaggtgacgc tgaatggggt tccagcccag      2220
ccactgggcc cgagggccca gctcctgctg aaggccaccc cagaggacaa cgggcgcagc      2280
ttctcctgct ctgcaaccct ggaggtggcc ggccagctta tacacaagaa ccagacccgg      2340
gagcttcgtg tcctgtatgg ccccgactg gacgagaggg attgtccggg aaactggacg       2400
tggccagaaa attcccagca gactccaatg tgccaggctt gggggaaccc attgcccgag      2460
ctcaagtgtc taaaggatgg cactttccca ctgcccatcg gggaatcagt gactgtcact      2520
cgagatcttg agggcaccta cctctgtcgg gccaggagca ctcaagggga ggtcacccgc      2580
gaggtgaccg tgaatgtgac tagtgggagc tcagcatccc cgaccagccc caaggtcttc      2640
ccgctgagcc tcgacagcac cccccaagat gggaacgtgg tcgtcgcatg cctggtccag      2700
ggcttcttcc cccaggagcc actcagtgtg acctggagcg aaagcggaca gaacgtgacc      2760
gccagaaact tcccacctag ccaggatgcc tccggggacc tgtacaccac gagcagccag      2820
ctgaccctgc cggccacaca gtgcccagac ggcaagtccg tgacatgcca cgtgaagcac      2880
tacacgaatt ccagccagga tgtgactgtg ccctgccgag ttccccccacc tcccccatgc      2940 tgccaccccc gactgtcgct gcaccgaccg gccctcgagg acctgctctt aggttcagaa      3000
gcgaacctca cgtgcacact gaccggcctg agagatgcct ctggtgccac cttcacctgg      3060
acgccctcaa gtgggaagag cgctgttcaa ggaccacctg agcgtgacct ctgtggctgc      3120
tacagcgtgt ccagagtact tcctggctgt gcccagccat ggaaccatgg ggagaccttc      3180
acctgcactg ctgcccaccc cgagttgaag accccactaa ccgccaacat cacaaaatcc      3240
ggaaacacat tccggcccga ggtccacctg ctgccgccgc cgtcggagga gctggccctg      3300
aacgagctgg tgacgctgac gtgcctggca cgtggcttca gccccaagga tgtgctggtt      3360
cgctggctgc aggggtcaca ggagctgccc cgcgagaagt acctgacttg gcatccccgg      3420
caggagccca gccagggcac caccacctat gctgtgacca gcatactgcg cgtggcagcc      3480
gaggactgga gaaggggga gaccttctcc tgcatggtgg ccacgaggc cctgccgctg      3540 gccttcacac agaagaccat cgaccgcttg gcgggtaaac ccacccatat caatgtgtct      3600
gttgtcatgg cggaggcgga cggcacctgc tacagatctg aaaaggatga actttagaat      3660
tcgatatcaa gctaattccc gatcgttcaa acatttggca ataaagtttc ttaagattga      3720
atcctgttgc cggtcttgcg atgattatca tataatttct gttgaattac gttaagcatg      3780
taataattaa catgtaatgc atgacgttat ttatgagatg gttttttatg attagagtcc      3840
cgcaattata catttaatac gcgatagaaa acaaaatata gcgcgcaaac taggataaat      3900
tatcgcgcgc ggtgtcatct atgttactag atcgggatc tgccggtctc cctatagtga      3960
gtcgtattaa tttcgataag ccaggttaac ctgcattaat gaatcggcca acgcgcgggg      4020
agaggcggtt tgcgtattgg gcgctcttcc gcttcctcgc tcactgactc gctgcgctcg      4080
gtcgttcggc tgcggcgagc ggtatcagct cactcaaagg cggtaatacg gttatccaca      4140
gaatcagggg ataacgcagg aaagaacatg tgagcaaaag gccagcaaaa ggccaggaac      4200
cgtaaaaagg ccgcgttgct ggcgtttttc cataggctcc gccccctga cgagcatcac       4260 aaaaatcgac gctcaagtca gaggtggcga aacccgacag gactataaag ataccaggcg      4320
tttccccctg gaagctccct cgtgcgctct cctgttccga ccctgccgct taccggatac      4380
```

```
ctgtccgcct ttctcccttc gggaagcgtg gcgctttctc aatgctcacg ctgtaggtat   4440
ctcagttcgg tgtaggtcgt tcgctccaag ctgggctgtg tgcacgaacc ccccgttcag   4500
cccgaccgct gcgccttatc cggtaactat cgtcttgagt ccaacccggt aagacacgac   4560
ttatcgccac tggcagcagc cactggtaac aggattagca gagcgaggta tgtaggcggt   4620
gctacagagt tcttgaagtg gtggcctaac tacggctaca ctagaaggac agtatttggt   4680
atctgcgctc tgctgaagcc agttaccttc ggaaaaagag ttggtagctc ttgatccggc   4740
aaacaaacca ccgctggtag cggtggtttt tttgtttgca agcagcagat tacgcgcaga   4800
aaaaaaggat ctcaagaaga tcctttgatc ttttctacgg ggtctgacgc tcagtggaac   4860
gaaaactcac gttaagggat tttggtcatg agattatcaa aaaggatctt cacctagatc   4920
cttttaaatt aaaaatgaag ttttaaatca atctaaagta tatatgagta aacttggtct   4980
gacagttacc aatgcttaat cagtgaggca cctatctcag cgatctgtct atttcgttca   5040
tccatagttg cctgactccc cgtcgtgtag ataactacga tacgggaggg cttaccatct   5100
ggccccagtg ctgcaatgat accgcgagac ccacgctcac cggctccaga tttatcagca   5160
ataaaccagc cagccggaag ggccgagcgc agaagtggtc ctgcaacttt atccgcctcc   5220
atccagtcta ttaattgttg ccgggaagct agagtaagta gttcgccagt taatagtttg   5280
cgcaacgttg ttgccattgc tacaggcatc gtggtgtcac gctcgtcgtt tggtatggct   5340
tcattcagct ccggttccca acgatcaagg cgagttacat gatccccat gttgtgcaaa   5400 aaagcggtta gctccttcgg tcctccgatc gttgtcagaa gtaagttggc cgcagtgtta   5460
tcactcatgg ttatggcagc actgcataat tctcttactg tcatgccatc cgtaagatgc   5520
ttttctgtga ctggtgagta ctcaaccaag tcattctgag aatagtgtat gcggcgaccg   5580
agttgctctt gcccggcgtc aatacgggat aataccgcgc cacatagcag aactttaaaa   5640
gtgctcatca ttggaaaacg ttcttcgggg cgaaaactct caaggatctt accgctgttg   5700
agatccagtt cgatgtaacc cactcgtgca cccaactgat cttcagcatc ttttactttc   5760
accagcgttt ctgggtgagc aaaaacagga aggcaaaatg ccgcaaaaaa gggaataagg   5820
gcgacacgga aatgttgaat actcatactc ttcctttttc aatattattg aagcatttat   5880
cagggttatt gtctcatgag cggatacata tttgaatgta tttagaaaaa taaacaaata   5940
ggggttccgc gcacatttcc ccgaaaagtg ccacctgacg tctaagaaac cattattatc   6000
atgacattaa cctataaaaa taggcgtatc acgaggccct ttcgtctcgc gcgtttcggt   6060
gatgacggtg aaaacctctg acacatgcag ctcccggaga cggtcacagc ttgtctgtaa   6120
gcggatgccg ggagcagaca agcccgtcag ggcgcgtcag cgggtgttgg cgggtgtcgg   6180
ggctggctta actatgcggc atcagagcag attgtactga gagtgcacca tatgcacata   6240
ttgtcgttag aacgcggcta caattaatac ataaccttat gtatcataca catacgattt   6300
aggtgacact ata                                                     6313
```

<210> SEQ ID NO 10
<211> LENGTH: 22
<212> TYPE: PRT
<213> ORGANISM: Phaseolus vulgaris
<400> SEQUENCE: 10

```
Met Ser Lys Pro Phe Leu Ser Leu Leu Ser Leu Ser Leu Leu Leu Phe
 1               5                  10                  15

Thr Ser Thr Cys Leu Ala
            20
```

<210> SEQ ID NO 11
<211> LENGTH: 508
<212> TYPE: DNA
<213> ORGANISM: Artificial Sequence
<220> FEATURE:
<223> OTHER INFORMATION: Description of Artificial Sequence: Protein
      coding region of the plasmid pSHuJ

<400> SEQUENCE: 11

```
aggatctatc gattcccggg taccatggag aaccatttgc ttttctgggg agtcctggcg      60
gttttattta aggctgttca tgtgaaagcc caagaagatg aaaggattgt tcttgttgac     120
aacaaatgta agtgtgcccg gattacttcc aggatcatcc gttcttccga agatcctaat     180
gaggacattg tggagagaaa catccgaatt attgttcctc tgaacaacag ggagaatatc     240
tctgatccca cctcaccatt gagaaccaga tttgtgtacc atttgtctga cctctgtaaa     300
aaatgtgatc ctacagaagt ggagctggat aatcagatag ttactgctac ccagagcaat     360
atctgtgatg aagacagtgc tacagagacc tgctacactt atgacagaaa caagtgctac     420
acagctgtgg tcccactcgt atatggtggt gagaccaaaa tggtggaaac agccttaacc     480
ccagatgcct gctatcctga ctgaattc                                       508
```

<210> SEQ ID NO 12
<211> LENGTH: 1845
<212> TYPE: DNA
<213> ORGANISM: Artificial Sequence
<220> FEATURE:
<223> OTHER INFORMATION: Description of Artificial Sequence: Protein
      coding region of plasmid pSHuSC

<400> SEQUENCE: 12

```
gtcgattccc gggtaccatg gtgctcttcg tgctcacctg cctgctggcg gtcttcccag      60
ccatctccac gaagagtccc atatttggtc ccgaggaggt gaatagtgtg aaggtaact     120
cagtgtccat cacgtgctac tacccaccca cctctgtcaa ccggcacacc cggaagtact     180
ggtgccggca gggagctaga ggtggctgca taaccctcat ctcctcggag ggctacgtct     240
ccagcaaata tgcaggcagg gctaacctca ccaacttccc ggagaacggc acatttgtgg     300
tgaacattgc ccagctgagc caggatgact ccgggcgcta caagtgtggc ctgggcatca     360
atagccgagg cctgtccttt gatgtcagcc tggaggtcag ccagggtcct gggctcctaa     420
atgacactaa agtctacaca gtggacctgg gcagaacggt gaccatcaac tgcccttca     480
agactgagaa tgctcaaaag aggaagtcct tgtacaagca gataggcctg taccctgtgc     540
tggtcatcga ctccagtggt tatgtgaatc caactatac aggaagaata cgccttgata     600
ttcagggtac tggccagtta ctgttcagcg ttgtcatcaa ccaactcagg ctcagcgatg     660
ctgggcagta tctctgccag gctggggatg attccaatag taataagaag aatgctgacc     720
tccaagtgct aaagcccgag cccgagctgg tttatgaaga cctgagggc tcagtgacct     780
tccactgtgc cctgggccct gaggtggcaa acgtggccaa atttctgtgc gacagagca     840
gtggggaaaa ctgtgacgtg gtcgtcaaca ccctggggaa gagggcccca gcctttgagg     900
gcaggatcct gctcaacccc caggacaagg atggctcatt cagtgtggtg atcacaggcc     960
tgaggaagga ggatgcaggg cgctaccgt gtggagccca ttcggatggt cagctgcagg    1020
aaggctcgcc tatccaggcc tggcaactct tcgtcaatga ggagtccacg attccccgca    1080
gccccactgt ggtgaagggg gtggcaggaa gctctgtggc cgtgctctgc ccctacaacc    1140
gtaaggaaag caaaagcatc aagtactggt gtctctggga aggggcccag aatggccgct    1200
```

| | | | | |
|---|---|---|---|---|
| gcccccctgct | ggtggacagc | gaggggtggg | ttaaggccca | gtacgagggc cgcctctccc | 1260 |
| tgctggagga | gccaggcaac | ggcaccttca | ctgtcatcct | caaccagctc accagccggg | 1320 |
| acgccggctt | ctactggtgt | ctgaccaacg | gcgatactct | ctggaggacc accgtggaga | 1380 |
| tcaagattat | cgaaggagaa | ccaaacctca | aggttcccgg | gaatgtcacg gctgtgctgg | 1440 |
| gagagactct | caaggtcccc | tgtcactttc | catgcaaatt | ctcctcgtac gagaaatact | 1500 |
| ggtgcaagtg | aataacacg | ggctgccagg | ccctgcccag | ccaagacgaa ggccccagca | 1560 |
| aggccttcgt | gaactgtgac | gagaacagcc | ggcttgtctc | cctgaccctg aacctggtga | 1620 |
| ccagggctga | tgagggctgg | tactggtgtg | agtgaagca | gggccacttc tatgagaga | 1680 |
| ctgcagccgt | ctatgtggca | gttgaagaga | ggaaggcagc | ggggtcccgc gatgtcagcc | 1740 |
| tagcgaaggc | agacgctgct | cctgatgaga | aggtgctaga | ctctggtttt cgggagattg | 1800 |
| agaacaaagc | cattcaggat | cccaggcttt | ttgcagagtg | aattc | 1845 |

<210> SEQ ID NO 13
<211> LENGTH: 4465
<212> TYPE: DNA
<213> ORGANISM: Artificial Sequence
<220> FEATURE:
<223> OTHER INFORMATION: plasmid pBMSP-1
<220> FEATURE:
<221> NAME/KEY: VARIANT
<222> LOCATION: 2150, 2214, 2215
<223> OTHER INFORMATION: n = A,T,C or G

<400> SEQUENCE: 13

| | | | | |
|---|---|---|---|---|
| ctggccggcg | ccagatctgg | ggaacctgtg | gttggcatgc | acatacaaat ggacgaacgg | 60 |
| ataaaccttt | tcacgccctt | ttaaatatcc | gattattcta | ataaacgctc ttttctctta | 120 |
| ggtttacccg | ccaatatatc | ctgtcaaaca | ctgatagttt | aaactgaagg cgggaaacga | 180 |
| caatctgatc | atgagcggag | aattaaggga | gtcacgttat | gaccccgcc gatgacgcgg | 240 |
| gacaagccgt | tttacgtttg | gaactgacag | aaccgcaacg | attgaaggag ccactcagcc | 300 |
| gatctgaatt | aattcccgat | ctagtaacat | agatgacacc | gcgcgcgata atttatccta | 360 |
| gttttgcgcg | ctatattttgt | tttctatcgc | gtattaaatg | tataattgcg ggactctaat | 420 |
| cataaaaacc | catctcataa | ataacgtcat | gcattacatg | ttaattatta catgcttaac | 480 |
| gtaattcaac | agaaattata | tgataatcat | cgcaagaccg | gcaacaggat tcaatcttaa | 540 |
| gaaactttat | tgccaaatgt | ttgaacgatc | ggggaaattc | gagctccacc gcggtggcgg | 600 |
| ccgctctaga | actagtggat | ccccccgggct | gcaggaattc | gatcagatct gatcaagctt | 660 |
| atcgataccg | tcgacctcga | gggggggccc | ggtaccccta | gagtcgattt ggtgtatcga | 720 |
| gattggttat | gaaattcaga | tgctagtgta | atgtattggt | aatttgggaa gatataatag | 780 |
| gaagcaaggc | tatttatcca | tttctgaaaa | ggcgaaatgg | cgtcaccgcg agcgtcacgc | 840 |
| gcattccgtt | cttgctgtaa | agcgttgttt | ggtacacttt | tgactagcga ggcttggcgt | 900 |
| gtcagcgtat | ctattcaaaa | gtcgttaatg | gctgcggatc | aagaaaaagt tggaatagaa | 960 |
| acagaatacc | cgcgaaattc | aggcccggtt | gccatgtcct | acacgccgaa ataaacgacc | 1020 |
| aaattagtag | aaaaataaaa | actgactcgg | atacttacgt | cacgtcttgc gcactgattt | 1080 |
| gaaaaatctc | cctcgatcga | aaagagatc | aatgttgagc | tgcttcaaaa gcaatgggat | 1140 |
| tgaccagctc | gcggatccta | caggccaaat | tcgctcttag | ccgtacaata ttactcaccg | 1200 |
| gtgcgatgcc | cccatcgta | ggtgaaggtg | gaaattaatg | atccatcttg agaccacagg | 1260 |
| cccacaacag | ctaccagttt | cctcaagggt | ccaccaaaaa | cgtaagcgct tacgtacatg | 1320 |

```
gtcgataaga aaaggcaatt tgtagatgtt aacatccaac gtcgctttca gggatcctac    1380
aggccaaatt cgctcttagc cgtacaatat tactcaccgg tgcgatgccc ccatcgtag     1440 gtgaaggtgg aaattaatga tccatcttga ccacaggc ccacaacagc taccagtttc      1500
ctcaagggtc caccaaaaac gtaagcgctt acgtacatgg tcgataagaa aaggcaattt    1560
gtagatgtta acatccaacg tcgctttcag ggatcctaca ggccaaattc gctcttagcc    1620
gtacaatatt actcaccggt gcgatgcccc ccatcgtagg tgaaggtgga aattaatgat    1680
ccatcttgag accacaggcc cacaacagct accagtttcc tcaagggtcc accaaaaacg    1740
taagcgctta cgtacatggt cgataagaaa aggcaatttg tagatgttaa catccaacgt    1800
cgctttcagg gatccgcgag cttatcgcga taccgtcgaa tataataatt atatttgtaa    1860
gaatattatt ataataatat aaaatatata tatataaatt ataatatatt aattattgtt    1920
aattattaat aatatatata ttaatcattt agatatataa ttctatagcc ttagactcct    1980
catcaataga agactacgta taaaataat cagataacat ctaaaacatg tagataaata     2040
atagttgttt catatccaac atgatgtcca gagcttcacg ctgccgcaag cactcagggc    2100
gcaagggctg ctaaaggaag cggaacacgt agaaagccag tccgcagaan cggtgctgac    2160
cccggatgaa tgtcagctac tgggctatct ggacaaggga aaacgcaagc gcannagaga    2220
aagcaggtag cttgcagtgg gcttacatgg cgatagctag actgggcggt tttatggaca    2280
gcaagcgaac cggaattgcc agctggggcg ccctctggta aggttgggaa gccctgcaaa    2340
gtaaactgga tggctttctt gccgccaagg atctgatggc gcaggggatc aagatcatga    2400
gcggagaatt aagggagtca cgttatgacc cccgccgatg acgcgggaca agccgtttta    2460
cgtttggaac tgacagaacc gcaacgttga aggagccact cagccgcggg tttctggagt    2520
ttaatgagct aagcacatac gtcagaaacc attattgcgc gttcaaaagt cgcctaaggt    2580
cactatcagc tagcaaatat ttcttgtcaa aaatgctcca ctgacgttcc ataaattccc    2640
ctcggtatcc aattagagtc tcatattcac tctcaatcca gatctggatc gtttcgcatg    2700
attgaacaag atggattgca cgcaggttct ccggccgctt gggtggagag ctattcggc    2760 tatgactggg cacaacagac aatcggctgc tctgatgccg ccgtgttccg gctgtcagcg    2820
caggggcgcc cggttctttt tgtcaagacc gacctgtccg gtgccctgaa tgaactgcag    2880
gacgaggcag cgcggctatc gtggctggcc acgacgggcg ttccttgcgc agctgtgctc    2940
gacgttgtca ctgaagcggg aagggactgg ctgctattgg gcgaagtgcc ggggcaggat    3000
ctcctgtcat ctcaccttgc tcctgccgag aaagtatcca tcatggctga tgcaatgcgg    3060
cggctgcata cgcttgatcc ggctacctgc ccattcgacc accaagcgaa acatcgcatc    3120
gagcgagcac gtactcggat ggaagccggt cttgtcgatc aggatgatct ggacgaagag    3180 catcagggc tcgcgccagc cgaactgttc gccaggctca aggcgcgcat gcccgacggc    3240
gatgatctcg tcgtgaccca tggcgatgcc tgcttgccga atatcatggt ggaaaatggc    3300
cgcttttctg gattcatcga ctgtggccgg ctgggtgtgg cggaccgcta tcaggacata    3360
gcgttggcta cccgtgatat tgctgaagag cttggcggcg aatgggctga ccgcttcctc    3420
gtgctttacg gtatcgccgc tcccgattcg cagcgcatcg ccttctatcg ccttcttgac    3480
gagttcttct gagcgggact ctgaggatcc cccgatgagc taagctagct atatcatcaa    3540
tttatgtatt acacataata tcgcactcag tctttcatct acggcaatgt accagctgat    3600
ataatcagtt attgaaatat ttctgaattt aaacttgcat caataaattt atgttttgc     3660 ttggactata atacctgact tgttatttta tcaataaata tttaaactat atttctttca    3720
```

-continued

| | |
|---|---|
| agatgggaat taattcactg gccgtcgttt acaacgtcg tgactgggaa accctggcg | 3780 |
| ttacccaact taatcgcctt gcagcacatc cccctttcgc cagctggcgt aatagcgaag | 3840 |
| aggcccgcac cgatcgccct tcccaacagt tgcgcagcct gaatggcgcc cgctcctttc | 3900 |
| gctttcttcc cttcctttct cgccacgttc gccggctttc cccgtcaagc tctaaatcgg | 3960 |
| gggctcccct tagggttccg atttagtgct ttacggcacc tcgaccccaa aaaacttgat | 4020 |
| ttgggtgatg gttcacgtag tgggccatcg ccctgataga cggttttttcg ccctttgacg | 4080 |
| ttggagtcca cgttctttaa tagtggactc ttgttccaaa ctggaacaac actcaaccct | 4140 |
| atctcgggct attctttga tttataaggg attttgccga tttcggaacc accatcaaac | 4200 |
| aggatttcg cctgctgggg caaaccagcg tggaccgctt gctgcaactc tctcagggcc | 4260 |
| aggcggtgaa gggcaatcag ctgttgcccg tctcactggt gaaagaaaaa accaccccag | 4320 |
| tacattaaaa acgtccgcaa tgtgttatta agttgtctaa gcgtcaattt gtttacacca | 4380 |
| caatatatcc tgccaccagc cagccaacag ctccccgacc ggcagctcgg cacaaaatca | 4440 |
| ccactcgata caggcagccc atcag | 4465 |

<210> SEQ ID NO 14
<211> LENGTH: 8074
<212> TYPE: DNA
<213> ORGANISM: Artificial Sequence
<220> FEATURE:
<223> OTHER INFORMATION: plasmid pBMSP-1spJSC
<221> NAME/KEY: VARIANT
<222> LOCATION: 2315
<223> OTHER INFORMATION: n = A,T,C or G
<220> FEATURE:
<223> OTHER INFORMATION: Vector

<400> SEQUENCE: 14

| | |
|---|---|
| ctgatgggct gcctgtatcg agtggtgatt ttgtgccgag ctgccggtcg gggagctgtt | 60 |
| ggctggctgg tggcaggata tattgtggtg taaacaaatt gacgcttaga caacttaata | 120 |
| acacattgcg gacgttttta atgtactggg gtggtttttc ttttcaccag tgagacgggc | 180 |
| aacagctgat tgcccttcac cgcctggccc tgagagagtt gcagcaagcg gtccacgctg | 240 |
| gtttgcccca gcaggcgaaa atcctgtttg atggtggttc cgaaatcggc aaaatccctt | 300 |
| ataaatcaaa agaatagccc gagatagggt tgagtgttgt tccagtttgg aacaagagtc | 360 |
| cactattaaa gaacgtggac tccaacgtca agggcgaaa aaccgtctat cagggcgatg | 420 |
| gcccactacg tgaaccatca cccaaatcaa gttttttggg gtcgaggtgc cgtaaagcac | 480 |
| taaatcggaa ccctaaaggg agcccccgat ttagagcttg acggggaaag ccggcgaacg | 540 |
| tggcgagaaa ggaagggaag aaagcgaaag gagcgggcgc cattcaggct gcgcaactgt | 600 |
| tgggaagggc gatcggtgcg ggcctcttcg ctattacgcc agctggcgaa aggggggatgt | 660 |
| gctgcaaggc gattaagttg gtaacgcca gggttttccc agtcacgacg ttgtaaaacg | 720 |
| acggccagtg aattaattcc catcttgaaa gaaatatagt ttaaatattt attgataaaa | 780 |
| taacaagtca ggtattatag tccaagcaaa aacataaatt tattgatgca agtttaaatt | 840 |
| cagaaatatt tcaataactg attatatcag ctggtacatt gccgtagatg aaagactgag | 900 |
| tgcgatatta tgtgtaatac ataaattgat gatatagcta gcttagctca tcggggatc | 960 |
| ctcagagtcc cgctcagaag aactcgtcaa gaaggcgata gaaggcgatg cgctgcgaat | 1020 |
| cgggagcggc gataccgtaa agcacgagga agcggtcagc ccattcgccg ccaagctctt | 1080 |
| cagcaatatc acgggtagcc aacgctatgt cctgatagcg gtccgccaca cccagccggc | 1140 |
| cacagtcgat gaatccagaa aagcggccat tttccaccat gatattcggc aagcaggcat | 1200 |

```
cgccatgggt cacgacgaga tcatcgccgt cgggcatgcg cgccttgagc ctggcgaaca    1260
gttcggctgg cgcgagcccc tgatgctctt cgtccagatc atcctgatcg acaagaccgg    1320
cttccatccg agtacgtgct cgctcgatgc gatgtttcgc ttggtggtcg aatgggcagg    1380
tagccggatc aagcgtatgc agccgccgca ttgcatcagc catgatggat actttctcgg    1440
caggagcaag gtgagatgac aggagatcct gccccggcac ttcgcccaat agcagccagt    1500
cccttcccgc ttcagtgaca acgtcgagca cagctgcgca aggaacgccc gtcgtggcca    1560
gccacgatag ccgcgctgcc tcgtcctgca gttcattcag gcaccggac aggtcggtct     1620 tgacaaaaag aaccgggcgc ccctgcgctg acagccggaa cacggcggca tcagagcagc    1680
cgattgtctg ttgtgcccag tcatagccga atagcctctc cacccaagcg gccggagaac    1740
ctgcgtgcaa tccatcttgt tcaatcatgc gaaacgatcc agatctggat tgagagtgaa    1800
tatgagactc taattggata ccgaggggaa tttatggaac gtcagtggag cattttgac     1860 aagaaatatt tgctagctga tagtgacctt aggcgacttt tgaacgcgca ataatggttt    1920
ctgacgtatg tgcttagctc attaaactcc agaaacccgc ggctgagtgg ctccttcaac    1980
gttgcggttc tgtcagttcc aaacgtaaaa cggcttgtcc cgcgtcatcg gcggggtca     2040 taacgtgact cccttaattc tccgctcatg atcttgatcc cctgcgccat cagatccttg    2100
gcggcaagaa agccatccag tttactttgc agggcttccc aaccttacca gagggcgccc    2160
cagctggcaa ttccggttcg cttgctgtcc ataaaaccgc ccagtctagc tatcgccatg    2220
taagcccact gcaagctacc tgctttctct ttgcgcttgc gttttccctt gtccagatag    2280
cccagtagct gacattcatc cggggtcagc accgnttctg cggactggct ttctacgtgt    2340
tccgcttcct ttagcagccc ttgcgccctg agtgcttgcg gcagcgtgaa gctctggaca    2400
tcatgttgga tatgaaacaa ctattattta tctacatgtt ttagatgtta tctgattatt    2460
tttatacgta gtcttctatt gatgaggagt ctaaggctat agaattatat atctaaatga    2520
ttaatatata tattattaat aattaacaat aattaatata ttataattta tatatatata    2580
ttttatatta ttataataat attcttacaa atataattat tatattcgac ggtatcgcga    2640
taagctcgcg gatccctgaa agcgacgttg gatgttaaca tctacaaatt gccttttctt    2700
atcgaccatg tacgtaagcg cttacgtttt tggtggaccc ttgaggaaac tggtagctgt    2760
tgtgggcctg tggtctcaag atggatcatt aatttccacc ttcacctacg atgggggca    2820 tcgcaccggt gagtaatatt gtacggctaa gagcgaattt ggcctgtagg atccctgaaa    2880
gcgacgttgg atgttaacat ctacaaattg ccttttctta tcgaccatgt acgtaagcgc    2940
ttacgttttt ggtggaccct tgaggaaact ggtagctgtt gtgggcctgt ggtctcaaga    3000
tggatcatta atttccacct tcacctacga tgggggcat cgcaccggtg agtaatattg     3060
tacggctaag agcgaatttg gcctgtagga tccctgaaag cgacgttgga tgttaacatc    3120
tacaaattgc cttttcttat cgaccatgta cgtaagcgct acgttttg gtggaccctt      3180 gaggaaactg gtagctgttg tgggcctgtg gtctcaagat ggatcattaa tttccacctt    3240
cacctacgat gggggcatc gcaccggtga gtaatattgt acggctaaga gcgaatttgg     3300
cctgtaggat ccgcgagctg gtcaatccca ttgcttttga agcagctcaa cattgatctc    3360
tttctcgatc gagggagatt tttcaaatca gtgcgcaaga cgtgacgtaa gtatccgagt    3420 cagttttat tttctacta atttggtcgt ttatttcggc gtgtaggaca tggcaaccgg      3480
gcctgaattt cgcgggtatt ctgtttctat tccaactttt tcttgatccg cagccattaa    3540
cgacttttga atagatacgc tgacacgcca agcctcgcta gtcaaaagtg taccaaacaa    3600
```

```
cgctttacag caagaacgga atgcgcgtga cgctcgcggt gacgccattt cgccttttca   3660
gaaatggata aatagccttg cttcctatta tatcttccca aattaccaat acattacact   3720
agcatctgaa tttcataacc aatctcgata caccaaatcg actctagggg taccatggtg   3780
ctcttcgtgc tcacctgcct gctggcggtc ttcccagcca tctccacgaa gagtcccata   3840
tttggtcccg aggaggtgaa tagtgtggaa ggtaactcag tgtccatcac gtgctactac   3900
ccacccacct ctgtcaaccg gcacacccgg aagtactggt gccggcaggg agctagaggt   3960
ggctgcataa ccctcatctc ctcggagggc tacgtctcca gcaaatatgc aggcagggct   4020
aacctcacca acttcccgga gaacggcaca tttgtggtga acattgccca gctgagccag   4080
gatgactccg ggcgctacaa gtgtggcctg gcatcaata gccgaggcct gtcctttgat   4140
gtcagcctgg aggtcagcca gggtcctggg ctcctaaatg cactaaagt ctacacagtg   4200 gacctgggca gaacggtgac catcaactgc cctttcaaga ctgagaatgc tcaaaagagg   4260
aagtccttgt acaagcagat aggcctgtac cctgtgctgg tcatcgactc cagtggttat   4320
gtgaatccca actatacagg aagaatacgc cttgatattc agggtactgg ccagttactg   4380
ttcagcgttg tcatcaacca actcaggctc agcgatgctg gcagtatct ctgccaggct   4440 ggggatgatt ccaatagtaa taagaagaat gctgacctcc aagtgctaaa gcccgagccc   4500
gagctggttt atgaagacct gagggctca gtgaccttcc actgtgccct gggccctgag   4560
gtggcaaacg tggccaaatt tctgtgccga cagagcagtg gggaaaactg tgacgtggtc   4620
gtcaacaccc tggggaagag ggccccagcc tttgagggca ggatcctgct caaccccag   4680 gacaaggatg gctcattcag tgtggtgatc acaggcctga ggaaggagga tgcagggcgc   4740
tacctgtgtg gagcccattc ggatggtcag ctgcaggaag gctcgcctat ccaggcctgg   4800
caactcttcg tcaatgagga gtccacgatt ccccgcagcc ccactgtggt gaaggggtg   4860 gcaggaagct ctgtggccgt gctctgcccc tacaaccgta aggaaagcaa aagcatcaag   4920
tactggtgtc tctgggaagg ggcccagaat ggccgctgcc ccctgctggt ggacagcgag   4980 gggtggtta aggcccagta cgagggccgc ctctccctgc tggaggagcc aggcaacggc   5040
accttcactg tcatcctcaa ccagctcacc agccgggacg ccggcttcta ctggtgtctg   5100
accaacggcg atactctctg gaggaccacc gtggagatca agattatcga aggaaacca   5160 aacctcaagg ttcccgggaa tgtcacggct gtgctgggag agactctcaa ggtcccctgt   5220
cactttccat gcaaattctc ctcgtacgag aaatactggt gcaagtggaa taacacgggc   5280
tgccaggccc tgcccagcca agacgaaggc cccagcaagg ccttcgtgaa ctgtgacgag   5340
aacagccggc ttgtctccct gacccctgaac ctggtgacca gggctgatga gggctggtac   5400
tggtgtggag tgaagcaggg ccacttctat ggagagactg cagccgtcta tgtggcagtt   5460
gaagagagga aggcagcggg gtcccgcgat gtcagcctag cgaaggcaga cgctgctcct   5520
gatgagaagg tgctagactc tggttttcgg gagattgaga acaaagccat tcaggatccc   5580 aggcttttg cagagtgaat tcccgatcgt tcaaacattt ggcaataaag tttcttaaga   5640
ttgaatcctg ttgccggtct tgcgatgatt atcatataat ttctgttgaa ttacgttaag   5700
catgtaataa ttaacatgta atgcatgacg ttatttatga gatgggtttt tatgattaga   5760
gtcccgcaat tatacattta atacgcgata gaaaacaaaa tatagcgcgc aaactaggat   5820
aaattatcgc gcgcggtgtc atctatgtta ctagatcggg gatccgtcga cggtatcgat   5880
aaggatccct gaaagcgacg ttggatgtta acatctacaa attgccttt cttatcgacc   5940 atgtacgtaa gcgcttacgt ttttggtgga cccttgagga aactggtagc tgttgtgggc   6000
```

```
ctgtggtctc aagatggatc attaatttcc accttcacct cgatgggggg gcatcgcacc    6060
ggtgagtaat attgtacggc taagagcgaa tttggcctgt aggatccctg aaagcgacgt    6120
tggatgttaa catctacaaa ttgccttttc ttatcgacca tgtacgtaag cgcttacgtt    6180
tttggtggac ccttgaggaa actggtagct gttgtgggcc tgtggtctca agatggatca    6240
ttaatttcca ccttcaccta cgatgggggg catcgcaccg gtgagtaata ttgtacggct    6300
aagagcgaat ttggcctgta ggatccctga aagcgacgtt ggatgttaac atctacaaat    6360
tgccttttct tatcgaccat gtacgtaagc gcttacgttt ttggtggacc cttgaggaaa    6420
ctggtagctg ttgtgggcct gtggtctcaa gatggatcat taatttccac cttcacctac    6480
gatggggggc atcgcaccgg tgagtaatat tgtacggcta agagcgaatt tggcctgtag    6540
gatccgcgag ctggtcaatc ccattgcttt tgaagcagct caacattgat ctctttctcg    6600
agggagattt ttcaaatcag tgcgcaagac gtgacgtaag tatccgagtc agttttttatt    6660
tttctactaa tttggtcgtt tatttcggcg tgtaggacat ggcaaccggg cctgaatttc    6720
gcgggtattc tgtttctatt ccaactttttt cttgatccgc agccattaac gacttttgaa    6780
tagatacgct gacacgccaa gcctcgctag tcaaaagtgt accaaacaac gctttacagc    6840
aagaacggaa tgcgcgtgac gctcgcggtg acgccatttc gccttttcag aaatggataa    6900
atagccttgc ttcctattat atcttcccaa attaccaata cattcactca gcatctgaat    6960
ttcataacca atctcgatac accaaatcga ctctagagga tctaaccatg gatctaaac    7020
cttttttgtc tcttctttca ttgtcattgc ttttgtttac atctactagt ttggcacaag    7080
aagatgaaag gattgttctt gttgacaaca aatgtaagtg tgcccggatt acttccagga    7140
tcatccgttc ttccgaagat cctaatgagg acattgtgga gagaaacatc cgaattattg    7200
ttcctctgaa caacagggag aatatctctg atcccacctc accattgaga accagatttg    7260
tgtaccattt gtctgacctc tgtaaaaaat gtgatcctac agaagtggag ctggataatc    7320
agatagttac tgctacccag agcaatatct gtgatgaaga cagtgctaca gagacctgct    7380
acacttatga cagaaacaag tgctacacag ctgtggtccc actcgtatat ggtggtgaga    7440
ccaaaatggt ggaaacagcc ttaaccccag atgcctgcta tcctgactga gctcgaattt    7500
ccccgatcgt tcaaacattt ggcaataaag tttcttaaga ttgaatcctg ttgccggtct    7560
tgcgatgatt atcatataat ttctgttgaa ttacgttaag catgtaataa ttaacatgta    7620
atgcatgacg ttatttatga gatgggtttt tatgattaga gtcccgcaat tatacattta    7680
atacgcgata gaaaacaaaa tatagcgcgc aaactaggat aaattatcgc gcgcggtgtc    7740
atctatgtta ctagatcggg aattaattca gatcggctga gtggctccctt caatcgttgc    7800
ggttctgtca gttccaaacg taaaacggct tgtcccgcgt catcggcggg ggtcataacg    7860
tgactcccctt aattctccgc tcatgatcag attgtcgttt cccgccttca gtttaaacta    7920
tcagtgtttg acaggatata ttggcgggta aacctaagag aaaagagcgt ttattagaat    7980
aatcggatat ttaaaagggc gtgaaaaggt ttatccgttc gtccatttgt atgtgcatgc    8040
caaccacagg ttccccagat ctggcgccgg ccag                                8074
```

<210> SEQ ID NO 15
<211> LENGTH: 1062
<212> TYPE: DNA
<213> ORGANISM: Homo sapiens

<400> SEQUENCE: 15

```
gcatccccga ccagccccaa ggtcttcccg ctgagcctct gcagcaccca gccagatggg      60
```

-continued

```
aacgtggtca tcgcctgcct ggtccagggc ttcttccccc aggagccact cagtgtgacc    120
tggagcgaaa gcggacaggg cgtgaccgcc agaaacttcc cacccagcca ggatgcctcc    180
ggggacctgt acaccacgag cagccagctg accctgccgg ccacacagtg cctagccggc    240
aagtccgtga catgccacgt gaagcactac acgaatccca gccaggatgt gactgtgccc    300
tgcccagttc cctcaactcc acctacccca tctccctcaa ctccacctac cccatctccc    360
tcatgctgcc accccgact gtcactgcac cgaccggccc tcgaggacct gctcttaggt     420
tcagaagcga acctcacgtg cacactgacc ggcctgagag atgcctcagg tgtcaccttc    480
acctggacgc cctcaagtgg aagagcgct gttcaaggac cacctgagcg tgacctctgt     540
ggctgctaca gcgtgtccag tgtcctgccg ggctgtgccg agccatggaa ccatgggaag    600
accttcactt gcactgctgc ctaccccgag tccaagaccc gctaaccgc cacctctca     660 aaatccggaa acacattccg gcccgaggtc cacctgctgc cgccgccgtc ggaggagctg    720
gccctgaacg agctggtgac gctgacgtgc ctggcacgcg gcttcagccc caaggacgtg    780
ctggttcgct ggctgcaggg gtcacaggag ctgccccgcg agaagtacct gacttgggca    840
tcccggcagg agcccagcca gggcaccacc accttcgctg tgaccagcat actgcgcgtg    900
gcagccgagg actggaagaa gggggacacc ttctcctgca tggtgggcca cgaggccctg    960
ccgctggcct tcacacagaa gaccatcgac cgcttggcgg gtaaacccac ccatgtcaat   1020
gtgtctgttg tcatggcgga ggtggacggc acctgctact ga                     1062
```

<210> SEQ ID NO 16
<211> LENGTH: 353
<212> TYPE: PRT
<213> ORGANISM: Homo sapiens

<400> SEQUENCE: 16

```
Ala Ser Pro Thr Ser Pro Lys Val Phe Pro Leu Ser Leu Cys Ser Thr
 1               5                  10                  15

Gln Pro Asp Gly Asn Val Val Ile Ala Cys Leu Val Gln Gly Phe Phe
             20                  25                  30

Pro Gln Glu Pro Leu Ser Val Thr Trp Ser Glu Ser Gly Gln Gly Val
         35                  40                  45

Thr Ala Arg Asn Phe Pro Pro Ser Gln Asp Ala Ser Gly Asp Leu Tyr
     50                  55                  60

Thr Thr Ser Ser Gln Leu Thr Leu Pro Ala Thr Gln Cys Leu Ala Gly
 65                  70                  75                  80

Lys Ser Val Thr Cys His Val Lys His Tyr Thr Asn Pro Ser Gln Asp
                 85                  90                  95

Val Thr Val Pro Cys Pro Val Pro Ser Thr Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
```

```
                195                 200                 205
Pro Glu Ser Lys Thr Pro Leu Thr Ala Thr Leu Ser Lys Ser Gly Asn
            210                 215                 220

Thr Phe Arg Pro Glu Val His Leu Leu Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
            275                 280                 285

Thr Thr Thr Phe Ala Val Thr Ser Ile Leu Arg Val Ala Ala Glu Asp
            290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350

Tyr
```

```
<210> SEQ ID NO 17
<211> LENGTH: 1023
<212> TYPE: DNA
<213> ORGANISM: Homo sapiens

<400> SEQUENCE: 17
gcatccccga ccagccccaa ggtcttcccg ctgagcctcg acagcacccc ccaagatggg      60
aacgtggtcg tcgcatgcct ggtccagggc ttcttccccc aggagccact cagtgtgacc     120
tggagcgaaa gcggacagaa cgtgaccgcc agaaacttcc cacctagcca ggatgcctcc    180
ggggacctgt acaccacgag cagccagctg accctgccgg ccacacagtg cccagacggc    240
aagtccgtga catgccacgt gaagcactac acgaatccca gccaggatgt gactgtgccc    300
tgcccagttc ccccacctcc cccatgctgc caccccgac tgtcgctgca ccgaccggcc     360
ctcgaggacc tgctcttagg ttcagaagcg aacctcacgt gcacactgac cggcctgaga    420
gatgcctctg gtgccacctt cacctggacg ccctcaagtg gaagagcgc tgttcaagga     480
ccacctgagc gtgaccctct ggctgctac agcgtgtcca gtgtcctgcc tggctgtgcc     540
cagccatgga accatgggga ccttcacc tgcactgctg cccaccccga gttgaagacc      600
ccactaaccg ccaacatcac aaaatccgga aacacattcc ggcccgaggt ccacctgctg    660
ccgccgccgt cggaggagct ggccctgaac gagctggtga cgctgacgtg cctggcacgt    720
ggcttcagcc ccaaggatgt gctggttcgc tggctgcagg ggtcacagga gctgccccgc    780
gagaagtacc tgacttgggc atcccggcag gagcccagcc agggcaccac caccttcgct    840
gtgaccagca tactgcgcgt ggcagccgag gactggaaga aggggacac cttctcctgc    900
atggtgggcc acgaggccct gccgctggcc ttcacacaga gaccatcga ccgcttggcg    960
ggtaaaccca cccatgtcaa tgtgtctgtt gtcatggcgg aggtggacgg cacctgctac   1020
tga                                                                 1023
```

```
<210> SEQ ID NO 18
<211> LENGTH: 340
<212> TYPE: PRT
<213> ORGANISM: Homo sapiens
```

```
<400> SEQUENCE: 18

Ala Ser Pro Thr Ser Pro Lys Val Phe Pro Leu Ser Leu Asp Ser Thr
1               5                   10                  15

Pro Gln Asp Gly Asn Val Val Ala Cys Leu Val Gln Gly Phe Phe
            20                  25                  30

Pro Gln Glu Pro Leu Ser Val Thr Trp Ser Glu Ser Gly Gln Asn Val
            35                  40                  45

Thr Ala Arg Asn Phe Pro Pro Ser Gln Asp Ala Ser Gly Asp Leu Tyr
        50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Pro Pro Pro Cys Cys His Pro
            100                 105                 110

Arg Leu Ser Leu His Arg Pro Ala Leu Glu Asp Leu Leu Leu Gly Ser
            115                 120                 125

Glu Ala Asn Leu Thr Cys Thr Leu Thr Gly Leu Arg Asp Ala Ser Gly
130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
            165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
            195                 200                 205

Ser Gly Asn Thr Phe Arg Pro Glu Val His Leu Leu Pro Pro Pro Ser
210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
            245                 250                 255

Glu Leu Pro Arg Glu Lys Tyr Leu Thr Trp Ala Ser Arg Gln Glu Pro
            260                 265                 270

Ser Gln Gly Thr Thr Thr Phe Ala Val Thr Ser Ile Leu Arg Val Ala
            275                 280                 285

Ala Glu Asp Trp Lys Lys Gly Asp Thr Phe Ser Cys Met Val Gly His
290                 295                 300

Glu Ala Leu Pro Leu Ala Phe Thr Gln Lys Thr Ile Asp Arg Leu Ala
305                 310                 315                 320

Gly Lys Pro Thr His Val Asn Val Ser Val Val Met Ala Glu Val Asp
                325                 330                 335

Gly Thr Cys Tyr
            340

<210> SEQ ID NO 19
<211> LENGTH: 993
<212> TYPE: DNA
<213> ORGANISM: Homo sapiens

<400> SEQUENCE: 19
gcctccacca agggcccatc ggtcttcccc ctggcaccct cctccaagag cacctctggg    60
ggcacagcgg ccctgggctg cctggtcaag gactacttcc ccgaaccggt gacggtgtcg   120
```

```
tggaactcag gcgccctgac cagcggcgtg cacaccttcc cggctgtcct acagtcctca    180
ggactctact ccctcagcag cgtggtgacc gtgccctcca gcagcttggg cacccagacc    240
tacatctgca acgtgaatca caagcccagc aacaccaagg tggacaagaa agttgagccc    300
aaatcttgtg acaaaactca cacatgccca ccgtgcccag cacctgaact cctgggggga    360
ccgtcagtct tcctcttccc cccaaaaccc aaggacaccc tcatgatctc ccggaccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gggtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa tga                                 993
```

<210> SEQ ID NO 20
<211> LENGTH: 330
<212> TYPE: PRT
<213> ORGANISM: Homo sapiens

<400> SEQUENCE: 20

```
Ala Ser Thr Lys Gly Pro Ser Val Phe Pro Leu Ala Pro Ser Ser Lys
  1               5                  10                  15
Ser Thr Ser Gly Gly Thr Ala Ala Leu Gly Cys Leu Val Lys Asp Tyr
             20                  25                  30
Phe Pro Glu Pro Val Thr Val Ser Trp Asn Ser Gly Ala Leu Thr Ser
         35                  40                  45
Gly Val His Thr Phe Pro Ala Val Leu Gln Ser Ser Gly Leu Tyr Ser
     50                  55                  60
Leu Ser Ser Val Val Thr Val Pro Ser Ser Ser Leu Gly Thr Gln Thr
 65                  70                  75                  80
Tyr Ile Cys Asn Val Asn His Lys Pro Ser Asn Thr Lys Val Asp Lys
                 85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
```

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 21
<211> LENGTH: 978
<212> TYPE: DNA
<213> ORGANISM: Homo sapiens

<400> SEQUENCE: 21
gcctccacca agggcccatc ggtcttcccc ctggcgccct gctccaggag cacctccgag      60
agcacagccg ccctgggctg cctggtcaag gactacttcc ccgaaccggt gacggtgtcg     120
tggaactcag gcgctctgac cagcggcgtg cacaccttcc cagctgtcct acagtcctca     180
ggactctact ccctcagcag cgtggtgacc gtgccctcca gcaacttcgg cacccagacc     240
tacacctgca acgtagatca caagcccagc aacaccaagg tggacaagac agttgagcgc     300
aaatgttgtg tcgagtgccc accgtgccca gcaccacctg tggcaggacc gtcagtcttc     360
ctcttccccc caaaacccaa ggacaccctc atgatctccc ggaccccctga ggtcacgtgc     420
gtggtggtgg acgtgagcca cgaagacccc gaggtccagt tcaactggta cgtggacggc     480
gtggaggtgc ataatgccaa gacaaagcca cgggaggagc agttcaacag cacgttccgt     540
gtggtcagcg tcctcaccgt tgtgcaccag gactggctga acggcaagga gtacaagtgc     600
aaggtctcca acaaaggcct cccagccccc atcgagaaaa ccatctccaa aaccaagggg     660
cagccccgag aaccacaggt gtacaccctg cccccatccc gggaggagat gaccaagaac     720
caggtcagcc tgacctgcct ggtcaaaggc ttctacccca gcgacatcgc cgtggagtgg     780
gagagcaatg ggcagccgga gaacaactac aagaccacac ctcccatgct ggactccgac     840
ggctccttct tcctctacag caagctcacc gtggacaaga gcaggtggca gcaggggaac     900
gtcttctcat gctccgtgat gcatgaggct ctgcacaacc actacacgca gaagagcctc     960
tccctgtctc cgggtaaa                                                   978

<210> SEQ ID NO 22
<211> LENGTH: 326
<212> TYPE: PRT
<213> ORGANISM: Homo sapiens

<400> SEQUENCE: 22

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

```
Gly Val His Thr Phe Pro Ala Val Leu Gln Ser Ser Gly Leu Tyr Ser
             50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 23
<211> LENGTH: 1134
<212> TYPE: DNA
<213> ORGANISM: Homo sapiens

<400> SEQUENCE: 23
gcttccacca agggcccatc ggtcttcccc ctggcgccct gctccaggag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacacctgca acgtgaatca caagcccagc aacaccaagg tggacaagag agttgagctc     300
aaaaccccac ttggtgacac aactcacaca tgcccacggt gcccagagcc caaatcttgt     360
gacacacctc cccgtgccc acggtgccca gagcccaaat cttgtgacac acctccccca     420
tgcccacggt gccagagcc caaatcttgt gacacacctc cccgtgccc aaggtgccca     480 gcacctgaac tcctgggagg accgtcagtc ttcctcttcc ccccaaaacc caaggatacc     540
```

```
cttatgattt cccggacccc tgaggtcacg tgcgtggtgg tggacgtgag ccacgaagac      600
cccgaggtcc agttcaagtg gtacgtggac ggcgtggagg tgcataatgc caagacaaag      660
ccgcgggagg agcagtacaa cagcacgttc cgtgtggtca gcgtcctcac cgtcctgcac      720
caggactggc tgaacggcaa ggagtacaag tgcaaggtct ccaacaaagc cctcccagcc      780
cccatcgaga aaaccatctc caaaaccaaa ggacagcccc gagaaccaca ggtgtacacc      840
ctgcccccat cccgggagga gatgaccaag aaccaggtca gcctgacctg cctggtcaaa      900
ggcttctacc ccagcgacat cgccgtggag tgggagagca atgggcagcc ggagaacaac      960
tacaacacca cgcctcccat gctggactcc gacggctcct tcttcctcta cagcaagctc     1020
accgtggaca agagcaggtg gcagcagggg aacatcttct catgctccgt gatgcatgag     1080
gctctgcaca accgcttcac gcagaagagc ctctccctgt ctccgggtaa atga           1134
```

<210> SEQ ID NO 24
<211> LENGTH: 377
<212> TYPE: PRT
<213> ORGANISM: Homo sapiens

<400> SEQUENCE: 24

```
Ala Ser Thr Lys Gly Pro Ser Val Phe Pro Leu Ala Pro Cys Ser Arg
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
 65                  70                  75                  80

Tyr Thr Cys Asn Val Asn His Lys Pro Ser Asn Thr Lys Val Asp Lys
                 85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270
```

```
Pro Arg Glu Pro Gln Val Tyr Thr Leu Pro Pro Ser Arg Glu Glu Met
        275                 280                 285
Thr Lys Asn Gln Val Ser Leu Thr Cys Leu Val Lys Gly Phe Tyr Pro
        290                 295                 300
Ser Asp Ile Ala Val Glu Trp Glu Ser Ser Gly Gln Pro Glu Asn Asn
305                 310                 315                 320
Tyr Asn Thr Thr Pro Pro Met Leu Asp Ser Asp Gly Ser Phe Phe Leu
                325                 330                 335
Tyr Ser Lys Leu Thr Val Asp Lys Ser Arg Trp Gln Gln Gly Asn Ile
                340                 345                 350
Phe Ser Cys Ser Val Met His Glu Ala Leu His Asn Arg Phe Thr Gln
                355                 360                 365
Lys Ser Leu Ser Leu Ser Pro Gly Lys
        370                 375

<210> SEQ ID NO 25
<211> LENGTH: 984
<212> TYPE: DNA
<213> ORGANISM: Homo sapiens

<400> SEQUENCE: 25
gcttccacca agggcccatc cgtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc ccccatgccc atcatgccca gcacctgagt tcctgggggg accatcagtc     360
ttcctgttcc ccccaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gcgtcctcac cgtcctgcac caggactggc tgaacggcaa ggagtacaag     600
tgcaaggtct ccaacaaagg cctcccgtcc tccatcgaga aaaccatctc caaagccaaa     660
gggcagcccc gagagccaca ggtgtacacc ctgcccccat cccaggagga gatgaccaag     720
aaccaggtca gcctgacctg cctggtcaaa ggcttctacc ccagcgacat cgccgtggag     780
tgggagagca atgggcagcc ggagaacaac tacaagacca cgcctcccgt gctggactcc     840
gacggctcct tcttcctcta cagcaggcta accgtggaca agagcaggtg gcaggagggg     900
aatgtcttct catgctccgt gatgcatgag gctctgcaca accactacac acagaagagc     960
ctctccctgt ctctgggtaa atga                                            984

<210> SEQ ID NO 26
<211> LENGTH: 327
<212> TYPE: PRT
<213> ORGANISM: Homo sapiens

<400> SEQUENCE: 26

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
```

```
Gly Val His Thr Phe Pro Ala Val Leu Gln Ser Ser Gly Leu Tyr Ser
 50                  55                  60
Leu Ser Ser Val Val Thr Val Pro Ser Ser Ser Leu Gly Thr Lys Thr
 65                  70                  75                  80
Tyr Thr Cys Asn Val Asp His Lys Pro Ser Asn Thr Lys Val Asp Lys
                 85                  90                  95
Arg Val Glu Ser Lys Tyr Gly Pro Pro Cys Pro Ser Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 27
<211> LENGTH: 300
<212> TYPE: DNA
<213> ORGANISM: Homo sapiens

<400> SEQUENCE: 27
taggctgcct gtgcccccca cctgcctgtc cacaacccag cctctggtac atccatgccc        60
tctgccctaa gctcacctg cactttcct tggatttcag agtctccaaa ggcacaggcc        120
tcctccgtgc ccactgcaca accccaagca gagggcagcc tcgccaaggc aaccacagcc       180
ccagccacca cccgtaacac aggtgagaag ccccttccct gcacactcca cccccaccca       240
cctgctcatt cctcagccgc ctcctccagg cagcccttca taactccttg tctgagtctc       300

<210> SEQ ID NO 28
<211> LENGTH: 383
<212> TYPE: PRT
<213> ORGANISM: Homo sapiens

<400> SEQUENCE: 28
```

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
            20                  25                  30

Tyr His Pro Thr Ser Val Thr Val Thr Trp Tyr Met Gly Thr Gln Ser
        35                  40                  45

Gln Pro Gln Arg Thr Phe Pro Glu Ile Gln Arg Arg Asp Ser Tyr Tyr
    50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro Glu Ser Pro Lys Ala Gln Ala Ser Ser Val Pro
                100                 105                 110

Thr Ala Gln Pro Gln Ala Glu Gly Ser Leu Ala Lys Ala Thr Thr Ala
            115                 120                 125

Pro Ala Thr Thr Arg Asn Thr Gly Arg Gly Gly Glu Glu Lys Lys Lys
130                 135                 140

Glu Lys Glu Lys Glu Glu Gln Glu Glu Arg Glu Thr Lys Thr Pro Glu
145                 150                 155                 160

Cys Pro Ser His Thr Gln Pro Leu Gly Val Tyr Leu Leu Thr Pro Ala
                165                 170                 175

Val Gln Asp Leu Trp Leu Arg Asp Lys Ala Thr Phe Thr Cys Phe Val
            180                 185                 190

Val Gly Ser Asp Leu Lys Asp Ala His Leu Thr Trp Glu Val Ala Gly
            195                 200                 205

Lys Val Pro Thr Gly Gly Val Glu Glu Gly Leu Leu Glu Arg His Ser
210                 215                 220

Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
                245                 250                 255

Pro Pro Gln Arg Leu Met Ala Leu Arg Glu Pro Ala Ala Gln Ala Pro
            260                 265                 270

Val Lys Leu Ser Leu Asn Leu Leu Ala Ser Ser Asp Pro Pro Glu Ala
            275                 280                 285

Ala Ser Trp Leu Leu Cys Glu Val Ser Gly Phe Ser Pro Pro Asn Ile
            290                 295                 300

Leu Leu Met Trp Leu Glu Asp Gln Arg Glu Val Asn Thr Ser Gly Phe
305                 310                 315                 320

Ala Pro Ala Arg Pro Pro Gln Pro Gly Ser Thr Thr Phe Trp Ala
                325                 330                 335

Trp Ser Val Leu Arg Val Pro Ala Pro Pro Ser Pro Gln Pro Ala Thr
            340                 345                 350

Tyr Thr Cys Val Val Ser His Glu Asp Ser Arg Thr Leu Leu Asn Ala
            355                 360                 365

Ser Arg Ser Leu Glu Val Ser Tyr Val Thr Asp His Gly Pro Met
370                 375                 380

<210> SEQ ID NO 29
<211> LENGTH: 300
<212> TYPE: DNA
<213> ORGANISM: Homo sapiens

<400> SEQUENCE: 29

```
gtcattagct ggatttagcc attccacaat gtacacatat ttcaaacatt gtgttgtata    60
tgataaacat gtataatttt tgtcaattaa aaattttttag gaagaggagg agaagagaag   120
aagaaggaga aggagaaaga ggaacaagaa gagagagaga caaagacacc aggttttttc   180 tgaccccctgg gctatcaaaa cacctattgc ccaataacta gttggccgtt ggtgccctaa   240
actattgaag cgattgctgt tatgtggatg ggccccggac acttagaaac tcgtgacccc   300
```

<210> SEQ ID NO 30
<211> LENGTH: 429
<212> TYPE: PRT
<213> ORGANISM: Homo sapiens

<400> SEQUENCE: 30

```
Pro Thr Lys Ala Pro Asp Val Phe Pro Ile Ile Ser Gly Cys Arg His
  1               5                  10                  15

Pro Lys Asp Asn Ser Pro Val Val Leu Ala Cys Leu Ile Thr Gly Tyr
                 20                  25                  30

His Pro Thr Ser Val Thr Val Thr Trp Tyr Met Gly Thr Gln Ser Gln
             35                  40                  45

Pro Gln Arg Thr Phe Pro Glu Ile Gln Arg Arg Asp Ser Tyr Tyr Met
         50                  55                  60

Thr Ser Ser Gln Leu Ser Thr Pro Leu Gln Gln Trp Arg Gln Gly Glu
 65                  70                  75                  80

Tyr Lys Cys Val Val Gln His Thr Ala Ser Lys Ser Lys Glu Ile
                 85                  90                  95

Phe Arg Trp Pro Glu Ser Pro Lys Ala Gln Ala Ser Ser Val Pro Thr
                100                 105                 110

Ala Gln Pro Gln Ala Glu Gly Ser Leu Ala Lys Ala Thr Thr Ala Pro
            115                 120                 125

Ala Thr Thr Arg Asn Thr Gly Arg Gly Gly Glu Glu Lys Lys Lys Glu
        130                 135                 140

Lys Glu Lys Glu Glu Gln Glu Glu Arg Glu Thr Lys Thr Pro Glu Cys
145                 150                 155                 160

Pro Ser His Thr Gln Pro Leu Gly Val Tyr Leu Leu Thr Pro Ala Val
                165                 170                 175

Gln Asp Leu Trp Leu Arg Asp Lys Ala Thr Phe Thr Cys Phe Val Val
            180                 185                 190

Gly Ser Asp Leu Lys Asp Ala His Leu Thr Trp Glu Val Ala Gly Lys
        195                 200                 205

Val Pro Thr Gly Gly Val Glu Glu Gly Leu Leu Glu Arg His Ser Asn
    210                 215                 220

Gly Ser Gln Ser Gln His Ser Arg Leu Thr Leu Pro Arg Ser Leu Trp
225                 230                 235                 240

Asn Ala Gly Thr Ser Val Thr Cys Thr Leu Asn His Pro Ser Leu Pro
                245                 250                 255

Pro Gln Arg Leu Met Ala Leu Arg Glu Pro Ala Ala Gln Ala Pro Val
            260                 265                 270

Lys Leu Ser Leu Asn Leu Leu Ala Ser Ser Asp Pro Pro Glu Ala Ala
        275                 280                 285

Ser Trp Leu Leu Cys Glu Val Ser Gly Phe Ser Pro Pro Asn Ile Leu
    290                 295                 300

Leu Met Trp Leu Glu Asp Gln Arg Glu Val Asn Thr Ser Gly Phe Ala
305                 310                 315                 320

Pro Ala Arg Pro Pro Pro Gln Pro Arg Ser Thr Thr Phe Trp Ala Trp
                325                 330                 335
```

```
Ser Val Leu Arg Val Pro Ala Pro Pro Ser Pro Gln Pro Ala Thr Tyr
            340                 345                 350

Thr Cys Val Val Ser His Glu Asp Ser Arg Thr Leu Leu Asn Ala Ser
        355                 360                 365

Arg Ser Leu Glu Val Ser Tyr Leu Ala Met Thr Pro Leu Ile Pro Gln
    370                 375                 380

Ser Lys Asp Glu Asn Ser Asp Asp Tyr Thr Thr Phe Asp Asp Val Gly
385                 390                 395                 400

Ser Leu Trp Thr Thr Leu Ser Thr Phe Val Ala Leu Phe Ile Leu Thr
                405                 410                 415

Leu Leu Tyr Ser Gly Ile Val Thr Phe Ile Lys Val Lys
            420                 425
```

<210> SEQ ID NO 31
<211> LENGTH: 500
<212> TYPE: DNA
<213> ORGANISM: Homo sapiens

<400> SEQUENCE: 31

```
gaagctgggg agaggagagc acagtggtta agtcagtccc tgcagcccaa ctgctcccga      60
aggtccggcc acagctgctc tcgtttgctc tcccctgcag agtgtccgag ccacacccag     120
cctcttggcg tctacctgct aaccccctgca gtgcaggacc tgtggctccg ggacaaagcc    180
accttcacct gcttcgtggt gggcagtgac ctgaaggatg ctcacctgac ctgggaggtg    240
gctgggaagg tccccacagg gggcgtggag aagggctgc tggagcggca cagcaacggc    300
tcccagagcc agcacagccg tctgaccctg cccaggtcct tgtggaacgc ggggacctcc    360
gtcacctgca cactgaacca tcccagcctc ccaccccaga ggttgatggc gctgagagaa    420
cccggtgagc ctggctccca ggtggggaga cgagggtgcc cacagcctgc tgaccccctac   480
gcccgcccca gggccatgac                                                500
```

<210> SEQ ID NO 32
<211> LENGTH: 383
<212> TYPE: PRT
<213> ORGANISM: Homo sapiens

<400> SEQUENCE: 32

```
Pro Thr Lys Ala Pro Asp Val Phe Pro Ile Ile Ser Gly Cys Arg His
1               5                  10                  15

Pro Lys Asp Asn Ser Pro Val Val Leu Ala Cys Leu Ile Thr Gly Tyr
            20                  25                  30

His Pro Thr Ser Val Thr Val Thr Trp Tyr Met Gly Thr Gln Ser Gln
        35                  40                  45

Pro Gln Arg Thr Phe Pro Glu Ile Gln Arg Arg Asp Ser Tyr Tyr Met
    50                  55                  60

Thr Ser Ser Gln Leu Ser Thr Pro Leu Gln Gln Trp Arg Gln Gly Glu
65                  70                  75                  80

Tyr Lys Cys Val Val Gln His Thr Ala Ser Lys Ser Lys Lys Glu Ile
                85                  90                  95

Phe Arg Trp Pro Glu Ser Pro Lys Ala Gln Ala Ser Ser Val Pro Thr
            100                 105                 110

Ala Gln Pro Gln Ala Glu Gly Ser Leu Ala Lys Ala Thr Thr Ala Pro
        115                 120                 125

Ala Thr Thr Arg Asn Thr Gly Arg Gly Gly Glu Glu Lys Lys Lys Glu
    130                 135                 140
```

Lys Glu Lys Glu Glu Gln Glu Arg Glu Thr Lys Thr Pro Glu Cys
145                 150                 155                 160

Pro Ser His Thr Gln Pro Leu Gly Val Tyr Leu Leu Thr Pro Ala Val
            165                 170                 175

Gln Asp Leu Trp Leu Arg Asp Lys Ala Thr Phe Thr Cys Phe Val Val
        180                 185                 190

Gly Ser Asp Leu Lys Asp Ala His Leu Thr Trp Glu Val Ala Gly Lys
    195                 200                 205

Val Pro Thr Gly Gly Val Glu Glu Gly Leu Leu Glu Arg His Ser Asn
210                 215                 220

Gly Ser Gln Ser Gln His Ser Arg Leu Thr Leu Pro Arg Ser Leu Trp
225                 230                 235                 240

Asn Ala Gly Thr Ser Val Thr Cys Thr Leu Asn His Pro Ser Leu Pro
            245                 250                 255

Pro Gln Arg Leu Met Ala Leu Arg Glu Pro Ala Ala Gln Ala Pro Val
        260                 265                 270

Lys Leu Ser Leu Asn Leu Leu Ala Ser Ser Asp Pro Pro Glu Ala Ala
    275                 280                 285

Ser Trp Leu Leu Cys Glu Val Ser Gly Phe Ser Pro Pro Asn Ile Leu
290                 295                 300

Leu Met Trp Leu Glu Asp Gln Arg Glu Val Asn Thr Ser Gly Phe Ala
305                 310                 315                 320

Pro Ala Arg Pro Pro Pro Gln Pro Arg Ser Thr Thr Phe Trp Ala Trp
            325                 330                 335

Ser Val Leu Arg Val Pro Ala Pro Pro Ser Pro Gln Pro Ala Thr Tyr
        340                 345                 350

Thr Cys Val Val Ser His Glu Asp Ser Arg Thr Leu Leu Asn Ala Ser
    355                 360                 365

Arg Ser Leu Glu Val Ser Tyr Val Thr Asp His Gly Pro Met Lys
370                 375                 380

<210> SEQ ID NO 33
<211> LENGTH: 500
<212> TYPE: DNA
<213> ORGANISM: Homo sapiens

<400> SEQUENCE: 33
ccacaggaaa ggagaaggga ggcaccacac cctggccggc cccacttctc tcccagtgcc      60
cccgtggcca gagcctgaca gcccccccac ctccccgcag ctgcgcaggc accgtcaag     120 ctttctctga acctgctggc ctcgtctgac cctcccgagg cggcctcgtg gctcctgtgt     180
gaggtgtctg gcttctcgcc ccccaacatc ctcctgatgt ggctggagga ccagcgtgag     240
gtgaacactt ctgggtttgc cccgcacgc ccccctccac agcccaggag caccacgttc      300
tgggcctgga gtgtgctgcg tgtcccagcc ccgcccagcc ctcagccagc cacctacacg     360
tgtgtggtca gccacgagga ctcccggact ctgctcaacg ccagccggag cctagaagtc     420
agctgtgagt cacccccagg ccagggttgg gacggggact ctgagggggg ccataaggag     480
ctggaatcca tactaggcag                                                 500

<210> SEQ ID NO 34
<211> LENGTH: 429
<212> TYPE: PRT
<213> ORGANISM: Homo sapiens

<400> SEQUENCE: 34

Pro Thr Lys Ala Pro Asp Val Phe Pro Ile Ile Ser Gly Cys Arg His

-continued

```
              1               5              10              15
Pro Lys Asp Asn Ser Pro Val Val Leu Ala Cys Leu Ile Thr Gly Tyr
                 20              25              30

His Pro Thr Ser Val Thr Val Thr Trp Tyr Met Gly Thr Gln Ser Gln
                 35              40              45

Pro Gln Arg Thr Phe Pro Glu Ile Gln Arg Arg Asp Ser Tyr Tyr Met
 50              55              60

Thr Ser Ser Gln Leu Ser Thr Pro Leu Gln Gln Trp Arg Gln Gly Glu
 65              70              75                              80

Tyr Lys Cys Val Val Gln His Thr Ala Ser Lys Ser Lys Lys Glu Ile
                 85              90              95

Phe Arg Trp Pro Glu Ser Pro Lys Ala Gln Ala Ser Ser Val Pro Thr
                100             105             110

Ala Gln Pro Gln Ala Glu Gly Ser Leu Ala Lys Ala Thr Thr Ala Pro
                115             120             125

Ala Thr Thr Arg Asn Thr Gly Arg Gly Gly Glu Glu Lys Lys Lys Glu
    130             135             140

Lys Glu Lys Glu Glu Gln Glu Glu Arg Glu Thr Lys Thr Pro Glu Cys
145             150             155                             160

Pro Ser His Thr Gln Pro Leu Gly Val Tyr Leu Leu Thr Pro Ala Val
                165             170             175

Gln Asp Leu Trp Leu Arg Asp Lys Ala Thr Phe Thr Cys Phe Val Val
                180             185             190

Gly Ser Asp Leu Lys Asp Ala His Leu Thr Trp Glu Val Ala Gly Lys
                195             200             205

Val Pro Thr Gly Gly Val Glu Glu Gly Leu Leu Glu Arg His Ser Asn
    210             215             220

Gly Ser Gln Ser Gln His Ser Arg Leu Thr Leu Pro Arg Ser Leu Trp
225             230             235                             240

Asn Ala Gly Thr Ser Val Thr Cys Thr Leu Asn His Pro Ser Leu Pro
                245             250             255

Pro Gln Arg Leu Met Ala Leu Arg Glu Pro Ala Ala Gln Ala Pro Val
                260             265             270

Lys Leu Ser Leu Asn Leu Leu Ala Ser Ser Asp Pro Pro Glu Ala Ala
    275             280             285

Ser Trp Leu Leu Cys Glu Val Ser Gly Phe Ser Pro Pro Asn Ile Leu
    290             295             300

Leu Met Trp Leu Glu Asp Gln Arg Glu Val Asn Thr Ser Gly Phe Ala
305             310             315                             320

Pro Ala Arg Pro Pro Pro Gln Pro Arg Ser Thr Thr Phe Trp Ala Trp
                325             330             335

Ser Val Leu Arg Val Pro Ala Pro Pro Ser Pro Gln Pro Ala Thr Tyr
                340             345             350

Thr Cys Val Val Ser His Glu Asp Ser Arg Thr Leu Leu Asn Ala Ser
    355             360             365

Arg Ser Leu Glu Val Ser Tyr Leu Ala Met Thr Pro Leu Ile Pro Gln
370             375             380

Ser Lys Asp Glu Asn Ser Asp Asp Tyr Thr Thr Phe Asp Asp Val Gly
385             390             395                             400

Ser Leu Trp Thr Thr Leu Ser Thr Phe Val Ala Leu Phe Ile Leu Thr
                405             410             415

Leu Leu Tyr Ser Gly Ile Val Thr Phe Ile Lys Val Lys
                420             425
```

<210> SEQ ID NO 35
<211> LENGTH: 26
<212> TYPE: PRT
<213> ORGANISM: Homo sapiens

<400> SEQUENCE: 35

Pro Thr Lys Ala Pro Asp Val Phe Pro Ile Ile Ser Gly Cys Arg His
1               5                   10                  15

Pro Lys Asp Asn Ser Pro Val Val Leu Ala
            20                  25

<210> SEQ ID NO 36
<211> LENGTH: 100
<212> TYPE: DNA
<213> ORGANISM: Homo sapiens

<400> SEQUENCE: 36
gacacgccga tttttttgtta ttagatgtaa cagaccatgg ccccatgaaa tgatcccgga    60
ccagatccgt ccgcacccgc cactcagcag ctctggccga                         100

<210> SEQ ID NO 37
<211> LENGTH: 383
<212> TYPE: PRT
<213> ORGANISM: Homo sapiens

<400> SEQUENCE: 37

Pro Thr Lys Ala Pro Asp Val Phe Pro Ile Ile Ser Gly Cys Arg His
1               5                   10                  15

Pro Lys Asp Asn Ser Pro Val Val Leu Ala Cys Leu Ile Thr Gly Tyr
            20                  25                  30

His Pro Thr Ser Val Thr Val Thr Trp Tyr Met Gly Thr Gln Ser Gln
        35                  40                  45

Pro Gln Arg Thr Phe Pro Glu Ile Gln Arg Arg Asp Ser Tyr Tyr Met
    50                  55                  60

Thr Ser Ser Gln Leu Ser Thr Pro Leu Gln Gln Trp Arg Gln Gly Glu
65                  70                  75                  80

Tyr Lys Cys Val Val Gln His Thr Ala Ser Lys Ser Lys Lys Glu Ile
                85                  90                  95

Phe Arg Trp Pro Glu Ser Pro Lys Ala Gln Ala Ser Ser Val Pro Thr
            100                 105                 110

Ala Gln Pro Gln Ala Glu Gly Ser Leu Ala Lys Ala Thr Thr Ala Pro
        115                 120                 125

Ala Thr Thr Arg Asn Thr Gly Arg Gly Gly Glu Lys Lys Lys Glu
    130                 135                 140

Lys Glu Lys Glu Glu Gln Glu Glu Arg Glu Thr Lys Thr Pro Glu Cys
145                 150                 155                 160

Pro Ser His Thr Gln Pro Leu Gly Val Tyr Leu Leu Thr Pro Ala Val
                165                 170                 175

Gln Asp Leu Trp Leu Arg Asp Lys Ala Thr Phe Thr Cys Phe Val Val
            180                 185                 190

Gly Ser Asp Leu Lys Asp Ala His Leu Thr Trp Glu Val Ala Gly Lys
        195                 200                 205

Val Pro Thr Gly Gly Val Glu Glu Gly Leu Leu Glu Arg His Ser Asn
    210                 215                 220

Gly Ser Gln Ser Gln His Ser Arg Leu Thr Leu Pro Arg Ser Leu Trp
225                 230                 235                 240

Asn Ala Gly Thr Ser Val Thr Cys Thr Leu Asn His Pro Ser Leu Pro

```
                      245                 250                 255
Pro Gln Arg Leu Met Ala Leu Arg Glu Pro Ala Ala Gln Ala Pro Val
            260                 265                 270

Lys Leu Ser Leu Asn Leu Leu Ala Ser Ser Asp Pro Pro Glu Ala Ala
        275                 280                 285

Ser Trp Leu Leu Cys Glu Val Ser Gly Phe Ser Pro Pro Asn Ile Leu
    290                 295                 300

Leu Met Trp Leu Glu Asp Gln Arg Glu Val Asn Thr Ser Gly Phe Ala
305                 310                 315                 320

Pro Ala Arg Pro Pro Pro Gln Pro Arg Ser Thr Thr Phe Trp Ala Trp
                325                 330                 335

Ser Val Leu Arg Val Pro Ala Pro Pro Ser Pro Gln Pro Ala Thr Tyr
            340                 345                 350

Thr Cys Val Val Ser His Glu Asp Ser Arg Thr Leu Leu Asn Ala Ser
        355                 360                 365

Arg Ser Leu Glu Val Ser Tyr Val Thr Asp His Gly Pro Met Lys
    370                 375                 380

<210> SEQ ID NO 38
<211> LENGTH: 200
<212> TYPE: DNA
<213> ORGANISM: Homo sapiens

<400> SEQUENCE: 38
cgctcggccc ccgttcctcc ccagacctgg ccatgacccc cctgatccct cagagcaagg      60
atgagaacag cgatgactac acgacctttg atgatgtggg cagcctgtgg accaccctgt     120
ccacgtttgt ggccctcttc atcctcaccc tcctctacag cggcattgtc actttcatca     180
aggtcagggg agcggccagg                                                 200

<210> SEQ ID NO 39
<211> LENGTH: 429
<212> TYPE: PRT
<213> ORGANISM: Homo sapiens

<400> SEQUENCE: 39

Pro Thr Lys Ala Pro Asp Val Phe Pro Ile Ile Ser Gly Cys Arg His
1               5                   10                  15

Pro Lys Asp Asn Ser Pro Val Val Leu Ala Cys Leu Ile Thr Gly Tyr
            20                  25                  30

His Pro Thr Ser Val Thr Val Thr Trp Tyr Met Gly Thr Gln Ser Gln
        35                  40                  45

Pro Gln Arg Thr Phe Pro Glu Ile Gln Arg Arg Asp Ser Tyr Tyr Met
    50                  55                  60

Thr Ser Ser Gln Leu Ser Thr Pro Leu Gln Gln Trp Arg Gln Gly Glu
65                  70                  75                  80

Tyr Lys Cys Val Val Gln His Thr Ala Ser Lys Ser Lys Lys Glu Ile
                85                  90                  95

Phe Arg Trp Pro Glu Ser Pro Lys Ala Gln Ala Ser Ser Val Pro Thr
            100                 105                 110

Ala Gln Pro Gln Ala Glu Gly Ser Leu Ala Lys Ala Thr Thr Ala Pro
        115                 120                 125

Ala Thr Thr Arg Asn Thr Gly Arg Gly Gly Glu Glu Lys Lys Lys Glu
    130                 135                 140

Lys Glu Lys Glu Glu Gln Glu Glu Arg Glu Thr Lys Thr Pro Glu Cys
145                 150                 155                 160
```

```
Pro Ser His Thr Gln Pro Leu Gly Val Tyr Leu Leu Thr Pro Ala Val
            165                 170                 175

Gln Asp Leu Trp Leu Arg Asp Lys Ala Thr Phe Thr Cys Phe Val Val
        180                 185                 190

Gly Ser Asp Leu Lys Asp Ala His Leu Thr Trp Glu Val Ala Gly Lys
    195                 200                 205

Val Pro Thr Gly Gly Val Glu Glu Gly Leu Leu Glu Arg His Ser Asn
210                 215                 220

Gly Ser Gln Ser Gln His Ser Arg Leu Thr Leu Pro Arg Ser Leu Trp
225                 230                 235                 240

Asn Ala Gly Thr Ser Val Thr Cys Thr Leu Asn His Pro Ser Leu Pro
                245                 250                 255

Pro Gln Arg Leu Met Ala Leu Arg Glu Pro Ala Ala Gln Ala Pro Val
            260                 265                 270

Lys Leu Ser Leu Asn Leu Leu Ala Ser Ser Asp Pro Pro Glu Ala Ala
        275                 280                 285

Ser Trp Leu Leu Cys Glu Val Ser Gly Phe Ser Pro Pro Asn Ile Leu
    290                 295                 300

Leu Met Trp Leu Glu Asp Gln Arg Glu Val Asn Thr Ser Gly Phe Ala
305                 310                 315                 320

Pro Ala Arg Pro Pro Gln Pro Arg Ser Thr Thr Phe Trp Ala Trp
                325                 330                 335

Ser Val Leu Arg Val Pro Ala Pro Pro Ser Pro Gln Pro Ala Thr Tyr
            340                 345                 350

Thr Cys Val Val Ser His Glu Asp Ser Arg Thr Leu Leu Asn Ala Ser
        355                 360                 365

Arg Ser Leu Glu Val Ser Tyr Leu Ala Met Thr Pro Leu Ile Pro Gln
370                 375                 380

Ser Lys Asp Glu Asn Ser Asp Asp Tyr Thr Thr Phe Asp Asp Val Gly
385                 390                 395                 400

Ser Leu Trp Thr Thr Leu Ser Thr Phe Val Ala Leu Phe Ile Leu Thr
                405                 410                 415

Leu Leu Tyr Ser Gly Ile Val Thr Phe Ile Lys Val Lys
            420                 425

<210> SEQ ID NO 40
<211> LENGTH: 100
<212> TYPE: DNA
<213> ORGANISM: Homo sapiens

<400> SEQUENCE: 40
tcaggcttct agcccctgtc tgaccccagg ggctgtcttt caggtgaagt agccccagaa    60
gagcaggacg ccctgtacct gcagagaagg gaagcagcct                         100

<210> SEQ ID NO 41
<211> LENGTH: 429
<212> TYPE: PRT
<213> ORGANISM: Homo sapiens

<400> SEQUENCE: 41

Pro Thr Lys Ala Pro Asp Val Phe Pro Ile Ile Ser Gly Cys Arg His
1               5                   10                  15

Pro Lys Asp Asn Ser Pro Val Val Leu Ala Cys Leu Ile Thr Gly Tyr
            20                  25                  30

His Pro Thr Ser Val Thr Val Thr Trp Tyr Met Gly Thr Gln Ser Gln
        35                  40                  45
```

Pro Gln Arg Thr Phe Pro Glu Ile Gln Arg Arg Asp Ser Tyr Tyr Met
    50                  55                  60

Thr Ser Ser Gln Leu Ser Thr Pro Leu Gln Gln Trp Arg Gln Gly Glu
65                  70                  75                  80

Tyr Lys Cys Val Val Gln His Thr Ala Ser Lys Ser Lys Lys Glu Ile
                85                  90                  95

Phe Arg Trp Pro Glu Ser Pro Lys Ala Gln Ala Ser Ser Val Pro Thr
            100                 105                 110

Ala Gln Pro Gln Ala Glu Gly Ser Leu Ala Lys Ala Thr Thr Ala Pro
        115                 120                 125

Ala Thr Thr Arg Asn Thr Gly Arg Gly Gly Glu Glu Lys Lys Lys Glu
    130                 135                 140

Lys Glu Lys Glu Glu Gln Glu Glu Arg Glu Thr Lys Thr Pro Glu Cys
145                 150                 155                 160

Pro Ser His Thr Gln Pro Leu Gly Val Tyr Leu Leu Thr Pro Ala Val
                165                 170                 175

Gln Asp Leu Trp Leu Arg Asp Lys Ala Thr Phe Thr Cys Phe Val Val
            180                 185                 190

Gly Ser Asp Leu Lys Asp Ala His Leu Thr Trp Glu Val Ala Gly Lys
        195                 200                 205

Val Pro Thr Gly Gly Val Glu Glu Gly Leu Leu Glu Arg His Ser Asn
    210                 215                 220

Gly Ser Gln Ser Gln His Ser Arg Leu Thr Leu Pro Arg Ser Leu Trp
225                 230                 235                 240

Asn Ala Gly Thr Ser Val Thr Cys Thr Leu Asn His Pro Ser Leu Pro
                245                 250                 255

Pro Gln Arg Leu Met Ala Leu Arg Glu Pro Ala Ala Gln Ala Pro Val
            260                 265                 270

Lys Leu Ser Leu Asn Leu Leu Ala Ser Ser Asp Pro Pro Glu Ala Ala
        275                 280                 285

Ser Trp Leu Leu Cys Glu Val Ser Gly Phe Ser Pro Pro Asn Ile Leu
    290                 295                 300

Leu Met Trp Leu Glu Asp Gln Arg Glu Val Asn Thr Ser Gly Phe Ala
305                 310                 315                 320

Pro Ala Arg Pro Pro Pro Gln Pro Arg Ser Thr Thr Phe Trp Ala Trp
                325                 330                 335

Ser Val Leu Arg Val Pro Ala Pro Pro Ser Pro Gln Pro Ala Thr Tyr
            340                 345                 350

Thr Cys Val Val Ser His Glu Asp Ser Arg Thr Leu Leu Asn Ala Ser
        355                 360                 365

Arg Ser Leu Glu Val Ser Tyr Leu Ala Met Thr Pro Leu Ile Pro Gln
    370                 375                 380

Ser Lys Asp Glu Asn Ser Asp Asp Tyr Thr Thr Phe Asp Asp Val Gly
385                 390                 395                 400

Ser Leu Trp Thr Thr Leu Ser Thr Phe Val Ala Leu Phe Ile Leu Thr
                405                 410                 415

Leu Leu Tyr Ser Gly Ile Val Thr Phe Ile Lys Val Lys
            420                 425

<210> SEQ ID NO 42
<211> LENGTH: 495
<212> TYPE: DNA
<213> ORGANISM: Homo sapiens

<400> SEQUENCE: 42

-continued

```
tttccctgcc tcccgtcacc ctgccgccag ggcctctgcc ctgccctgcc ccttgtcctc    60
aggtttccag cctcagactc ccactgtgtc tgtcttccag cacccaccaa ggctccggat   120
gtgttcccca tcatatcagg gtgcagacac ccaaaggata acagccctgt ggtcctggca   180
tgcttgataa ctgggtacca cccaacgtcc gtgactgtca cctggtacat ggggacacag   240
agccagcccc agagaaacctt ccctgagata caaagacggg acagctacta catgacaagc   300
agccagctct ccaccccct ccagcagtgg cgcaaggcg agtacaaatg cgtggtccag   360
cacaccgcca gcaagagtaa aaggagatc ttccgctggc caggtaggtc gcaccggaga   420
tcacccagaa gggccccca ggaccccag caccttccac tcagggcctg accacaaaga   480
cagaagcaag ggctg                                                   495
```

<210> SEQ ID NO 43
<211> LENGTH: 429
<212> TYPE: PRT
<213> ORGANISM: Homo sapiens

<400> SEQUENCE: 43

```
Pro Thr Lys Ala Pro Asp Val Phe Pro Ile Ile Ser Gly Cys Arg His
1               5                   10                  15

Pro Lys Asp Asn Ser Pro Val Val Leu Ala Cys Leu Ile Thr Gly Tyr
            20                  25                  30

His Pro Thr Ser Val Thr Val Thr Trp Tyr Met Gly Thr Gln Ser Gln
        35                  40                  45

Pro Gln Arg Thr Phe Pro Glu Ile Gln Arg Arg Asp Ser Tyr Tyr Met
    50                  55                  60

Thr Ser Ser Gln Leu Ser Thr Pro Leu Gln Gln Trp Arg Gln Gly Glu
65                  70                  75                  80

Tyr Lys Cys Val Val Gln His Thr Ala Ser Lys Ser Lys Lys Glu Ile
                85                  90                  95

Phe Arg Trp Pro Glu Ser Pro Lys Ala Gln Ala Ser Ser Val Pro Thr
            100                 105                 110

Ala Gln Pro Gln Ala Glu Gly Ser Leu Ala Lys Ala Thr Thr Ala Pro
        115                 120                 125

Ala Thr Thr Arg Asn Thr Gly Arg Gly Gly Glu Glu Lys Lys Lys Glu
    130                 135                 140

Lys Glu Lys Glu Glu Gln Glu Glu Arg Glu Thr Lys Thr Pro Glu Cys
145                 150                 155                 160

Pro Ser His Thr Gln Pro Leu Gly Val Tyr Leu Leu Thr Pro Ala Val
                165                 170                 175

Gln Asp Leu Trp Leu Arg Asp Lys Ala Thr Phe Thr Cys Phe Val Val
            180                 185                 190

Gly Ser Asp Leu Lys Asp Ala His Leu Thr Trp Glu Val Ala Gly Lys
        195                 200                 205

Val Pro Thr Gly Gly Val Glu Glu Gly Leu Leu Glu Arg His Ser Asn
    210                 215                 220

Gly Ser Gln Ser Gln His Ser Arg Leu Thr Leu Pro Arg Ser Leu Trp
225                 230                 235                 240

Asn Ala Gly Thr Ser Val Thr Cys Thr Leu Asn His Pro Ser Leu Pro
                245                 250                 255

Pro Gln Arg Leu Met Ala Leu Arg Glu Pro Ala Ala Gln Ala Pro Val
            260                 265                 270

Lys Leu Ser Leu Asn Leu Leu Ala Ser Ser Asp Pro Pro Glu Ala Ala
        275                 280                 285
```

```
Ser Trp Leu Leu Cys Glu Val Ser Gly Phe Ser Pro Pro Asn Ile Leu
        290                 295                 300

Leu Met Trp Leu Glu Asp Gln Arg Glu Val Asn Thr Ser Gly Phe Ala
305                 310                 315                 320

Pro Ala Arg Pro Pro Gln Pro Arg Ser Thr Thr Phe Trp Ala Trp
                325                 330                 335

Ser Val Leu Arg Val Pro Ala Pro Ser Pro Gln Pro Ala Thr Tyr
                340                 345                 350

Thr Cys Val Val Ser His Glu Asp Ser Arg Thr Leu Leu Asn Ala Ser
        355                 360                 365

Arg Ser Leu Glu Val Ser Tyr Leu Ala Met Thr Pro Leu Ile Pro Gln
        370                 375                 380

Ser Lys Asp Glu Asn Ser Asp Asp Tyr Thr Thr Phe Asp Asp Val Gly
385                 390                 395                 400

Ser Leu Trp Thr Thr Leu Ser Thr Phe Val Ala Leu Phe Ile Leu Thr
                405                 410                 415

Leu Leu Tyr Ser Gly Ile Val Thr Phe Ile Lys Val Lys
                420                 425

<210> SEQ ID NO 44
<211> LENGTH: 1725
<212> TYPE: DNA
<213> ORGANISM: Homo sapiens

<400> SEQUENCE: 44
atggactgga cctggatcct cttcttggtg gcagcagcca cgcgagtcca ctcccagacg        60
cagttggtgc agtctggggc tgaggtgagg aagcctgggg catcagtgag ggtctcctgc       120
aaggcttctg gatacacctt catcgactcc tatatccact ggatacgaca ggcccctggg       180
cacgggcttg agtgggtggg atggatcaac cctaacagtg gtggcacaaa ctatgctccg       240
agatttcagg gcagggtcac catgaccaga gacgcgtcct tcagtacagc ctacatggac       300
ctgagaagtc tgagatctga cgactcggcc gtgttttact gtgcgaaaag tgaccctttt       360
tggagtgatt attataactt tgactactcg tacactttgg acgtctgggg ccaagggacc       420
acggtcaccg tctcctcagc ctccacacag agcccatccg tcttcccctt gacccgctgc       480
tgcaaaaaca ttccctccaa tgccacctcc gtgactctgg ctgcctggc acgggctac        540 ttcccggagc cggtgatggt gacctgggac acaggctccc tcaacgggac aactatgacc       600
ttaccagcca ccaccctcac gctctctggt cactatgcca ccatcagctt gctgaccgtc       660
tcgggtgcgt gggccaagca gatgttcacc tgccgtgtgg cacacactcc atcgtccaca       720
gactgggtcg acaacaaaac cttcagcgtc tgctccaggg acttcacccc gcccaccgtg       780
aagatcttac agtcgtcctg cgacggcggc gggcacttcc ccccgaccat ccagctcctg       840
tgcctcgtct ctgggtacac cccagggact atcaacatca cctggctgga ggacgggcag       900
gtcatggacg tggacttgtc caccgcctct accacgcagg agggtgagct ggcctccaca       960
caaagcgagc tcaccctcag ccagaagcac tggctgtcag accgcaccta cacctgccag      1020
gtcacctatc aaggtcacac ctttgaggac agcaccaaga gtgtgcaga ttccaacccg       1080 agagggtgtga cgcctacct aagccggccc agccgttcg acctgttcat ccgcaagtcg       1140
cccacgatca cctgtctggt ggtggacctg cacccagca aggggaccgt gaacctgacc       1200
tggtcccggg ccagtgggaa gcctgtgaac actccacca gaaaggagga gaagcagcgc       1260
aatggcacgt taaccgtcac gtccaccctg cggtgggca cccgagactg gatcgagggg       1320
gagacctacc agtgcagggt gacccacccc cacctgccca gggccctcat gcggtccacg       1380
```

```
accaagacca gcggcccgcg tgctgccccg gaagtctatg cgtttgcgac gccggagtgg    1440
ccggggagcc gggacaagcg caccctcgcc tgcctgatcc agaacttcat gcctgaggac    1500
atctcggtgc agtggctgca acgaggtg cagctcccgg acgcccggca cagcacgacg      1560
cagccccgca agaccaaggg ctccggcttc ttcgtcttca gccgcctgga ggtgaccagg    1620
gccgaatggg agcagaaaga tgagttcatc tgccgtgcag tccatgaggc agcgagcccc    1680
tcacagaccg tccagcgagc ggtgtctgta atcccggta aatga                     1725
```

<210> SEQ ID NO 45
<211> LENGTH: 428
<212> TYPE: PRT
<213> ORGANISM: Homo sapiens

<400> SEQUENCE: 45

```
Ala Ser Thr Gln Ser Pro Ser Val Phe Pro Leu Thr Arg Cys Cys Lys
 1               5                  10                  15
Asn Ile Pro Ser Asn Ala Thr Ser Val Thr Leu Gly Cys Leu Ala Thr
            20                  25                  30
Gly Tyr Phe Pro Glu Pro Val Met Val Thr Trp Asp Thr Gly Ser Leu
        35                  40                  45
Asn Gly Thr Thr Met Thr Leu Pro Ala Thr Thr Leu Thr Leu Ser Gly
    50                  55                  60
His Tyr Ala Thr Ile Ser Leu Leu Thr Val Ser Gly Ala Trp Ala Lys
65                  70                  75                  80
Gln Met Phe Thr Cys Arg Val Ala His Thr Pro Ser Ser Thr Asp Trp
                85                  90                  95
Val Asp Asn Lys Thr Phe Ser Val Cys Ser Arg Asp Phe Thr Pro Pro
            100                 105                 110
Thr Val Lys Ile Leu Gln Ser Ser Cys Asp Gly Gly Gly His Phe Pro
        115                 120                 125
Pro Thr Ile Gln Leu Leu Cys Leu Val Ser Gly Tyr Thr Pro Gly Thr
    130                 135                 140
Ile Asn Ile Thr Trp Leu Glu Asp Gly Gln Val Met Asp Val Asp Leu
145                 150                 155                 160
Ser Thr Ala Ser Thr Thr Gln Glu Gly Glu Leu Ala Ser Thr Gln Ser
                165                 170                 175
Glu Leu Thr Leu Ser Gln Lys His Trp Leu Ser Asp Arg Thr Tyr Thr
            180                 185                 190
Cys Gln Val Thr Tyr Gln Gly His Thr Phe Glu Asp Ser Thr Lys Lys
        195                 200                 205
Cys Ala Asp Ser Asn Pro Arg Gly Val Ser Ala Tyr Leu Ser Arg Pro
    210                 215                 220
Ser Pro Phe Asp Leu Phe Ile Arg Lys Ser Pro Thr Ile Thr Cys Leu
225                 230                 235                 240
Val Val Asp Leu Ala Pro Ser Lys Gly Thr Val Asn Leu Thr Trp Ser
                245                 250                 255
Arg Ala Ser Gly Lys Pro Val Asn His Ser Thr Arg Lys Glu Glu Lys
            260                 265                 270
Gln Arg Asn Gly Thr Leu Thr Val Thr Ser Thr Leu Pro Val Gly Thr
        275                 280                 285
Arg Asp Trp Ile Glu Gly Glu Thr Tyr Gln Cys Arg Val Thr His Pro
    290                 295                 300
His Leu Pro Arg Ala Leu Met Arg Ser Thr Thr Lys Thr Ser Gly Pro
305                 310                 315                 320
```

```
Arg Ala Ala Pro Glu Val Tyr Ala Phe Ala Thr Pro Glu Trp Pro Gly
            325                 330                 335

Ser Arg Asp Lys Arg Thr Leu Ala Cys Leu Ile Gln Asn Phe Met Pro
        340                 345                 350

Glu Asp Ile Ser Val Gln Trp Leu His Asn Glu Val Gln Leu Pro Asp
    355                 360                 365

Ala Arg His Ser Thr Thr Gln Pro Arg Lys Thr Lys Gly Ser Gly Phe
370                 375                 380

Phe Val Phe Ser Arg Leu Glu Val Thr Arg Ala Glu Trp Glu Gln Lys
385                 390                 395                 400

Asp Glu Phe Ile Cys Arg Ala Val His Glu Ala Ala Ser Pro Ser Gln
                405                 410                 415

Thr Val Gln Arg Ala Val Ser Val Asn Pro Gly Lys
            420                 425

<210> SEQ ID NO 46
<211> LENGTH: 1884
<212> TYPE: DNA
<213> ORGANISM: Homo sapiens

<400> SEQUENCE: 46
atggactgga cctggaggtt cctctttgtg gtggcagcag ctacaggtgt ccagtcccag     60
gtgcagctgg tgcagtctgg ggctgaggtg aagaagcctg gtcctcggt gaaggtctcc    120 tgcaaggctt ctggaggcac cttcagcagc tatgctatca gctgggtgcg acaggcccct    180
ggacaagggc ttgagtggat gggagggatc atccctatct tggtacagc aaactacgca    240 cagaagttcc agggcagagt cacgattacc gcggacgaat ccacgagcac agcctacatg    300
gagctgagca gcctgagatc tgaggacacg gccgtgtatt actgtgcgaa aaccgggatc    360
ctggggccgt atagcagtgg ctggtacccg aactcggact actactacta cggtatggac    420
gtctggggcc aagggaccac ggtcaccgtc tcctcaggga gtgcatccgc cccaaccctt    480
ttccccctcg tctcctgtga aattccccg tcggatacga gcagcgtggc cgttggctgc    540
ctcgcacagg acttccttcc cgactccatc actttctcct ggaaatacaa gaacaactct    600
gacatcagca gcacccgggg cttcccatca gtcctgagag ggggcaagta cgcagccacc    660
tcacaggtgc tgctgccttc caaggacgtc atgcagggca gacgaaca cgtggtgtgc    720 aaagtccagc accccaacgg caacaaagaa aagaacgtgc ctcttccagt gattgctgag    780
ctgcctccca agtgagcgt cttcgtccca cccgcgacg gcttcttcgg caaccccgc    840 agcaagtcca agctcatctg ccaggccacg gtttcagtc cccggcagat tcaggtgtcc    900
tggctgcgcg aggggaagca ggtggggtct ggcgtcacca cggaccaggt gcaggctgag    960
gccaaagagt ctgggcccac gacctacaag gtgaccagca cactgaccat caaagagagc   1020
gactggctca gccagagcat gttcacctgc cgcgtggatc acaggggcct gaccttccag   1080
cagaatgcgt cctccatgtg tgtccccgat caagacacag ccatccgggt cttcgccatc   1140 ccccatcct ttgccagcat cttcctcacc aagtccacca gttgacctg cctggtcaca   1200 gacctgacca cctatgacag cgtgaccatc tcctggaccc gccagaatgg cgaagctgtg   1260
aaaacccaca ccaacatctc cgagagccac cccaatgcca ctttcagcgc cgtgggtgag   1320
gccagcatct gcgaggatga ctggaattcc ggggagaggt tcacgtgcac cgtgacccac   1380
acagacctgc cctcgccact gaagcagacc atccccggc caaggggt ggccctgcac   1440 aggcccgatg tctacttgct gccaccagcc cgggagcagc tgaacctgcg ggagtcggcc   1500
```

```
accatcacgt gcctggtgac gggcttctct cccgcggacg tcttcgtgca gtggatgcag    1560
agggggcagc ccttgtcccc ggagaagtat gtgaccagcg ccccaatgcc tgagccccag    1620
gccccaggcc ggtacttcgc ccacagcatc ctgaccgtgt ccgaagagga atggaacacg    1680
ggggagacct acacctgcgt ggtggcccat gaggccctgc caacagggt caccgagagg    1740 accgtggaca agtccaccga gggggaggtg agcgccgacg aggagggctt tgagaacctg    1800
tgggccaccg cctccacctt catcgtcctc ttcctcctga gcctcttcta cagtaccacc    1860
gtcaccttgt tcaaggtgaa atga                                           1884

<210> SEQ ID NO 47
<211> LENGTH: 454
<212> TYPE: PRT
<213> ORGANISM: Homo sapiens

<400> SEQUENCE: 47
```

Gly Ser Ala Ser Ala Pro Thr Leu Phe Pro Leu Val Ser Cys Glu Asn
 1               5                  10                  15

Ser Pro Ser Asp Thr Ser Ser Val Ala Val Gly Cys Leu Ala Gln Asp
             20                  25                  30

Phe Leu Pro Asp Ser Ile Thr Phe Ser Trp Lys Tyr Lys Asn Asn Ser
         35                  40                  45

Asp Ile Ser Ser Thr Arg Gly Phe Pro Ser Val Leu Arg Gly Gly Lys
     50                  55                  60

Tyr Ala Ala Thr Ser Gln Val Leu Leu Pro Ser Lys Asp Val Met Gln
 65                  70                  75                  80

Gly Thr Asp Glu His Val Val Cys Lys Val Gln His Pro Asn Gly Asn
                 85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Ser Lys Ser Lys Leu Ile Cys Gln Ala Thr Gly Phe Ser Pro Arg Gln
    130                 135                 140

Ile Gln Val Ser Trp Leu Arg Glu Gly Lys Gln Val Gly Ser Gly Val
145                 150                 155                 160

Thr Thr Asp Gln Val Gln Ala Glu Ala Lys Glu Ser Gly Pro Thr Thr
                165                 170                 175

Tyr Lys Val Thr Ser Thr Leu Thr Ile Lys Glu Ser Asp Trp Leu Ser
            180                 185                 190

Gln Ser Met Phe Thr Cys Arg Val Asp His Arg Gly Leu Thr Phe Gln
        195                 200                 205

Gln Asn Ala Ser Ser Met Cys Val Pro Asp Gln Asp Thr Ala Ile Arg
    210                 215                 220

Val Phe Ala Ile Pro Pro Ser Phe Ala Ser Ile Phe Leu Thr Lys Ser
225                 230                 235                 240

Thr Lys Leu Thr Cys Leu Val Thr Asp Leu Thr Thr Tyr Asp Ser Val
                245                 250                 255

Thr Ile Ser Trp Thr Arg Gln Asn Gly Glu Ala Val Lys Thr His Thr
            260                 265                 270

Asn Ile Ser Glu Ser His Pro Asn Ala Thr Phe Ser Ala Val Gly Glu
        275                 280                 285

Ala Ser Ile Cys Glu Asp Asp Trp Asn Ser Gly Glu Arg Phe Thr Cys
    290                 295                 300

Thr Val Thr His Thr Asp Leu Pro Ser Pro Leu Lys Gln Thr Ile Ser

```
                    305                 310                 315                 320
Arg Pro Lys Gly Val Ala Leu His Arg Pro Asp Val Tyr Leu Leu Pro
                325                 330                 335

Pro Ala Arg Glu Gln Leu Asn Leu Arg Glu Ser Ala Thr Ile Thr Cys
            340                 345                 350

Leu Val Thr Gly Phe Ser Pro Ala Asp Val Phe Val Gln Trp Met Gln
        355                 360                 365

Arg Gly Gln Pro Leu Ser Pro Glu Lys Tyr Val Thr Ser Ala Pro Met
    370                 375                 380

Pro Glu Pro Gln Ala Pro Gly Arg Tyr Phe Ala His Ser Ile Leu Thr
385                 390                 395                 400

Val Ser Glu Glu Glu Trp Asn Thr Gly Glu Thr Tyr Thr Cys Val Val
                405                 410                 415

Ala His Glu Ala Leu Pro Asn Arg Val Thr Glu Arg Thr Val Asp Lys
            420                 425                 430

Ser Thr Gly Lys Pro Thr Leu Tyr Asn Val Ser Leu Val Met Ser Asp
        435                 440                 445

Thr Ala Gly Thr Cys Tyr
    450

<210> SEQ ID NO 48
<211> LENGTH: 822
<212> TYPE: PRT
<213> ORGANISM: Artificial Sequence
<220> FEATURE:
<223> OTHER INFORMATION: Description of Artificial Sequence: Protein
      encoded by plasmid pSSPICAMHuA2

<400> SEQUENCE: 48

Met Gly Ser Lys Pro Phe Leu Ser Leu Leu Ser Leu Ser Leu Leu Leu
 1               5                  10                  15

Phe Thr Ser Thr Ser Leu Ala Gln Thr Ser Val Ser Pro Ser Lys Val
            20                  25                  30

Ile Leu Pro Arg Gly Gly Ser Val Leu Val Thr Cys Ser Thr Ser Cys
        35                  40                  45

Asp Gln Pro Lys Leu Leu Gly Ile Glu Thr Pro Leu Pro Lys Lys Glu
    50                  55                  60

Leu Leu Leu Pro Gly Asn Asn Arg Lys Val Tyr Glu Leu Ser Asn Val
65                  70                  75                  80

Gln Glu Asp Ser Gln Pro Met Cys Tyr Ser Asn Cys Pro Asp Gly Gln
                85                  90                  95

Ser Thr Ala Lys Thr Phe Leu Thr Val Tyr Trp Thr Pro Glu Arg Val
            100                 105                 110

Glu Leu Ala Pro Leu Pro Ser Trp Gln Pro Val Gly Lys Asn Leu Thr
        115                 120                 125

Leu Arg Cys Gln Val Glu Gly Gly Ala Pro Arg Ala Asn Leu Thr Val
    130                 135                 140

Val Leu Leu Arg Gly Glu Lys Glu Leu Lys Arg Glu Pro Ala Val Gly
145                 150                 155                 160

Glu Pro Ala Glu Val Thr Thr Thr Val Leu Val Arg Arg Asp His His
                165                 170                 175

Gly Ala Asn Phe Ser Cys Arg Thr Glu Leu Asp Leu Arg Pro Gln Gly
            180                 185                 190

Leu Glu Leu Phe Glu Asn Thr Ser Ala Pro Tyr Gln Leu Gln Thr Phe
        195                 200                 205

Val Leu Pro Ala Thr Pro Pro Gln Leu Val Ser Pro Arg Val Leu Glu
```

```
                210                 215                 220
Val Asp Thr Gln Gly Thr Val Val Cys Ser Leu Asp Gly Leu Phe Pro
225                 230                 235                 240

Val Ser Glu Ala Gln Val His Leu Ala Leu Gly Asp Gln Arg Leu Asn
            245                 250                 255

Pro Thr Val Thr Tyr Gly Asn Asp Ser Phe Ser Ala Lys Ala Ser Val
                260                 265                 270

Ser Val Thr Ala Glu Asp Glu Gly Thr Gln Arg Leu Thr Cys Ala Val
            275                 280                 285

Ile Leu Gly Asn Gln Ser Gln Glu Thr Leu Gln Thr Val Thr Ile Tyr
        290                 295                 300

Ser Phe Pro Ala Pro Asn Val Ile Leu Thr Lys Pro Glu Val Ser Glu
305                 310                 315                 320

Gly Thr Glu Val Thr Val Lys Cys Glu Ala His Pro Arg Ala Lys Val
                325                 330                 335

Thr Leu Asn Gly Val Pro Ala Gln Pro Leu Gly Pro Arg Ala Gln Leu
            340                 345                 350

Leu Leu Lys Ala Thr Pro Glu Asp Asn Gly Arg Ser Phe Ser Cys Ser
        355                 360                 365

Ala Thr Leu Glu Val Ala Gly Gln Leu Ile His Lys Asn Gln Thr Arg
370                 375                 380

Glu Leu Arg Val Leu Tyr Gly Pro Arg Leu Asp Glu Arg Asp Cys Pro
385                 390                 395                 400

Gly Asn Trp Thr Trp Pro Glu Asn Ser Gln Gln Thr Pro Met Cys Gln
                405                 410                 415

Ala Trp Gly Asn Pro Leu Pro Glu Leu Lys Cys Leu Lys Asp Gly Thr
            420                 425                 430

Phe Pro Leu Pro Ile Gly Glu Ser Val Thr Val Thr Arg Asp Leu Glu
        435                 440                 445

Gly Thr Tyr Leu Cys Arg Ala Arg Ser Thr Gln Gly Glu Val Thr Arg
450                 455                 460

Glu Val Thr Val Asn Val Thr Ser Gly Ser Ser Ala Ser Pro Thr Ser
465                 470                 475                 480

Pro Lys Val Phe Pro Leu Ser Leu Asp Ser Thr Pro Gln Asp Gly Asn
                485                 490                 495

Val Val Val Ala Cys Leu Val Gln Gly Phe Phe Pro Gln Glu Pro Leu
            500                 505                 510

Ser Val Thr Trp Ser Glu Ser Gly Gln Asn Val Thr Ala Arg Asn Phe
        515                 520                 525

Pro Pro Ser Gln Asp Ala Ser Gly Asp Leu Tyr Thr Thr Ser Ser Gln
530                 535                 540

Leu Thr Leu Pro Ala Thr Gln Cys Pro Asp Gly Lys Ser Val Thr Cys
545                 550                 555                 560

His Val Lys His Tyr Thr Asn Ser Ser Gln Asp Val Thr Val Pro Cys
                565                 570                 575

Arg Val Pro Pro Pro Pro Pro Cys Cys His Pro Arg Leu Ser Leu His
            580                 585                 590

Arg Pro Ala Leu Glu Asp Leu Leu Leu Gly Ser Glu Ala Asn Leu Thr
        595                 600                 605

Cys Thr Leu Thr Gly Leu Arg Asp Ala Ser Gly Ala Thr Phe Thr Trp
610                 615                 620

Thr Pro Ser Ser Gly Lys Ser Ala Val Gln Gly Pro Pro Glu Arg Asp
625                 630                 635                 640
```

```
Leu Cys Gly Cys Tyr Ser Val Ser Arg Val Leu Pro Gly Cys Ala Gln
            645                 650                 655

Pro Trp Asn His Gly Glu Thr Phe Thr Cys Thr Ala Ala His Pro Glu
            660                 665                 670

Leu Lys Thr Pro Leu Thr Ala Asn Ile Thr Lys Ser Gly Asn Thr Phe
            675                 680                 685

Arg Pro Glu Val His Leu Leu Pro Pro Ser Glu Glu Leu Ala Leu
            690                 695                 700

Asn Glu Leu Val Thr Leu Thr Cys Leu Ala Arg Gly Phe Ser Pro Lys
705                 710                 715                 720

Asp Val Leu Val Arg Trp Leu Gln Gly Ser Gln Glu Leu Pro Arg Glu
                725                 730                 735

Lys Tyr Leu Thr Trp Ala Ser Arg Gln Glu Pro Ser Gln Gly Thr Thr
                740                 745                 750

Thr Tyr Ala Val Thr Ser Ile Leu Arg Val Ala Ala Glu Asp Trp Lys
                755                 760                 765

Lys Gly Glu Thr Phe Ser Cys Met Val Gly His Glu Ala Leu Pro Leu
                770                 775                 780

Ala Phe Thr Gln Lys Thr Ile Asp Arg Leu Ala Gly Lys Pro Thr His
785                 790                 795                 800

Ile Asn Val Ser Val Val Met Ala Glu Ala Asp Gly Thr Cys Tyr Arg
                805                 810                 815

Ser Glu Lys Asp Glu Leu
                820

<210> SEQ ID NO 49
<211> LENGTH: 428
<212> TYPE: PRT
<213> ORGANISM: Homo sapiens

<400> SEQUENCE: 49

Ala Ser Thr Gln Ser Pro Ser Val Phe Pro Leu Thr Arg Cys Cys Lys
 1               5                  10                  15

Asn Ile Pro Ser Asn Ala Thr Ser Val Thr Leu Gly Cys Leu Ala Thr
                20                  25                  30

Gly Tyr Phe Pro Glu Pro Val Met Val Thr Trp Asp Thr Gly Ser Leu
            35                  40                  45

Asn Gly Thr Thr Met Thr Leu Pro Ala Thr Thr Leu Thr Leu Ser Gly
        50                  55                  60

His Tyr Ala Thr Ile Ser Leu Leu Thr Val Ser Gly Ala Trp Ala Lys
65                  70                  75                  80

Gln Met Phe Thr Cys Arg Val Ala His Thr Pro Ser Ser Thr Asp Trp
                85                  90                  95

Val Asp Asn Lys Thr Phe Ser Val Cys Ser Arg Asp Phe Thr Pro Pro
                100                 105                 110

Thr Val Lys Ile Leu Gln Ser Ser Cys Asp Gly Gly Gly His Phe Pro
            115                 120                 125

Pro Thr Ile Gln Leu Leu Cys Leu Val Ser Gly Tyr Thr Pro Gly Thr
        130                 135                 140

Ile Asn Ile Thr Trp Leu Glu Asp Gly Gln Val Met Asp Val Asp Leu
145                 150                 155                 160

Ser Thr Ala Ser Thr Thr Gln Glu Gly Glu Leu Ala Ser Thr Gln Ser
                165                 170                 175

Glu Leu Thr Leu Ser Gln Lys His Trp Leu Ser Asp Arg Thr Tyr Thr
            180                 185                 190
```

```
Cys Gln Val Thr Tyr Gln Gly His Thr Phe Glu Asp Ser Thr Lys Lys
            195                 200                 205

Cys Ala Asp Ser Asn Pro Arg Gly Val Ser Ala Tyr Leu Ser Arg Pro
    210                 215                 220

Ser Pro Phe Asp Leu Phe Ile Arg Lys Ser Pro Thr Ile Thr Cys Leu
225                 230                 235                 240

Val Val Asp Leu Ala Pro Ser Lys Gly Thr Val Asn Leu Thr Trp Ser
                245                 250                 255

Arg Ala Ser Gly Lys Pro Val Asn His Ser Thr Arg Lys Glu Glu Lys
            260                 265                 270

Gln Arg Asn Gly Thr Leu Thr Val Thr Ser Thr Leu Pro Val Gly Thr
        275                 280                 285

Arg Asp Trp Ile Glu Gly Glu Thr Tyr Gln Cys Arg Val Thr His Pro
290                 295                 300

His Leu Pro Arg Ala Leu Met Arg Ser Thr Thr Lys Thr Ser Gly Pro
305                 310                 315                 320

Arg Ala Ala Pro Glu Val Tyr Ala Phe Ala Thr Pro Glu Trp Pro Gly
                325                 330                 335

Ser Arg Asp Lys Arg Thr Leu Ala Cys Leu Ile Gln Asn Phe Met Pro
            340                 345                 350

Glu Asp Ile Ser Val Gln Trp Leu His Asn Glu Val Gln Leu Pro Asp
        355                 360                 365

Ala Arg His Ser Thr Thr Gln Pro Arg Lys Thr Lys Gly Ser Gly Phe
370                 375                 380

Phe Val Phe Ser Arg Leu Glu Val Thr Arg Ala Glu Trp Glu Gln Lys
385                 390                 395                 400

Asp Glu Phe Ile Cys Arg Ala Val His Glu Ala Ala Ser Pro Ser Gln
                405                 410                 415

Thr Val Gln Arg Ala Val Ser Val Asn Pro Gly Lys
            420                 425

<210> SEQ ID NO 50
<211> LENGTH: 159
<212> TYPE: PRT
<213> ORGANISM: Homo sapiens

<400> SEQUENCE: 50

Met Glu Asn His Leu Leu Phe Trp Gly Val Leu Ala Val Phe Ile Lys
1               5                   10                  15

Ala Val His Val Lys Ala Gln Glu Asp Glu Arg Ile Val Leu Val Asp
            20                  25                  30

Asn Lys Cys Lys Cys Ala Arg Ile Thr Ser Arg Ile Ile Arg Ser Ser
        35                  40                  45

Glu Asp Pro Asn Glu Asp Ile Val Glu Arg Asn Ile Arg Ile Ile Val
    50                  55                  60

Pro Leu Asn Asn Arg Glu Asn Ile Ser Asp Pro Thr Ser Pro Leu Arg
65                  70                  75                  80

Thr Arg Phe Val Tyr His Leu Ser Asp Leu Cys Lys Lys Cys Asp Pro
                85                  90                  95

Thr Glu Val Glu Leu Asp Asn Gln Ile Val Thr Ala Thr Gln Ser Asn
            100                 105                 110

Ile Cys Asp Glu Asp Ser Ala Thr Glu Thr Cys Tyr Thr Tyr Asp Arg
        115                 120                 125

Asn Lys Cys Tyr Thr Ala Val Val Pro Leu Val Tyr Gly Gly Glu Thr
    130                 135                 140
```

```
Lys Met Val Glu Thr Ala Leu Thr Pro Asp Ala Cys Tyr Pro Asp
145                 150                 155
```

<210> SEQ ID NO 51
<211> LENGTH: 602
<212> TYPE: PRT
<213> ORGANISM: Homo sapiens

<400> SEQUENCE: 51

```
Met Val Leu Phe Val Leu Thr Cys Leu Leu Ala Val Phe Pro Ala Ile
1               5                   10                  15

Ser Thr Lys Ser Pro Ile Phe Gly Pro Glu Glu Val Asn Ser Val Glu
            20                  25                  30

Gly Asn Ser Val Ser Ile Thr Cys Tyr Tyr Pro Pro Thr Ser Val Asn
                35                  40                  45

Arg Thr Arg Lys Tyr Trp Cys Arg Gln Gly Ala Arg Gly Gly Cys Ile
    50                  55                  60

Thr Leu Ile Ser Ser Glu Gly Tyr Val Ser Ser Lys Tyr Ala Gly Arg
65                  70                  75                  80

Ala Asn Leu Thr Asn Phe Pro Glu Asn Gly Thr Phe Val Val Asn Ile
                85                  90                  95

Ala Gln Leu Ser Gln Asp Asp Ser Gly Arg Tyr Lys Cys Gly Leu Gly
            100                 105                 110

Ile Asn Ser Arg Gly Leu Ser Phe Asp Val Ser Leu Glu Val Ser Gln
        115                 120                 125

Gly Pro Gly Leu Leu Asn Asp Thr Lys Val Tyr Thr Val Asp Leu Gly
130                 135                 140

Arg Thr Val Thr Ile Asn Cys Pro Phe Lys Thr Glu Asn Ala Gln Lys
145                 150                 155                 160

Arg Lys Ser Leu Tyr Lys Gln Ile Gly Leu Tyr Pro Val Leu Val Ile
                165                 170                 175

Asp Ser Ser Gly Tyr Val Asn Pro Asn Tyr Thr Gly Arg Ile Arg Leu
            180                 185                 190

Asp Ile Gln Gly Thr Gly Gln Leu Leu Phe Ser Val Val Ile Asn Gln
        195                 200                 205

Leu Arg Leu Ser Asp Ala Gly Gln Tyr Leu Cys Gln Ala Gly Asp Asp
210                 215                 220

Ser Asn Ser Asn Lys Lys Asn Ala Asp Leu Gln Val Leu Lys Pro Glu
225                 230                 235                 240

Pro Glu Leu Val Tyr Glu Asp Leu Arg Gly Ser Val Thr Phe Cys Ala
                245                 250                 255

Leu Gly Pro Glu Val Ala Asn Val Ala Lys Phe Leu Cys Arg Gln Ser
            260                 265                 270

Ser Gly Glu Asn Cys Asp Val Val Asn Thr Leu Gly Lys Arg Ala
        275                 280                 285

Pro Ala Phe Glu Gly Arg Ile Leu Leu Asn Pro Gln Asp Lys Asp Gly
290                 295                 300

Ser Phe Ser Val Val Ile Thr Gly Leu Arg Lys Glu Asp Ala Gly Arg
305                 310                 315                 320

Tyr Leu Cys Gly Ala Ser Asp Gly Gln Leu Gln Glu Gly Ser Pro Ile
                325                 330                 335

Gln Ala Trp Gln Leu Phe Val Asn Glu Glu Ser Thr Ile Pro Arg Ser
            340                 345                 350

Pro Thr Val Val Lys Gly Val Ala Gly Ser Ser Val Ala Val Leu Cys
        355                 360                 365
```

```
Pro Tyr Asn Arg Lys Glu Ser Lys Ser Ile Lys Tyr Trp Cys Leu Trp
    370                 375                 380

Glu Gly Ala Gln Asn Gly Arg Cys Pro Leu Leu Val Asp Ser Glu Gly
385                 390                 395                 400

Trp Val Lys Ala Gln Tyr Glu Gly Arg Leu Ser Leu Leu Glu Glu Pro
                405                 410                 415

Gly Asn Gly Thr Phe Thr Val Ile Leu Asn Gln Leu Thr Ser Arg Asp
                420                 425                 430

Ala Gly Phe Tyr Trp Cys Leu Thr Asn Gly Asp Thr Leu Trp Arg Thr
            435                 440                 445

Thr Val Glu Ile Lys Ile Ile Glu Gly Glu Pro Asn Leu Lys Val Pro
    450                 455                 460

Gly Asn Val Thr Ala Val Leu Gly Glu Thr Leu Lys Val Pro Cys Phe
465                 470                 475                 480

Pro Cys Lys Phe Ser Ser Tyr Glu Lys Tyr Trp Cys Lys Trp Asn Asn
                485                 490                 495

Thr Gly Cys Gln Ala Leu Pro Ser Gln Asp Glu Gly Pro Ser Lys Ala
                500                 505                 510

Phe Val Asn Cys Asp Glu Asn Ser Arg Leu Val Ser Leu Thr Leu Asn
            515                 520                 525

Leu Val Thr Arg Ala Asp Glu Gly Trp Tyr Trp Cys Gly Val Lys Gln
    530                 535                 540

Gly Phe Tyr Gly Glu Thr Ala Ala Val Tyr Val Ala Val Glu Glu Arg
545                 550                 555                 560

Lys Ala Ala Gly Ser Arg Asp Val Ser Leu Ala Lys Ala Asp Ala Ala
                565                 570                 575

Pro Asp Glu Lys Val Leu Asp Ser Gly Phe Arg Glu Ile Glu Asn Lys
                580                 585                 590

Ala Ile Gln Asp Pro Arg Leu Phe Ala Glu
            595                 600

<210> SEQ ID NO 52
<211> LENGTH: 2533
<212> TYPE: DNA
<213> ORGANISM: Homo sapiens

<400> SEQUENCE: 52
ggtccaactg caggcctgtg gtgcaggagc tgtgtgacca tggggctgtc accaggcctc      60
tctgtgctgg gttcctccag tatagaggag aggcagtata gaggagaggg ccgcgtcctc     120
acagtgcatt ctgtgttcca gcatccccga ccagccccaa ggtcttcccg ctgagcctct     180
gcagcaccca gccagatggg aacgtggtca tcgcctgcct ggtccagggc ttcttccccc     240
aggagccact cagtgtgacc tggagcgaaa gcggacaggg cgtgaccgcc agaaacttcc     300
cacccagcca ggatgcctcc ggggacctgt acaccacgag cagccagctg acctgccgg      360 ccacacagtg cctagccggc aagtccgtga catgccacgt gaagcactac acgaatccca     420
gccaggatgt gactgtgccc tgcccaggtc agagggcagg ctgggagtg gggcggggcc      480 accccgtcgt gccctgacac tgcgcctgca cccgtgttcc ccacagggag ccgccccttc     540
actcacacca gagtggaccc cgggccgagc cccaggaggt ggtggtggac aggccaggag     600
gggcgaggcg ggggcatggg gaagtatgtg ctgaccagct caggccatct tccactcca     660 gttccctcaa ctccacctac cccatctccc tcaactccac ctaccccatc tcctcatgc     720 tgccacccc gactgtcact gcaccgaccg ccctcgagg acctgctctt aggttcagaa     780
gcgaacctca cgtgcacact gaccggcctg agagatgcct caggtgtcac cttcacctgg     840
```

| | |
|---|---|
| acgccctcaa gtgggaagag cgctgttcaa ggaccacctg agcgtgacct ctgtggctgc | 900 |
| tacagcgtgt ccagtgtcct gccgggctgt gccgagccat ggaaccatgg aagaccttc | 960 |
| acttgcactg ctgcctaccc cgagtccaag accccgctaa ccgccaccct ctcaaaatcc | 1020 |
| ggtgggtcca gaccctgctc ggggccctgc tcagtgctct ggtttgcaaa gcatattcct | 1080 |
| ggcctgcctc ctccctccca atcctgggct ccagtgctca tgccaagtac acagggaaac | 1140 |
| tgaggcaggc tgaggggcca ggacacagcc cggggtgccc accagagcag aggggctctc | 1200 |
| tcatcccctg cccagccccc tgacctggct ctctaccctc caggaaacac attccggccc | 1260 |
| gaggtccacc tgctgccgcc gccgtcggag gagctggccc tgaacgagct ggtgacgctg | 1320 |
| acgtgcctgg cacgcggctt cagccccaag gacgtgctgg ttcgctggct gcaggggtca | 1380 |
| caggagctgc cccgcgagaa gtacctgact tgggcatccc ggcaggagcc cagccagggc | 1440 |
| accaccacct tcgctgtgac cagcatactg cgcgtggcag ccgaggactg gaagaagggg | 1500 |
| gacaccttct cctgcatggt gggccacgag gccctgccgc tggccttcac acagaagacc | 1560 |
| atcgaccgct ggcgggtaa acccacccat gtcaatgtgt ctgttgtcat ggcggaggtg | 1620 |
| gacggcacct gctactgagc cgcccgcctg tccccacccc tgaataaact ccatgctccc | 1680 |
| ccaagcagcc ccacgcttcc atccggcgcc tgtctgtcca tcctcagggt ctcagcactt | 1740 |
| gggaaagggc cagggcatgg acagggaaga atacccctg ccctgagcct cggggggccc | 1800 |
| ctggcacccc catgagactt tccaccctgg tgtgagtgtg agttgtgagt gtgagagtgt | 1860 |
| gtggtgcagg aggcctcgct ggtgtgagat cttaggtctg ccaaggcagg cacagcccag | 1920 |
| gatgggttct gagagacgca catgccccgg acagttctga gtgagcagtg gcatggccgt | 1980 |
| ttgtccctga gagagccgcc tctggctgta gctgggaggg aatagggagg gtaaaaggag | 2040 |
| caggctagcc aagaaaggcg caggtagtgg caggagcggc gagggagtga ggggctggac | 2100 |
| tccagggccc cactgggagg acaagctcca ggagggcccc accacccctag tgggtgggcc | 2160 |
| tcaggacgtc ccactgacgc atgcaggaag gggcacctcc ccttaaccac actgctctgt | 2220 |
| acggggcacg tgggcacagg tgcacactca cactcacata tatgcctgag ccctgcagga | 2280 |
| gcggaacgtt cacagcccag acccagttcc agaaaagcca ggggagtccc ctcccaagcc | 2340 |
| cccaagctca gcctgctccc ctaggcccct ctggcttccc tgtgtttcca ctgtgcacag | 2400 |
| atcaggcacc aactccacag acccctccca ggcagcccct gctccctgcc tggccaagtc | 2460 |
| tcccatccct tcctaagccc aactaggacc caaagcatag acagggaggg gccacgtggg | 2520 |
| gtggcatcag aag | 2533 |

<210> SEQ ID NO 53
<211> LENGTH: 2516
<212> TYPE: DNA
<213> ORGANISM: Homo sapiens

<400> SEQUENCE: 53

| | |
|---|---|
| ggtccaaccg caggcccatg gtgcaggagc tgtgtaacct atgggctgt caccaggcct | 60 |
| ctctgtgctg ggttcctcca gtgtagagga gaggcaggta cagcctgtcc tcctggggac | 120 |
| atggcatgag ggccgcgtcc tcacagcgca ttctgtgttc cagcatcccc gaccagcccc | 180 |
| aaggtcttcc cgctgagcct cgacagcacc ccccaagatg gaacgtggt cgtcgcatgc | 240 |
| ctggtccagg gcttcttccc ccaggagcca ctcagtgtga cctggagcga agcggacag | 300 |
| aacgtgaccc ccagaaactt cccacctagc caggatgcct ccggggacct gtacaccacg | 360 |
| agcagccagc tgaccctgcc ggccacacag tgcccagacg gcaagtccgt gacatgccac | 420 |

```
gtgaagcact acacgaatcc cagccaggat gtgactgtgc cctgcccagg tcagagggca      480
ggctggggag tggggcgggg ccacccccgtc ctgccctgac actgcgcctg cacccgtgtt     540
ccccacaggg agccgcccct tcactcacac cagagtggac cccggccgga gccccaggag     600
gtggtggtgg acaggccagg aggggcgagg cgggggcacg gggaagggcg ttctgaccag     660
ctcaggccat ctctccactc cagttccccc acctccccca tgctgccacc ccgactgtc     720 gctgcaccga ccggccctcg aggacctgct cttaggttca gaagcgaacc tcacgtgcac     780
actgaccggc ctgagagatg cctctggtgc caccttcacc tggacgccct caagtgggaa     840
gagcgctgtt caaggaccac ctgagcgtga cctctgtggc tgctacagcg tgtccagtgt     900
cctgcctggc tgtgcccagc catggaacca tggggagacc ttcacctgca ctgctgccca     960
ccccgagttg aagaccccac taaccgccaa catcacaaaa tccggtgggt ccagaccctg    1020
ctcggggccc tgctcagtgc tctggtttgc aaagcatatt cccggcctgc ctcctccctc    1080
ccaatcctgg gctccagtgc tcatgccaag tacacaggga aactgaggca ggctgagggg    1140
ccaggacaca gcccagggtg cccaccagag cagaggggct ctctcatccc ctgcccagcc    1200
ccctgacctg gctctctacc ctccaggaaa cacattccgg cccgaggtcc acctgctgcc    1260
gccgccgtcg gaggagctgg ccctgaacga gctggtgacg ctgacgtgcc tggcacgtgg    1320
cttcagcccc aaggatgtgc tggttcgctg gctgcagggg tcacaggagc tgccccgcga    1380
gaagtacctg acttgggcat cccggcagga gcccagccag ggcaccacca ccttcgctgt    1440
gaccagcata ctgcgcgtgg cagccgagga ctggaagaag ggggacacct tctcctgcat    1500
ggtgggccac gaggccctgc cgctggcctt cacacagaag accatcgacc gcttggcggg    1560
taaacccacc catgtcaatg tgtctgttgt catggcggag gtggacggca cctgctactg    1620
agccgcccgc ctgtccccac ccctgaataa actccatgct cccccaagca gccccacgct    1680
tccatccggc gcctgtctgt ccatcctcag ggtctcagca cttgggaaag gccagggca    1740 tggacaggga agaataccccc ctgccctgag cctcggggg cccctggcac ccccatgaga    1800
ctttccaccc tggtgtgagt gtgagttgtg agtgtgagag tgtgtggtgc aggaggcctc    1860
gctggtgtga gatcttaggt ctgccaaggc aggcacagcc caggatgggt tctgagagac    1920
gcacatgccc cggacagttc tgagtgagca gtggcatggc cgtttgtccc tgagagagcc    1980
gcctctggct gtagctggga gggaatagg agggtaaaag gagcaggcta gccaagaaag    2040
gcgcaggtag tggcaggagc ggcgagggag tgaggggctg gactccaggg ccccactggg    2100
aggacaagct ccaggagggc cccaccaccc tagtgggtgg gcctcaggac gtcccactga    2160
cgcatgcagg aagggcacc tcccttaac cacactgctc tgtacggggc acgtgggcac    2220
acatgcacac tcacactcac atatacgcct gagccctgca ggagtggaac gttcacagcc    2280
cagacccagt tccagaaaag ccaggggagt cccctcccaa gccccaagc tcagcctgct    2340 cccccaggcc cctctggctt ccctgtgttt ccactgtgca cagatcaggc accaactcca    2400 cagaccctc ccaggcagcc cctgctccct gcctggccaa gtctcccatc ccttcctaag    2460
cccaactagg acccaaagca tagacaggga ggggccgcgt ggggtggcat cagaag       2516

<210> SEQ ID NO 54
<211> LENGTH: 2009
<212> TYPE: DNA
<213> ORGANISM: Homo sapiens

<400> SEQUENCE: 54
agctttctgg ggcaggccag gcctgacctt ggctttgggg cagggagggg gctaaggtga        60
```

-continued

```
ggcaggtggc gccagcaggt gcacacccaa tgcccatgag cccagacact ggacgctgaa      120
cctcgcggac agttaagaac ccaggggcct ctgcgcctgg gcccagctct gtcccacacc      180
gcggtcacat ggcaccacct ctcttgcagc ctccaccaag gcccatcgg tcttcccct       240 ggcaccctcc tccaagagca cctctggggg cacagcggcc ctgggctgcc tggtcaagga      300
ctacttcccc gaaccggtga cggtgtcgtg gaactcaggc gccctgacca gcggcgtgca      360
caccttcccg gctgtcctac agtcctcagg actctactcc ctcagcagcg tggtgaccgt      420
gccctccagc agcttgggca cccagaccta catctgcaac gtgaatcaca agcccagcaa      480
caccaaggtg gacaagaaag ttggtgagag gccagcacag ggagggaggg tgtctgctgg      540
aagcaggctc agcgctcctg cctggacgca tcccggctat gcagcccag tccagggcag       600 caaggcaggc cccgtctgcc tcttcacccg gagcctctgc ccgccccact catgctcagg      660
gagagggtct tctggctttt tcccaggctc tgggcaggca caggctaggt gccctaacc       720 caggccctgc acacaagggg gcaggtgctg ggctcagacc tgccaagagc catatccggg      780
aggaccctgc ccctgaccta agcccacccc aaaggccaaa ctctccactc cctcagctcg      840
gacaccttct ctcctcccag attccagtaa ctcccaatct tctctctgca gagcccaaat      900
cttgtgacaa aactcacaca tgcccaccgt gcccaggtaa gccagcccag gcctcgccct      960
ccagctcaag gcgggacagg tgccctagag tagcctgcat ccaggacag gccccagccg       1020 ggtgctgaca cgtccacctc catctcttcc tcagcacctg aactcctggg ggaccgtca      1080 gtcttcctct tccccccaaa acccaaggac accctcatga tctcccggac ccctgaggtc      1140
acatgcgtgg tggtggacgt gagccacgaa gaccctgagg tcaagttcaa ctggtacgtg      1200
gacggcgtgg aggtgcataa tgccaagaca aagccgcggg aggagcagta acagcacg       1260 taccgggtgg tcagcgtcct caccgtcctg caccaggact ggctgaatgg caaggagtac      1320
aagtgcaagg tctccaacaa agccctccca gcccccatcg agaaaaccat ctccaaagcc      1380
aaaggtggga cccgtggggt gcgagggcca catggacaga ggccggctcg gcccaccctc      1440
tgccctgaga gtgaccgctg taccaacctc tgtcctacag gcagccccg agaaccacag       1500 gtgtacaccc tgcccccatc ccgggatgag ctgaccaaga accaggtcag cctgacctgc      1560
ctggtcaaag gcttctatcc cagcgacatc gccgtggagt gggagagcaa tgggcagccg      1620
gagaacaact acaagaccac gcctcccgtg ctggactccg acggctcctt cttcctctac      1680
agcaagctca ccgtggacaa gagcaggtgg cagcagggga acgtcttctc atgctccgtg      1740
atgcatgagg ctctgcacaa ccactacacg cagaagagcc tctccctgtc tccgggtaaa      1800
tgagtgcgac ggccggcaag ccccgctccc cgggctctcg cggtcgcacg aggatgcttg      1860
gcacgtaccc cctgtacata cttcccgggc gcccagcatg gaaataaagc acccagcgct      1920
gccctgggcc cctgcgagac tgtgatggtt ctttccacgg gtcaggccga gtctgaggcc      1980
tgagtggcat gagggaggca gagcgggtc                                        2009
```

<210> SEQ ID NO 55
<211> LENGTH: 2009
<212> TYPE: DNA
<213> ORGANISM: Homo sapiens

<400> SEQUENCE: 55

```
agctttctgg ggcgagccgg gcctgacttt ggctttgggg cagggagtgg gctaaggtga       60
ggcaggtggc gccagccagg tgcacaccca atgcccgtga gccagacac tggaccctgc       120 ctggaccctc gtggatagac aagaaccgag gggcctctgc gcctgggccc agctctgtcc      180
```

```
cacaccgcgg tcacatggca ccacctctct tgcagcctcc accaagggcc catcggtctt    240
ccccctggcg ccctgctcca ggagcacctc cgagagcaca gccgccctgg gctgcctggt    300
caaggactac ttccccgaac cggtgacggt gtcgtggaac tcaggcgctc tgaccagcgg    360
cgtgcacacc ttcccagctg tcctacagtc ctcaggactc tactccctca gcagcgtggt    420
gaccgtgccc tccagcaact tcggcaccca gacctacacc tgcaacgtag atcacaagcc    480
cagcaacacc aaggtggaca agacagttgg tgagaggcca gctcagggag ggagggtgtc    540
tgctggaagc caggctcagc cctcctgcct ggacgcaccc cggctgtgca gccccagccc    600
agggcagcaa gcaggcccc atctgtctcc tcacccggag gcctctgccc gccccactca    660
tgctcaggga gagggtcttc tggctttttc caccaggctc caggcaggca caggctgggt    720 gccctaccc caggcccttc acacacaggg gcaggtgctt ggctcagacc tgccaaaagc    780
catatccggg aggaccctgc ccctgaccta agccgacccc aaaggccaaa ctgtccactc    840
cctcagctcg gacaccttct ctcctcccag atccgagtaa ctcccaatct tctctctgca    900
gagcgcaaat gttgtgtcga gtgcccaccg tgcccaggta gccagccca ggcctcgccc    960 tccagctcaa ggcgggacag gtgccctaga gtagcctgca tccagggaca ggccccagct   1020
gggtgctgac acgtccacct ccatctcttc ctcagcacca cctgtggcag gaccgtcagt   1080
cttcctcttc cccccaaaac ccaaggacac cctcatgatc tcccgacccc tgaggtcac   1140 gtgcgtggtg gtggacgtga gccacgaaga ccccgaggtc cagttcaact ggtacgtgga   1200
cggcgtggag gtgcataatg ccaagacaaa gccacgggag gagcagttca acagcacgtt   1260
ccgtgtggtc agcgtcctca ccgttgtgca ccaggactgg ctgaacggca aggagtacaa   1320
gtgcaaggtc tccaacaaag gcctcccagc ccccatcgag aaaaccatct ccaaaaccaa   1380
aggtgggacc cgcggggtat gagggccaca tggacagagg ccggctcggc ccaccctctg   1440
ccctgggagt gaccgctgtg ccaacctctg tccctacagg gcagcccga gaaccacagg   1500 tgtacaccct gcccccatcc cgggaggaga tgaccaagaa ccaggtcagc ctgacctgcc   1560
tggtcaaagg cttctacccc agcgacatcg ccgtggagtg ggagagcaat gggcagccgg   1620
agaacaacta caagaccaca cctcccatgc tggactccga cggctccttc ttcctctaca   1680
gcaagctcac cgtggacaag agcaggtggc agcaggggaa cgtcttctca tgctccgtga   1740
tgcatgaggc tctgcacaac cactacacgc agaagagcct ctccctgtct ccgggtaaat   1800
gagtgccacg gccggcaagc ccccgctccc caggctctcg gggtcgcgtg aggatgcttg   1860
gcacgtaccc cgtgtacata cttcccaggc acccagcatg gaaataaagc acccagcgct   1920
gccctgggcc cctgcgagac tgtgatggtt ctttccgtgg gtcaggccga gtctgaggcc   1980
tgagtggcat gagggaggca gagtgggtc                                    2009
```

<210> SEQ ID NO 56
<211> LENGTH: 2590
<212> TYPE: DNA
<213> ORGANISM: Homo sapiens

<400> SEQUENCE: 56

```
agctttctgg ggcaggccag gcctgactt ggctgggggc agggaggggg ctaaggtgac     60
gcaggtggcg ccagccaggc gcacacccaa tgcccgtgag cccagacact ggaccctgcc    120
tggaccctcg tggatagaca agaaccgagg ggcctctgcg ccctgggccc agctctgtcc    180
cacaccgcag tcatggcg ccatctctct tgcagcttcc accaagggcc catcggtctt     240
ccccctggcg ccctgctcca ggagcacctc tgggggcaca gcggccctgg gctgcctggt    300
```

```
caaggactac ttccccgaac cggtgacggt gtcgtggaac tcaggcgccc tgaccagcgg    360
cgtgcacacc ttcccggctg tcctacagtc ctcaggactc tactccctca gcagcgtggt    420
gaccgtgccc tccagcagct tgggcaccca gacctacacc tgcaacgtga atcacaagcc    480
cagcaacacc aaggtggaca agagagttgg tgagaggcca gcgcagggag ggagggtgtc    540
tgctggaagc caggctcagc cctcctgcct ggacgcatcc cggctgtgca gtcccagccc    600
agggcagcaa ggcaggcccc gtctgactcc tcacccggag cctctgcccg ccccactcat    660
gctcagggag agggtcttct ggcttttttcc accaggctcc gggcaggcac aggctggatg    720
cccctacccc aggcccttca cacacagggg caggtgctgc gctcagagct gccaaaagcc    780
atatccagga ggaccctgcc cctgacctaa gcccacccca aggccaaac tctctactca     840 ctcagctcag acaccttctc tcttcccaga tctgagtaac tcccaatctt ctctctgcag    900
agctcaaaac cccacttggt gacacaactc acacatgccc acggtgccca ggtaagccag    960
cccaggactc gccctccagc tcaaggcggg acaagagccc tagagtggcc tgagtccagg   1020
gacaggcccc agcagggtgc tgacgcatcc acctccatcc cagatccccg taactcccaa   1080
tcttctctct gcagagccca aatcttgtga cacacctccc ccgtgcccac ggtgcccagg   1140
taagccagcc caggcctcac cctccagctc aaggcaggac aagagcccta gagtggcctg   1200
agtccaggga caggccccag cagggtgctg acgcgtccac ctccatccca gatccccgta   1260
actcccaatc ttctctctgc agagcccaaa tcttgtgaca cacctccccc atgcccacgg   1320
tgcccaggta agccagccca ggcctcgccc tccagctcaa gcgggacaa gagccctaga   1380 gtggcctgag tccagggaca ggccccagca gggtgctgac gcatccacct ccatcccaga   1440
tccccgtaac tcccaatctt ctctctgcag agcccaaatc ttgtgacaca cctccccgt    1500 gcccaaggtg cccaggtaag ccagcccagg cctcgccctc agctcaagg caggacaggt    1560 gccctagagt ggcctgcatc cagggacagg tcccagtcgg gtgctgacac atctgcctcc   1620
atctcttcct cagcacctga actcctggga ggaccgtcag tcttcctctt cccccaaaa    1680 cccaaggata cccttatgat ttcccggacc cctgaggtca cgtgcgtggt ggtggacgtg   1740
agccacgaag accccgaggt ccagttcaag tggtacgtgg acggcgtgga ggtgcataat   1800
gccaagacaa agccgcggga ggagcagtac aacagcacgt ccgtgtggt cagcgtcctc    1860 accgtcctgc accaggactg gctgaacggc aaggagtaca agtgcaaggt ctccaacaaa   1920 gcctcccag cccccatcga gaaaaccatc tccaaaacca aggtgggac ccgcggggta    1980 tgagggccac atggacagag gccagcttga cccaccctct gccctgggag tgaccgctgt   2040
gccaacctct gtccctacag gacagccccg agaaccacag gtgtacaccc tgcccccatc   2100
ccgggaggag atgaccaaga accaggtcag cctgacctgc ctggtcaaag gcttctaccc   2160
cagcgacatc gccgtggagt gggagagcag cgggcagccg gagaacaact acaacaccac   2220
gcctcccatg ctggactccg acggctcctt cttcctctac agcaagctca ccgtggacaa   2280
gagcaggtgg cagcagggga acatcttctc atgctccgtg atgcatgagg ctctgcacaa   2340
ccgcttcacg cagaagagcc tctccctgtc tccgggtaaa tgagtgcgac agccggcaag   2400
cccccgctcc ccgggctctc ggggtcgcgc gaggatgctt ggcacgtacc ccgtgtacat   2460
acttcccggg cacccagcat ggaaataaag cacccagcgc tgcctgggc ccctgtgaga    2520 ctgtgatggt tctttccacg ggtcaggccg agtctgaggc ctgagtgaca tgagggaggc   2580
agagcgggtc                                                         2590
```

<210> SEQ ID NO 57
<211> LENGTH: 2028
<212> TYPE: DNA
<213> ORGANISM: Homo sapiens

<400> SEQUENCE: 57

```
agctttctgg ggcaggccgg gcctgacttt ggctggggc agggagggggg ctaaggtgac      60
gcaggtggcg ccagccaggt gcacacccaa tgcccatgag cccagacact ggaccctgca     120
tggaccatcg cggatagaca agaaccgagg ggcctctgcg ccctgggccc agctctgtcc     180
cacaccgcgg tcacatggca ccacctctct tgcagcttcc accaagggcc catccgtctt     240
cccccctggcg ccctgctcca ggagcacctc cgagagcaca gccgccctgg gctgcctggt     300
caaggactac ttccccgaac cggtgacggt gtcgtggaac tcaggcgccc tgaccagcgg     360
cgtgcacacc ttcccggctg tcctacagtc ctcaggactc tactccctca gcagcgtggt     420
gaccgtgccc tccagcagct tgggcacgaa gacctacacc tgcaacgtag atcacaagcc     480
cagcaacacc aaggtggaca gagagttgg tgagaggcca gcacagggag ggagggtgtc     540
tgctggaagc caggctcagc cctcctgcct ggacgcaccc cggctgtgca gccccagccc     600
agggcagcaa ggcatgcccc atctgtctcc tcacccggag gcctctgacc accccactca     660
tgctcaggga gagggtcttc tggattttc caccaggctc ccggcaccac aggctggatg     720
cccctacccc aggccctgcg catacagggc aggtgctgcg ctcagacctg ccaagagcca     780
tatccgggag gaccctgccc ctgacctaag cccaccccaa aggccaaact ctccactccc     840
tcagctcaga caccttctct cctcccagat ctgagtaact cccaatcttc tctctgcaga     900
gtccaaatat ggtcccccat gcccatcatg cccaggtaag ccaacccagg cctcgccctc     960
cagctcaagg cgggacaggt gccctagagt agcctgcatc cagggacagg ccccagccgg    1020
gtgctgacgc atccacctcc atctcttcct cagcacctga gttcctgggg ggaccatcag    1080
tcttcctgtt cccccaaaaa cccaaggaca ctctcatgat ctcccggacc cctgaggtca    1140
cgtgcgtggt ggtggacgtg agccaggaag accccgaggt ccagttcaac tggtacgtgg    1200
atggcgtgga ggtgcataat gccaagacaa agccgcggga ggagcagttc aacagcacgt    1260
accgtgtggt cagcgtcctc accgtcctgc accaggactg gctgaacggc aaggagtaca    1320
agtgcaaggt ctccaacaaa ggcctcccgt cctccatcga aaaaccatc tccaaagcca    1380
aaggtgggac ccacggggtg cgagggccac acggacagag gccagctcgg cccaccctct    1440
gccctgggag tgaccgctgt gccaacctct gtccctacag ggcagccccg agagccacag    1500
gtgtacaccc tgcccccatc ccaggaggag atgaccaaga accaggtcag cctgacctgc    1560
ctggtcaaag gcttctaccc cagcgacatc gccgtggagt gggagagcaa tgggcagccg    1620
gagaacaact acaagaccac gcctcccgtg ctggactccg acggctcctt cttcctctac    1680
agcaggctaa ccgtggacaa gagcaggtgg caggagggga atgtcttctc atgctccgtg    1740
atgcatgagg ctctgcacaa ccactacaca cagaagagcc tctccctgtc tctgggtaaa    1800
tgagtgccag gccggcaag ccccgctctc ccgggctctc ggggtcgcgc gaggatgctt    1860
ggcacgtacc ccgtctacat acttcccagg cacccagcat ggaaataaag cacccaccac    1920
tgccctgggc cctgtgaga ctgtgatggt tctttccacg ggtcaggccg agtctgaggc    1980
ctgagtgaca tgagggaggc agagcgggtc ccactgtccc cacactgg                 2028
```

<210> SEQ ID NO 58
<211> LENGTH: 106
<212> TYPE: DNA
<213> ORGANISM: Homo sapiens

<400> SEQUENCE: 58

```
tgccacccca ggactctgtc ttccagcacc caccaaggct ccggatgtgt tccccatcat    60
atcagggtgc agacacccaa aggataacag ccctgtggtc ctggca                  106
```

<210> SEQ ID NO 59
<211> LENGTH: 1920
<212> TYPE: DNA
<213> ORGANISM: Homo sapiens

<400> SEQUENCE: 59

```
ggatccctgc cacggggtcc ccagctcccc catccaggcc ccccaggctg atgggcgctg    60
gcctgaggct ggcactgact aggttctgtc ctcacagcct ccacacagag cccatccgtc   120
ttccccttga cccgctgctg caaaaacatt ccctccaatg ccacctccgt gactctgggc   180
tgcctggcca cgggctactt cccggagccg gtgatggtga cctgggacac aggctccctc   240
aacgggacaa ctatgacctt accagccacc accctcacgc tctctggtca ctatgccacc   300
atcagcttgc tgaccgtctc gggtgcgtgg gccaagcaga tgttcacctg ccgtgtggca   360
cacactccat cgtccacaga ctgggtcgac aacaaaacct tcagcggtaa gagagggcca   420
agctcagaga ccacagttcc caggagtgcc aggctgaggg ctggcagagt gggcaggggt   480
tgaggggtg ggtgggctca aacgtgggaa cacccagcat gcctgggac ccgggccagg    540
acgtgggggc aagaggaggg cacacagagc tcagagaggc caacaaccct catgaccacc   600
agctctcccc cagtctgctc cagggacttc accccgccca ccgtgaagat cttacagtcg   660
tcctgcgacg gcggcgggca cttcccccg accatccagc tcctgtgcct cgtctctggg   720
tacaccccag ggactatcaa catcacctgg ctggaggacg gcaggtcat ggacgtggac    780
ttgtccaccg cctctaccac gcaggagggt gagctggcct ccacacaaag cgagctcacc   840
ctcagccaga agcactggct gtcagaccgc acctacacct gccaggtcac ctatcaaggt   900
cacacctttg aggacagcac caagaagtgt gcaggtacgt tcccacctgc cctggtggcc   960
gccacggagg ccagagaaga ggggcgggtg ggcctcacac agccctccgg tgtaccacag  1020
attccaaccc gagaggggtg agcgcctacc taagccggcc cagcccgttc gacctgttca  1080
tccgcaagtc gcccacgatc acctgtctgg tggtggacct ggcacccagc aaggggaccg  1140
tgaacctgac ctggtcccgg gccagtggga agcctgtgaa ccactccacc agaaaggagg  1200
agaagcagcg caatggcacg ttaaccgtca cgtccaccct gccggtgggc acccgagact  1260
ggatcgaggg ggagacctac cagtgcaggg tgacccaccc ccacctgccc agggccctca  1320
tgcggtccac gaccaagacc agcggtgagc catgggcagg ccggggtcgt ggggaaggg   1380
agggagcgag tgagcgggc ccgggctgac cccacgtctg gccacaggcc cgcgtgctgc   1440
cccggaagtc tatgcgtttg cgacgccgga gtggccgggg agcgggaca agcgcaccct   1500
cgcctgcctg atccagaact tcatgcctga ggacatctcg gtgcagtggc tgcacaacga  1560
ggtgcagctc ccggacgccc ggcacagcac gacgcagccc cgcaagacca agggctccgg  1620
cttcttcgtc ttcagccgcc tggaggtgac cagggccgaa tgggagcaga agatgagtt   1680
catctgccgt gcagtccatg aggcagcgag cccctcacag accgtccagc gagcggtgtc  1740
tgtaaatccc ggtaaatgac gtactcctgc ctccctccct cccagggctc catccagctg  1800
tgcagtgggg aggactggcc agaccttctg tccactgttg caatgacccc aggaagctac  1860
ccccaataaa ctgtgcctgc tcagagcccc agtacaccca ttcttgggag cgggcagggc  1920
```

```
<210> SEQ ID NO 60
<211> LENGTH: 574
<212> TYPE: PRT
<213> ORGANISM: Homo sapiens

<400> SEQUENCE: 60

Met Asp Trp Thr Trp Ile Leu Phe Leu Val Ala Ala Thr Arg Val
 1               5                  10                  15

His Ser Gln Thr Gln Leu Val Gln Ser Gly Ala Glu Val Arg Lys Pro
             20                  25                  30

Gly Ala Ser Val Arg Val Ser Cys Lys Ala Ser Gly Tyr Thr Phe Ile
         35                  40                  45

Asp Ser Tyr Ile His Trp Ile Arg Gln Ala Pro Gly His Gly Leu Glu
     50                  55                  60

Trp Val Gly Trp Ile Asn Pro Asn Ser Gly Thr Asn Tyr Ala Pro
 65                  70                  75                  80

Arg Phe Gln Gly Arg Val Thr Met Thr Arg Asp Ala Ser Phe Ser Thr
                 85                  90                  95

Ala Tyr Met Asp Leu Arg Ser Leu Arg Ser Asp Ser Ala Val Phe
            100                 105                 110

Tyr Cys Ala Lys Ser Asp Pro Phe Trp Ser Asp Tyr Asn Phe Asp
            115                 120                 125

Tyr Ser Tyr Thr Leu Asp Val Trp Gly Gln Gly Thr Val Thr Val
            130                 135                 140

Ser Ser Ala Ser Thr Gln Ser Pro Ser Val Phe Pro Leu Thr Arg Cys
145                 150                 155                 160

Cys Lys Asn Ile Pro Ser Asn Ala Thr Ser Val Thr Leu Gly Cys Leu
                165                 170                 175

Ala Thr Gly Tyr Phe Pro Glu Pro Val Met Val Thr Trp Asp Thr Gly
            180                 185                 190

Ser Leu Asn Gly Thr Thr Met Thr Leu Pro Ala Thr Thr Leu Thr Leu
            195                 200                 205

Ser Gly His Tyr Ala Thr Ile Ser Leu Leu Thr Val Ser Gly Ala Trp
            210                 215                 220

Ala Lys Gln Met Phe Thr Cys Arg Val Ala His Thr Pro Ser Ser Thr
225                 230                 235                 240

Asp Trp Val Asp Asn Lys Thr Phe Ser Val Cys Ser Arg Asp Phe Thr
                245                 250                 255

Pro Pro Thr Val Lys Ile Leu Gln Ser Ser Cys Asp Gly Gly His
            260                 265                 270

Phe Pro Pro Thr Ile Gln Leu Leu Cys Leu Val Ser Gly Tyr Thr Pro
            275                 280                 285

Gly Thr Ile Asn Ile Thr Trp Leu Glu Asp Gly Gln Val Met Asp Val
            290                 295                 300

Asp Leu Ser Thr Ala Ser Thr Thr Gln Glu Gly Glu Leu Ala Ser Thr
305                 310                 315                 320

Gln Ser Glu Leu Thr Leu Ser Gln Lys His Trp Leu Ser Asp Arg Thr
                325                 330                 335

Tyr Thr Cys Gln Val Thr Tyr Gln Gly His Thr Phe Glu Asp Ser Thr
            340                 345                 350

Lys Lys Cys Ala Asp Ser Asn Pro Arg Gly Val Ser Ala Tyr Leu Ser
            355                 360                 365

Arg Pro Ser Pro Phe Asp Leu Phe Ile Arg Lys Ser Pro Thr Ile Thr
            370                 375                 380

Cys Leu Val Val Asp Leu Ala Pro Ser Lys Gly Thr Val Asn Leu Thr
```

```
            385                 390                 395                 400
Trp Ser Arg Ala Ser Gly Lys Pro Val Asn His Ser Thr Arg Lys Glu
                405                 410                 415
Glu Lys Gln Arg Asn Gly Thr Leu Thr Val Thr Ser Thr Leu Pro Val
            420                 425                 430
Gly Thr Arg Asp Trp Ile Glu Gly Glu Thr Tyr Gln Cys Arg Val Thr
                435                 440                 445
His Pro His Leu Pro Arg Ala Leu Met Arg Ser Thr Thr Lys Thr Ser
        450                 455                 460
Gly Pro Arg Ala Ala Pro Glu Val Tyr Ala Phe Ala Thr Pro Glu Trp
465                 470                 475                 480
Pro Gly Ser Arg Asp Lys Arg Thr Leu Ala Cys Leu Ile Gln Asn Phe
                485                 490                 495
Met Pro Glu Asp Ile Ser Val Gln Trp Leu His Asn Glu Val Gln Leu
                500                 505                 510
Pro Asp Ala Arg His Ser Thr Thr Gln Pro Arg Lys Thr Lys Gly Ser
            515                 520                 525
Gly Phe Phe Val Phe Ser Arg Leu Glu Val Thr Arg Ala Glu Trp Glu
        530                 535                 540
Gln Lys Asp Glu Phe Ile Cys Arg Ala Val His Glu Ala Ala Ser Pro
545                 550                 555                 560
Ser Gln Thr Val Gln Arg Ala Val Ser Val Asn Pro Gly Lys
                565                 570

<210> SEQ ID NO 61
<211> LENGTH: 2213
<212> TYPE: DNA
<213> ORGANISM: Homo sapiens
<400> SEQUENCE: 61
gctctagaac tagtggatcc cccgggctgc aggaattctc taaagaagcc cctgggagca      60
cagctcatca ccatggactg gacctggagg ttcctctttg tggtggcagc agctacaggt     120
gtccagtccc aggtgcagct ggtgcagtct ggggctgagg tgaagaagcc tgggtcctcg     180
gtgaaggtct cctgcaaggc ttctggaggc accttcagca gctatgctat cagctgggtg     240
cgacaggccc ctggacaagg gcttgagtgg atgggaggga tcatccctat ctttggtaca     300
gcaaactacg cacagaagtt ccagggcaga gtcacgatta ccgcggacga atccacgagc     360
acagcctaca tggagctgag cagcctgaga tctgaggaca cggccgtgta ttactgtgcg     420
aaaaccggga tcctggggcc gtatagcagt ggctggtacc gaactcgga ctactactac      480
tacggtatgg acgtctgggg ccaagggacc acggtcaccg tctcctcagg gagtgcatcc     540
gccccaaccc ttttccccct cgtctcctgt gagaattccc cgtcggatac gagcagcgtg     600
gccgttggct gcctcgcaca ggacttcctt cccgactcca tcactttctc ctggaaatac     660
aagaacaact ctgacatcag cagcacccgg ggcttcccat cagtcctgag agggggcaag     720
tacgcagcca cctcacaggt gctgctgcct tccaaggacg tcatgcaggg cacagacgaa     780
cacgtggtgt gcaaagtcca gcaccccaac ggcaacaaag aaaagaacgt gcctcttcca     840
gtgattgctg agctgcctcc aaagtgagc gtcttcgtcc caccccgcga cggcttcttc      900
ggcaaccccc gcagcaagtc caagctcatc tgccaggcca cgggtttcag tcccggcag      960
attcaggtgt cctggctgcg cgaggggaag caggtgggt ctggcgtcac cacggaccag     1020
gtgcaggctg aggccaaaga gtctgggccc acgacctaca aggtgaccag cacactgacc     1080
atcaaagaga gcgactggct cagccagagc atgttcacct gccgcgtgga tcacagggc     1140
```

```
ctgaccttcc agcagaatgc gtcctccatg tgtgtccccg atcaagacac agccatccgg    1200
gtcttcgcca tcccccatc ctttgccagc atcttcctca ccaagtccac caagttgacc    1260
tgcctggtca cagacctgac cacctatgac agcgtgacca tctcctggac ccgccagaat    1320
ggcgaagctg tgaaaaccca caccaacatc tccgagagcc accccaatgc cactttcagc    1380
gccgtgggtg aggccagcat ctgcgaggat gactggaatt ccggggagag gttcacgtgc    1440
accgtgaccc acacagacct gccctcgcca ctgaagcaga ccatctcccg gcccaagggg    1500
gtggccctgc acaggcccga tgtctacttg ctgccaccag cccggagca gctgaacctg    1560 cgggagtcgg ccaccatcac gtgcctggtg acgggcttct ctcccgcgga cgtcttcgtg    1620
cagtggatgc agagggggca gcccttgtcc ccggagaagt atgtgaccag cgccccaatg    1680
cctgagcccc aggcccccagg ccggtacttc gcccacagca tcctgaccgt gtccgaagag    1740
gaatggaaca cggggagac ctacacctgc gtggtggccc atgaggccct gcccaacagg    1800
gtcaccgaga ggaccgtgga caagtccacc gaggggagg tgagcgccga cgaggagggc    1860
tttgagaacc tgtgggccac cgcctccacc ttcatcgtcc tcttcctcct gagcctcttc    1920
tacagtacca ccgtcacctt gttcaaggtg aaatgatccc aacagaagaa catcggagac    1980
cagagagagg aactcaaagg ggcgctgcct ccgggtctgg ggtcctggcc tgcgtggcct    2040
gttggcacgt gtttctcttc ccgcccggcc tccagttgtg tgctctcaca caggcttcct    2100
tctcgaccgg caggggctgg ctggcttgca ggccacgagg tgggctctac cccacactgc    2160
tttgctgtgt atacgcttgt tgccctgaaa taaatatgca cattttatcc atg           2213
```

<210> SEQ ID NO 62
<211> LENGTH: 627
<212> TYPE: PRT
<213> ORGANISM: Homo sapiens

<400> SEQUENCE: 62

```
Met Asp Trp Thr Trp Arg Phe Leu Phe Val Val Ala Ala Ala Thr Gly
 1               5                  10                  15

Val Gln Ser Gln Val Gln Leu Val Gln Ser Gly Ala Glu Val Lys Lys
            20                  25                  30

Pro Gly Ser Ser Val Lys Val Ser Cys Lys Ala Ser Gly Gly Thr Phe
        35                  40                  45

Ser Ser Tyr Ala Ile Ser Trp Val Arg Gln Ala Pro Gly Gln Gly Leu
    50                  55                  60

Glu Trp Met Gly Gly Ile Ile Pro Ile Phe Gly Thr Ala Asn Tyr Ala
65                  70                  75                  80

Gln Lys Phe Gln Gly Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Lys Thr Gly Ile Leu Gly Pro Tyr Ser Ser Gly Trp
        115                 120                 125

Tyr Pro Asn Ser Asp Tyr Tyr Tyr Gly Met Asp Val Trp Gly Gln
    130                 135                 140

Gly Thr Thr Val Thr Val Ser Ser Gly Ser Ala Ser Ala Pro Thr Leu
145                 150                 155                 160

Phe Pro Leu Val Ser Cys Glu Asn Ser Pro Ser Asp Thr Ser Ser Val
                165                 170                 175

Ala Val Gly Cys Leu Ala Gln Asp Phe Leu Pro Asp Ser Ile Thr Phe
            180                 185                 190
```

-continued

```
Ser Trp Lys Tyr Lys Asn Asn Ser Asp Ile Ser Ser Thr Arg Gly Phe
            195                 200                 205

Pro Ser Val Leu Arg Gly Gly Lys Tyr Ala Ala Thr Ser Gln Val Leu
            210                 215                 220

Leu Pro Ser Lys Asp Val Met Gln Gly Thr Asp Glu His Val Val Cys
225                 230                 235                 240

Lys Val Gln His Pro Asn Gly Asn Lys Glu Lys Asn Val Pro Leu Pro
                245                 250                 255

Val Ile Ala Glu Leu Pro Pro Lys Val Ser Val Phe Val Pro Pro Arg
            260                 265                 270

Asp Gly Phe Phe Gly Asn Pro Arg Ser Lys Ser Lys Leu Ile Cys Gln
            275                 280                 285

Ala Thr Gly Phe Ser Pro Arg Gln Ile Gln Val Ser Trp Leu Arg Glu
            290                 295                 300

Gly Lys Gln Val Gly Ser Gly Val Thr Thr Asp Gln Val Gln Ala Glu
305                 310                 315                 320

Ala Lys Glu Ser Gly Pro Thr Thr Tyr Lys Val Thr Ser Thr Leu Thr
                325                 330                 335

Ile Lys Glu Ser Asp Trp Leu Ser Gln Ser Met Phe Thr Cys Arg Val
            340                 345                 350

Asp His Arg Gly Leu Thr Phe Gln Gln Asn Ala Ser Ser Met Cys Val
            355                 360                 365

Pro Asp Gln Asp Thr Ala Ile Arg Val Phe Ala Ile Pro Pro Ser Phe
            370                 375                 380

Ala Ser Ile Phe Leu Thr Lys Ser Thr Lys Leu Thr Cys Leu Val Thr
385                 390                 395                 400

Asp Leu Thr Thr Tyr Asp Ser Val Thr Ile Ser Trp Thr Arg Gln Asn
                405                 410                 415

Gly Glu Ala Val Lys Thr His Thr Asn Ile Ser Glu Ser His Pro Asn
            420                 425                 430

Ala Thr Phe Ser Ala Val Gly Glu Ala Ser Ile Cys Glu Asp Asp Trp
            435                 440                 445

Asn Ser Gly Glu Arg Phe Thr Cys Thr Val Thr His Thr Asp Leu Pro
450                 455                 460

Ser Pro Leu Lys Gln Thr Ile Ser Arg Pro Lys Gly Val Ala Leu His
465                 470                 475                 480

Arg Pro Asp Val Tyr Leu Leu Pro Pro Ala Arg Glu Gln Leu Asn Leu
                485                 490                 495

Arg Glu Ser Ala Thr Ile Thr Cys Leu Val Thr Gly Phe Ser Pro Ala
            500                 505                 510

Asp Val Phe Val Gln Trp Met Gln Arg Gly Gln Pro Leu Ser Pro Glu
            515                 520                 525

Lys Tyr Val Thr Ser Ala Pro Met Pro Glu Pro Gln Ala Pro Gly Arg
            530                 535                 540

Tyr Phe Ala His Ser Ile Leu Thr Val Ser Glu Glu Trp Asn Thr
545                 550                 555                 560

Gly Glu Thr Tyr Thr Cys Val Val Ala His Glu Ala Leu Pro Asn Arg
                565                 570                 575

Val Thr Glu Arg Thr Val Asp Lys Ser Thr Glu Gly Glu Val Ser Ala
            580                 585                 590
```

-continued

```
Asp Glu Glu Gly Phe Glu Asn Leu Trp Ala Thr Ala Ser Thr Phe Ile
        595                 600                 605

Val Leu Phe Leu Leu Ser Leu Phe Tyr Ser Thr Thr Val Thr Leu Phe
    610                 615                 620

Lys Val Lys
625
```

The invention claimed is:

1. An immunoadhesin which is capable of binding to human rhinovirus comprising:

a chimeric ICAM-1 molecule, said chimeric ICAM-1 molecule having a rhinovirus receptor protein linked to at least a portion of an immunoglobulin heavy chain, wherein said rhinovirus receptor protein comprises extracellular domains 1 and 2 of ICAM-1, wherein said portion of said immunoglobulin heavy chain allows said heavy chain to bind to a J chain a J chain and a secretory component, wherein said J chain and secretory component are associated with said chimeric ICAM-1 molecule; and wherein said immunoadhesin is expressed in a plant and wherein all polypeptide sequences of the chimeric ICAM-1 molecule, J chain and secretory component are human.

2. The immunoadhesin of claim 1 wherein said rhinovirus receptor protein further comprises extracellular domains 3, 4, or 5 of ICAM-1.

3. The immunoadhesin of claim 1 wherein said immunoglobulin is selected from the group of IgA, $IgA_1$, $IgA_2$, IgM, and chimeric immunoglobulin heavy chains.

4. A composition comprising the immunoadhesin of claim 1 and at least one additional chimeric ICAM-1 molecule.

5. The immunoadhesin of claim 1 wherein said rhinovirus receptor protein further comprises extracellular domains 3, 4, or 5 of ICAM-1; and said portion of said immunoglobulin heavy chain is a portion of $IgA_2$ heavy chain.

6. The immunoadhesin of claim 1 expressed in monocotyledonous plants.

7. The immunoadhesin of claim 1 expressed in dicotyledonous plants.

8. The immunoadhesin of claim 1 expressed in hairy root cultures.

9. The immunoadhesin of claim 1 expressed in plant cells in tissue culture.

10. An immunoadhesin which is capable of binding to human rhinovirus comprising:

a chimeric ICAM-1 molecule, said chimeric ICAM-1 molecule having a rhinovirus receptor protein linked to at least a portion of an immunoglobulin heavy chain sufficient to confer effector function, wherein said rhinovirus receptor protein comprises extracellular domains 1 and 2 of ICAM-1, and wherein said immunoadhesin is expressed in a plant and wherein all polypeptide sequences of the chimeric ICAM-1 molecule are human.

11. The immunoadhesin of claim 10 wherein said immunoadhesin further comprises J chain and secretory component associated with said chimeric ICAM-1 molecule.

12. The immunoadhesin of claim 10 wherein said rhinovirus receptor protein further comprises extracellular domains 3, 4, or 5 of ICAM-1.

13. The immunoadhesin of claim 10 wherein said immunoglobulin heavy chain is selected from the group of IgA, $IgA_1$, $IgA_2$, $IgG_1$, $IgG_2$, $IgG_3$, $IgG_4$, IgM, IgD, IgE and a chimeric ICAM-1 molecule.

14. A composition comprising the immunoadhesin of claim 10 and at least one additional chimeric ICAM-1 molecule.

15. The immunoadhesin of claim 10 wherein said rhinovirus receptor protein further comprises extracellular domains 3, 4, or 5 of ICAM-1; and said immunoglobulin heavy chain comprises at least a portion of an $IgA_2$ heavy chain.

16. The immunoadhesin of claim 10 expressed in heterologous cells derived from plants.

17. The immunoadhesin of claim 10 expressed in hairy root cultures.

18. The immunoadhesin of claim 10 expressed in plant cells in tissue culture.

19. The immunoadhesin of claim 10 expressed in monocotyledonous plants.

20. The immunoadhesin of claim 10 expressed in dicotyledonous plants.

21. A composition comprising an immunoadhesin and plant material, wherein said immunoadhesin which is capable of binding to human rhinovirus comprises a chimeric ICAM-1 molecule, said chimeric ICAM-1 molecule comprising a rhinovirus receptor protein linked to at least a portion of an immunoglobulin heavy chain sufficient to confer effector function, wherein said rhinovirus receptor protein comprises extracellular domains 1 and 2 of ICAM-1, and wherein said immunoadhesin is expressed in a plant and wherein all polypeptide sequences of the chimeric ICAM-1 molecule are human.

22. The composition of claim 21 further comprising J chain and secretory component associated with said chimeric ICAM-1 molecule.

23. A composition of claim 21 wherein said rhinovirus receptor protein further comprises extracellular domains 3, 4, or 5 of ICAM-1.

24. A composition of claim 21 wherein said immunoglobulin is selected from the group of IgA, $IgA_1$, $IgA_2$, $IgG_1$, $IgG_2$, $IgG_3$, $IgG_4$, IgM, IgD, IgE, and chimeric immunoglobulin heavy chain.

25. A composition of claim 21 further comprising at least one additional chimeric ICAM-1 molecule.

26. A composition of claim 21 wherein said rhinovirus receptor protein further comprises extracellular domains 3, 4, or 5 of ICAM-1; and said immunoglobulin heavy chain is an $IgA_2$ heavy chain.

27. A method for reducing the infection by human rhinovirus of host cells susceptible to infection by human rhinovirus, said method comprising:

contacting the virus with an immunoadhesin of claim 1 or 10, and wherein said immunoadhesin binds to human rhinovirus and reduces infectivity thereof.

28. A method for the treatment of human rhinovirus infection in a human subject, said method comprising: administering to said subject an effective amount of an immunoadhesin of claim 1 or 10, and wherein said immunoadhesin reduces human rhinovirus infectivity thereof.

29. A method for the treatment of human rhinovirus infection in a subject, said method comprising: intranasally administering to said subject an effective amount of an immunoadhesin of claim 1 or 10, and wherein said immunoadhesin reduces human rhinovirus infectivity thereof.

30. A method for the treatment of human rhinovirus infection in a subject, said method comprising: administering through the oral cavity to said subject an effective amount of an immunoadhesin of claim 1 or 10, and wherein said immunoadhesin reduces human rhinovirus infectivity thereof.

31. A pharmaceutical composition comprising an immunoadhesin of claim 1 or 10, in a pharmaceutically acceptable buffer.

32. An expression vector comprising a gene encoding a chimeric ICAM-1 molecule operatively linked to a plant promoter, said chimeric ICAM-1 molecule being capable of binding to human rhinovirus and comprising a rhinovirus receptor protein linked to at least a portion of an immunoglobulin heavy chain sufficient to confer effector function, wherein said rhinovirus receptor protein comprises extracellular domains 1 and 2 of ICAM-1 wherein all encoded polypeptide sequences of the chimeric ICAM-1 molecule are human.

33. An immunoadhesin which is capable of binding to human rhinovirus comprising:
a chimeric ICAM-1 molecule, said chimeric ICAM-1 molecule having a rhinovirus receptor protein linked to at least a portion of an immunoglobulin heavy chain, wherein said rhinovirus receptor protein comprises extracellular domains 1 and 2 of ICAM-1, and wherein said portion of said immunoglobulin heavy chain allows said heavy chain to bind to a J chain;
a J chain and a secretory component, wherein said J chain and secretory component are associated with said chimeric ICAM-1 molecule; and wherein said immunoadhesin is a tetramer of said chimeric ICAM-1 molecule and is expressed in a plant; and wherein all polypeptide sequences of the chimeric ICAM-1 molecule, J chain and secretory component are human.

34. The immunoadhesin of claim 33 wherein said rhinovirus receptor protein further comprises extracellular domains 3, 4, or 5 of ICAM-1.

35. The immunoadhesin of claim 33 wherein said immunoglobulin is selected from the group of IgA, $IgA_1$, $IgA_2$, IgM, and chimeric immunoglobulin heavy chains.

36. A composition comprising the immunoadhesin of claim 33 and at least one additional chimeric ICAM-1 molecule.

37. The immunoadhesin of claim 33 wherein said rhinovirus receptor protein further comprises extracellular domains 3, 4, or 5 of ICAM-1; and said immunoglobulin heavy chain comprises at least a portion of $IgA_2$ heavy chain.

38. A method for reducing the infection by human rhinovirus of host cells susceptible to infection by human rhinovirus, said method comprising:
contacting the virus with the composition of claim 21; and wherein the immunoadhesin of said composition binds to human rhinovirus and reduces infectivity thereof.

39. A method for the treatment of human rhinovirus infection in a human subject, said method comprising:
administering to said subject an effective amount of the composition of claim 21; and
wherein said composition reduces human rhinovirus infectivity thereof.

40. A method for the treatment of human rhinovirus infection in a subject, said method comprising:
intranasally administering to said subject an effective amount of the composition of claim 21; and
wherein said composition reduces human rhinovirus infectivity thereof.

41. A method for the treatment of human rhinovirus infection in a subject, said method comprising:
administering through the oral cavity to said subject an effective amount of the composition of claim 21; and
wherein said composition reduces human rhinovirus infectivity thereof.

42. A pharmaceutical composition comprising the composition of claim 21 in a pharmaceutically acceptable buffer.

43. The immunoadhesin of claim 1 or 10 further comprising an endoplasmic reticulum retention signal.

44. The composition of claim 21 wherein the immunoadhesin of the composition further comprises an endoplasmic reticulum retention signal.

45. The expression vector of claim 32 further comprising an endoplasmic reticulum retention signal.

46. The immunoadhesin of claim 33 further comprising an endoplasmic reticulum retention signal.

47. A method for reducing the infection by human rhinovirus of host cells susceptible to infection by human rhinovirus, said method comprising:
contacting the virus with the immunoadhesin of claim 43; and
wherein the immunoadhesin of said composition binds to human rhinovirus and reduces infectivity thereof.

48. A method for reducing the infection by human rhinovirus of host cells susceptible to infection by human rhinovirus, said method comprising:
contacting the virus with the composition of claim 44; and
wherein the immunoadhesin of said composition binds to human rhinovirus and reduces infectivity thereof.

49. A method for reducing the infection by human rhinovirus of host cells susceptible to infection by human rhinovirus, said method comprising:
contacting the virus with the immunoadhesin of claim 46; and
wherein said immunoadhesin binds to human rhinovirus and reduces infectivity thereof.

* * * * *